United States Patent
Skucas et al.

(10) Patent No.: US 11,613,531 B2
(45) Date of Patent: Mar. 28, 2023

(54) INHIBITORS OF RHO ASSOCIATED COILED-COIL CONTAINING PROTEIN KINASE

(71) Applicant: Kadmon Corporation, LLC, New York, NY (US)

(72) Inventors: Eduardas Skucas, Medford, MA (US); Kevin G. Liu, West Windsor, NJ (US); Ji-In Kim, Princeton, NJ (US); Masha V. Poyurovsky, New York, NY (US); Rigen Mo, Livingston, NJ (US)

(73) Assignee: Kadmon Corporation, LLC, New York, NY (US)

( * ) Notice: Subject to any disclaimer, the term of this patent is extended or adjusted under 35 U.S.C. 154(b) by 0 days.

(21) Appl. No.: 16/641,465

(22) PCT Filed: Jun. 13, 2018

(86) PCT No.: PCT/US2018/037305
§ 371 (c)(1),
(2) Date: Feb. 24, 2020

(87) PCT Pub. No.: WO2019/045824
PCT Pub. Date: Mar. 7, 2019

(65) Prior Publication Data
US 2020/0199109 A1  Jun. 25, 2020

Related U.S. Application Data

(60) Provisional application No. 62/553,619, filed on Sep. 1, 2017.

(51) Int. Cl.
| | |
|---|---|
| C07D 403/14 | (2006.01) |
| C07D 401/14 | (2006.01) |
| C07D 413/14 | (2006.01) |
| C07D 471/10 | (2006.01) |
| C07D 487/08 | (2006.01) |
| C07D 487/10 | (2006.01) |
| C07D 491/048 | (2006.01) |
| C07D 491/052 | (2006.01) |
| C07D 495/04 | (2006.01) |
| C07D 498/10 | (2006.01) |
| C07D 519/00 | (2006.01) |
| A61P 11/00 | (2006.01) |

(52) U.S. Cl.
CPC ............ *C07D 403/14* (2013.01); *A61P 11/00* (2018.01); *C07D 401/14* (2013.01); *C07D 413/14* (2013.01); *C07D 471/10* (2013.01); *C07D 487/08* (2013.01); *C07D 487/10* (2013.01); *C07D 491/048* (2013.01); *C07D 491/052* (2013.01); *C07D 495/04* (2013.01); *C07D 498/10* (2013.01); *C07D 519/00* (2013.01)

(58) Field of Classification Search
CPC .. C07D 495/04; C07D 498/10; C07D 519/00; C07D 403/14; C07D 401/14; C07D 491/052; C07D 491/048; C07D 413/14; C07D 471/10; C07D 487/08; C07D 487/10
See application file for complete search history.

(56) References Cited

U.S. PATENT DOCUMENTS

| | | | |
|---|---|---|---|
| 6,156,751 A | 12/2000 | Hutchison et al. | |
| 7,648,986 B2* | 1/2010 | Nagarathnam | C07D 471/04 514/234.2 |
| 8,741,450 B2 | 6/2014 | Iwakuma et al. | |
| 2009/0318684 A1 | 12/2009 | Sebti et al. | |
| 2016/0237095 A1 | 8/2016 | Kim et al. | |

FOREIGN PATENT DOCUMENTS

| | | |
|---|---|---|
| WO | 2003059913 A1 | 7/2003 |
| WO | 2006111549 A1 | 10/2006 |
| WO | 2009103652 A1 | 8/2009 |
| WO | 2014055999 A2 | 4/2014 |
| WO | 2015054317 A1 | 4/2015 |
| WO | 2015157556 A1 | 10/2015 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL;http;//www.cnn/com/2003/HEALTH/conditions/09/24/alzheimers.drug.ap/index.html>.*
Extended Search Report dated Nov. 18, 2020 in related European Patent Application No. 18850603.4, 8 pgs.
O'Donnell, Michael et al., "A complementary route to diaminopyrimidines through regioselective SNAr amination reactions", Tetrahedron 71 (2015) 1515-1522.
Singla, Prinka et al., "Novel pyrazolo[3,4-d]pyrimidine with 4-(1H-benzimidazol-2-yl)-phenylamine as broad spectrum anticancer agents: Synthesis, cell based assay, topoisomerase inhibition, DNA intercalation and bovine serum albumin studies", European Journal of Medicinal Chemistry, 126 (2017) 24-35.
Office Action from JP2020-512675 dated May 31, 2022, 5 pages.

\* cited by examiner

*Primary Examiner* — Rebecca L Anderson
(74) *Attorney, Agent, or Firm* — McNeill Baur PLLC

(57) ABSTRACT

The invention relates to inhibitors of ROCK1 and/or ROCK2. Also provided are methods of inhibiting ROCK1 and/or ROCK2 that are useful for the treatment of disease.

17 Claims, 17 Drawing Sheets

Fig. 1a.
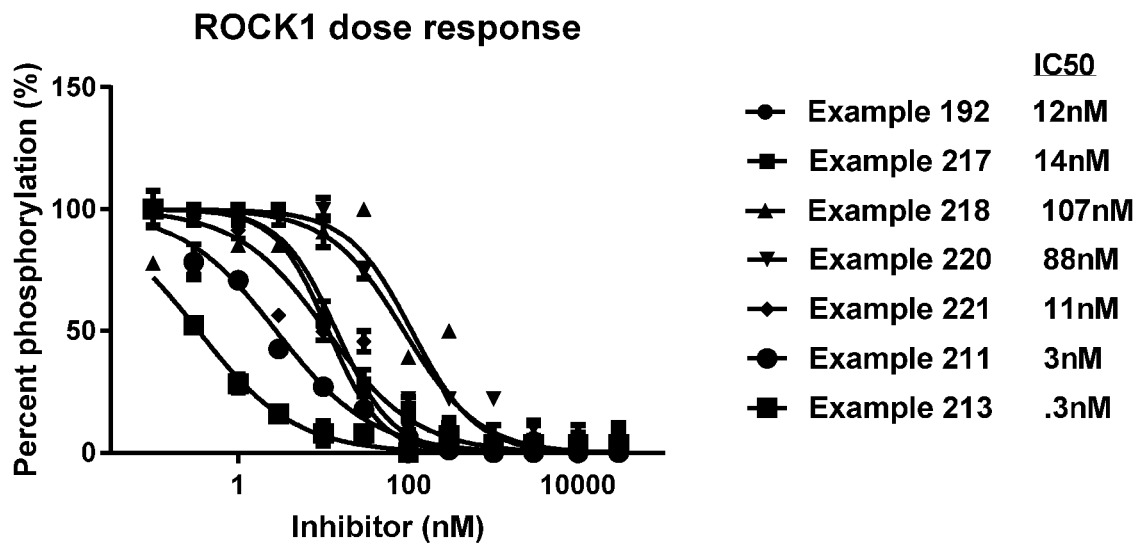
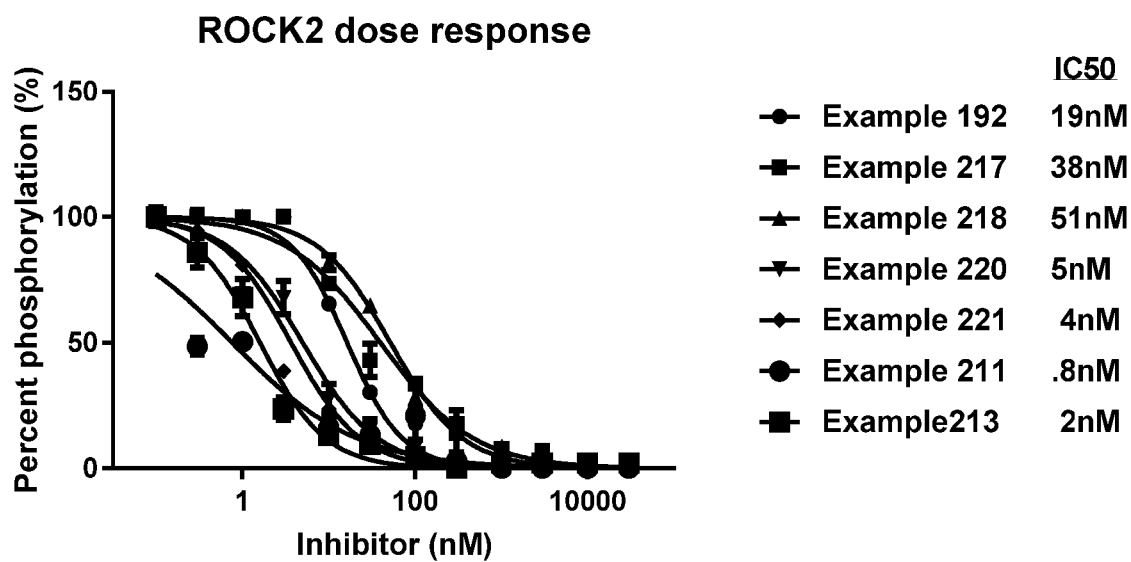
Figure 1

Fig. 1b.
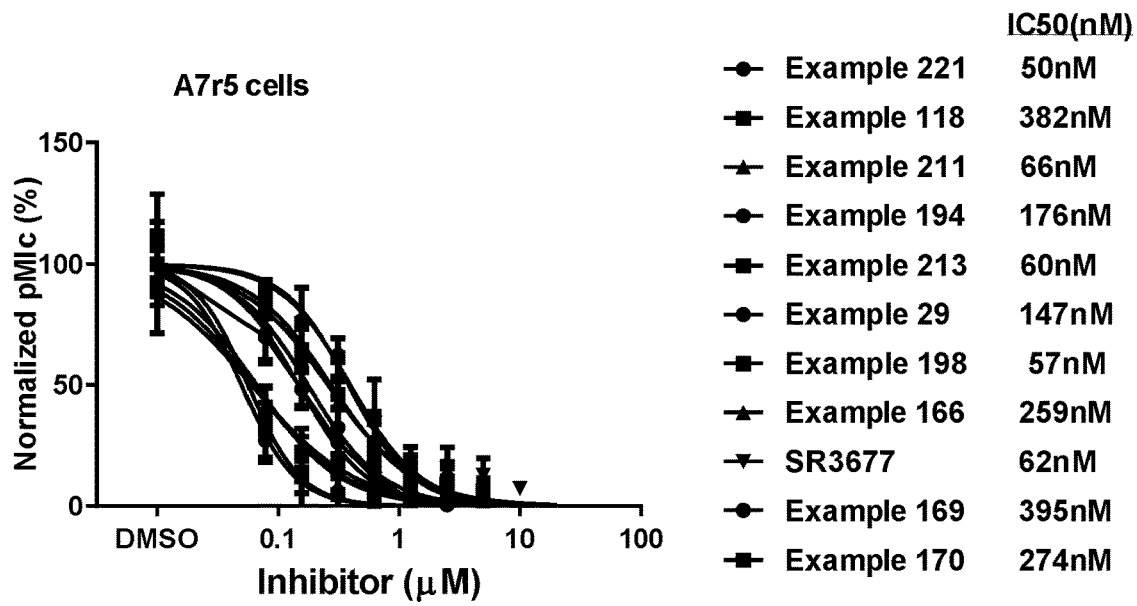
Fig. 1c.
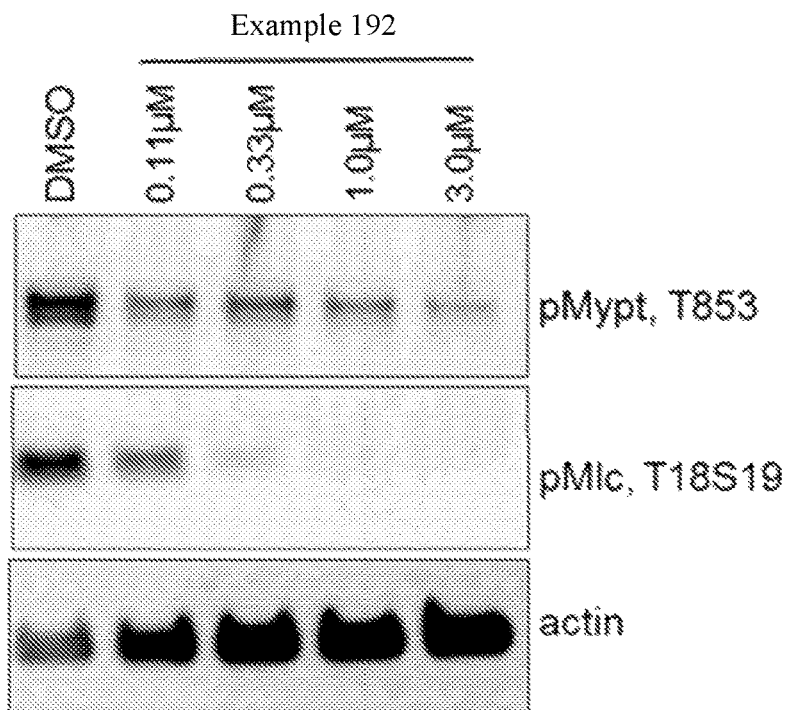
Figure 1 (cont.)

Fig. 2a.
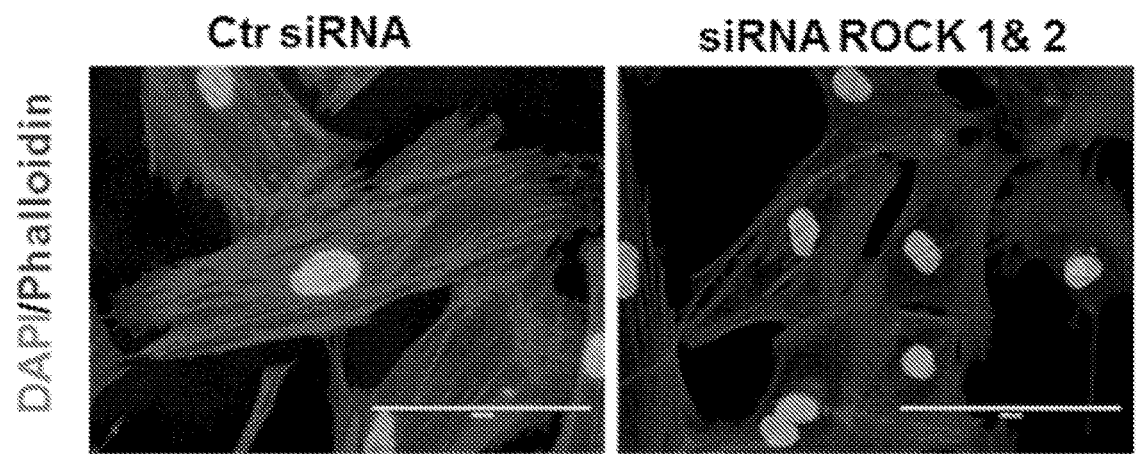
Fig. 2b.
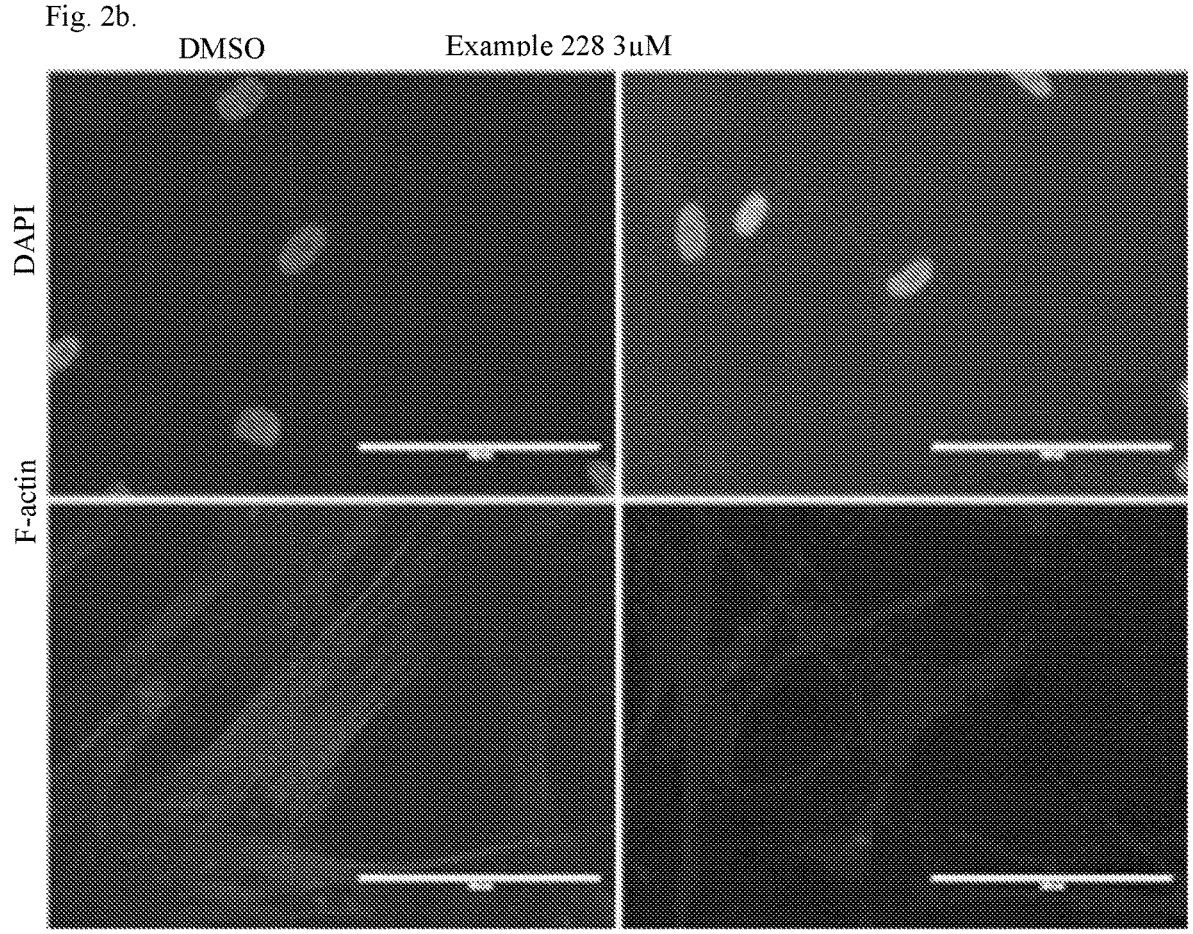
Figure 2

Fig. 4a.
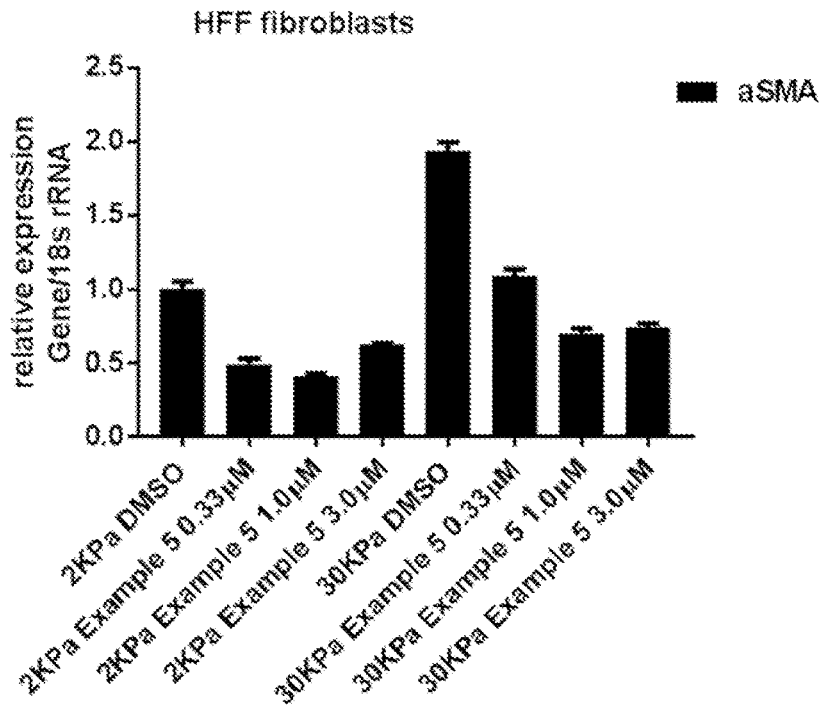
Fig 4b.
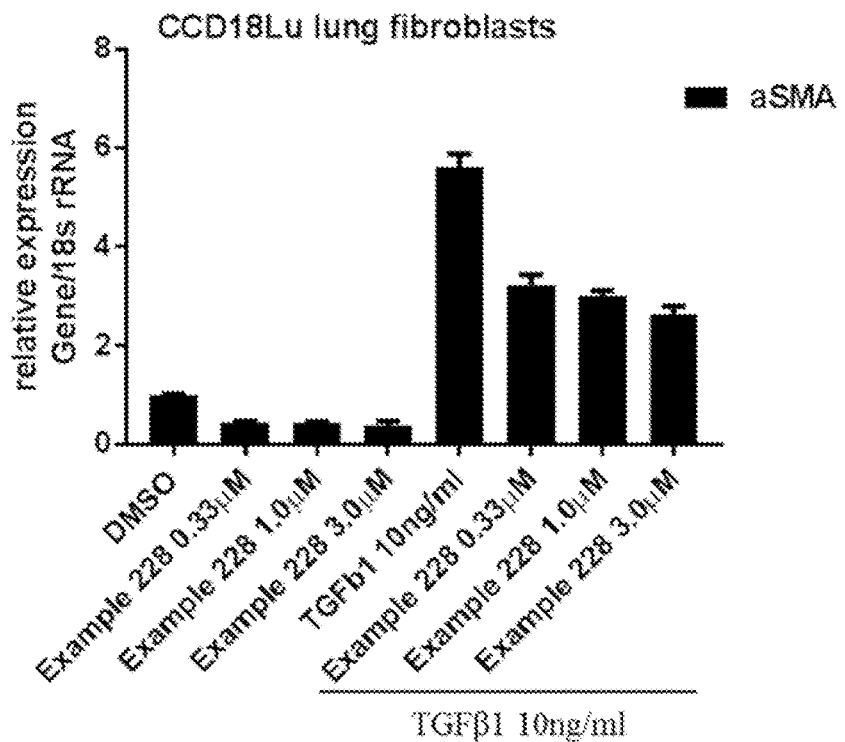
Figure 4

Fig. 4c.
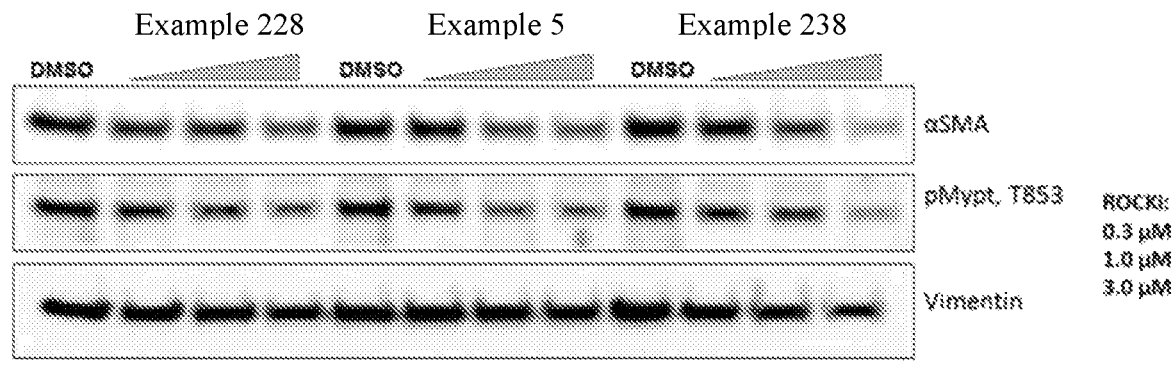
Fig 4d.
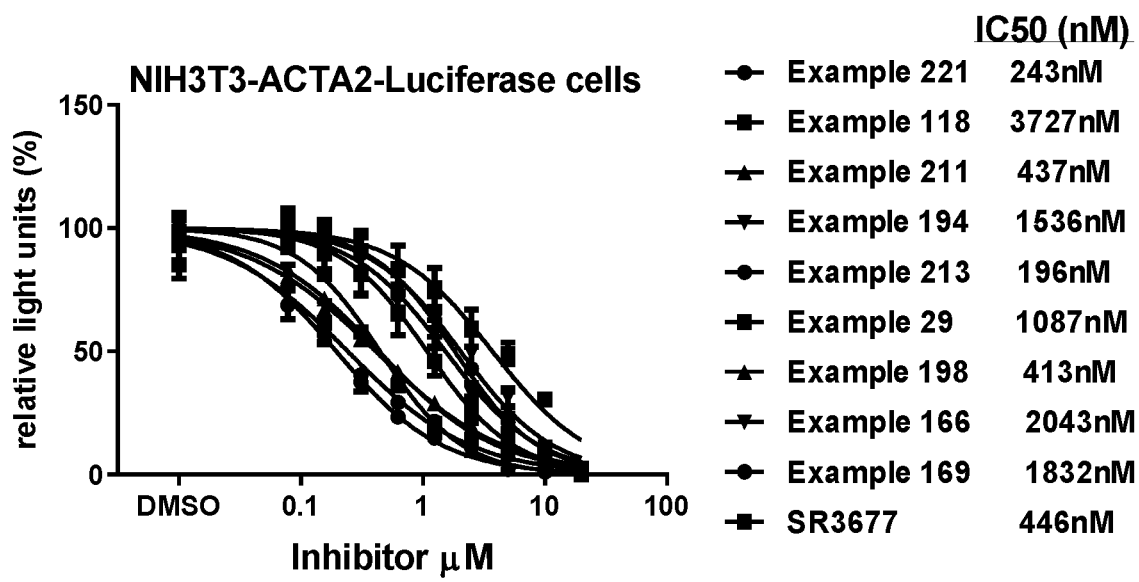
Figure 4 (cont.)

Fig. 7a.
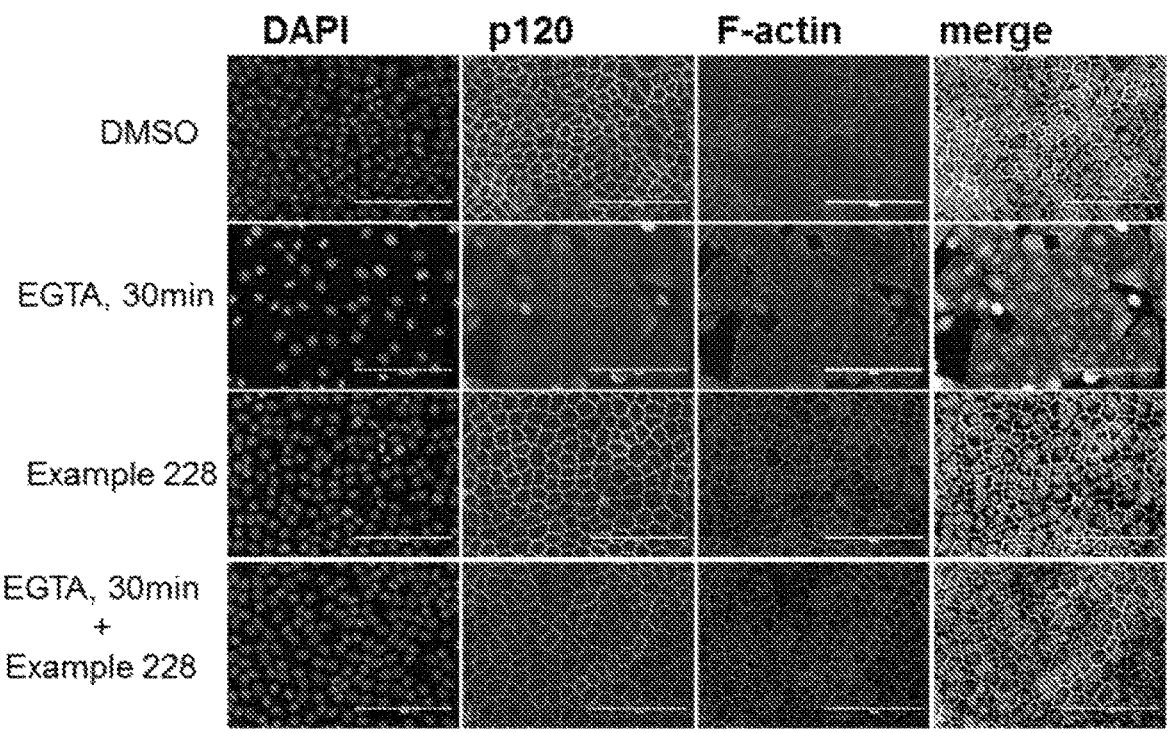
Fig. 7b.
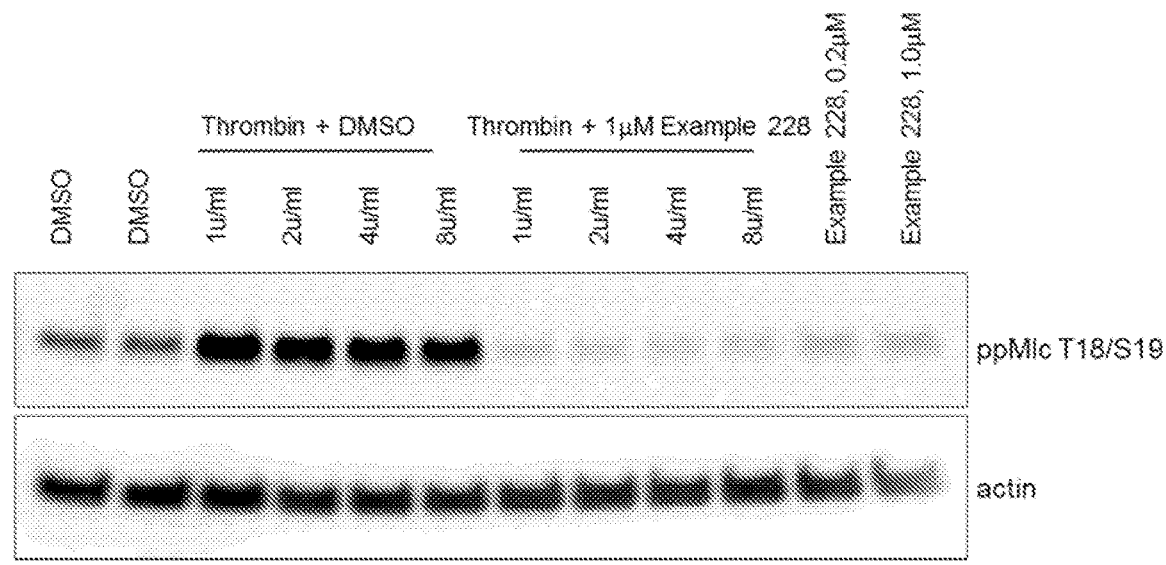
Figure 7

Fig. 11A
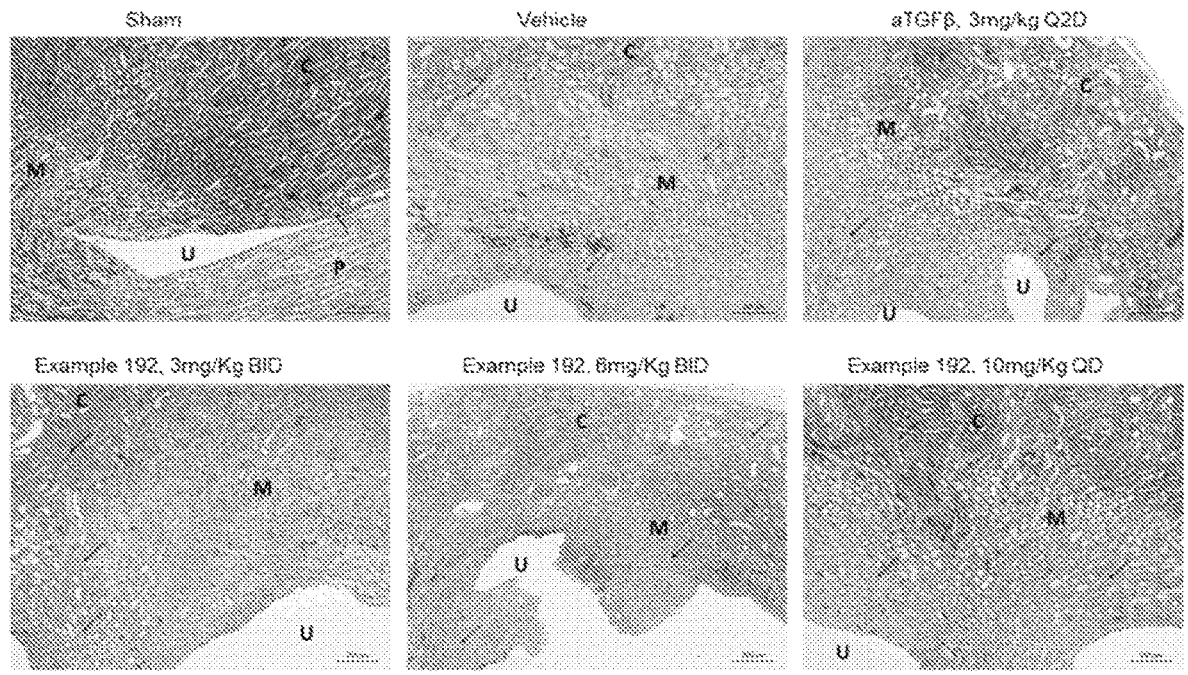
Fig. 11B
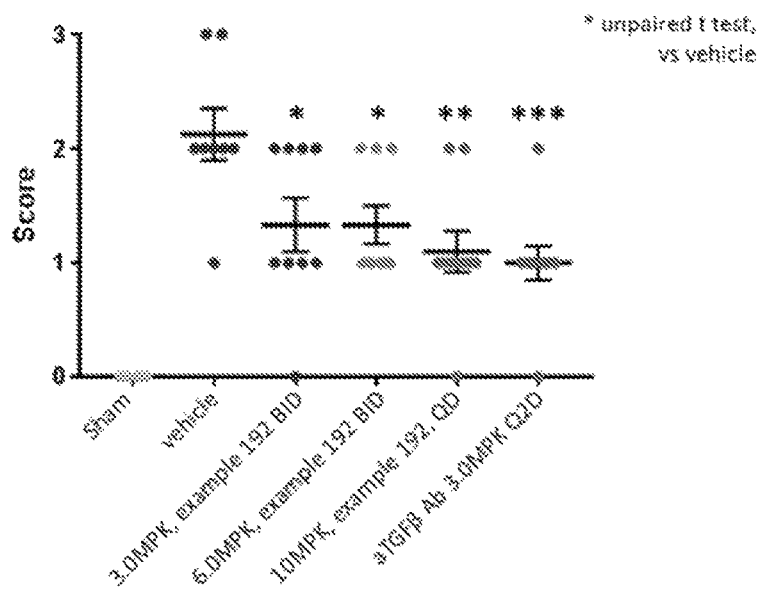
Figure 11

Fig. 12A
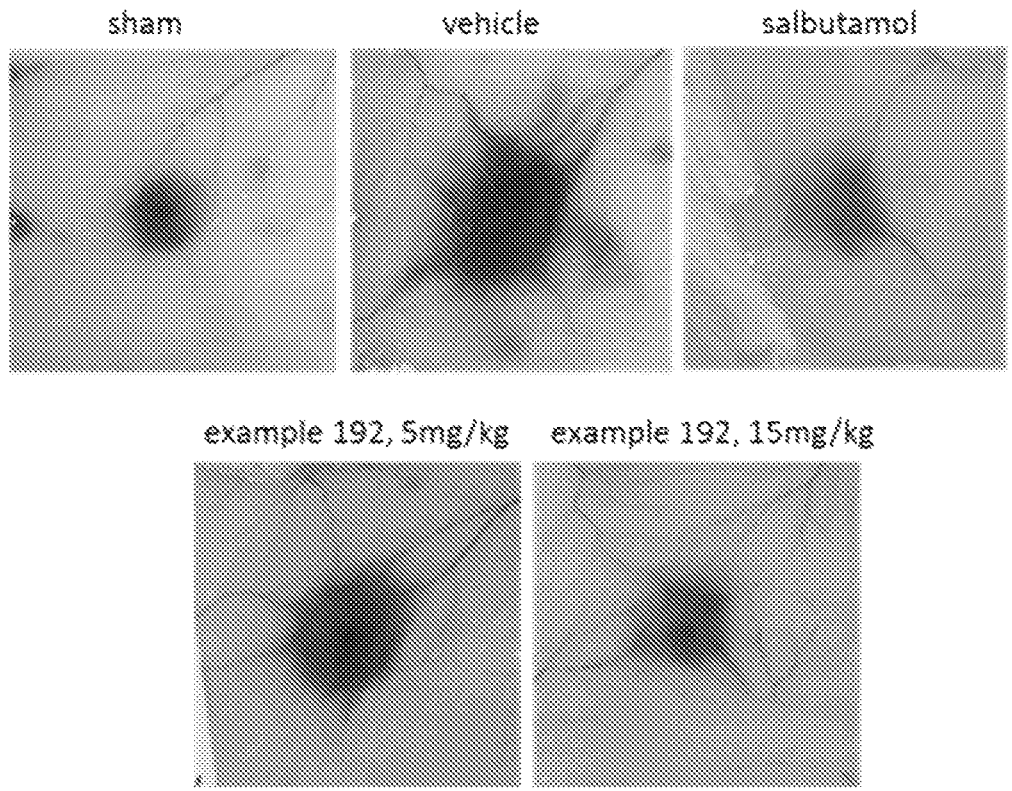
Fig. 12B
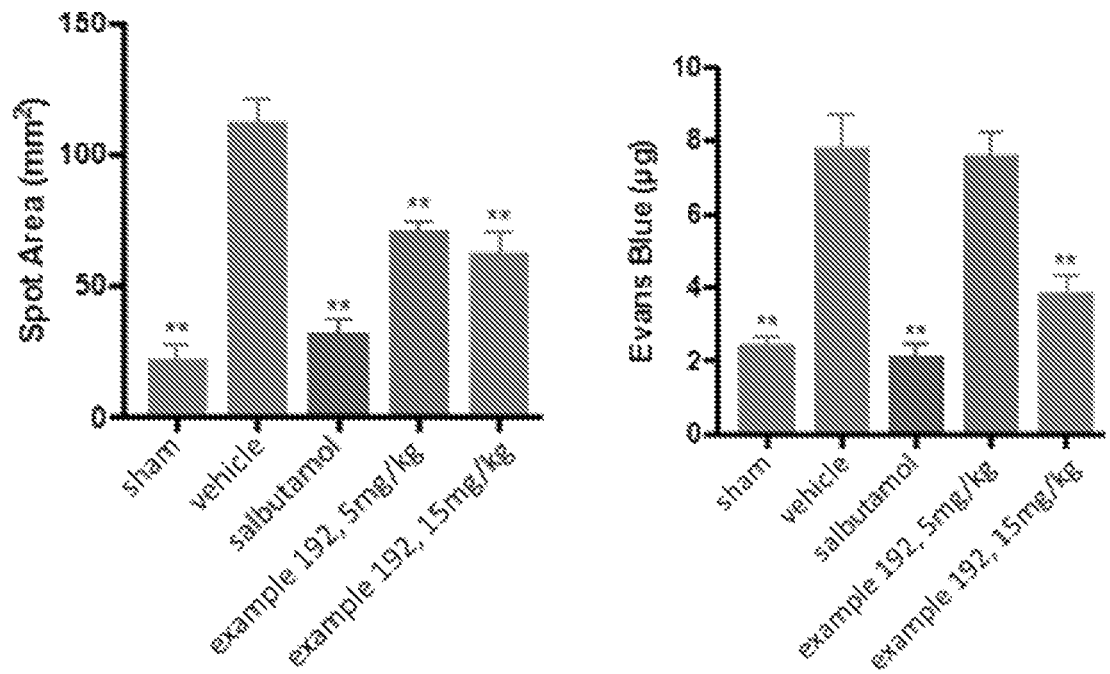
Figure 12

INHIBITORS OF RHO ASSOCIATED COILED-COIL CONTAINING PROTEIN KINASE

FIELD OF THE INVENTION

The invention relates to inhibitors of ROCK1 and/or ROCK2. Also provided are methods of inhibiting ROCK1 and/or ROCK2 that are useful for the treatment of disease.

BACKGROUND OF THE INVENTION

The Rho Associated Coiled-Coil Containing Protein Kinases (ROCK) are members of the serine/threonine kinase family. Two isoforms, ROCK1 and ROCK2, have been identified. Both isoforms are activated by GTP-bound forms of Rho GTPase and when activated phosphorylate a variety of downstream substrates. ROCKs play important roles in numerous cellular processes including smooth muscle cell contraction, cell proliferation, adhesion and migration. As such, ROCK inhibitors have potential therapeutic applicability in a wide variety of pathological conditions including, for example, asthma, cancer, erectile dysfunction, glaucoma, insulin resistance, kidney failure, pulmonary hypertension, neuronal degeneration, and osteoporosis.

Fibrosis is defined by the excessive accumulation of fibrous extracellular matrix (ECM) components, such as collagen and fibronectin, in the damaged tissue and ultimately leads to permanent scarring, organ failure as seen in idiopathic pulmonary fibrosis (IPF), end-stage liver disease, kidney disease, and heart failure (Julian and Olson, 2014). Regardless of tissue type and etiology, organ fibrosis is now understood to be the final pathological outcome of an aberrant wound healing response to tissue injury. The initial or repetitive damages occur to the outermost epithelial cells, which trigger wound healing responses. A feature common to all fibrotic diseases is the activation of ECM producing myofibroblasts, which is the key cell type dominating fibrotic tissue remodeling and normal wound healing. Unlike in controlled wound healing, in which myofibroblasts undergo apoptosis after the healing process, myofibroblasts become resistance to apoptosis in fibrosis and over-produce extracellular matrix. Together with excessive ECM deposition and increased cross linking of collagen matrix turn ECM more rigid in the fibrotic tissue. The increase in matrix stiffness has been recognized as active participant in disease progression by establishing a feedback loop termed mechanotransduction (Moraes, 2015). The pro-fibrotic cells response to the mounting extracellular mechanical forces by exhibiting stiffer cytoskeletal features and consequently alter their intracellular signaling cascades toward disease prone direction.

ROCK kinases, as major effector proteins of small GTPase Rho, are key regulators of the cell cytoskeleton and actomyosin contractility. Upon activation, ROCKs phosphorylate multiple downstream substrates, including myosin-light-chain (MLC, at threonine 18 & serine 19) and myosin light-chain phosphatase (MYPT1, at threonine 853), to drive the polymerization of globular G-actin into filamentous F-actin and assemble actomyosin contractile machinery. ROCKs are key regulators of mechanotransduction signaling, and the cells involved in tissue fibrotic responses, namely epithelial cells, endothelial cells and myofibroblasts, are fundamentally regulated by ROCK activities. Thus, ROCK inhibitors ("ROCKi") may have therapeutic utilities in fibrotic disease.

SUMMARY OF THE INVENTION

Compounds according to the present invention include those having the formula I:

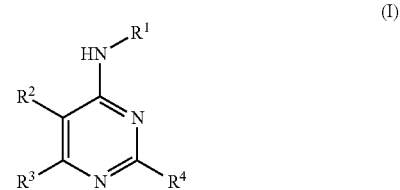

wherein:

$R^1$ is a selected from the group consisting of the following structures:

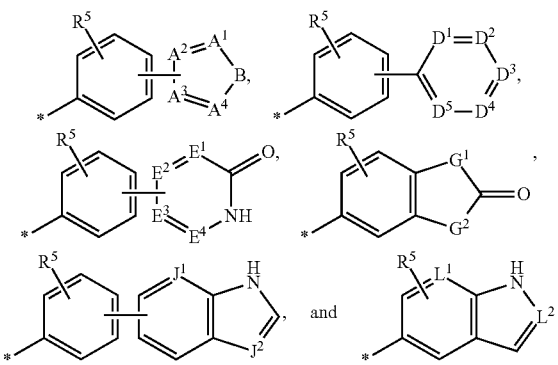

$R^5$ is selected from H, halo, hydroxy, —NRR', —(CH$_2$)NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

each of $A^1$, $A^2$, $A^3$ and $A^4$ are independently selected from N, C—$R^a$ and CH, wherein the maximum number of N among $A^1$, $A^2$, $A^3$ and $A^4$ is 3;

B is selected from group consisting of NH, O and S;

each of $D^1$, $D^2$, $D^3$, $D^4$ and $D^5$ are independently selected from N, C—$R^a$ and CH; wherein the maximum number of N among $D^1$, $D^2$, $D^3$, $D^4$ and $D^5$ is 3;

each of $E^1$, $E^2$, $E^3$ and $E^4$ are independently selected from N, C—$R^a$ and CH, wherein the maximum number of N among $E^1$, $E^2$, $E^3$ and $E^4$ is 2;

each of $G^1$ and $G^2$ are independently selected from NH, CH—$R^a$ and CH$_2$;

each of $J^1$ and $J^2$ are independently selected from N and CH, each of $L^1$ and $L^2$ are independently selected from N and CH, each $R^a$ is independently selected from the group consisting of lower alkyl, halo and amino;

$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively R² and R³ are taken together to form a 4- to 7-membered fused ring having from 0 to 3 ring heteroatoms, and is unsubstituted or is substituted with halo, hydroxy, amino, —C(=O)-lower alkyl, lower alkyl, and lower alkoxy;

R⁴ is a selected from the group consisting of the following structures:

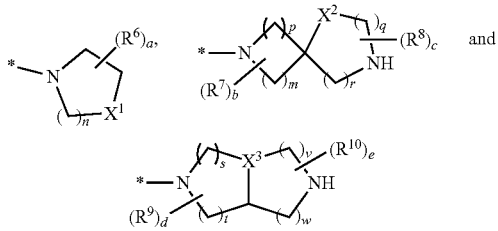

X¹ is selected from the group consisting of O, NH, and CHR⁶;

each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)$_f$NRR', —O—(CH₂)$_g$NRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;

additionally or alternatively, two R⁶ substituents attached to the same ring carbon may be taken together to form an oxo group (i.e., =O), or a C₃ to C₇ spiro cyclic group; and additionally or alternatively, two R⁶ substituents attached to different ring carbons may be taken together to form a ring, wherein the ring formed when taking the two R⁶ groups together has from 4 to 7 ring atoms including from 0 to 3 ring heteroatoms.

each R⁷ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;

each R⁸ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;

each R⁹ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;

each R¹⁰ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;

X² is selected from CH₂, CHR⁸, O, NH and N-(lower alkyl);
X³ is selected from CH, CR⁹ and N;
each R is independently selected from H and lower alkyl;
each R' is independently selected from H, lower alkyl, aryl, substituted aryl, aralkyl, and
substituted aralkyl;
a is selected from 0 to 3;
b is selected from 0 to 2;
c is selected from 0 to 2;
d is selected from 0 to 2;
e is selected from 0 to 2;
each f is independently 1 to 3;
each g is independently 2 or 3;
n is selected from 0 to 4;
m is selected from 1 to 3;
p is selected from 1 to 3;
q is selected from 0 to 3;
r is selected from 0 to 3;
wherein q and r are not simultaneously selected to be 0;
s is selected from 0 to 3;
t is selected from 0 to 3;
wherein s and t are not simultaneously selected to be 0;
v is selected from 0 to 3; and
w is selected from 0 to 3.

The present invention includes pharmaceutical compositions comprising the compounds of the invention and a pharmaceutically acceptable carrier. The present invention includes compositions comprising a substantially pure compound of the invention and a pharmaceutically acceptable salt, stereoisomer, or hydrate thereof, and a pharmaceutically acceptable carrier.

In one aspect, the invention provides a method of inhibiting a ROCK (i.e., ROCK1 and/or ROCK2) in a mammal comprising administering an effective amount of one or more compounds of Formula I. The invention provides a method of treating a patient suffering from a disease comprising administering to the patient in need of such treatment a therapeutically effective amount of a compound of Formula I. In certain such embodiments, the compound of Formula I inhibits ROCK2. In certain such embodiments, the compound of Formula I selectively inhibits ROCK1 and/or ROCK2. Non-limiting diseases and conditions treated according to the instant invention include fibrotic disease, central nervous system disorders such as neuronal degeneration and spinal cord injury, cardiovascular diseases such as hypertension, atherosclerosis, restenosis, cardiac hypertrophy, ocular hypertension, cerebral ischemia, cerebral vasospasm, penile erectile dysfunction, arterial thrombotic disorders such as platelet aggregation and leukocyte aggregation, asthma, regulation of intraocular pressure, and bone resorption.

The invention provides a method of treating a fibrotic disorder in a subject comprising administering to the subject a therapeutically effective amount of a compound of Formula I. Non-limiting examples of fibrotic disorders are pulmonary fibrosis including cystic and idiopathic pulmonary fibrosis, radiation induced lung injury, liver fibrosis including cirrhosis, cardiac fibrosis including arterial fibrosis, endomyocardial fibrosis, old myocardial infraction, arterial stiffness, atherosclerosis, restenosis, arthrofibrosis, Crohn's disease, myelofibrosis, Peyronie's diseases, nephrogenic systemic fibrosis, progressive massive fibrosis, retroperitoneal cavity fibrosis, schleroderma/systemic sclerosis, mediastinal fibrosis, Keloids and hypertrophic scars, glial scaring, or renal fibrosis.

The invention provides a method of treating a central nervous system disorder in a subject comprising administering to the subject a therapeutically effective amount of a compound of Formula I. Central nervous system disorders include, without limitation, neuronal degeneration or spinal cord injury, as well as Huntington's disease, Parkinson's disease, Alzheimer's disease, Amyotrophic lateral sclerosis (ALS), or multiple sclerosis.

The invention provides a method of treating an autoimmune disorder in a subject comprising administering to the subject a therapeutically effective amount of a compound of Formula I. Autoimmune disorders include, without limitation, rheumatoid arthritis, (multiple sclerosis), systemic lupus erythematosus (SLE; lupus), psoriasis, Crohn's disease, atopic dermatitis, eczema, or graft-versus-host disease (GVHD).

The invention provides a method of treating a cardiovascular disorder in a subject comprising administering to the subject a therapeutically effective amount of a compound of Formula I. Cardiovascular disorders include, without limitation, hypertension, atherosclerosis, angina, arterial obstruction, peripheral arterial disease, peripheral circulatory disorder, cerebral cavernous malformation, restenosis, cardiac hypertrophy, ocular hypertension, cerebral ischemia, cerebral vasospasm, acute respiratory distress syndrome (ARDS) or erectile dysfunction.

The invention provides a method of treating inflammation in a subject comprising administering to the subject a therapeutically effective amount of a compound of Formula I. Inflammation includes, without limitation, asthma, cardiovascular inflammation, renal inflammation or arteriosclerosis.

The invention provides a method of treating an arterial thrombotic disorder in a subject comprising administering to the subject a therapeutically effective amount of a compound of Formula I. Non-limiting examples of arterial thrombotic disorders are platelet aggregation, or leukocyte aggregation.

The invention provides a method of maintaining epithelial stability comprising administering to the subject a therapeutically effective amount of a compound of Formula I.

The invention provides a method of treating glaucoma or regulating intraocular pressure in a subject comprising administering to the subject a therapeutically effective amount of a compound of Formula I. Non-limiting examples of glaucoma include primary open-angle glaucoma, acute angle-closure glaucoma, pigmentary glaucoma, neovascular glaucoma, congenital glaucoma, normal tension glaucoma, or secondary glaucoma.

The invention provides a method of treating a neoplastic disease in a subject comprising administering to the subject a therapeutically effective amount of a compound of Formula I. Neoplastic diseases include, without limitation, a lymphoma, carcinoma, leukemia, sarcoma, or blastoma, such as squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, or head and neck cancer.

The invention also provides a method of treating metabolic syndrome, insulin resistance, hyperinsulinemia, type 2 diabetes, or glucose intolerance in a subject comprising administering to the subject a therapeutically effective amount of a compound of Formula I.

Further, the invention provides a method of treating osteoporosis or promoting bone formation a subject comprising administering to the subject a therapeutically effective amount of a compound of Formula I.

The invention also provides a method of regulating TH17 and Treg function, as well as IL-17 and IL-21 production in immune system cells. Accordingly, the invention provides a method of regulating immunological responses using ROCK inhibitors of Formula I.

The invention provides a method of treating an ocular disorder having an angiogenic component comprising administering to the subject a therapeutically effective amount of a compound of Formula I and an angiogenesis inhibitor. Non-limiting examples of such ocular disorders include age related macular degeneration (AMD), choroidal neovascularization (CNV), diabetic macular edema (DME), iris neovascularization, uveitis, neovascular glaucoma, or retinitis of prematurity (ROP).

BRIEF DESCRIPTION OF THE FIGURES

FIG. 1a. Representative Z'-Lyte assay results. ROCK inhibitors of the invention show single digit nanomolar potencies towards both isoforms of ROCK.

FIG. 1b. A7R5 in-cell Elisa assay. A7R5 cells were treated with 9 points 2 fold serial dilution of compounds and ppMlc (T18/S19) levels were determined to calculate cellular IC50 values of the compounds. Compounds of the invention gave in cell IC50s under 100 nM.

FIG. 1c. Western blot of A7R5 cell lysates to visualize ppMlc (T18/S19) levels following treatment with the compound of Example 192 ("Example 192") for 90 min. A7R5 cells were treated with the compound and ppMlc (T18/S19) levels were visualized by western blotting. Kadmon ROCK efficiently blocked ROCK targets MLC and MYPT1 phosphorylation at 110 nM.

FIG. 2a. Silencing of ROCK1 and ROCK2 protein expression in HFF human fibroblasts reduced stress fiber formation. ROCK1 and ROCK2 expressions were simultaneously silenced with transfection of targeting siRNAs and F-actin contents were visualized by phalloidin staining.

FIG. 2b. The Example 228 compound inhibited F-actin stress fiber formation in CCD18lu human lung fibroblasts.

FIG. 4a. ROCK inhibitor blocked mechanotransduction. HFF cells were cultured on Prime Coat dishes coated with silicone gel with increasing rigidities (2 KPa or 30 KPa). Cells were treated for 24 hours with compounds and mRNA expressions were quantified by Taqman qPCR.

FIG. 4b. ROCK inhibitor decreased basal, as well as TGFβ1 induced, expression of αSMA in human lung fibroblasts. LL24 cells were treated for 24 hours and mRNA expressions were quantified by Taqman qPCR.

FIG. 4c. ROCK inhibitor reduced αSMA protein levels in fibroblasts. CCD18Lu human lung fibroblasts were cultured on plastic substrate for 5 days with or without inhibitors. αSMA and control proteins were visualized by western blots.

FIG. 4d. ROCK inhibitors can be effectively rank ordered by ACTA2-promoter-driven-luciferase reporter cell assay. NIH3T3 cells stably expressing ACTA2-promoter-driven-luciferase were plated in 96 well plates to confluence and treated with 9 points serial dilution of compounds in combination with TGFβ1 for 24 hr. Luciferase activities were measured and compound's IC50s were calculated. By this assay multiple compounds of the invention gave IC50s under 200 nM.

FIG. 7a. ROCK inhibitors protected epithelial junctional integrity. MDCK cells were cultured in confluence for 3 days and extracellular calcium was chelated by adding 5 mM of EGTA with or without addition of ROCK inhibitor. Cellular junctional integrity was visualized by immunofluorescent staining of adhesion molecule p120. F-actin and nucleus were counterstained.

FIG. 7b. ROCK inhibitors blocked thrombin induced MLC phosphorylation. Mouse endothelial cell line SVEC4-10 cells were cultured and treated with increasing doses of thrombin in combination with ROCKi for 10 min. ppMLC signal was detected by western blot.

FIG. 11a. ROCK inhibitor is active in a mouse model of renal fibrosis. Representative images of kidney sections stained with Masson's trichrome to visualize collagen and fibrosis in mice treated with ROCK inhibitor in the ureteral obstruction (UUO) induced renal fibrosis mouse model.

FIG. 11b. Quantitation of the decrease in the interstitial fibrosis index in the histopathological analysis of the images from ROCK inhibitor and vehicle treated mice in the UUO induced renal fibrosis mouse model.

FIG. 12a. ROCK inhibition stabilizes the endothelial barrier function in a histamine-induced vascular permeability model in mice. Representative images of Evan's Blue dye extravasation induced by histamine in the skin of ROCK inhibitor and vehicle treated mice, relative to the control compound (salbutamol). ROCK inhibitor induces vascular barrier stabilization following single dose of compound administered 1 hr. prior to histamine injection.

FIG. 12b. Quantitation of the decrease in spot area size and Evan's Blue dye amount in the skin of ROCK inhibitor treated mice following the induction of capillary leakage by histamine injection.

DETAILED DESCRIPTION OF THE INVENTION

ROCK Inhibitors

Figure 3:
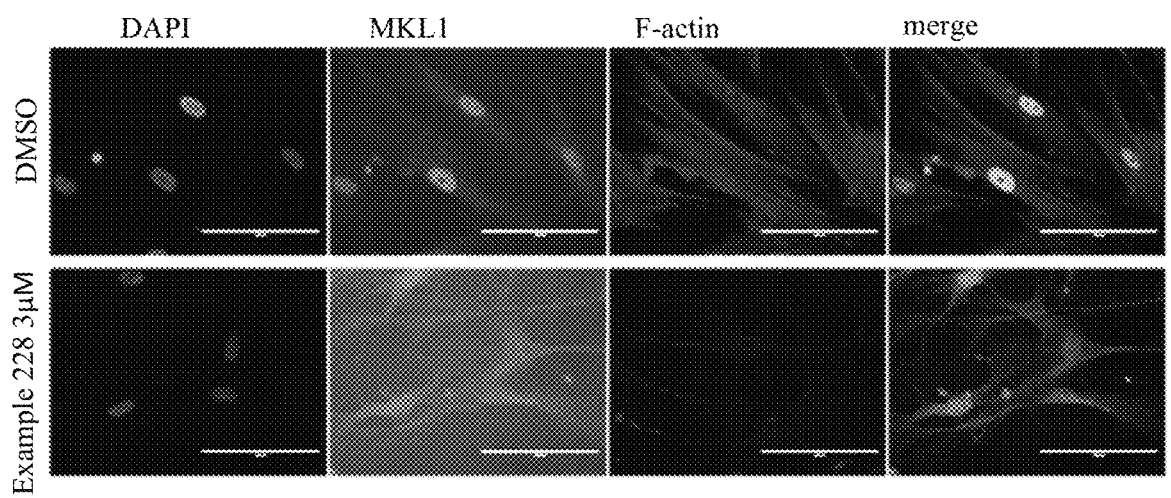
FIG. 3. Immunofluorescent staining of MKL1 in human lung fibroblasts. CCD18Lu human lung fibroblasts were treated with compounds for 3 hours and fixed and stained for MKL1, F-actin and DAPI. Note that ROCKi efficiently cleared stress fiber formation while blocked nuclear accumulation of MKL1.

Compounds according to the present invention include those having the formula I:

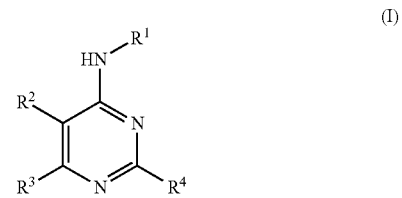

wherein:
R$^1$ is a selected from the group consisting of the following structures:

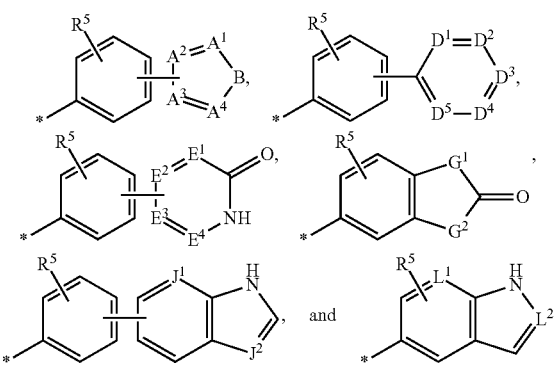

R$^5$ is selected from H, halo, hydroxy, —NRR', —(CH$_2$)NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;

each of A$^1$, A$^2$, A$^3$ and A$^4$ are independently selected from N, C—R$^a$ and CH, wherein the maximum number of N among A$^1$, A$^2$, A$^3$ and A$^4$ is 3;

B is selected from group consisting of NH, O and S;

each of D$^1$, D$^2$, D$^3$, D$^4$ and D$^5$ are independently selected from N, C—R$^a$ and CH; wherein the maximum number of N among D$^1$, D$^2$, D$^3$, D$^4$ and D$^5$ is 3;

each of E$^1$, E$^2$, E$^3$ and E$^4$ are independently selected from N, C—R$^a$ and CH, wherein the maximum number of N among E$^1$, E$^2$, E$^3$ and E$^4$ is 2;

each of G$^1$ and G$^2$ are independently selected from NH, CH—R$^a$ and CH$_2$;

each of $J^1$ and $J^2$ are independently selected from N and CH, each of $L^1$ and $L^2$ are independently selected from N and CH, each $R^a$ is independently selected from the group consisting of lower alkyl, halo and amino;

$R^2$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxy, amino, —C(=O)-lower alkyl, lower alkyl, and lower alkoxy;

$R^4$ is a selected from the group consisting of the following structures:

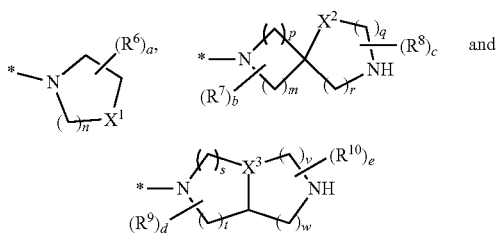

$X^1$ is selected from the group consisting of O, NH, and $CHR^6$;

each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —$(CH_2)_f$NRR', —O—$(CH_2)_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

additionally or alternatively, two $R^6$ substituents attached to the same ring carbon may be taken together to form an oxo group (i.e., =O), or a $C_3$ to $C_7$ spiro cyclic group; and additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms.

each $R^7$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^8$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^9$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^{10}$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy; $X^2$ is selected from $CH_2$, $CHR^8$, O, NH and N-(lower alkyl); $X^3$ is selected from CH, $CR^9$ and N;

each R is independently selected from H and lower alkyl;

each R' is independently selected from H, lower alkyl, aryl, substituted aryl, aralkyl, and substituted aralkyl;

a is selected from 0 to 3;

b is selected from 0 to 2;

c is selected from 0 to 2;

d is selected from 0 to 2;

e is selected from 0 to 2;

each f is independently 1 to 3;

each g is independently 2 or 3;

n is selected from 0 to 4;

m is selected from 1 to 3;

p is selected from 1 to 3;

q is selected from 0 to 3;

r is selected from 0 to 3;

wherein q and r are not simultaneously selected to be 0;

s is selected from 0 to 3;

t is selected from 0 to 3;

wherein s and t are not simultaneously selected to be 0;

v is selected from 0 to 3; and w is selected from 0 to 3.

In embodiments of the invention, one of $R^2$ and $R^3$ is H and the other is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl.

When $R^2$ and $R^3$ are taken together to form a 4- to 7-membered fused ring having from 0 to 3 ring heteroatoms, the resulting ring may be aromatic or non-aromatic. Preferably, when $R^2$ and $R^3$ are taken together to form a fused ring, the ring has 5 or 6 ring atoms. The term "fused" in this context refers to the adjoining rings sharing two adjacent ring atoms. Examples of the ring systems that may be formed when $R^2$ and $R^3$ are taken together to form a 5- or 6-membered fused ring include:

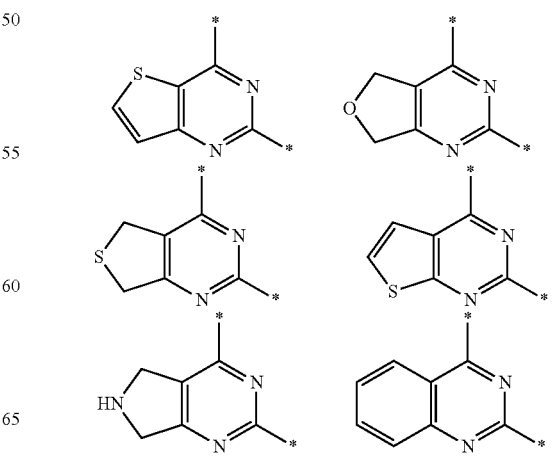

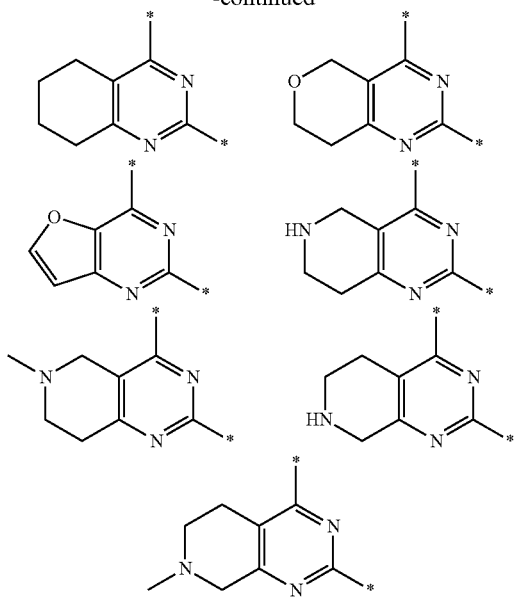

When $R^4$ is a selected from the structure:

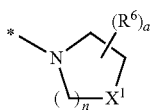

in certain embodiments, $X^1$ is NH, providing the structure:

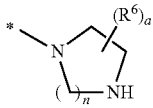

Also, when $R^4$ is the above structure, two $R^6$ substituents attached to the same ring carbon may be taken together to form an oxo group (i.e., =O), or a $C_3$ to $C_6$ spiro cyclic group. Accordingly, such structures include:

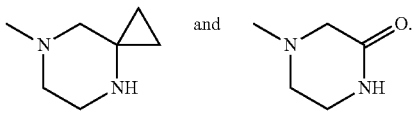

In certain embodiments, n is selected to be 1 to 4.

Also, when two $R^6$ substituents attached to different ring carbons are taken together to form a ring, the ring formed when taking the two $R^6$ groups together has from 4 to 7 ring atoms including from 0 to 3 ring heteroatoms. Accordingly, such structures include:

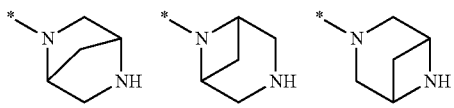

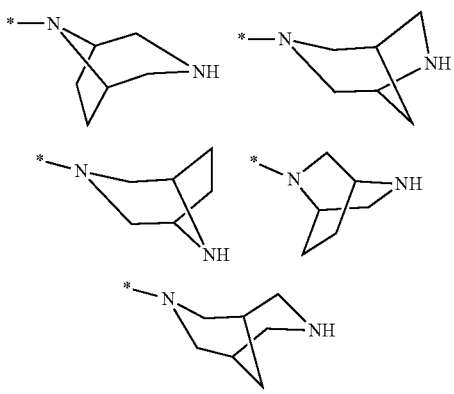

In preferred embodiments of the present invention, $R^5$ is selected to be H.

In embodiments of the invention, $R^1$ may be selected from the groups having the following structures:

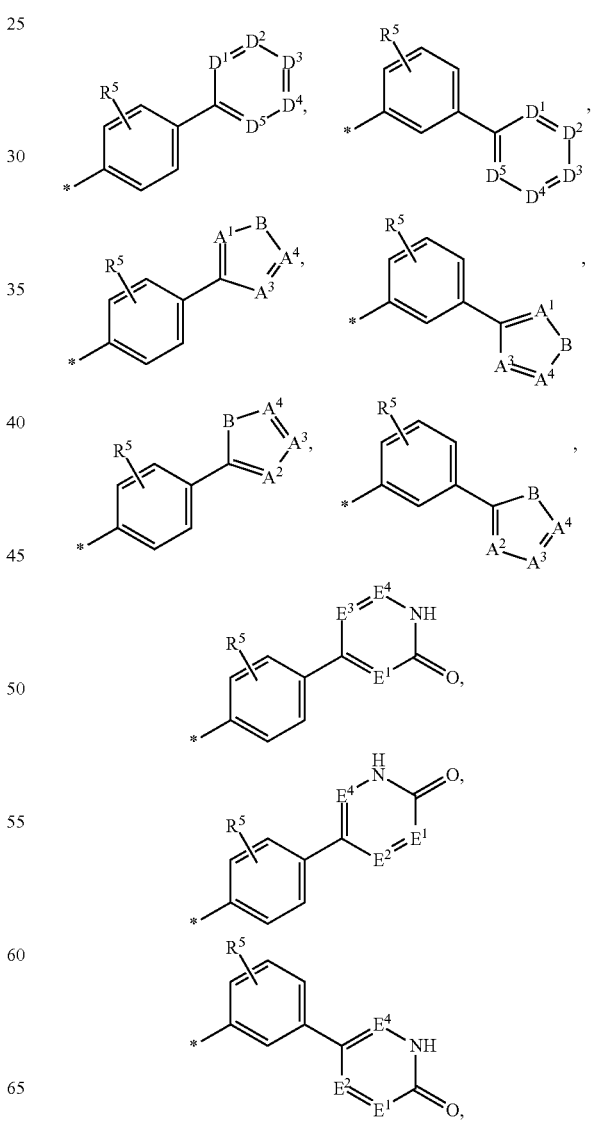

-continued

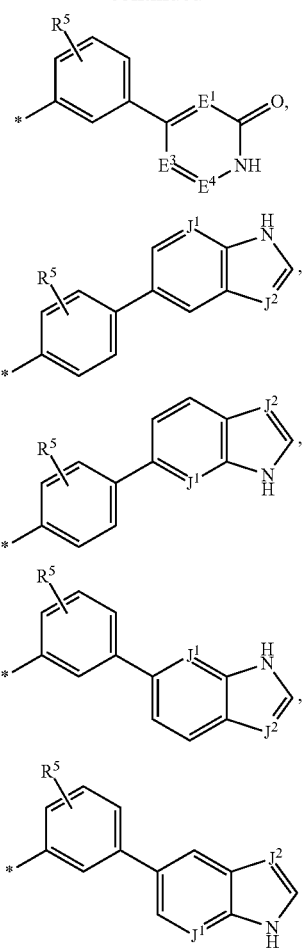

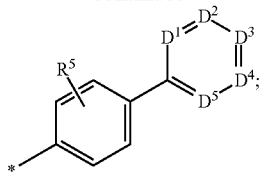

$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

each of $A^1$ and $A^3$ are independently selected from N and CH;

each of $D^1$, $D^2$, $D^3$, $D^4$ and $D^5$ are independently selected from N and CH; wherein the maximum number of N among $D^1$, $D^2$, $D^3$, $D^4$ and $D^5$ is 3;

$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

$R^4$ is a selected from the group consisting of the following structures:

Compounds according to the present invention include those having the formula Ia:

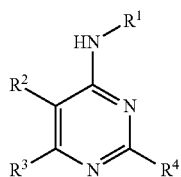

(Ia)

wherein:
$R^1$ is a selected from the group consisting of the following structures:

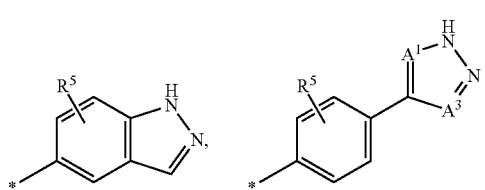

and

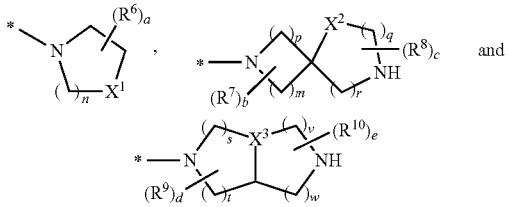

$X^1$ is selected from the group consisting of O, NH, and CHR$^6$;

each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

additionally or alternatively, two $R^6$ substituents attached to the same ring carbon may be taken together to form an oxo group (i.e., =O), or a $C_3$ to $C_7$ spiro cyclic group; and additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms.

each $R^7$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^8$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^9$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^{10}$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

$X^2$ is selected from $CH_2$, $CHR^8$, O, NH and N-(lower alkyl);
$X^3$ is selected from CH and N;
each R is independently selected from H and lower alkyl;
each R' is independently selected from H, lower alkyl, aryl, substituted aryl, aralkyl, and substituted aralkyl;
a is selected from 0 to 3;
b is selected from 0 to 2;
c is selected from 0 to 2;
d is selected from 0 to 2;
e is selected from 0 to 2;
each f is independently 1 to 3;
each g is independently 2 or 3;
n is selected from 0 to 4;
m is selected from 1 to 3;
p is selected from 1 to 3;
q is selected from 0 to 3;
r is selected from 0 to 3;
  wherein q and r are not simultaneously selected to be 0;
s is selected from 0 to 3;
t is selected from 0 to 3;
  wherein s and t are not simultaneously selected to be 0;
v is selected from 0 to 3; and
w is selected from 0 to 3.

Compounds according to the present invention include those having the formula Ib:

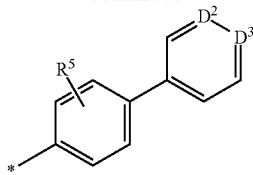

(Ib)

wherein:
$R^1$ is a selected from the group consisting of the following structures:

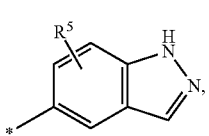 , 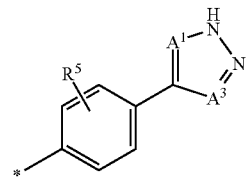 and

-continued

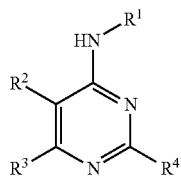

wherein
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each of $A^1$ and $A^3$ are independently selected from N and CH;
each of $D^2$ and $D^3$ are independently selected from N and CH; wherein at least one of $D^2$ and $D^3$ is N;
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^4$ is a selected from the group consisting of the following structures:

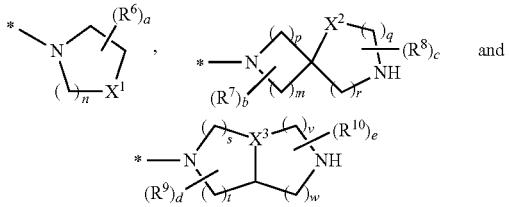

$X^1$ is selected from the group consisting of O, NH, and $CHR^6$;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
additionally or alternatively, two $R^6$ substituents attached to the same ring carbon may be taken together to form an oxo group (i.e., =O), or a $C_3$ to $C_7$ spiro cyclic group; and
additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms.

each R⁷ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each R⁸ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each R⁹ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each R¹⁰ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

X² is selected from $CH_2$, CHR⁸, O, NH and N-(lower alkyl);
X³ is selected from CH and N;
each R is independently selected from H and lower alkyl;
each R' is independently selected from H, lower alkyl, aryl, substituted aryl, aralkyl, and substituted aralkyl;
a is selected from 0 to 3;
b is selected from 0 to 2;
c is selected from 0 to 2;
d is selected from 0 to 2;
e is selected from 0 to 2;
each f is independently 1 to 3;
each g is independently 2 or 3;
n is selected from 0 to 4;
m is selected from 1 to 3;
p is selected from 1 to 3;
q is selected from 0 to 3;
r is selected from 0 to 3;
wherein q and r are not simultaneously selected to be 0;
s is selected from 0 to 3;
t is selected from 0 to 3;
wherein s and t are not simultaneously selected to be 0;
v is selected from 0 to 3; and
w is selected from 0 to 3.

In a certain embodiments of the present invention, there is provided a compound of the formula II:

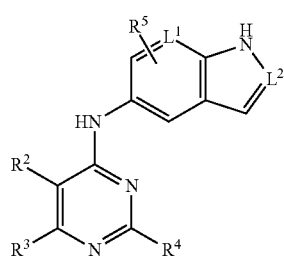

(II)

R⁵ is selected from H, halo, hydroxy, —NRR', —(CH₂)$_f$NRR', —O—(CH₂)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each of L¹ and L² are independently selected from N and CH;
R² is selected from the group consisting of H, halo, hydroxy, —NRR', —(CH₂)$_f$NRR', —O—(CH₂)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

R³ is selected from the group consisting of H, halo, hydroxy, —NRR', —(CH₂)$_f$NRR', —O—(CH₂)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively R² and R³ are taken together to form a 4- to 7-membered fused ring having from 0 to 3 ring heteroatoms, and is unsubstituted or is substituted with halo, hydroxy, amino, —C(=O)-lower alkyl, lower alkyl, and lower alkoxy;
R⁴ is a selected from the group consisting of the following structures:

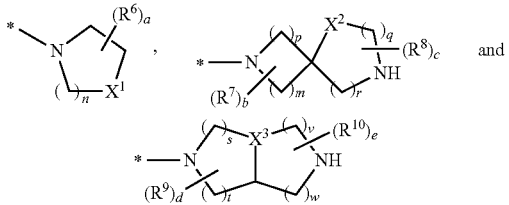

X¹ is selected from the group consisting of O, NH, and CHR⁶;
each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)$_f$NRR', —O—(CH₂)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
additionally or alternatively, two R⁶ substituents attached to the same ring carbon may be taken together to form an oxo group (i.e., =O), or a $C_3$ to $C_7$ spiro cyclic group; and
additionally or alternatively, two R⁶ substituents attached to different ring carbons may be taken together to form a ring, wherein the ring formed when taking the two R⁶ groups together has from 4 to 7 ring atoms including from 0 to 3 ring heteroatoms.

each R⁷ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each R⁸ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each R⁹ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each R¹⁰ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

$X^2$ is selected from $CH_2$, $CHR^8$, O, NH and N-(lower alkyl);
$X^3$ is selected from CH, $CR^9$ and N;
each R is independently selected from H and lower alkyl;
each R' is independently selected from H, lower alkyl, aryl, substituted aryl, aralkyl, and substituted aralkyl;
a is selected from 0 to 3;
b is selected from 0 to 2;
c is selected from 0 to 2;
d is selected from 0 to 2;
e is selected from 0 to 2;
each f is independently 1 to 3;
each g is independently 2 or 3;
n is selected from 0 to 4;
m is selected from 1 to 3;
p is selected from 1 to 3;
q is selected from 0 to 3;
r is selected from 0 to 3;
   wherein q and r are not simultaneously selected to be 0;
s is selected from 0 to 3;
t is selected from 0 to 3;
   wherein s and t are not simultaneously selected to be 0;
v is selected from 0 to 3; and
w is selected from 0 to 3.

In a certain embodiments of the present invention, there is provided a compound of the formula IIa:

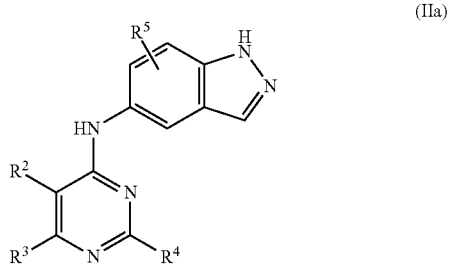

(IIa)

wherein:
$R^2$ is selected from the group consisting of H, halo, hydroxy, —NRR', —$(CH_2)$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^4$ is a selected from the group consisting of the following structures:

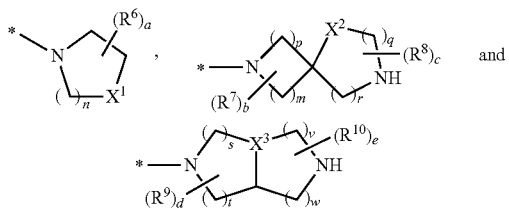

$X^1$ is selected from the group consisting of O, NH, and $CHR^6$;
$R^5$ is selected from H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —$(CH_2)_f$NRR', —O—$(CH_2)_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
additionally or alternatively, two $R^6$ substituents attached to the same ring carbon may be taken together to form an oxo group (i.e., =O), or a $C_3$ to $C_7$ spiro cyclic group; and
additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;
each $R^7$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;
each $R^8$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;
each $R^9$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;
each $R^{10}$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;
$X^2$ is selected from $CH_2$, $CHR^8$, O, NH and N-(lower alkyl);
$X^3$ is selected from CH and N;
each R is independently selected from H and lower alkyl;
each R' is independently selected from H, lower alkyl, aryl, substituted aryl, aralkyl, and substituted aralkyl;
a is selected from 0 to 3;
b is selected from 0 to 2;
c is selected from 0 to 2;
d is selected from 0 to 2;
e is selected from 0 to 2;
each f is independently 1 to 3;
each g is independently 2 or 3;
n is selected from 0 to 4;
m is selected from 1 to 3;
p is selected from 1 to 3;
q is selected from 0 to 3;
r is selected from 0 to 3;
   wherein q and r are not simultaneously selected to be 0;
s is selected from 0 to 3;
t is selected from 0 to 3;
   wherein s and t are not simultaneously selected to be 0;
v is selected from 0 to 3; and
w is selected from 0 to 3.

In a certain embodiments of the present invention, there is provided a compound of the formula IIb:

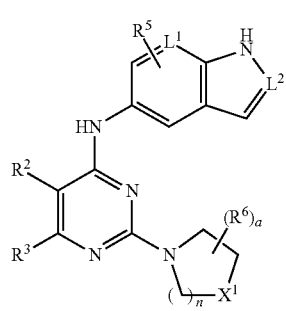

(IIb)

wherein
each of L¹ and L² are independently selected from N and CH;
R² is selected from the group consisting of H, halo, hydroxy, —NRR', —(CH₂)$_f$NRR', —O—(CH₂)$_g$NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)$_f$NRR', —O—(CH₂)$_g$NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁵ is selected from H, halo, hydroxy, —NRR', —(CH₂)$_f$NRR', —O—(CH₂)$_g$NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
X¹ is selected from the group consisting of O, NH, and CHR⁶;
each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)$_f$NRR', —O—(CH₂)$_g$NRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;
  additionally or alternatively, two R⁶ substituents attached to the same ring carbon may be taken together to form an oxo group (i.e., =O), or a C₃ to C₇ spiro cyclic group; and
  additionally or alternatively, two R⁶ substituents attached to different ring atoms may be taken together to form a ring, wherein the ring formed when taking the two R⁶ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
n is selected from 0 to 4.

In a certain embodiments of the present invention, there is provided a compound of the formula IIc:

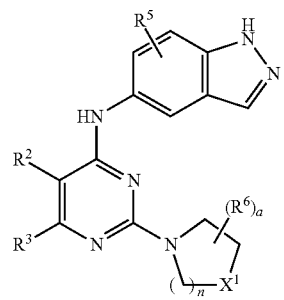

(IIc)

wherein:
R² is selected from the group consisting of H, halo, hydroxy, —NRR', —(CH₂)$_f$NRR', —O—(CH₂)$_g$NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)$_f$NRR', —O—(CH₂)$_g$NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁵ is selected from H, halo, hydroxy, —NRR', —(CH₂)NRR', —O—(CH₂)$_g$NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
X¹ is selected from the group consisting of O, NH, and CHR⁶;
each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)$_f$NRR', —O—(CH₂)$_g$NRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;
  additionally or alternatively, two R⁶ substituents attached to the same ring carbon may be taken together to form an oxo group (i.e., =O), or a C₃ to C₇ spiro cyclic group; and
  additionally or alternatively, two R⁶ substituents attached to different ring atoms may be taken together to form a ring, wherein the ring formed when taking the two R⁶ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
n is selected from 0 to 4.

In a certain embodiments of the present invention, there is provided a compound of the formula IId:

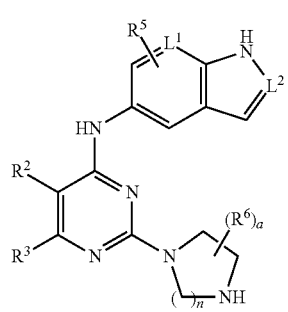

(IId)

wherein
each of $L^1$ and $L^2$ are independently selected from N and CH;
$R^2$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(═O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(═O)—NRR', —C(═O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
additionally or alternatively, two $R^6$ substituents attached to the same ring carbon may be taken together to form an oxo group (i.e., ═O), or a $C_3$ to $C_7$ spiro cyclic group; and
additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
n is selected from 0 to 4.

In a certain embodiments of the present invention, there is provided a compound of the formula IIe:

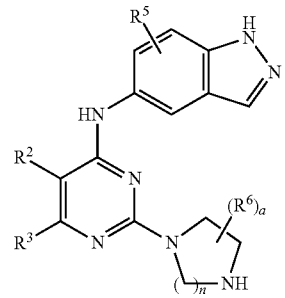

(IIe)

wherein:
$R^2$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(═O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(═O)—NRR', —C(═O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
additionally or alternatively, two $R^6$ substituents attached to the same ring carbon may be taken together to form an oxo group (i.e., ═O), or a $C_3$ to $C_7$ spiro cyclic group; and
additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
n is selected from 0 to 4.

In a certain embodiments of the present invention, there is provided a compound of the formula IIf:

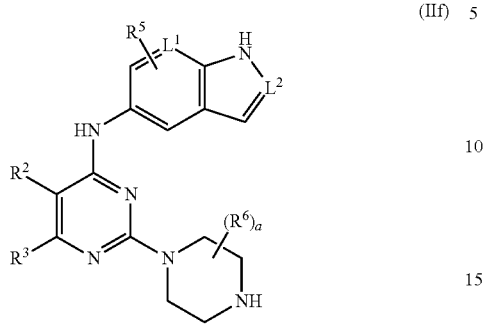
(IIf)

wherein
each of $L^1$ and $L^2$ are independently selected from N and CH;
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
additionally or alternatively, two $R^6$ substituents attached to the same ring carbon may be taken together to form an oxo group (i.e., =O), or a $C_3$ to $C_7$ spiro cyclic group; and
additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3; and
each g is independently 2 or 3.

In a certain embodiments of the present invention, there is provided a compound of the formula IIg:

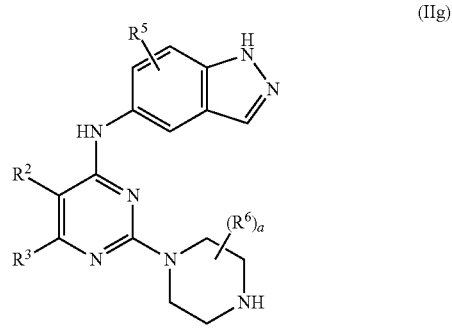
(IIg)

wherein:
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
additionally or alternatively, two $R^6$ substituents attached to the same ring carbon may be taken together to form an oxo group (i.e., =O), or a $C_3$ to $C_7$ spiro cyclic group; and
additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3; and
each g is independently 2 or 3.

In a certain embodiments of the present invention, there is provided a compound of the formula IIh:

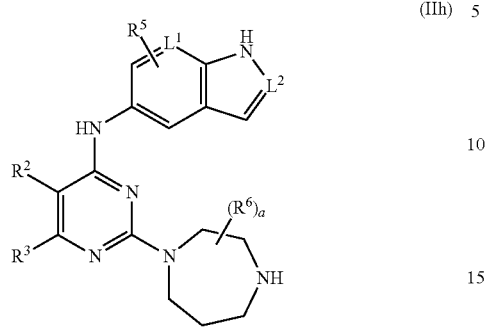

(IIh)

wherein
each of $L^1$ and $L^2$ are independently selected from N and CH;
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, C$_3$-C$_6$ cyclic alkyl, C$_1$-C$_3$ perfluoro alkyl, C$_1$-C$_3$ perfluoro alkoxy and carboxyl;
additionally or alternatively, two $R^6$ substituents attached to the same ring carbon may be taken together to form an oxo group (i.e., =O), or a C$_3$ to C$_7$ spiro cyclic group; and
additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3; and
each g is independently 2 or 3.

In a certain embodiments of the present invention, there is provided a compound of the formula IIi:

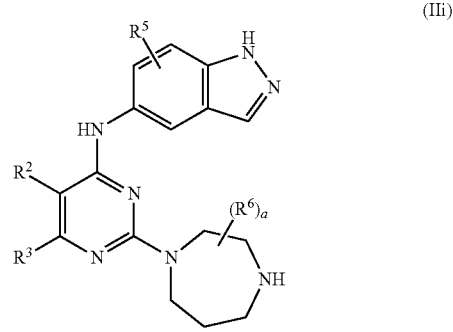

(IIi)

wherein:
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, C$_3$-C$_6$ cyclic alkyl, C$_1$-C$_3$ perfluoro alkyl, C$_1$-C$_3$ perfluoro alkoxy and carboxyl;
additionally or alternatively, two $R^6$ substituents attached to the same ring carbon may be taken together to form an oxo group (i.e., =O), or a C$_3$ to C$_7$ spiro cyclic group; and
additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3; and
each g is independently 2 or 3.

In a certain embodiments of the present invention, there is provided a compound of the formula IIj:

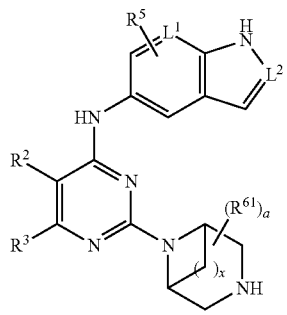

(IIj)

wherein
each of $L^1$ and $L^2$ are independently selected from N and CH;
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^{61}$ is independently selected from the group consisting of H, halo, hydroxy, lower alkyl, substituted lower alkyl, lower alkoxy, aryl, aralkyl, heterocycle, —NRR', —(CH$_2$)NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIk:

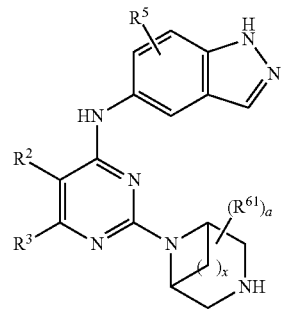

(IIk)

wherein:
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^{61}$ is independently selected from the group consisting of H, halo, hydroxy, lower alkyl, substituted lower alkyl, lower alkoxy, aryl, aralkyl, heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIm:

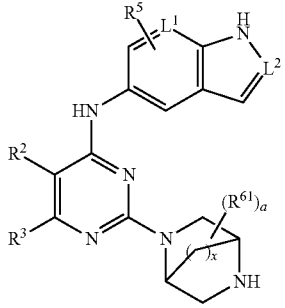

(IIm)

wherein
each of $L^1$ and $L^2$ are independently selected from N and CH;
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^{61}$ is independently selected from the group consisting of H, halo, hydroxy, lower alkyl, substituted lower alkyl, lower alkoxy, aryl, aralkyl, heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIn:

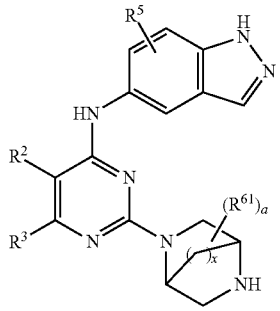

(IIm)

wherein:
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^{61}$ is independently selected from the group consisting of H, halo, hydroxy, lower alkyl, substituted lower alkyl, lower alkoxy, aryl, aralkyl, heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIo:

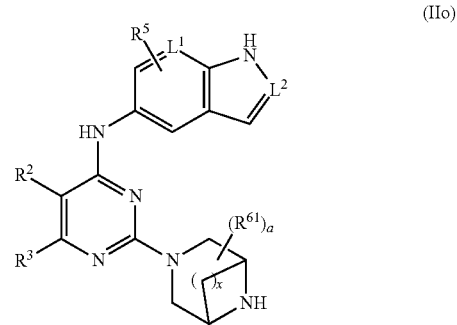

(IIo)

wherein
each of $L^1$ and $L^2$ are independently selected from N and CH;
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^{61}$ is independently selected from the group consisting of H, halo, hydroxy, lower alkyl, substituted lower alkyl, lower alkoxy, aryl, aralkyl, heterocycle, —NRR',
—(CH$_2$)$_f$NRR', —O—(CH$_2$)$_g$NRR', —C(=O)—NRR',
—C(=O)—OR, cyano, lower alkyl, C$_3$-C$_6$ cyclic alkyl,
C$_1$-C$_3$ perfluoro alkyl, C$_1$-C$_3$ perfluoro alkoxy and carboxyl;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIp:

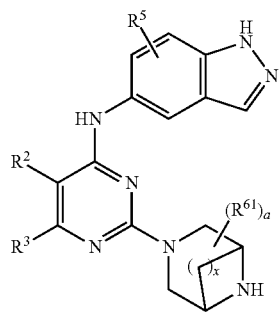

(IIp)

wherein:
R$^2$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
R$^3$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
alternatively R$^2$ and R$^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R$^5$ is selected from H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
each R$^{61}$ is independently selected from the group consisting of H, halo, hydroxy, lower alkyl, substituted lower alkyl, lower alkoxy, aryl, aralkyl, heterocycle, —NRR', —(CH$_2$)$_f$NRR', —O—(CH$_2$)$_g$NRR', —C(=O)—NRR', —C(=O)—OR, cyano, lower alkyl, C$_3$-C$_6$ cyclic alkyl, C$_1$-C$_3$ perfluoro alkyl, C$_1$-C$_3$ perfluoro alkoxy and carboxyl;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIq:

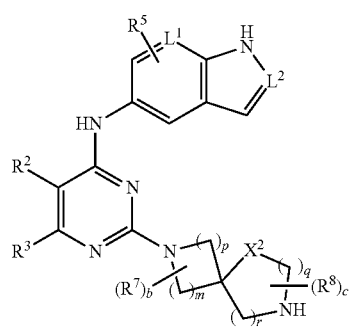

(IIq)

wherein
each of L$^1$ and L$^2$ are independently selected from N and CH;
R$^2$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
R$^3$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
alternatively R$^2$ and R$^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R$^5$ is selected from H, halo, hydroxy, —NRR', —(CH$_2$)$_f$NRR', —O—(CH$_2$)$_g$NRR', —C(=O)—NRR', —C(=O)—OR, cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
each R$^7$ is independently selected from the group consisting of H, halo, hydroxy, lower alkyl, substituted lower alkyl, lower alkoxy, —NRR', —C(=O)—NRR', —C(=O)—OR, cyano, oxo, C$_1$-C$_3$ perfluoro alkyl, and C$_1$-C$_3$ perfluoro alkoxy;
each R$^8$ is independently selected from the group consisting of H, halo, hydroxy, lower alkyl, substituted lower alkyl, lower alkoxy, —NRR', —C(=O)—NRR', —C(=O)—OR, cyano, oxo, C$_1$-C$_3$ perfluoro alkyl, and C$_1$-C$_3$ perfluoro alkoxy;
X$^2$ is selected from CH$_2$, CHR$^8$, O, NH and N-(lower alkyl);
each R is independently selected from H and lower alkyl;
each R' is independently selected from H, lower alkyl, aryl, substituted aryl, aralkyl, and substituted aralkyl;
b is selected from 0 to 2;
c is selected from 0 to 2;
each f is independently 1 to 3;
each g is independently 2 or 3;
m is selected from 1 to 3;
p is selected from 1 to 3;
q is selected from 0 to 3; and
r is selected from 0 to 3;
wherein q and r are not simultaneously selected to be 0.

In a certain embodiments of the present invention, there is provided a compound of the formula IIr:

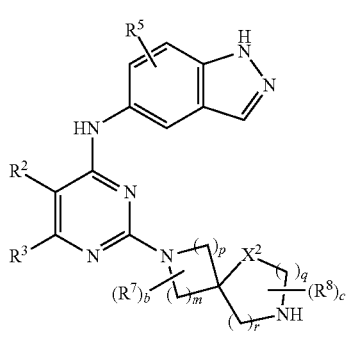

(IIr)

wherein:
R² is selected from the group consisting of H, halo, hydroxy, —NRR', —(CH₂)_fNRR', —O—(CH₂)_gNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)_fNRR', —O—(CH₂)_gNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁵ is selected from H, halo, hydroxy, —NRR', —(CH₂)_fNRR', —O—(CH₂)_gNRR', —C(=O)—NRR', —C(=O)—OR, cyano, lower alkyl, C₃-C₆ cyclic alkyl, lower alkoxy, C₁-C₃ perfluoro alkyl, C₁-C₃ perfluoro alkoxy and carboxyl;
each R⁷ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;
each R⁸ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;
X² is selected from CH₂, CHR⁸, O, NH and N-(lower alkyl);
each R is independently selected from H and lower alkyl;
each R' is independently selected from H, lower alkyl, aryl, substituted aryl, aralkyl, and substituted aralkyl;
b is selected from 0 to 2;
c is selected from 0 to 2;
each f is independently 1 to 3;
each g is independently 2 or 3;
m is selected from 1 to 3;
p is selected from 1 to 3;
q is selected from 0 to 3; and
r is selected from 0 to 3;
wherein q and r are not simultaneously selected to be 0.

In a certain embodiments of the present invention, there is provided a compound of the formula IIs:

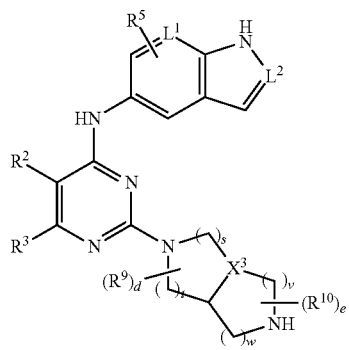

(IIs)

wherein
each of L¹ and L² are independently selected from N and CH;
R² is selected from the group consisting of H, halo, hydroxy, —NRR', —(CH₂)_fNRR', —O—(CH₂)_gNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)_fNRR', —O—(CH₂)_gNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁵ is selected from H, halo, hydroxy, —NRR', —(CH₂)_fNRR', —O—(CH₂)_gNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
each R⁹ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;
each R¹⁰ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;
X³ is selected from CH and N;
each R is independently selected from H and lower alkyl;
each R' is independently selected from H, lower alkyl, aryl, substituted aryl, aralkyl, and substituted aralkyl;
d is selected from 0 to 2;
e is selected from 0 to 2;
each f is independently 1 to 3;
each g is independently 2 or 3;
s is selected from 0 to 3;
t is selected from 0 to 3;
wherein s and t are not simultaneously selected to be 0;
v is selected from 0 to 3; and
w is selected from 0 to 3.

In a certain embodiments of the present invention, there is provided a compound of the formula IIt:

(IIt)

wherein:
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^9$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;
each $R^{10}$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;
$X^3$ is selected from CH and N;
each R is independently selected from H and lower alkyl;
each R' is independently selected from H, lower alkyl, aryl, substituted aryl, aralkyl, and substituted aralkyl;
d is selected from 0 to 2;
e is selected from 0 to 2;
each f is independently 1 to 3;
each g is independently 2 or 3;
s is selected from 0 to 3;
t is selected from 0 to 3;
wherein s and t are not simultaneously selected to be 0;
v is selected from 0 to 3; and
w is selected from 0 to 3.

In a certain embodiments of the present invention, there is provided a compound of the formula III:

(III)

wherein:
each of $A^1$, $A^3$ and $A^4$ are independently selected from N, C—$R^a$ and CH, wherein the maximum number of N among $A^1$, $A^3$ and $A^4$ is 3;
B is selected from group consisting of NH, O and S;
each $R^a$ is independently selected from the group consisting of lower alkyl, halo and amino;
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^4$ is a selected from the group consisting of the following structures:

$X^1$ is selected from the group consisting of O, NH, and CHR$^6$;
$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

additionally or alternatively, two $R^b$ substituents attached to the same ring carbon may be taken together to form an oxo group (i.e., =O), or a $C_3$ to $C_7$ spiro cyclic group; and additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;

each $R^7$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^8$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^9$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^{10}$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

$X^2$ is selected from $CH_2$, $CHR^8$, O, NH and N-(lower alkyl);

$X^3$ is selected from CH and N;

each R is independently selected from H and lower alkyl;

each R' is independently selected from H, lower alkyl, aryl, substituted aryl, aralkyl, and substituted aralkyl;

a is selected from 0 to 3;

b is selected from 0 to 2;

c is selected from 0 to 2;

d is selected from 0 to 2;

e is selected from 0 to 2;

each f is independently 1 to 3;

each g is independently 2 or 3;

n is selected from 0 to 4;

m is selected from 1 to 3;

p is selected from 1 to 3;

q is selected from 0 to 3;

r is selected from 0 to 3;

wherein q and r are not simultaneously selected to be 0;

s is selected from 0 to 3;

t is selected from 0 to 3;

wherein s and t are not simultaneously selected to be 0;

v is selected from 0 to 3; and w is selected from 0 to 3.

In a certain embodiments of the present invention, there is provided a compound of the formula IIIa:

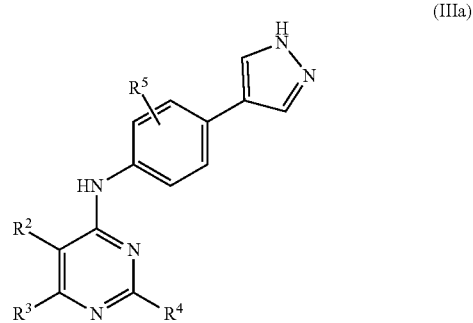

(IIIa)

wherein:

$R^2$ is selected from the group consisting of H, halo, hydroxy, —NRR', —(CH$_2$)NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —(CH$_2$)NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

$R^4$ is a selected from the group consisting of the following structures:

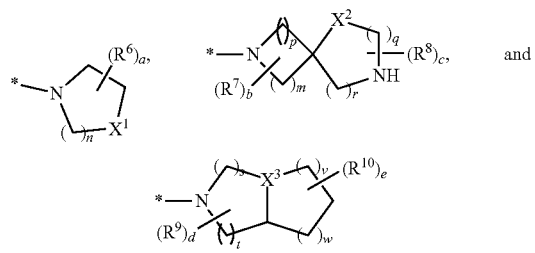

$X^1$ is selected from the group consisting of O, NH, and $CHR^6$;

$R^5$ is selected from H, halo, hydroxy, —NRR', —(CH$_2$)NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

additionally or alternatively, two $R^b$ substituents attached to the same ring carbon may be taken together to form an oxo group (i.e., =O), or a $C_3$ to $C_7$ spiro cyclic group; and additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;

each $R^7$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^8$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^9$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^{10}$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

$X^2$ is selected from $CH_2$, $CHR^8$, O, NH and N-(lower alkyl);
$X^3$ is selected from CH and N;
each R is independently selected from H and lower alkyl;
each R' is independently selected from H, lower alkyl, aryl, substituted aryl, aralkyl, and substituted aralkyl;
a is selected from 0 to 3;
b is selected from 0 to 2;
c is selected from 0 to 2;
d is selected from 0 to 2;
e is selected from 0 to 2;
each f is independently 1 to 3;
each g is independently 2 or 3;
n is selected from 0 to 4;
m is selected from 1 to 3;
p is selected from 1 to 3;
q is selected from 0 to 3;
r is selected from 0 to 3;
wherein q and r are not simultaneously selected to be 0;
s is selected from 0 to 3;
t is selected from 0 to 3;
wherein s and t are not simultaneously selected to be 0;
v is selected from 0 to 3; and
w is selected from 0 to 3.

In a certain embodiments of the present invention, there is provided a compound of the formula IIIb:

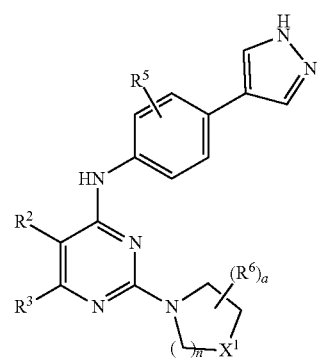

(IIIb)

wherein:
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

$R^5$ is selected from H, halo, hydroxy, —NRR', —(CH$_2$)$_f$NRR', —O—(CH$_2$)$_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$X^1$ is selected from the group consisting of O, NH, and $CHR^6$;

each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

additionally or alternatively, two $R^6$ substituents attached to the same ring carbon may be taken together to form an oxo group (i.e., =O), or a $C_3$ to $C_7$ spiro cyclic group; and additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;

each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
n is selected from 0 to 4.

In a certain embodiments of the present invention, there is provided a compound of the formula IIIc:

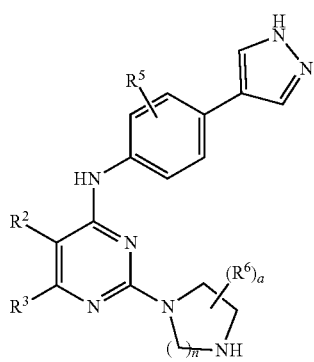

(IIIc)

wherein:
R² is selected from the group consisting of H, halo, hydroxy, —NRR', —(CH₂)<sub>f</sub>NRR', —O—(CH₂)<sub>g</sub>NRR', —C(═O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)<sub>f</sub>NRR', —O—(CH₂)<sub>g</sub>NRR', —C(═O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(═O)-lower alkyl, lower alkyl, and lower alkoxy;
R⁵ is selected from H, halo, hydroxy, —NRR', —(CH₂)<sub>f</sub>NRR', —O—(CH₂)<sub>g</sub>NRR', —C(═O)—NRR', cyano, lower alkyl, C₃-C₆ cyclic alkyl, lower alkoxy, C₁-C₃ perfluoro alkyl, C₁-C₃ perfluoro alkoxy and carboxyl;
each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)<sub>f</sub>NRR', —O—(CH₂)<sub>g</sub>NRR', —C(═O)—NRR', —C(═O)—OR, cyano, lower alkyl, C₃-C₆ cyclic alkyl, C₁-C₃ perfluoro alkyl, C₁-C₃ perfluoro alkoxy and carboxyl;
additionally or alternatively, two R⁶ substituents attached to the same ring carbon may be taken together to form an oxo group (i.e., ═O), or a C₃ to C₇ spiro cyclic group; and
additionally or alternatively, two R⁶ substituents attached to different ring carbons may be taken together to form a ring, wherein the ring formed when taking the two R⁶ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
n is selected from 0 to 4.

In a certain embodiments of the present invention, there is provided a compound of the formula IIId:

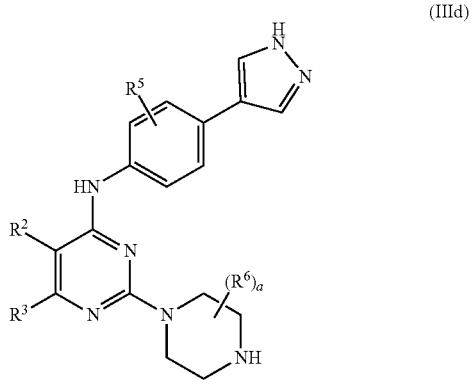

(IIId)

wherein:
R² is selected from the group consisting of H, halo, hydroxy, —NRR', —(CH₂)<sub>f</sub>NRR', —O—(CH₂)<sub>g</sub>NRR', —C(═O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)<sub>f</sub>NRR', —O—(CH₂)<sub>g</sub>NRR', —C(═O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(═O)-lower alkyl, lower alkyl, and lower alkoxy;
R⁵ is selected from H, halo, hydroxy, —NRR', —(CH₂)<sub>f</sub>NRR', —O—(CH₂)<sub>g</sub>NRR', —C(═O)—NRR', cyano, lower alkyl, C₃-C₆ cyclic alkyl, lower alkoxy, C₁-C₃ perfluoro alkyl, C₁-C₃ perfluoro alkoxy and carboxyl;
each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)<sub>f</sub>NRR', —O—(CH₂)<sub>g</sub>NRR', —C(═O)—NRR', —C(═O)—OR, cyano, lower alkyl, C₃-C₆ cyclic alkyl, C₁-C₃ perfluoro alkyl, C₁-C₃ perfluoro alkoxy and carboxyl;
additionally or alternatively, two R⁶ substituents attached to the same ring carbon may be taken together to form an oxo group (i.e., ═O), or a C₃ to C₇ spiro cyclic group; and
additionally or alternatively, two R⁶ substituents attached to different ring carbons may be taken together to form a ring, wherein the ring formed when taking the two R⁶ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3; and
each g is independently 2 or 3.

In a certain embodiments of the present invention, there is provided a compound of the formula IIIe:

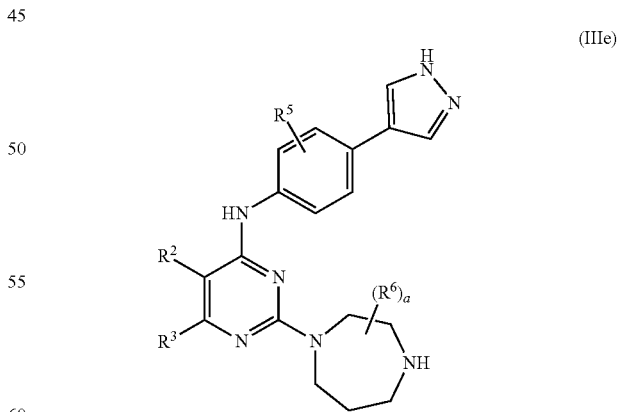

(IIIe)

wherein:
R² is selected from the group consisting of H, halo, hydroxy, —NRR', —(CH₂)<sub>f</sub>NRR', —O—(CH₂)<sub>g</sub>NRR', —C(═O)—NRR', cyano, lower alkyl, C₃-C₆ cyclic alkyl, lower alkoxy, C₁-C₃ perfluoro alkyl, C₁-C₃ perfluoro alkoxy and carboxyl;

R³ is selected from the group consisting of H, halo, hydroxy, —NRR', —(CH₂)_f NRR', —O—(CH₂)_g NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

R⁵ is selected from H, halo, hydroxy, —NRR', —(CH₂)_f NRR', —O—(CH₂)_g NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)_f NRR', —O—(CH₂)_g NRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;

additionally or alternatively, two R⁶ substituents attached to the same ring carbon may be taken together to form an oxo group (i.e., =O), or a C₃ to C₇ spiro cyclic group; and additionally or alternatively, two R⁶ substituents attached to different ring carbons may be taken together to form a ring, wherein the ring formed when taking the two R⁶ groups together has from 4 to 7 ring atoms including from 0 to 3 ring heteroatoms;

each R is independently selected from H and lower alkyl;
each R' is independently selected from H, lower alkyl, aryl, substituted aryl, aralkyl, and substituted aralkyl;
a is selected from 0 to 3;
each f is independently 1 to 3; and
each g is independently 2 or 3.

In a certain embodiments of the present invention, there is provided a compound of the formula IIIf:

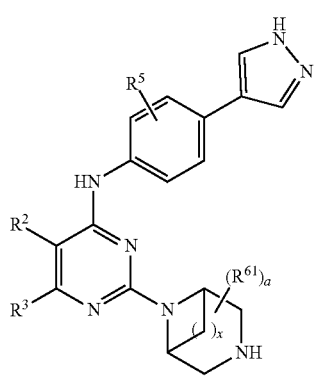

(IIIf)

wherein:
R² is selected from the group consisting of H, halo, hydroxy, —NRR', —(CH₂)_f NRR', —O—(CH₂)_g NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

R³ is selected from the group consisting of H, halo, hydroxy, —NRR', —(CH₂)_f NRR', —O—(CH₂)_g NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

R⁵ is selected from H, halo, hydroxy, —NRR', —(CH₂)_f NRR', —O—(CH₂)_g NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

each R⁶¹ is independently selected from the group consisting of H, halo, hydroxy, lower alkyl, substituted lower alkyl, lower alkoxy, aryl, aralkyl, heterocycle, —NRR', —(CH₂)_f NRR', —O—(CH₂)_g NRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;

each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIIg:

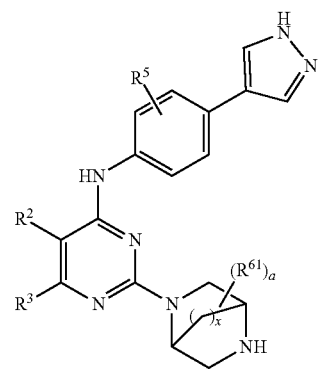

(IIIg)

wherein:
R² is selected from the group consisting of H, halo, hydroxy, —NRR', —(CH₂)_f NRR', —O—(CH₂)_g NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

R³ is selected from the group consisting of H, halo, hydroxy, —NRR', —(CH₂)_f NRR', —O—(CH₂)_g NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

R⁵ is selected from H, halo, hydroxy, —NRR', —(CH₂)_f NRR', —O—(CH₂)_g NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

each $R^{61}$ is independently selected from the group consisting of H, halo, hydroxy, lower alkyl, substituted lower alkyl, lower alkoxy, aryl, aralkyl, heterocycle, —NRR', —(CH$_2$)$_f$NRR', —O—(CH$_2$)$_g$NRR', —C(=O)—NRR', —C(=O)—OR, cyano, lower alkyl, C$_3$-C$_6$ cyclic alkyl, C$_1$-C$_3$ perfluoro alkyl, C$_1$-C$_3$ perfluoro alkoxy and carboxyl;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIIh:

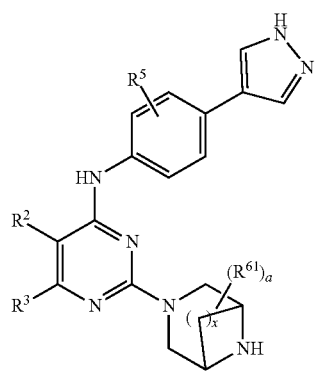

(IIIh)

wherein:
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
each $R^{61}$ is independently selected from the group consisting of H, halo, hydroxy, lower alkyl, substituted lower alkyl, lower alkoxy, aryl, aralkyl, heterocycle, —NRR', —(CH$_2$)$_f$NRR', —O—(CH$_2$)$_g$NRR', —C(=O)—NRR', —C(=O)—OR, cyano, lower alkyl, C$_3$-C$_6$ cyclic alkyl, C$_1$-C$_3$ perfluoro alkyl, C$_1$-C$_3$ perfluoro alkoxy and carboxyl;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IIIi:

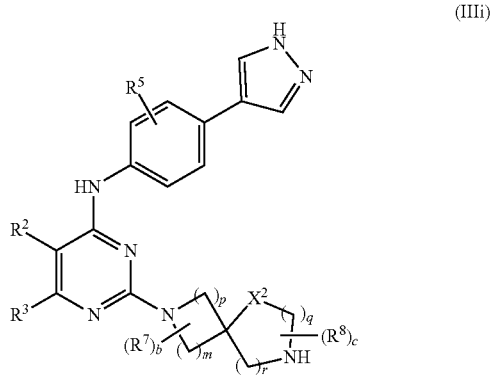

(IIIi)

wherein:
$R^2$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
$R^3$ is selected from the group consisting of H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
$R^5$ is selected from H, halo, hydroxy, —NRR', —(CH$_2$)$_f$NRR', —O—(CH$_2$)$_g$NRR', —C(=O)—NRR', cyano, lower alkyl, C$_3$-C$_6$ cyclic alkyl, lower alkoxy, C$_1$-C$_3$ perfluoro alkyl, C$_1$-C$_3$ perfluoro alkoxy and carboxyl;
each $R^7$ is independently selected from the group consisting of H, halo, hydroxy, lower alkyl, substituted lower alkyl, lower alkoxy, —NRR', —C(=O)—NRR', —C(=O)—OR, cyano, oxo, C$_1$-C$_3$ perfluoro alkyl, and C$_1$-C$_3$ perfluoro alkoxy;
each $R^8$ is independently selected from the group consisting of H, halo, hydroxy, lower alkyl, substituted lower alkyl, lower alkoxy, —NRR', —C(=O)—NRR', —C(=O)—OR, cyano, oxo, C$_1$-C$_3$ perfluoro alkyl, and C$_1$-C$_3$ perfluoro alkoxy;
$X^2$ is selected from CH$_2$, CHR$^8$, O, NH and N-(lower alkyl);
each R is independently selected from H and lower alkyl;
each R' is independently selected from H, lower alkyl, aryl, substituted aryl, aralkyl, and substituted aralkyl;
b is selected from 0 to 2;
c is selected from 0 to 2;
each f is independently 1 to 3;
each g is independently 2 or 3;
m is selected from 1 to 3;
p is selected from 1 to 3;
q is selected from 0 to 3; and
r is selected from 0 to 3;
   wherein q and r are not simultaneously selected to be 0.

In a certain embodiments of the present invention, there is provided a compound of the formula IIIj:

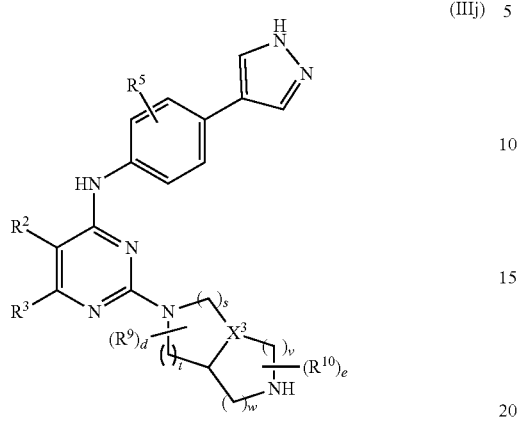

(IIIj)

wherein:
R² is selected from the group consisting of H, halo, hydroxy, —NRR', —(CH₂)ƒNRR', —O—(CH₂)ɡNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)ƒNRR', —O—(CH₂)ɡNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁵ is selected from H, halo, hydroxy, —NRR', —(CH₂)ƒNRR', —O—(CH₂)ɡNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
each R⁹ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;
each R¹⁰ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;
X³ is selected from CH and N;
each R is independently selected from H and lower alkyl;
each R' is independently selected from H, lower alkyl, aryl, substituted aryl, aralkyl, and substituted aralkyl;
d is selected from 0 to 2;
e is selected from 0 to 2;
each f is independently 1 to 3;
each g is independently 2 or 3;
s is selected from 0 to 2;
t is selected from 0 to 3;
  wherein s and t are not simultaneously selected to be 0;
v is selected from 0 to 3; and
w is selected from 0 to 3.

In a certain embodiments of the present invention, there is provided a compound of the formula IV:

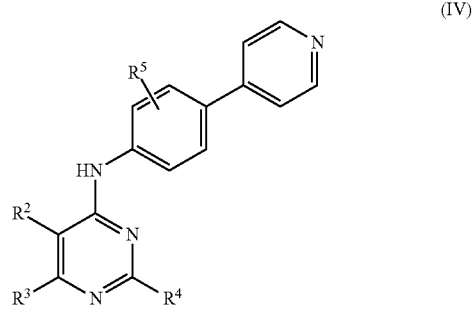

(IV)

wherein:
R² is selected from the group consisting of H, halo, hydroxy, —NRR', —(CH₂)NRR', —O—(CH₂)ɡNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)NRR', —O—(CH₂)ɡNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁴ is a selected from the group consisting of the following structures:

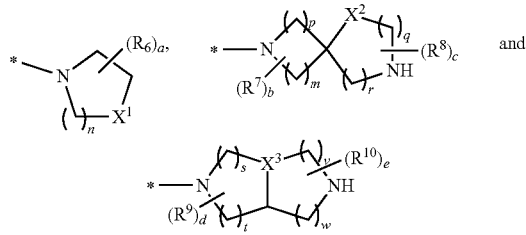

X¹ is selected from the group consisting of O, NH, and CHR⁶;
R⁵ is selected from H, halo, hydroxy, —NRR', —(CH₂)NRR', —O—(CH₂)ɡNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)ƒNRR', —O—(CH₂)ɡNRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;
additionally or alternatively, two R⁶ substituents attached to the same ring carbon may be taken together to form an oxo group (i.e., =O), or a C₃ to C₇ spiro cyclic group; and additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms.

each $R^7$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^8$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^9$ is independently selected from the group consisting of H, halo, hydroxy, lower alkyl, substituted lower alkyl, lower alkoxy, —NRR', —C(=O)—NRR', cyano, oxo, $C_1$-$C_3$ perfluoro alkyl, and $C_1$-$C_3$ perfluoro alkoxy;

each $R^{10}$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

$X^2$ is selected from $CH_2$, $CHR^8$, O, NH and N-(lower alkyl);
$X^3$ is selected from CH and N;
each R is independently selected from H and lower alkyl;
each R' is independently selected from H, lower alkyl, aryl, substituted aryl, aralkyl, and substituted aralkyl;
a is selected from 0 to 3;
b is selected from 0 to 2;
c is selected from 0 to 2;
d is selected from 0 to 2;
e is selected from 0 to 2;
each f is independently 1 to 3;
each g is independently 2 or 3;
n is selected from 0 to 4;
m is selected from 1 to 3;
p is selected from 1 to 3;
q is selected from 0 to 3;
r is selected from 0 to 3;
  wherein q and r are not simultaneously selected to be 0;
s is selected from 0 to 3;
t is selected from 0 to 3;
  wherein s and t are not simultaneously selected to be 0;
v is selected from 0 to 3; and
w is selected from 0 to 3.

In a certain embodiments of the present invention, there is provided a compound of the formula IVa:

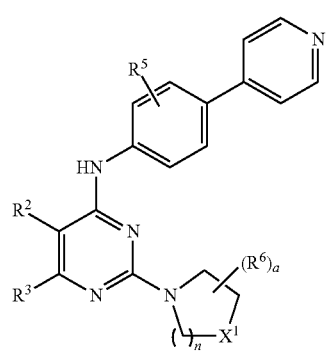

(IVa)

wherein:
$R^2$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

$R^5$ is selected from H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$X^1$ is selected from the group consisting of O, NH, and $CHR^6$;

each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —$(CH_2)_f$NRR', —O—$(CH_2)_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

additionally or alternatively, two $R^6$ substituents attached to the same ring carbon may be taken together to form an oxo group (i.e., =O), or a $C_3$ to $C_7$ spiro cyclic group; and additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;

each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
n is selected from 0 to 4.

In a certain embodiments of the present invention, there is provided a compound of the formula IVb:

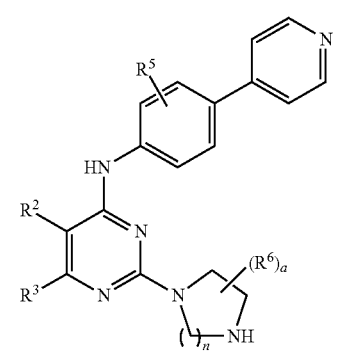

(IVb)

wherein:
R² is selected from the group consisting of H, halo, hydroxy, —NRR', —(CH₂)ₓNRR', —O—(CH₂)₉NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)ₓNRR', —O—(CH₂)₉NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁵ is selected from H, halo, hydroxy, —NRR', —(CH₂)ₓNRR', —O—(CH₂)₉NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)ₓNRR', —O—(CH₂)₉NRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;
additionally or alternatively, two R⁶ substituents attached to the same ring carbon may be taken together to form an oxo group (i.e., =O), or a C₃ to C₇ spiro cyclic group; and
additionally or alternatively, two R⁶ substituents attached to different ring carbons may be taken together to form a ring, wherein the ring formed when taking the two R⁶ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
n is selected from 0 to 4.

In a certain embodiments of the present invention, there is provided a compound of the formula IVc:

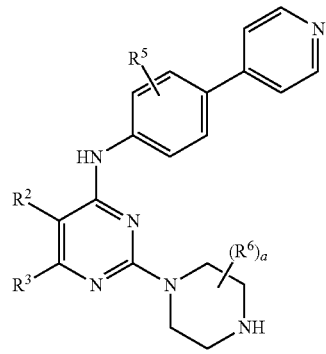

(IVc)

wherein:
R² is selected from the group consisting of H, halo, hydroxy, —NRR', —(CH₂)ₓNRR', —O—(CH₂)₉NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)ₓNRR', —O—(CH₂)₉NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁵ is selected from H, halo, hydroxy, —NRR', —(CH₂)ₓNRR', —O—(CH₂)₉NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
each R⁶ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH₂)ₓNRR', —O—(CH₂)₉NRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;
additionally or alternatively, two R⁶ substituents attached to the same ring carbon may be taken together to form an oxo group (i.e., =O), or a C₃ to C₇ spiro cyclic group; and
additionally or alternatively, two R⁶ substituents attached to different ring carbons may be taken together to form a ring, wherein the ring formed when taking the two R⁶ groups together has from 4 to 7 ring atoms including from 0 to 3 ring heteroatoms;
each R is independently selected from H and lower alkyl;
each R' is independently selected from H, lower alkyl, aryl, substituted aryl, aralkyl, and substituted aralkyl;
a is selected from 0 to 3;
each f is independently 1 to 3; and
each g is independently 2 or 3.

In a certain embodiments of the present invention, there is provided a compound of the formula IVd:

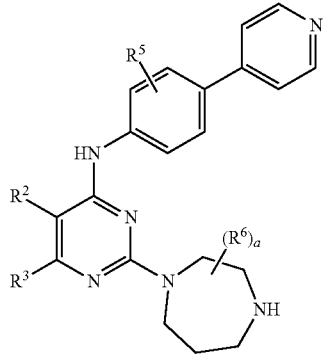

(IVd)

wherein:
R² is selected from the group consisting of H, halo, hydroxy, —NRR', —(CH₂)ₓNRR', —O—(CH₂)₉NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(═O)-lower alkyl, lower alkyl, and lower alkoxy;

$R^5$ is selected from H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

each $R^6$ is independently selected from the group consisting of H, halo, hydroxy, lower alkyl, substituted lower alkyl, lower alkoxy, aryl, substituted aryl, aralkyl, substituted aralkyl, heterocycle, substituted heterocycle, —NRR', —(CH$_2$)$_f$NRR', —O—(CH$_2$)$_g$NRR', —C(═O)—NRR', —C(═O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

additionally or alternatively, two $R^6$ substituents attached to the same ring carbon may be taken together to form an oxo group (i.e., ═O), or a $C_3$ to $C_7$ spiro cyclic group; and additionally or alternatively, two $R^6$ substituents attached to different ring carbons may be taken together to form a ring, wherein the ring formed when taking the two $R^6$ groups together has from 4 to 7 ring atoms including from 0 to 3 ring heteroatoms;

each R is independently selected from H and lower alkyl;
each R' is independently selected from H, lower alkyl, aryl, substituted aryl, aralkyl, and substituted aralkyl;
a is selected from 0 to 3;
each f is independently 1 to 3; and
each g is independently 2 or 3.

In a certain embodiments of the present invention, there is provided a compound of the formula IVe:

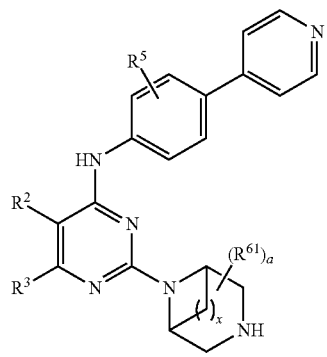

(IVe)

wherein:

$R^2$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(═O)-lower alkyl, lower alkyl, and lower alkoxy;

$R^5$ is selected from H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

each $R^{61}$ is independently selected from the group consisting of H, halo, hydroxy, lower alkyl, substituted lower alkyl, lower alkoxy, aryl, aralkyl, heterocycle, —NRR', —(CH$_2$)$_f$NRR', —O—(CH$_2$)$_g$NRR', —C(═O)—NRR', —C(═O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

each R is independently selected from H and lower alkyl;
each R' is independently selected from H, lower alkyl, aryl, substituted aryl, aralkyl, and substituted aralkyl;
a is selected from 0 to 3;
each f is independently 1 to 3;
each g is independently 2 or 3; and
x is selected from 1 to 3.

In a certain embodiments of the present invention, there is provided a compound of the formula IVf:

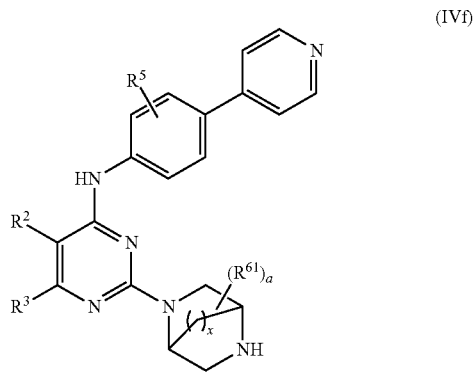

(IVf)

wherein:

$R^2$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(═O)-lower alkyl, lower alkyl, and lower alkoxy;

$R^5$ is selected from H, halo, hydroxy, —NRR', —(CH$_2$)$_f$NRR', —O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

each $R^{61}$ is independently selected from the group consisting of H, halo, hydroxy, lower alkyl, substituted lower alkyl, lower alkoxy, aryl, aralkyl, heterocycle, —NRR', —$(CH_2)_f$NRR', —O—$(CH_2)_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

each R is independently selected from H and lower alkyl;

each R' is independently selected from H, lower alkyl, aryl, substituted aryl, aralkyl, and substituted aralkyl;

a is selected from 0 to 3;

each f is independently 1 to 3;

each g is independently 2 or 3; and x is selected from 1 to 3.

In a certain embodiments of the present invention, there is provided a compound of the formula IVg:

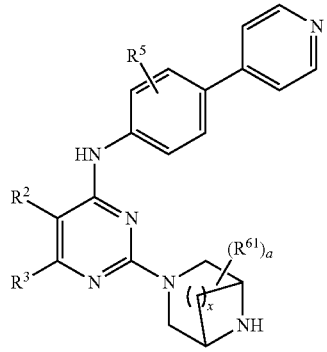

(IVg)

wherein:

$R^2$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

$R^5$ is selected from H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

each $R^{61}$ is independently selected from the group consisting of H, halo, hydroxy, lower alkyl, substituted lower alkyl, lower alkoxy, aryl, aralkyl, heterocycle, —NRR', —$(CH_2)_f$NRR', —O—$(CH_2)_g$NRR', —C(=O)—NRR', —C(=O)—OR, cyano, lower alkyl, $C_3$-$C_6$ cyclic alkyl, $C_1$-$C_3$ perfluoro alkyl, $C_1$-$C_3$ perfluoro alkoxy and carboxyl;

each R is independently selected from H and lower alkyl;

each R' is independently selected from H, lower alkyl, aryl, substituted aryl, aralkyl, and substituted aralkyl;

a is selected from 0 to 3;

each f is independently 1 to 3;

each g is independently 2 or 3; and x is selected from 1 to 3.

In a certain embodiments of the present invention, there is provided a compound of the formula IVh:

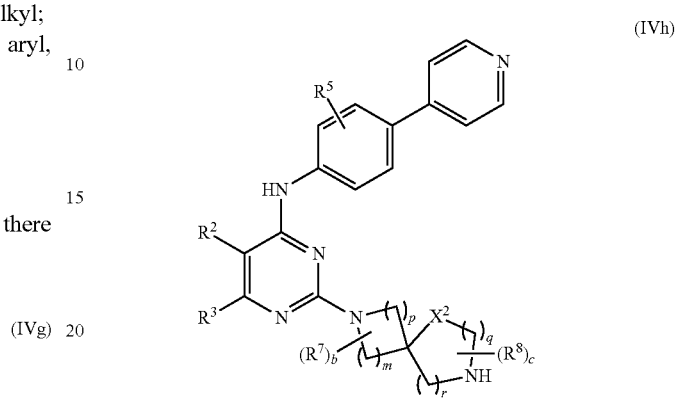

(IVh)

wherein:

$R^2$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

$R^3$ is selected from the group consisting of H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively $R^2$ and $R^3$ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

$R^5$ is selected from H, halo, hydroxy, —NRR', —$(CH_2)_f$NRR', —O—$(CH_2)_g$NRR', —C(=O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

each $R^7$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

each $R^8$ is independently selected from the group consisting of H, halo, hydroxy, lower alkyl, substituted lower alkyl, lower alkoxy, —NRR', —C(=O)—NRR', —C(=O)—OR, cyano, oxo, $C_1$-$C_3$ perfluoro alkyl, and $C_1$-$C_3$ perfluoro alkoxy;

$X^2$ is selected from $CH_2$, $CHR^8$, O, NH and N-(lower alkyl);

each R is independently selected from H and lower alkyl;

each R' is independently selected from H, lower alkyl, aryl, substituted aryl, aralkyl, and substituted aralkyl;

b is selected from 0 to 2;

c is selected from 0 to 2;

each f is independently 1 to 3;

each g is independently 2 or 3;

m is selected from 1 to 3;

p is selected from 1 to 3;

q is selected from 0 to 3; and r is selected from 0 to 3;

wherein q and r are not simultaneously selected to be 0.

In a certain embodiments of the present invention, there is provided a compound of the formula IVi:

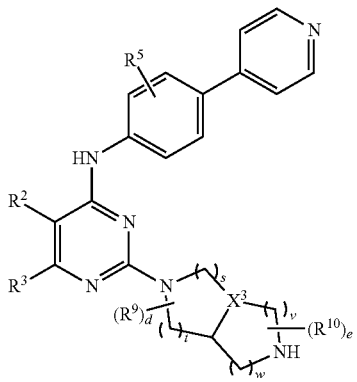

(IVi)

wherein:
R² is selected from the group consisting of H, halo, hydroxy, —NRR', —(CH₂)ₓNRR', —O—(CH₂)ₘNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
R³ is selected from the group consisting of H, halo, hydroxy, —NRR', —(CH₂)ₓNRR', —O—(CH₂)ₘNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;
R⁵ is selected from H, halo, hydroxy, —NRR', —(CH₂)ₓNRR', —O—(CH₂)ₘNRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;
each R⁹ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;
each R¹⁰ is independently selected from the group consisting of H, halo, hydroxy, lower alkyl, substituted lower alkyl, lower alkoxy, —NRR', —C(=O)—NRR', —C(=O)—OR, cyano, oxo, C₁-C₃ perfluoro alkyl, and C₁-C₃ perfluoro alkoxy;
X³ is selected from CH and N;
each R is independently selected from H and lower alkyl;
each R' is independently selected from H, lower alkyl, aryl, substituted aryl, aralkyl, and substituted aralkyl;
d is selected from 0 to 2;
e is selected from 0 to 2;
each f is independently 1 to 3;
each g is independently 2 or 3;
s is selected from 0 to 3;
t is selected from 0 to 3;
wherein s and t are not simultaneously selected to be 0;
v is selected from 0 to 3; and
w is selected from 0 to 3.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 8 or fewer carbon atoms in its backbone (e.g., C₁-C₈ for straight chain, C₃-C₈ for branched chain), and more preferably 6 or fewer. Likewise, preferred cycloalkyls have from 3-8 carbon atoms in their ring structure, and more preferably have 3 to 6 carbons in the ring structure.

Unless the number of carbons is otherwise specified, "lower alkyl" as used herein means an alkyl group, as defined above, but having from one to four carbons, and more preferably from one to three carbon atoms. In preferred embodiments, a substituent designated herein as alkyl is a lower alkyl. Lower alkyl groups include methyl, ethyl, propyl, isopropyl, n-butyl, iso-butyl, and tert-butyl.

The term "cycloalkyl" refers to saturated, carbocyclic groups having from 3 to 8 carbons in the ring. Cycloalkyl groups include cyclopropyl, cyclobutyl, cyclopentyl and cyclohexyl.

The term "substituted alkyl" refers to an alkyl group as defined above, and having one to three substituents. The substituents are selected from the group consisting of halo, hydroxy, lower alkoxy, amino, lower alkyl amino, nitro, cyano, perfluoro lower alkyl, perfluoro lower alkoxy and carboxyl.

"Substituted lower alkyl" refers to a lower alkyl group as defined above, and having one to three substituents. The substituents are selected from the group consisting of halo, hydroxy, lower alkoxy, amino, nitro, cyano, perfluoro lower alkyl, perfluoro lower alkoxy and carboxyl.

As used herein, the term "halogen" or "halo" designates —F, —Cl, —Br or —I, and preferably F, Cl or Br.

The terms "alkoxyl" or "alkoxy" as used herein refers to an alkyl group, as defined above, that is attached through an oxygen atom. Representative alkoxyl groups include methoxy, ethoxy, propyloxy, tert-butoxy and the like. The term "lower alkoxy" refers to an alkoxy substituent in which a lower alkyl is bonded through an oxygen atom, wherein the "lower alkyl" portion is as defined above.

The terms "amine" and "amino" refer to both unsubstituted and substituted amines, e.g., a moiety that can be represented by the general formula:

wherein R and R' are each independently selected from H and lower alkyl.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaryl" groups. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic.

The term "substituted aryl" refers to an aryl group as defined above, and having one to three substituents. The substituents are selected from the group consisting of halo, hydroxy, lower alkoxy, amino, lower alkyl amino, nitro, cyano, perfluoro lower alkyl, perfluoro lower alkoxy and carboxyl.

The term "aralkyl", as used herein, refers to an alkyl group substituted with an aryl group. Preferably, the alkyl group is a lower alkyl, as described above.

The term "substituted aralkyl" refers to an aralkyl group as defined above, and having one to three substituents on the aryl portion. The substituents are selected from the group consisting of halo, hydroxy, lower alkoxy, amino, lower alkyl amino, nitro, cyano, perfluoro lower alkyl, perfluoro lower alkoxy and carboxyl.

The term "heterocycle" of "heterocyclyl" refer to non-aromatic heterocycles having from 1 to 3 ring heteroatoms.

The term "substituted heterocycle" refers to a heterocycle group as defined above, and having one to three substituents. The substituents are selected from the group consisting of halo, hydroxy, lower alkoxy, amino, lower alkyl amino, nitro, cyano, perfluoro lower alkyl, perfluoro lower alkoxy and carboxyl.

The term "heteroatom" as used herein means an atom of any element other than carbon or hydrogen. Preferred heteroatoms are nitrogen, oxygen, and sulfur. Most preferred are nitrogen and oxygen.

As used herein, the definition of each expression, e.g. alkyl, m, n, $R^1$, $R^2$, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

In one aspect, the present invention provides compounds of Formulas I-IV (i.e., Formulas I, Ia, Ib, II, IIa, IIb, IIc, IId, IIe, IIf, IIg, IIh, Iii, IIj, IIk, IIm, IIn, IIo, IIp, IIq, IIr, IIs, IIt, III, IIIa, IIIb, IIIc, IIId, IIIe, IIIf, IIIg, IIIh, IIIi, IIIj, IV, Iva, IVb, IVc, IVd, IVe, IVf, IVg, IVh, IVi) that are inhibitors of ROCK. ROCK is found in two forms, ROCK 1 (ROCKβ; p160-ROCK) and ROCK 2 (ROCKα). In some embodiments, the compound of Formulas I-IV selectively inhibits ROCK1. In some embodiments, the compound of Formulas I-IV selectively inhibits ROCK2. In some embodiments, the compound of Formulas I-IV is non-selective with respect to inhibition of ROCK1 and ROCK2. In the context of this invention, selective means the inhibitor demonstrates an $IC_{50}$ that is at least 2-fold, at least 5-fold, at least 10-fold, or at least 25-fold lower for one kinase as compared to the $IC_{50}$ for the other kinase.

Methods of determining kinase inhibition are known in the art. For example, kinase activity of an enzyme and the inhibitory capacity of a test compound can be determined by measuring enzyme specific phosphorylation of a substrate. Commercial assays and kits are available and can be employed. For example, kinase inhibition can be determined using an IMAP® assay (Molecular Devices). This assay method involves the use of a fluorescently tagged peptide substrate. Phosphorylation of the tagged peptide by a kinase of interest promotes binding of the peptide to a trivalent metal-based nanoparticle via the specific, high affinity interaction between the phospho-group and the trivalent metal. Proximity to the nanoparticle results in increased fluorescence polarization. Inhibition of the kinase by a kinase inhibitor prevents phosphorylation of the substrate and thereby limits binding of the fluorescently-tagged substrate to the nanoparticle. Such an assay can be compatible with a microwell assay format, allowing simultaneous determination of $IC_{50}$ of multiple compounds.

Methods of Treating Disease

In one aspect of the present invention there is provided a method of treating a patient suffering from a disease comprising administering to a patient in need of such treatment a therapeutically effective amount of a compound of the present invention. The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g. reasonable side effects applicable to any medical treatment.

Fibrotic Disorders

ROCKs are key regulators of mechanotransduction signaling, and the cells involved in tissue fibrotic responses, namely epithelial cells, endothelial cells and myofibroblasts, are regulated by ROCK activities. Thus, the ROCK inhibitors of the invention may have therapeutic utilities in fibrotic disease. The invention provides a method of treating a fibrotic disorder in a subject comprising administering to the subject a therapeutically effective amount of a compound of Formulas I-IV. Non-limiting examples of fibrotic disorders are pulmonary fibrosis including cystic and idiopathic pulmonary fibrosis, radiation induced lung injury, liver fibrosis including cirrhosis, cardiac fibrosis including arterial fibrosis, endomyocardial fibrosis, old myocardial infraction, arterial stiffness, atherosclerosis, restenosis, arthrofibrosis, Crohn's disease, myelofibrosis, Peyronie's diseases, nephrogenic systemic fibrosis, progressive massive fibrosis, retroperitoneal cavity fibrosis, schleroderma/systemic sclerosis, mediastinal fibrosis, Keloids and hypertrophic scars, glial scaring, or renal fibrosis.

CNS Disorders

Compounds of Formulas I-IV are useful for treatment of central nervous system disorders. Such disorders may involve neuronal degeneration or physical injury to neural tissue, including without limitation, Huntington's disease, Parkinson's Disease, Alzheimer's, Amyotrophic lateral sclerosis (ALS), Batten disease, dementia, spinal muscular atrophy, motor neurone diseases, spinocerebellar ataxia, acute or chronic pain, dementia, neuronal degeneration, spinal cord injury, cerebral vasospasm or multiple sclerosis.

Cardiovascular and Other Diseases

Compounds of the invention that inhibit ROCK and/or ROCK mediated phosphorylation are useful for treatment of patients suffering from cardiovascular and non-cardiovascular diseases involving Rho-kinase function, such as hypertension, pulmonary hypertension, atherosclerosis, restenosis, coronary heart disease, cardiac hypertrophy, ocular hypertension, retinopathy, ischemic diseases, cerebral ischemia, cerebral vasospasm, penile erectile dysfunction, peripheral circulatory disorder, peripheral artery occlusive disease, glaucoma, (e.g., regulating intraocular pressure), fibroid lung, fibroid liver, fibroid kidney, chronic obstructive pulmonary disease (COPD), adult respiratory distress syndrome, central nervous system disorders such as neuronal degeneration and spinal cord injury. Further, ROCK inhibitors of the invention can be used to treat arterial thrombotic disorders such as platelet aggregation and leukocyte aggregation, and bone resorption.

In an embodiment of the invention, compounds are used to treat cerebral cavernous malformation (CCM). CCMs are vascular lesions consisting of clusters of leaky, dilated capillaries and are associated with central nervous system (CNS) disorders, including seizures and stroke. The loss of vascular integrity is thought to involve activation of RhoA and activation of ROCK, leading to changes in cytoskeletal stability and increased vascular permeability. The compounds of the invention inhibit ROCK activation and restore vascular endothelial function.

Glaucoma

In an embodiment of the invention, a compound of Formulas I-IV is used to treat glaucoma. The two most common, primary open-angle glaucoma and acute angle-closure glaucoma, are characterized by high ocular pressure. Pigmentary glaucoma and congenital glaucoma also are characterized by reduced fluid outflow and high intraocular pressure (IOP). Normal tension glaucoma is thought to be due to another mechanism, in particular poor blood flow to the optic nerve. Secondary glaucoma can result from injury, infection, inflammation, tumor or cataracts, and is also associated with prolonged use of steroids, systemic hypertension, diabetic retinopathy, and central retinal vein occlusion. Glaucomas having a neovascular component can benefit from administration of a angiogenesis inhibitor in addition to a ROCK inhibitor.

Inflammation

The invention provides a method of treating inflammation in a subject comprising administering to the subject a therapeutically effective amount of a compound of Formulas I-IV. Inflammation includes, without limitation, asthma, cardiovascular inflammation, renal inflammation, atherosclerosis and arteriosclerosis, and sepsis. Other inflammatory conditions that can be treated by methods of the invention include fibrotic conditions (including, e.g., idiopathic pulmonary fibrosis, NASH, scleroderma, systemic sclerosis, and cirrhosis).

Autoimmune Disorders

The invention provides a method of treating an autoimmune disorder in a subject comprising administering to the subject a therapeutically effective amount of a compound of Formulas I-IV. Autoimmune disorders include, without limitation, rheumatoid arthritis, multiple sclerosis, systemic lupus erythematosus (SLE; lupus), psoriasis, Crohn's disease, atopic dermatitis, eczema, or graft-versus-host disease (GVHD), Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, and Vitiligo.

According to the invention, targeting Th17 (IL-17-secreting) cells by ROCK inhibition provides a method for treating Th17 cell-mediated diseases, including but not limited to autoimmune disorders such as RA, MS, SLE, Psoriasis, and Crohn's disease, and GVHD in humans. In an embodiment of the invention, the ROCK inhibitor is a compound of Formula I-IV.

Regulatory T cells (Tregs) play a critical role in the maintenance of immunological tolerance to self-antigens and inhibition of autoimmune responses, but, at the same time, prevent an effective immune response against tumor cells. Indeed, Tregs isolated from the peripheral blood of patients with autoimmune disease, such as rheumatoid arthritis (RA) and multiple sclerosis (MS), show a defect in their ability to suppress effector T cell function, while increased accumulation of Tregs correlates with a poor prognosis in many cancers. Thus, the level of Treg function effects a balance between effective immunity and avoidance of pathological autoreactivity.

The development and function of Tregs depend on activation of specific signaling transduction pathways. TGF-β and IL-2 activate expression of Foxp3 and STAT5 transcription factors that both play an essential role in the control of Treg suppressive function. On the other hand, pro-inflammatory cytokines inhibit Foxp3 expression via up-regulation of STAT3 phosphorylation. According to the invention, pharmacological inhibition of ROCK may regulate Treg function.

Neoplastic Disease

ROCK inhibitors of the invention inhibit tumor cell growth and metastasis, and angiogenesis, and are useful for treating neoplastic diseases. Neoplastic diseases include any malignant growth or tumor caused by abnormal or uncontrolled cell division, and may spread to other parts of the body through the lymphatic system or the blood stream. Neoplastic disease includes, without limitation, lymphoma (a neoplasm of lymph tissue that is usually malignant), carcinoma (any malignant tumor derived from epithelial tissue), leukemia (malignant neoplasm of blood-forming tissues; characterized by abnormal proliferation of leukocytes), sarcoma (a usually malignant tumor arising from connective tissue (bone or muscle etc.), and blastoma (malignancy in precursor cells). Nonlimiting examples include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

Weight Gain/Loss

According to the invention, ROCK inhibitors are used to effect weight loss and/or limit weight gain. In a preferred embodiment, the ROCK inhibitor is a ROCK 1 and ROCK2 inhibitor. ROCK inhibitors promote weight loss in normal subjects, and limit weight gain in subjects prone to obesity.

Insulin Resistance

In an embodiment of the invention, a ROCK inhibitor is used to reduce or prevent insulin resistance or restore insulin sensitivity. Accordingly, in one embodiment, the compounds of the invention are used to promote or restore insulin-dependent glucose uptake. In another embodiment of the invention, a ROCK inhibitors of the invention is used to promote or restore glucose tolerance. In another embodiment of the invention, a ROCK inhibitor of the invention is used to treat metabolic syndrome. In another embodiment, a ROCK-inhibitors of the invention is used to reduce or prevent hyperinsulinemia. ROCK inhibitors of the invention may also be used to promote or restore insulin-mediated relaxation of vascular smooth muscle cells (VSMCs).

Angiogenesis

The invention provides methods and compounds for treating diseases and disorders with an angiogenic component. According to the invention, in certain embodiments, such diseases and disorders are treated by administering to a subject an effective amount of a ROCK inhibitor. According to the invention, such diseases and disorders can also be treated by administering an effective amount of a rho kinase inhibitor and an effective amount of an angiogenesis inhibitor. According to the invention, ocular diseases and disorders having an angiogenic component are treated in this manner. In one embodiment, the invention provides a method of treating age related macular degeneration (AMD), which occurs in "dry" and "wet" forms. The "wet" form of AMD causes vision loss due to abnormal blood vessel growth (neovascularization). Bleeding, leaking, and scarring from these retinal blood vessels eventually causes irreversible damage to the photoreceptors. The dry form results from atrophy of the retinal pigment epithelial layer, which causes vision loss through loss of photoreceptors (rods and cones) in the central part of the eye. In another embodiment, the invention provides a method of treating choroidal neovascularization (CNV). Choroidal neovascularization is a process in which new blood vessels grow in the choroid, through the Bruch membrane and invade the subretinal space, and is a symptom of, among other causes, age-related macular degeneration, myopia and ocular trauma. In another embodiment, the invention provides a method of treating diabetic macular edema (DME). In another embodiment, the invention provides a method of treating macular edema that is secondary to branch retinal vein occlusion (BRVO) or central retinal vein occlusion (CRVO). In other embodiments, the diseases to be treated include, without limitation, retinal neovascularization, infectious and non-infectious, corneal neovascularization infectious and non-infectious, iris neovascularization, uveitis, neovascular glaucoma, and retinitis of prematurity (ROP). The method of treatment can be prophylactic, such as to stave off corneal neovascularization after corneal transplant, or to modulate the wound healing process in trabeculectomy surgery. These diseases and disorders may be characterized as having an angiogenic component. According to the invention, such disorders are treated by administering a Rho-kinase inhibitor, and an angiogenesis inhibitor.

Accordingly, in one such embodiment, the disease or disorder is AMD, and a subject in need of treatment for AMD is administered an amount of a ROCK inhibitor effective to treat AMD. In another embodiment, the subject is administered a ROCK inhibitor and an angiogenesis inhibitor in amounts effective to treat AMD. In some embodiments, the angiogenesis inhibitor is a VEGFR2 antagonist. In certain such embodiments, the VEGFR2 antagonist binds to VEGF. In other such embodiments, the VEGFR2 antagonist binds to VEGFR2. Such VEGFR2-binding inhibitors include agents that bind to the extracellular domain of VEGFR2, including but not limited to antibodies and VEGFR2-binding fragments thereof, and agents that interact with the intracellular domain of VEGFR2 and block activation of VEGFR2-dependent signal transduction. VEGFR2 antagonists further include agents that interact with other cellular components to block VEGFR2-dependent signal transduction. In other embodiments of the invention, other ocular diseases and disorders having an angiogenic component, such as are indicated above, are similarly treated.

According to the invention, a ROCK inhibitor and an angiogenesis inhibitor are administered to a subject in amounts effective amount to treat or preventing a pathologic condition characterized by excessive angiogenesis. Such conditions, involving for example, vascularization and/or inflammation, include atherosclerosis, rheumatoid arthritis (RA), hemangiomas, angiofibromas, and psoriasis. Other non-limiting examples of angiogenic disease are retinopathy of prematurity (retrolental fibroplastic), corneal graft rejection, corneal neovascularization related to complications of refractive surgery, corneal neovascularization related to contact lens complications, corneal neovascularization related to pterygium and recurrent pterygium, corneal ulcer disease, and non-specific ocular surface disease, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osler-Weber syndrome, restinosis, and fungal, parasitic and viral infections, including cytomegaloviral infections.

The invention provides pan-ROCK inhibitors (i.e., compounds that inhibit ROCK1 and ROCK2). For example, one study observed that ROCK2 is frequently over expressed in hepatocellular cancer compared to non-tumorous livers while ROCK1 expression is unaltered. Other cancers that may benefit from treatment with a ROCK2 selective inhibitor include, but are not limited to, colon and bladder cancer. In contrast, ROCK1 expression levels have been observed to be higher in mammary tumors. Any cancer may be tested to determine whether there is overexpression of ROCK1 and/or ROCK2 and treated accordingly. In certain circumstances, ROCK 1 and ROCK2 isoforms show similarity in regulating certain downstream targets and neither isoform seems to be predominant. In such cases, a pan-ROCK inhibitor may be preferred.

Combinations with Other Agents

Compounds of the invention can be advantageously administered with second agents to patients in need thereof. When ROCK inhibitor is administered with a second agent, the ROCK inhibitor and the second agent can be administered sequentially or concomitantly. Sequentially means that one agent is administered for a time followed by administration of the other agent, which may be followed by administration of the first agent. When agents are administered sequentially, the level of one agent may not be maintained at a therapeutically effective level when the second agent is administered, and vice versa. Concomitantly means that the first and second agents are administered according to a schedule that maintains both agents at a substantially therapeutically effective level, even though the agents are not administered simultaneously. Each agent can be administered in single or multiple doses, and the doses can be administered on any schedule, including, without limitation, twice daily, daily, weekly, every two weeks, and monthly.

The invention also includes adjunctive administration. Adjunctive administration means that a second agent is administered to a patient in addition to a first agent that is already being administered to treat a disease or disease symptom. In some embodiments, adjunctive administration involves administering a second agent to a patient in which administration of the first agent did not sufficiently treat a disease or disease symptom. In other embodiments, adjunctive administration involves administration of the second agent to a patient whose disease has been effectively treated by administration of the first agent, with the expectation that the adjunctive treatment improves the outcome of the treatment. In some embodiments, the effect of administering the first and second agents is synergistic. In some embodiments, administration of the first and second agents prevents or lengthens the time until relapse, compared to administration of either of the agents alone. In some embodiments, administration of the first and second agents allows for reduced dosage and/or frequency of administration of the first and second agent.

Anti-inflammatories and immunosuppressants that can be administered in combination with the compounds of the present invention include steroid drugs such as glucocorticoids (e.g., dexamethasone), FK506 (tacrolimus), ciclosporin, fingolimod, interferon, such as IFNβ or IFNγ, a tumor necrosis factor-alpha (TNF-α) binding protein such as infliximab (Remicade), etanercept (Enbrel), or adalimumab (Humira), mycophenolic acid, MMF, Methotrexate, NSAID, Statins, Sirolimus/temsirolimus/everolimus, abatacept (Orencia), anakinra (Kineret), certolizumab (Cimzia), golimumab (Simponi), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), daclizumab (Zinbryta), muromonab (Orthoclone OKT3), Jakafi (Ruxolitinib), Xeljanz (Tofacitnib), and Otezla (Apremilast).

In an embodiment of the invention, a rho-kinase inhibitor of the invention and an anti-neoplastic agent are administered to a subject in need thereof. In another embodiment, a rho-kinase inhibitor of the invention and an angiogenesis inhibitor are administered to a subject in need thereof. In another embodiment, a rho-kinase inhibitor of the invention and an anti-inflammatory agent are administered to a subject in need thereof. In yet another embodiment, a ROCK inhibitor of the invention and an immunosuppressant are administered. The second agent can be, without limitation, a small molecule, an antibody or antigen binding fragment thereof, or radiation.

Antineoplastic agents include, without limitation, cytotoxic chemotherapeutic agents, targeted small molecules and biological molecules, and radiation. Compounds and agents that can be administered for oncological treatment, in addition to a rho kinase inhibitor of the invention, include the following: irinotecan, etoposide, camptothecin, 5-fluorouracil, hydroxyurea, tamoxifen, paclitaxel, capcitabine, carboplatin, cisplatin, bleomycin, dactomycin, gemcitabine, doxorubicin, danorubicin, cyclophosphamide, and radiotherapy, which can be external (e.g., external beam radiation therapy (EBRT)) or internal (e.g., brachytherapy (BT)).

Targeted small molecules and biological molecules include, without limitation, inhibitors of components of signal transduction pathways, such as modulators of tyrosine kinases and inhibitors of receptor tyrosine kinases, and agents that bind to tumor-specific antigens. Examples include inhibitors of epidermal growth factor receptor (EGFR), including gefitinib, erlotinib, and cetuximab, inhibitors of HER2 (e.g., trastuzumab, trastuzumab emtansine (trastuzumab-DM1; T-DM1) and pertuzumab), anti-VEGF antibodies and fragments (e.g., bevacizumab), antibodies that inhibit CD20 (e.g., rituximab, ibritumomab), anti-VEGFR antibodies (e.g., ramucirumab (IMC-1121B), IMC-1C11, and CDP791), anti-PDGFR antibodies, and imatinib. Small molecule kinase inhibitors can be specific for a particular tyrosine kinase or be inhibitors of two or more kinases. For example, the compound N-(3,4-dichloro-2-fluorophenyl)-7-({[(3aR,6aS)-2-methyloctahydrocyclopenta[c]pyrrol-5-yl]methyl}oxy)-6-(methyloxy)quinazolin-4-amine (also known as XL647, EXEL-7647 and KD-019) is an in vitro inhibitor of several receptor tyrosine kinases (RTKs), including EGFR, EphB4, KDR (VEGFR), Flt4 (VEGFR3) and ErbB2, and is also an inhibitor of the SRC kinase, which is involved in pathways that result in nonresponsiveness of tumors to certain TKIs. In an embodiment of the invention, treatment of a subject in need comprises administration of a ROCK inhibitor of Formulas I-V and administration of KD-019.

Dasatinib (BMS-354825; Bristol-Myers Squibb, New York) is another orally bioavailable, ATP-site competitive Src inhibitor. Dasatanib also targets Bcr-Abl (FDA-approved for use in patients with chronic myelogenous leukemia (CML) or Philadelphia chromosome positive (Ph+) acute lymphoblastic leukemia (ALL)) as well as c-Kit, PDGFR, c-FMS, EphA2, and Src family kinases. Two other oral tyrosine kinase inhibitor of Src and Bcr-Abl are bosutinib (SKI-606) and saracatinib (AZD0530).

According to the invention, angiogenesis inhibitors can be administered to a subject in conjunction with compounds of the invention. Angiogenesis inhibitors include any substance that inhibits the growth of new blood vessels. For example, angiogenesis inhibitors include antagonists of VEGF, PlGF, and VEGF receptors, including the antibodies disclosed herein. A VEGF antagonist reduces or blocks a function in a cell that is associated with VEGF. A VEGF antagonist may act on VEGF, by binding to VEGF and blocking binding to its receptors and/or may act on another cellular component involved in VEGF-mediated signal transduction. Similarly, a VEGFR2 antagonist is an agent that reduces or blocks VEGFR2-mediated signal transduction by binding to VEGFR2 and blocking ligand binding or interaction with a VEGFR2 substrate, or acts on another cellular component to reduce or block VEGFR2-mediated signal transduction. Thus, angiogenesis inhibitors include anti-VEGFR2 antibodies, and antagonists of, without limitation, VEGF, VEGFR1, VEGFR2, PDGF, PDGFR-β, neuropilin-1 (NRP1), and complement.

Angiogenesis inhibitors include intracellular agents that block signal transduction mediated by, for example, VEGF, PDGF, ligands of VEGF or PDGF receptors, or complement. Intracellular agents that inhibit angiogenesis inhibitors include the following, without limitation. Sunitinib (Sutent; SU11248) is a panspecific small-molecule inhibitor of VEGFR1-VEGFR3, PDGFRα and PDGFRβ, stem cell factor receptor (cKIT), Flt-3, and colony-stimulating factor-1 receptor (CSF-1R). Axitinib (AG013736; Inlyta) is another small molecule tyrosine kinase inhibitor that inhibits VEGFR-1-VEGFR-3, PDGFR, and cKIT. Cediranib (AZD2171) is an inhibitor of VEGFR-1-VEGFR-3, PDGFRβ, and cKIT. Sorafenib (Nexavar) is another small molecular inhibitor of several tyrosine protein kinases, including VEGFR, PDGFR, and Raf kinases. Pazopanib (Votrient; (GW786034) inhibits VEGFR-1, -2 and -3, cKIT and PDGFR. Foretinib (GSK1363089; XL880) inhibits VEGFR2 and MET. CP-547632 is as a potent inhibitor of the VEGFR-2 and basic fibroblast growth factor (FGF) kinases. E-3810 ((6-(7-((1-aminocyclopropyl) methoxy)-6-methoxyquinolin-4-yloxy)-N-methyl-1-naphthamide) inhibits VEGFR-1, -2, and -3 and FGFR-1 and -2 kinases in the nanomolar range. Brivanib (BMS-582664) is a VEGFR-2 inhibitor that also inhibits FGF receptor signaling. CT-322 (Adnectin) is a small protein based on a human fibronectin domain and binds to and inhibits activation of VEGFR2. Vandetanib (Caprelas; Zactima; ZD6474) is an inhibitor of VEGFR2, EGFR, and RET tyrosine kinases. X-82 (Xcovery) is a small molecule indolinone inhibitor of signaling through the growth factor receptors VEGFR and PDGFR Pharmaceutical Compositions In one aspect, the present invention provides pharmaceutically acceptable compositions which comprise a therapeutically-effective amount of one or more of the compounds of Formulas I-V, formulated together with one or more pharmaceutically excipients. As described below, the pharmaceutical compositions of the present invention may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, e.g., Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable excipients including a pharmaceutically-acceptable carrier, such as sodium citrate or dicalcium phosphate, and/or any of the following:

(1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides diluents, the oral compositions can also include additional excipients such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain additional excipients such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Routes of Administration and Dose

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

In certain embodiments, a dose of a compound or a composition is administered to a subject every day, every other day, every couple of days, every third day, once a week, twice a week, three times a week, or once every two weeks. If desired, the effective daily dose of the active compound may be administered as two, three, four, five, six or more sub-doses administered separately at appropriate intervals throughout the day, optionally, in unit dosage forms. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

The above-described administration schedules are provided for illustrative purposes only and should not be considered limiting. A person of ordinary skill in the art will readily understand that all doses are within the scope of the invention.

The patient receiving this treatment is any animal in need, including primates, in particular humans, and other mammals such as equines, cattle, swine and sheep; and poultry and pets in general.

The compounds for use in the methods of the invention can be administered as such or in admixtures with pharmaceutically acceptable carriers and can also be administered in conjunction with antimicrobial agents such as penicillins, cephalosporins, aminoglycosides and glycopeptides. Conjunctive therapy thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Microemulsification technology may be employed to improve bioavailability of lipophilic (water insoluble) pharmaceutical agents. Examples include Trimetrine (Dordunoo, S. K., et al., Drug Development and Industrial Pharmacy, 17(12), 1685-1713, 1991) and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

Controlled Release

The release characteristics of a formulation of the present invention depend on the encapsulating material, the concentration of encapsulated drug, and the presence of release modifiers. Release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients that modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references cited herein are hereby incorporated by reference in their entirety.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references cited herein are hereby incorporated by reference in their entirety.

EXAMPLES

Example 1

All solvents and reagents were obtained commercially and used as received. $^1$H NMR spectra were recorded on a Bruker instrument (300 MHz or 400 MHz) in the cited deuterated solvents. Chemical shifts are given in ppm, and coupling constants are in hertz. All final compounds were purified by flash chromatography using 220-400 mesh silica gel or reverse-phase HPLC with $CH_3CN$/water as the solvents. Thin-layer chromatography was done on silica gel 60 F-254 (0.25-nm thickness) plates. Visualization was accomplished with UV light and/or 10% phosphomolybdic acid in ethanol. Nominal (low resolution) mass spectra were acquired on either a Waters LCT or an Applied Biosystems API 3000 mass spectrometer. High resolution mass spectra (HRMS) were acquired on either a Waters LCT or an Agilent TOF mass spectrometer. All other LC-MS experiments were done on an Agilent 1100 HPLC coupled with an Agilent single quadrupole mass spectrometer. Compound purity was determined by a LC-MS with 230 nM and 254 nM wavelengths. All final compounds reported here have purity ≥95%.

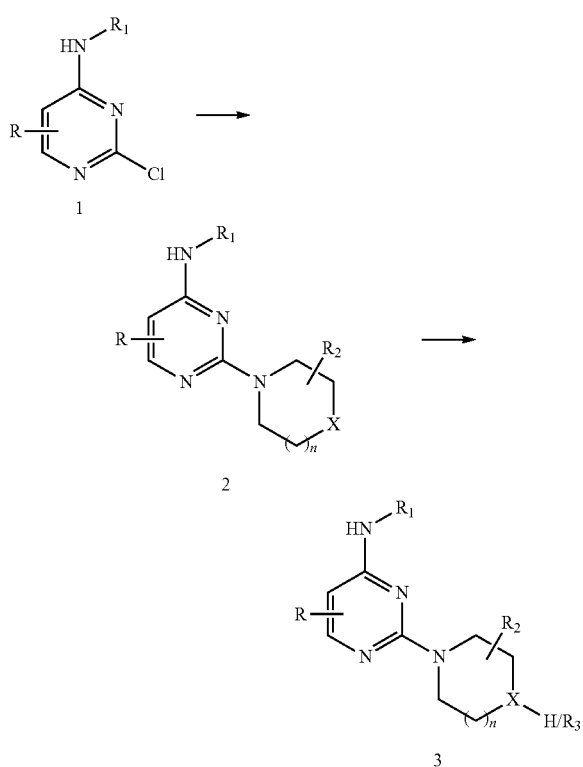

Method A:

A solution of compounds of general structure 1 (1 equiv), Boc protected amine (1-3 equiv) and DIPEA (3 equiv) in DMSO were reacted at 100-110° C. The reaction mixture was cooled to room temperature and quenched by addition of water and crude residue extracted with EtOAc. Combined organic layers were washed with brine, dried over $Na_2SO_4$, filtered and concentrated under reduced pressure to provide crude compound of general structure 2, which was used in the following step without further purification. To a solution of compounds of general structure 2 in $CH_2Cl_2$ was added HCl/dioxane (4 N) or TFA. The reaction was stirred at room temperature for 2 hrs and mixture was concentrated under reduced pressure. The residue was purified by reverse phase preparative HPLC to afford final compounds of general structure 3.

Method B:

A solution of compounds of general structure 1 (1 equiv), Bn protected amine (1-3 equiv) and DIPEA (3 equiv) in DMSO were reacted at 100-110° C. The reaction mixture was cooled to room temperature and quenched by addition of water and crude residue extracted with EtOAc. Combined organic layers were washed with brine, dried over $Na_2SO_4$, filtered and concentrated under reduced pressure to afford crude residue of general structure 2. The crude product was used into the next step without further purification or purified by prep-TLC. To a mixture of compound 2 in MeOH was added HCl (12 N, 2 equiv) and Pd/C (wet, 0.1 equiv). The reaction was stirred at room temperature for 16 hrs under an atmosphere of $H_2$. The mixture was filtered through a pad of Celite and the filtrate concentrated under reduced pressure. The residue was purified by reverse phase preparative HPLC to afford final compounds of general structure 3.

Method C:

A solution of compounds of general structure 1 (1 equiv), unprotected secondary amine (1-3 equiv) and DIPEA (2 equiv) in DMSO or DMF was stirred at 100-110° C. for several hours. The residue was purified by reverse phase preparative HPLC to afford final compounds of general structure 3.

Method D:

A solution of compounds of general structure 1 (1 equiv) in $CH_2Cl_2$ (300.00 uL) was added HCl/dioxane (4 N, 2 equiv). After the mixture was stirred at 15° C. for 30 minutes, the mixture was concentrated under reduced pressure to afford a crude residue. The residue was dispersed in t-BuOH (300.00 uL), amine (1 equiv) was added. Then the reaction was stirred at 90° C. for 16 hours. The reaction mixture was cooled to room temperature and dispersed in $CH_2Cl_2$. The removal of Boc protecting group was facilitated by TFA. The reaction mixture was concentrated under reduced pressure to give a residue. The residue was purified by reverse phase preparative HPLC to afford final compounds of general structure 3.

Method E:

A solution of compounds of general structure 1 (1 equiv), Boc protected amine or amino alcohol (1-1.2 equiv) in i-PrOH was stirred at 170° C. under microwave irradiation for 1 hr. The solution was purified by reverse phase preparative HPLC to afford compound of general structure 2. Compound of general structure 2 was dissolved in $CH_2Cl_2$ and TFA added. The reaction mixture was stirred at room temperature for 2 hours and concentrated under reduced pressure. The residue was purified by reverse phase preparative HPLC to afford final compounds of general structure 3.

Method F:

A solution of compounds of general structure 1 (1 equiv), Boc protected amine (1-3 equiv) and DIPEA (3 equiv) in DMSO were reacted at 100-110° C. The reaction mixture was cooled to room temperature and quenched by addition of water and crude residue extracted with EtOAc. Combined organic layers were washed with brine, dried over $Na_2SO_4$, filtered and concentrated under reduced pressure to provide crude compound of general structure 2, which was used in the following step without further purification. To a solution of compounds of general structure 2 in $CH_2Cl_2$ was added HCl/dioxane (4 N) or TFA. The reaction was stirred at room temperature for 2 hrs and mixture was concentrated under reduced pressure to afford compound of general structure 3. To a solution of compound 3 in MeOH and TEA (2 equiv) at room temperature was added the corresponding aldehyde. The reaction mixture was stirred at room temperature for 16 hours and $NaBH_3CN$ (2 equiv) added. Reaction stirred for 1 hour. Solvent removed under reduced pressure. Crude material dissolved in EtOAc and washed with water. Combined organic phases were dried and solvent removed under reduced pressure. The residue was purified by reverse phase preparative HPLC to afford final compound.

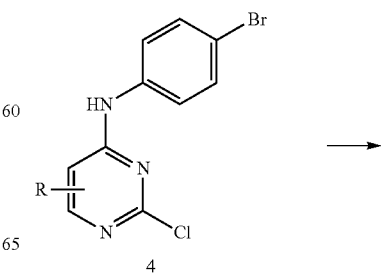

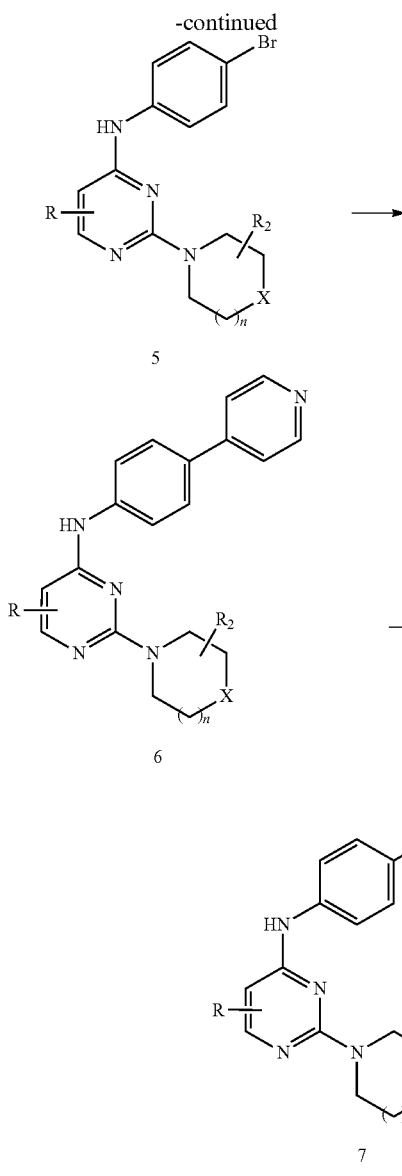

Method G:

A solution of compounds of general structure 4 (1 equiv), Boc protected amine (1-3 equiv) and DIPEA (3 equiv) in DMSO were reacted at 100-110° C. The reaction mixture was cooled to room temperature and quenched by addition of water and crude residue extracted with EtOAc. Combined organic layers were washed with brine, dried over $Na_2SO_4$, filtered and concentrated under reduced pressure to provide crude compound of general structure 5, which was purified using silica gel chromatography. To a solution of compounds of general structure 5 in dioxane and water was added 4-pyridinyl boronic acid (1 equiv), $K_2CO_3$ (2 equiv), Pd(dppf)Cl$_2$ (0.05 equiv). Reaction mixture was stirred for 16 hours at 100° C. Reaction solution was diluted with water and extracted with EtOAc, dried $Na_2SO_4$, filtered and concentrated under reduced pressure to provide crude compound of general structure 6. To a solution of compounds of general structure 6 in $CH_2Cl_2$ was added HCl/dioxane (4 N) or TFA. The reaction was stirred at room temperature for 2 hrs and mixture was concentrated under reduced pressure. The residue was purified by reverse phase preparative HPLC to afford final compounds of general structure 7.

Example 2

2-(3-benzyl-1,4-diazepan-1-yl)-N-(1H-indazol-5-yl)-5,7-dihydrofuro[3,4-d]pyrimidin-4-amine

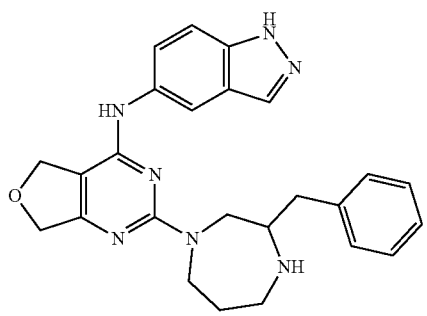 [SMILES: c1ccc(CC2CN(c3nc4c(c(Nc5ccc6[nH]ncc6c5)n3)COC4)CCCN2)cc1]

The reaction was conducted following general protocol C. The residue was purified by reverse phase preparative HPLC to afford 2-(3-benzyl-1,4-diazepan-1-yl)-N-(1H-indazol-5-yl)-5,7-dihydrofuro[3,4-d]pyrimidin-4-amine as a yellow solid (22%). $^1$H NMR (400 MHz, DMSO-d$_6$) δ 12.96 (s, 1H), 8.73 (s, 1H), 8.13 (s, 1H), 7.96-7.87 (m, 1H), 7.49-7.44 (m, 2H), 7.29-7.25 (m, 2H), 7.20-7.16 (m, 3H), 4.87 (s, 2H), 4.67 (s, 2H), 3.91-3.85 (m, 1H), 3.81-3.77 (m, 1H), 3.60-3.53 (m, 2H), 3.09-3.05 (m, 1H), 2.76-2.60 (m, 4H), 1.89-1.82 (m, 1H), 1.47-1.37 (m, 1H). MS (ES+) m/e 442.4 (M+H)$^+$.

Example 3

N-(2-(1,4-diazepan-1-yl)-5-methylpyrimidin-4-yl)-1H-indazol-5-amine

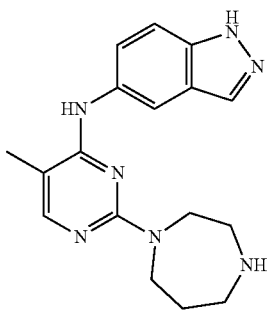 [SMILES: Cc1cnc(N2CCCNCC2)nc1Nc1ccc2[nH]ncc2c1]

The reaction was conducted following general protocol A. The reaction time of the first step was 32 hours and the crude material was further used without additional purification. The final residue was purified by reverse phase preparative HPLC to afford N-(2-(1,4-diazepan-1-yl)-5-methylpyrimidin-4-yl)-1H-indazol-5-amine as a white solid (35%). $^1$H NMR (400 MHz, DMSO-d$_6$) δ 12.93 (s, 1H), 8.05-8.19 (m, 2H), 7.94-7.99 (m, 1H), 7.71-7.76 (m, 1H), 7.60 (t, J=7.2 Hz, 1H), 7.41-7.47 (m, 1H), 3.58-3.74 (m, 4H), 3.46 (s, 1H), 3.27 (s, 1H), 2.79 (s, 1H), 2.64 (t, J=5.2 Hz, 1H), 2.05 (s, 3H), 1.72 (dd, J=11.2, J=5.6 Hz, 2H). MS (ES+) m/e 324.1 (M+H)$^+$.

Example 4

N-(5-chloro-2-(1,4-diazepan-1-yl)pyrimidin-4-yl)-1H-indazol-5-amine

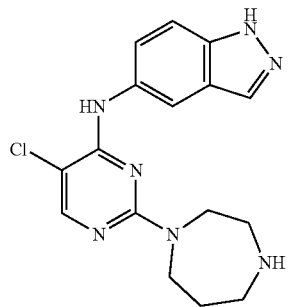 [SMILES: Clc1cnc(N2CCCNCC2)nc1Nc1ccc2[nH]ncc2c1]

The reaction was conducted following general protocol A. The reaction time of the first step was 32 hours and the crude material was further used without additional purification. The final residue was purified by reverse phase preparative HPLC to afford N-(5-chloro-2-(1,4-diazepan-1-yl)pyrimidin-4-yl)-1H-indazol-5-amine as a white solid (35%). $^1$H NMR (400 MHz, CD$_3$OD) δ 8.02 (s, 2H), 7.93 (s, 1H), 7.59 (dd, J=8.8, 1.6 Hz, 1H), 7.52 (d, J=8.8 Hz, 1H), 3.76 (t, J=6.0 Hz, 4H), 2.97 (t, J=4.8 Hz, 2H), 2.87 (t, J=6.0 Hz, 2H), 1.89 (t, J=4.8 Hz, 2H). MS (ES+) m/e 344.0 (M+H)$^+$.

Example 5

N-(2-(1,4-diazepan-1-yl)-6-methylpyrimidin-4-yl)-1H-indazol-5-amine

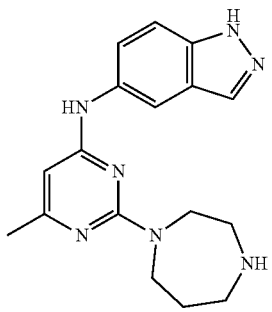 [SMILES: Cc1cc(Nc2ccc3[nH]ncc3c2)nc(N2CCCNCC2)n1]

The reaction was conducted following general protocol A. The reaction time of the first step was 16 hours and the crude material was further used without additional purification. The final residue was purified by reverse phase preparative HPLC to afford N-(2-(1,4-diazepan-1-yl)-6-methylpyrimidin-4-yl)-1H-indazol-5-amine as a white solid (50%). $^1$H NMR (400 MHz, CD$_3$OD) δ 8.10 (s, 1H), 7.97 (s, 1H), 7.49 (s, 2H), 5.92 (s, 1H), 3.94-3.88 (m, 4H), 3.12 (t, J=5.2 Hz, 2H), 2.97 (t, J=5.6 Hz, 2H), 2.22 (s, 3H), 2.02 (t, J=5.6 Hz, 2H). MS (ES+) m/e 324.1 (M+H)$^+$.

Example 6

2-(1,4-diazepan-1-yl)-N-(1H-indazol-5-yl)quinazolin-4-amine

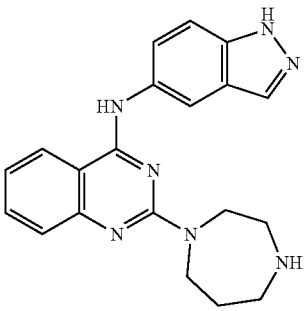 [SMILES: c1ccc2c(Nc3ccc4[nH]ncc4c3)nc(N3CCCNCC3)nc2c1]

The reaction was conducted following general protocol A. The reaction time of the first step was 16 hours and the crude material was further used without additional purification. The final residue was purified by reverse phase preparative HPLC to afford 2-(1,4-diazepan-1-yl)-N-(1H-indazol-5-yl)quinazolin-4-amine as a light red solid (51%). $^1$H NMR (400 MHz, DMSO-d$_6$) δ 13.02 (brs, 1H), 9.55-9.494 (m, 1H), 8.30-8.20 (m, 2H), 8.02 (d, J=11.2 Hz, 1H), 7.74-7.71 (m, 2H), 7.59-7.52 (m, 2H), 7.33 (t, J=8.4 Hz, 1H), 7.17-7.11 (m, 1H), 3.80-3.31 (m, 6H), 2.86 (m, 1H), 2.68 (d, J=5.6 Hz, 1H), 1.78 (m, 2H). MS (ES+) m/e 360.1 (M+H)$^+$.

Example 7

N-(2-(1,4-diazepan-1-yl)-5-methoxypyrimidin-4-yl)-1H-indazol-5-amine

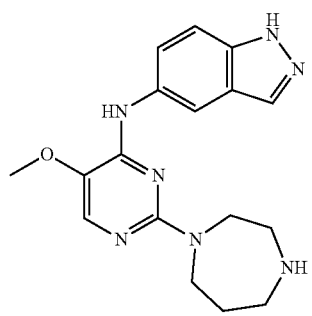 [SMILES: COc1cnc(N2CCCNCC2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(1,4-diazepan-1-yl)-5-methoxypyrimidin-4-yl)-1H-indazol-5-amine as a white solid (40%). $^1$H NMR (400 MHz, CD$_3$OD) δ 8.22 (s, 1H), 7.99 (s, 1H), 7.64 (dd, J=9.2 Hz, 2.0 Hz, 1H), 7.60 (s, 1H), 7.50 (d, J=9.2 Hz, 1H), 3.89 (s, 3H), 3.79 (t, J=5.6 Hz, 4H), 3.02 (t, J=5.2 Hz, 2H), 2.86 (t, J=5.6 Hz, 2H), 1.98-1.92 (m, 2H). MS (ES+) m/e 340.1 (M+H)$^+$.

Example 8

N-(2-(1,4-diazepan-1-yl)-5,6-dimethylpyrimidin-4-yl)-1H-indazol-5-amine

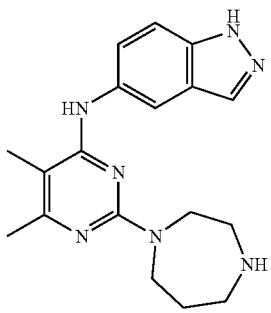 [SMILES: Cc1nc(N2CCCNCC2)nc(Nc2ccc3[nH]ncc3c2)c1C]

The reaction was conducted following general protocol A. The reaction time of the first step was 16 hours and the crude material was further used without additional purification. The final residue was purified by reverse phase preparative HPLC to afford N-(2-(1,4-diazepan-1-yl)-5,6-dimethylpyrimidin-4-yl)-1H-indazol-5-amine as a yellow solid (20%). $^1$H NMR (400 MHz, DMSO-$d_6$) δ 8.32 (s, 2H), 8.16 (s, 1H), 7.98 (s, 1H), 7.95 (s, 1H) 7.55 (d, J=7.6 Hz, 1H), 7.44 (d, J=8.8 Hz, 1H), 3.67-3.76 (m, 4H), 3.12 (s, 2H), 3.02 (s, 2H), 2.22 (s, 3H), 2.07 (s, 3H), 1.95 (s, 2H). MS (ES+) m/e 338.2 (M+H)$^+$.

Example 9

2-(1,4-diazepan-1-yl)-N-(1H-indazol-5-yl)-5,6,7,8-tetrahydroquinazolin-4-amine

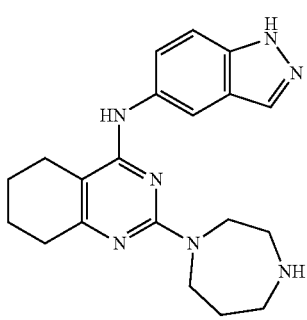 [SMILES: c1cc2[nH]ncc2cc1Nc1nc(N2CCCNCC2)nc2c1CCCC2]

The reaction was conducted following general protocol A. The reaction time of the first step was 16 hours and the crude material was further used without additional purification. The final residue was purified by reverse phase preparative HPLC to afford 2-(1,4-diazepan-1-yl)-N-(1H-indazol-5-yl)-5,6,7,8-tetrahydroquinazolin-4-amine as a white solid (43%). $^1$H NMR (400 MHz, DMSO-$d_6$) δ 12.19 (s, 1H), 9.73 (s, 1H), 9.50 (brs, 2H), 8.11 (s, 1H), 7.87 (s, 1H), 7.57 (d, J=8.8 Hz, 1H), 7.51 (d, J=8.8 Hz, 1H), 3.92 (m, 2H), 3.75 (m, 2H), 3.16 (m, 4H), 2.81 (m, 2H), 2.53 (m, 2H), 2.05 (m, 2H), 1.79 (m, 4H). MS (ES+) m/e 364.2 (M+H)$^+$.

Example 10

2-(1,4-diazepan-1-yl)-N-(1H-indazol-5-yl)thieno[3,2-d]pyrimidin-4-amine

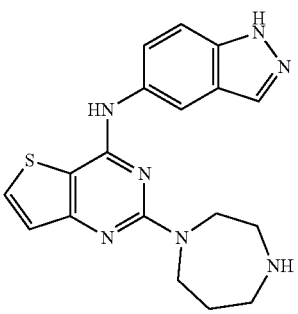 [SMILES: c1cc2nc(N3CCCNCC3)nc(Nc3ccc4[nH]ncc4c3)c2s1]

The reaction was conducted following general protocol A. The reaction time of the first step was 16 hours and the crude material was further used without additional purification. The final residue was purified by reverse phase preparative HPLC to afford 2-(1,4-diazepan-1-yl)-N-(1H-indazol-5-yl)thieno[3,2-d]pyrimidin-4-amine as a white solid (58%). $^1$H NMR (400 MHz, DMSO-$d_6$) δ 13.79 (brs, 1H), 11.14 (s, 1H), 9.54 (brs, 2H), 8.33 (s, 1H), 8.14 (s, 1H), 8.00 (s, 1H), 7.72-7.35 (m, 3H), 3.92 (m, 4H), 3.24 (m, 4H), 2.15 (m, 2H). MS (ES+) m/e 366.1 (M+H)$^+$.

Example 11

2-(1,4-diazepan-1-yl)-N-(1H-indazol-5-yl)-5,7-dihydrofuro[3,4-d]pyrimidin-4-amine

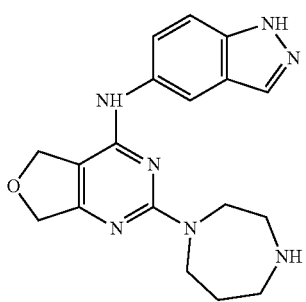 [SMILES: c1cc2[nH]ncc2cc1Nc1nc(N2CCCNCC2)nc2c1COC2]

The reaction was conducted following general protocol A. The reaction time of the first step was 16 hours and the crude material was further used without additional purification. The final residue was purified by reverse phase preparative HPLC to afford 2-(1,4-diazepan-1-yl)-N-(1H-indazol-5-yl)-5,7-dihydrofuro[3,4-d]pyrimidin-4-amine as a white solid (40%). $^1$H NMR (400 MHz, CD$_3$OD) δ 8.07 (s, 1H), 8.00 (s, 1H), 7.58 (d, J=8.8 Hz, 1H), 7.50 (d, J=8.8 Hz, 1H), 4.95-4.92 (m, 2H), 4.79-4.78 (m, 2H), 4.88-4.83 (m, 4H), 3.07-3.04 (m, 2H), 2.94-2.91 (m, 2H), 2.00-1.94 (m, 2H). MS (ES+) m/e 352.1 (M+H)$^+$.

Example 12

2-(1,4-diazepan-1-yl)-N-(1H-indazol-5-yl)-5,7-dihydrothieno[3,4-d]pyrimidin-4-amine

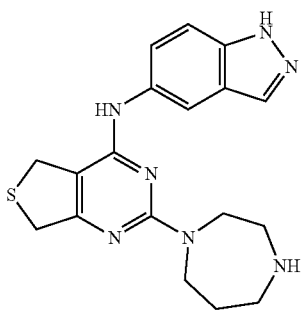 [SMILES: c1cc2[nH]ncc2cc1Nc1nc(N2CCCNCC2)nc2c1CSC2]

The reaction was conducted following general protocol A. The reaction time of the first step was 16 hours and the crude material was further used without additional purification. The final residue was purified by reverse phase preparative HPLC to afford 2-(1,4-diazepan-1-yl)-N-(1H-indazol-5-yl)-5,7-dihydrothieno[3,4-d]pyrimidin-4-amine as a yellow solid (40%). $^1$H NMR (400 MHz, DMSO-$d_6$) δ 12.99 (s, 1H), 8.49 (s, 1H), 8.14 (s, 1H), 7.98 (s, 1H), 7.60 (d, J=8.8 Hz, 1H), 7.46 (d, J=8.8 Hz, 1H), 4.04 (s, 2H), 3.98 (s, 2H), 3.73-3.65 (m, 4H), 2.86-2.80 (m, 2H), 2.68-2.67 (m, 2H), 1.76-1.73 (m, 2H). MS (ES+) m/e 352.1 (M+H)$^+$.

Example 13

N-(5,6-dimethyl-2-(3-methylpiperazin-1-yl)pyrimidin-4-yl)-1H-indazol-5-amine

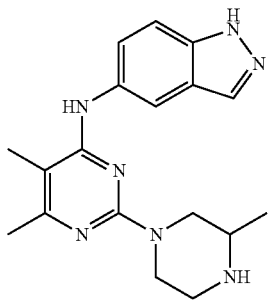

The reaction was conducted following general protocol A. The reaction time of the first step was 32 hours and the crude material was further used without additional purification. The final residue was purified by reverse phase preparative HPLC to afford N-(5,6-dimethyl-2-(3-methylpiperazin-1-yl)pyrimidin-4-yl)-1H-indazol-5-amine as a yellow solid (32%). $^1$H NMR (400 MHz, CD$_3$OD) δ 8.33 (s, 2H), 7.99 (s, 1H), 7.86 (s, 1H), 7.54-7.48 (m, 2H), 4.59 (d, J=14.2 Hz, 2H), 3.35 (m, 1H), 3.28-3.23 (m, 1H), 3.19-3.00 (m, 2H), 2.93-2.89 (m, 1H), 2.33 (s, 3H), 2.14 (s, 3H), 1.28 (d, J=6.4 Hz, 3H). MS (ES+) m/e 338.1 (M+H)$^+$.

Example 14

N-(2-(3-ethylpiperazin-1-yl)-5,6-dimethylpyrimidin-4-yl)-1H-indazol-5-amine

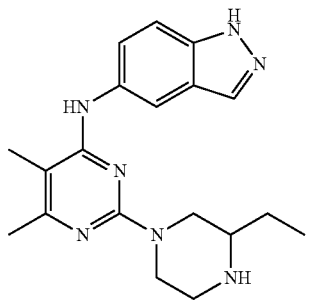 [SMILES: CCC1CN(c2nc(C)c(C)c(Nc3ccc4[nH]ncc4c3)n2)CCN1]

The reaction was conducted following general protocol A. The reaction time of the first step was 32 hours and the crude material was further used without additional purification. The final residue was purified by reverse phase preparative HPLC to afford N-(2-(3-ethylpiperazin-1-yl)-5,6-dimethylpyrimidin-4-yl)-1H-indazol-5-amine as a yellow solid (37%). $^1$H NMR (400 MHz, CD$_3$OD) δ 8.07 (s, 1H), 7.80 (d, J=1.6 Hz, 1H), 7.60 (d, J=8.8 Hz, 1H), 7.46 (dd, J=8.8, 2.0 Hz, 1H), 4.49 (d, J=13.6 Hz, 1H), 4.38 (d, J=14.8 Hz, 1H), 3.47-3.37 (m, 2H), 3.23-3.10 (m, 2H), 3.09-3.01 (m, 1H), 2.48 (s, 3H), 2.22 (s, 3H), 1.64-1.51 (m, 2H), 0.79 (t, J=7.6 Hz, 3H). MS (ES+) m/e 352.1 (M+H)$^+$.

Example 15

N-(2-(3-isopropylpiperazin-1-yl)-5,6-dimethylpyrimidin-4-yl)-1H-indazol-5-amine

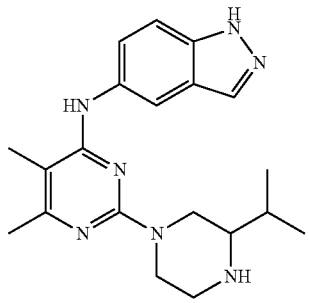

The reaction was conducted following general protocol A. The reaction time of the first step was 32 hours and the crude material was further used without additional purification. The final residue was purified by reverse phase preparative HPLC to afford N-(2-(3-isopropylpiperazin-1-yl)-5,6-dimethylpyrimidin-4-yl)-1H-indazol-5-amine as a yellow solid (25%). $^1$H NMR (400 MHz, CD$_3$OD) δ 8.46 (s, 2H), 7.97 (s, 1H), 7.85 (s, 1H), 7.53-7.47 (m, 2H), 4.78 (d, J=9.6 Hz, 1H), 4.66 (d, J=12.0 Hz, 1H), 3.34 (m, 1H), 3.14-3.03 (m, 2H), 2.84-2.81 (m, 2H), 2.32 (s, 3H), 2.16 (s, 3H), 1.85-1.78 (m, 1H), 0.99 (d, J=6.8 Hz, 3H), 0.91 (d, J=6.8 Hz, 3H). MS (ES+) m/e 366.2 (M+H)$^+$.

Example 16

N-(2-(3-isopropyl-1,4-diazepan-1-yl)-5,6-dimethylpyrimidin-4-yl)-1H-indazol-5-amine

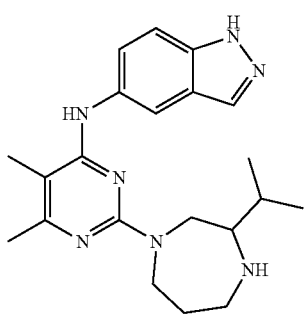 [SMILES: Cc1nc(N2CCCNC(C(C)C)C2)nc(Nc2ccc3[nH]ncc3c2)c1C]

The reaction was conducted following general protocol C. The residue was purified by reverse phase preparative HPLC to afford N-(2-(3-isopropyl-1,4-diazepan-1-yl)-5,6-dimethylpyrimidin-4-yl)-1H-indazol-5-amine as a yellow solid (12%). $^1$H NMR (400 MHz, CD$_3$OD) δ 8.45 (brs, 2H), 8.00 (s, 1H), 7.85 (s, 1H), 7.53-7.47 (m, 2H), 4.30-4.18 (m, 2H), 3.49-3.38 (m, 3H), 3.10 (m, 1H), 3.00 (m, 1H), 2.33 (s, 3H), 2.16-2.15 (m, 4H), 2.08-2.06 (m, 1H), 1.74 (m, 1H), 0.83-0.79 (m, 6H). MS (ES+) m/e 380.1 (M+H)$^+$.

Example 17

4-(4-((1H-indazol-5-yl)amino)pyrimidin-2-yl)piperazin-2-one

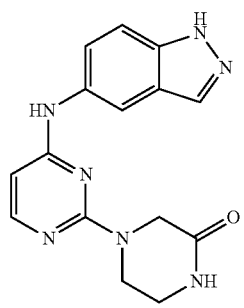 [SMILES: O=C1CN(c2nccc(Nc3ccc4[nH]ncc4c3)n2)CCN1]

The reaction was conducted following general protocol C. The residue was purified by reverse phase preparative HPLC to afford 4-(4-((1H-indazol-5-yl)amino)pyrimidin-2-yl)piperazin-2-one as a beige solid (62%). MS (ES+) m/e 310.1 (M+H)$^+$.

Example 18

2-(3-phenyl-1,4-diazepan-1-yl)-N-(4-(pyridin-4-yl)phenyl)pyrimidin-4-amine

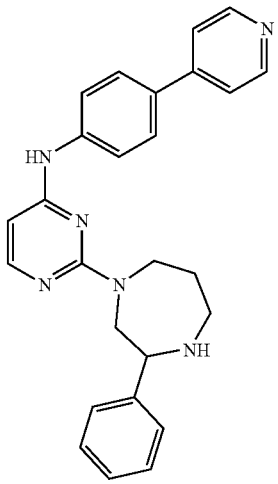 [SMILES: c1ccc(C2CN(c3nccc(Nc4ccc(-c5ccncc5)cc4)n3)CCCN2)cc1]

The reaction was conducted following general protocol G. The final residue was purified by reverse phase preparative HPLC to afford 2-(3-phenyl-1,4-diazepan-1-yl)-N-(4-(pyridin-4-yl)phenyl)pyrimidin-4-amine as a yellow solid (18%). $^1$H NMR (400 MHz, Methanol-d$_4$) δ 8.56-8.54 (m, 2H), 8.43 (s, 1H), 7.99 (d, J=6.0 Hz, 1H), 7.68 (m, 2H), 7.59 (m, 2H), 7.50-7.39 (m, 7H), 6.18 (d, J=6.0 Hz, 1H), 4.80-4.74 (m, 1H), 4.56 (dd, J=10.8, 2.4 Hz, 1H), 4.46 (m, 1H), 3.92 (dd, J=15.6, 10.4 Hz, 1H), 3.59-3.53 (m, 2H), 3.21-3.09 (m, 1H), 2.47-2.31 (m, 2H). MS (ES+) m/e 423.0 (M+H).

Example 19

N-(2-(5-isopropyl-1,4-diazepan-1-yl)-5,6-dimethylpyrimidin-4-yl)-1H-indazol-5-amine

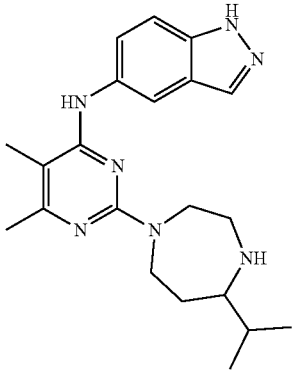 [SMILES: Cc1nc(N2CCNC(C(C)C)CC2)nc(Nc2ccc3[nH]ncc3c2)c1C]

The reaction was conducted following general protocol C. The residue was purified by reverse phase preparative HPLC to afford N-(2-(5-isopropyl-1,4-diazepan-1-yl)-5,6-dimethylpyrimidin-4-yl)-1H-indazol-5-amine as a white solid (44%). $^1$H NMR (400 MHz, CD$_3$OD) δ 8.51 (brs, 2H), 8.00 (s, 1H), 7.91 (d, J=0.8 Hz, 1H), 7.57-7.49 (m, 2H), 4.12-4.02 (m, 1H), 3.99-3.93 (m, 1H), 3.86-3.79 (m, 1H), 3.71-3.64

(m, 1H), 3.44-3.35 (m, 1H), 3.20-3.13 (m, 2H), 2.34 (s, 3H), 2.15 (s, 3H), 2.11-1.99 (m, 2H), 1.85-1.75 (m, 1H), 0.99 (t, J=6.4 Hz, 6H). MS (ES+) m/e 380.1 (M+H)⁺.

Example 20

N-(5,6-dimethyl-2-(3-phenyl-1,4-diazepan-1-yl)pyrimidin-4-yl)-1H-indazol-5-amine

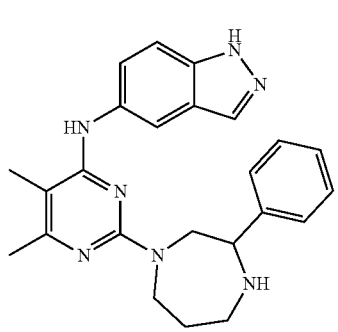 [SMILES: Cc1nc(N2CCCNC(c3ccccc3)C2)nc(Nc2ccc3[nH]ncc3c2)c1C]

The reaction was conducted following general protocol C. The residue was purified by reverse phase preparative HPLC to afford N-(5,6-dimethyl-2-(3-phenyl-1,4-diazepan-1-yl)pyrimidin-4-yl)-1H-indazol-5-amine as a light yellow oil (32%). ¹H NMR (400 MHz, CD₃OD) δ 8.42 (s, 2H), 7.83 (s, 1H), 7.80 (s, 1H), 7.46 (dd, J=8.8, 1.6 Hz, 1H), 7.34 (t, J=7.6 Hz, 1H), 7.28 (d, J=8.8 Hz, 1H), 7.16 (t, J=6.4 Hz, 2H), 7.02 (m, 2H), 4.52-4.40 (m, 2H), 4.30 (m, 1H), 3.64-3.57 (m, 1H), 3.48-3.43 (m, 2H), 3.03-2.96 (m, 1H), 2.41-2.28 (m, 4H), 2.24-2.14 (m, 4H). MS (ES+) m/e 414.1 (M+H)⁺.

Example 21

N-(5,6-dimethyl-2-(5-phenyl-1,4-diazepan-1-yl)pyrimidin-4-yl)-1H-indazol-5-amine

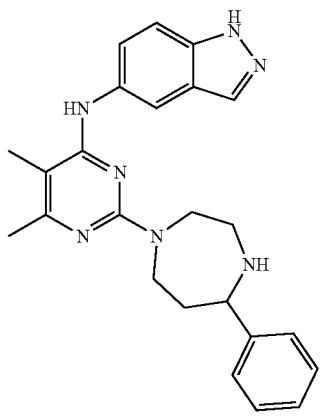 [SMILES: Cc1nc(N2CCNC(c3ccccc3)CC2)nc(Nc2ccc3[nH]ncc3c2)c1C]

The reaction was conducted following general protocol C. The residue was purified by reverse phase preparative HPLC to afford N-(5,6-dimethyl-2-(5-phenyl-1,4-diazepan-1-yl)pyrimidin-4-yl)-1H-indazol-5-amine as a yellow solid (9%). ¹H NMR (400 MHz, CD₃OD) δ 8.02 (s, 1H), 7.83 (d, J=0.8 Hz, 1H), 7.56 (d, J=9.2 Hz, 1H), 7.51-7.43 (m, 6H), 4.51 (d, J=10.8 Hz, 1H), 4.07-3.97 (m, 3H), 3.67 (t, J=11.2 Hz, 1H), 3.44 (m, 1H), 2.58 (m, 1H), 2.49 (s, 3H), 2.22 (s, 3H), 2.18-2.15 (m, 1H). MS (ES+) m/e 414.1 (M+H)⁺.

Example 22

N-(5,6-dimethyl-2-(3-methyl-1,4-diazepan-1-yl)pyrimidin-4-yl)-1H-indazol-5-amine

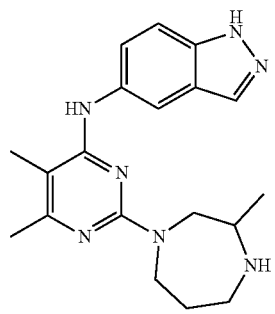

The reaction was conducted following general protocol A. The reaction time of the first step was 48 hours and the crude material was further used without additional purification. The final residue was purified by reverse phase preparative HPLC to afford N-(5,6-dimethyl-2-(3-methyl-1,4-diazepan-1-yl)pyrimidin-4-yl)-1H-indazol-5-amine as a yellow solid (22%). ¹H NMR (400 MHz, CD₃OD) δ 8.39 (s, 2H), 8.01 (s, 1H), 7.85 (s, 1H), 7.55-7.48 (m, 2H), 4.24-4.16 (m, 2H), 3.40-3.34 (m, 3H), 3.27-2.23 (m, 1H), 3.00-2.96 (m, 1H), 2.34 (s, 3H), 2.18-2.06 (m, 5H), 1.04-1.01 (m, 3H). MS (ES+) m/e 352.2 (M+H)⁺.

Example 23

N-(2-(5-ethyl-1,4-diazepan-1-yl)-5,6-dimethylpyrimidin-4-yl)-1H-indazol-5-amine

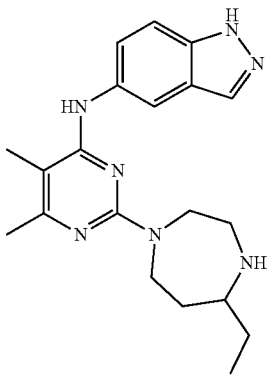 [SMILES: CCC1CCN(c2nc(C)c(C)c(Nc3ccc4[nH]ncc4c3)n2)CCN1]

The reaction was conducted following general protocol A. The reaction time of the first step was 46 hours and the crude material was further used without additional purification. The final residue was purified by reverse phase preparative HPLC to afford N-(2-(5-ethyl-1,4-diazepan-1-yl)-5,6-dimethylpyrimidin-4-yl)-1H-indazol-5-amine as a yellow solid (12%). ¹H NMR (400 MHz, CD₃OD) δ 8.09 (s, 1H), 7.83 (d, J=0.8 Hz, 1H), 7.61 (d, J=8.8 Hz, 1H), 7.50 (dd, J=8.8, 1.6 Hz, 1H), 3.96-3.91 (m, 2H), 3.87-3.85 (m, 1H), 3.59-3.58

(m, 1H), 3.30 (m, 2H), 3.21 (m, 1H), 2.49 (s, 3H), 2.22 (s, 3H), 2.12 (m, 1H), 2.00-1.98 (m, 1H), 1.78-1.68 (m, 2H), 1.03 (t, J=7.2 Hz, 3H). MS (ES+) m/e 366.1 (M+H)+.

Example 24

N-(2-(3,5-dimethylpiperazin-1-yl)-5,6-dimethylpyrimidin-4-yl)-1H-indazol-5-amine

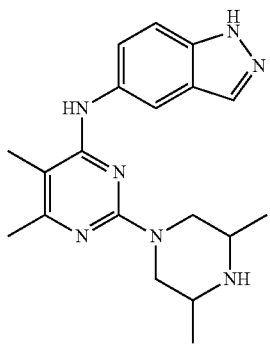

The reaction was conducted following general protocol A. The reaction time of the first step was 48 hours and the crude material was further used without additional purification. The final residue was purified by reverse phase preparative HPLC to afford N-(2-(3,5-dimethylpiperazin-1-yl)-5,6-dimethylpyrimidin-4-yl)-1H-indazol-5-amine as a yellow solid (12%). $^1$H NMR (400 MHz, CD$_3$OD) δ 8.50 (s, 2H), 8.01 (s, 1H), 7.89 (dd, J=1.6, 0.8 Hz, 1H), 7.56-7.50 (m, 2H), 4.75-4.71 (m, 2H), 3.30-3.22 (m, 2H), 2.76-2.69 (m, 2H), 2.34 (s, 3H), 2.15 (s, 3H), 1.29 (d, J=6.4 Hz, 6H). MS (ES+) m/e 352.1 (M+H)+.

Example 25

N-(5,6-dimethyl-2-(5-methyl-1,4-diazepan-1-yl)pyrimidin-4-yl)-1H-indazol-5-amine

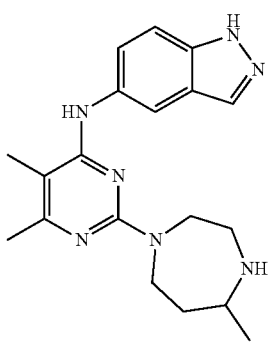 [SMILES: Cc1nc(N2CCNC(C)CC2)nc(Nc2ccc3[nH]ncc3c2)c1C]

The reaction was conducted following general protocol A. The reaction time of the first step was 48 hours and the crude material was further used without additional purification. The final residue was purified by reverse phase preparative HPLC to afford N-(5,6-dimethyl-2-(5-methyl-1,4-diazepan-1-yl)pyrimidin-4-yl)-1H-indazol-5-amine as a yellow solid (28%). $^1$H NMR (400 MHz, CD$_3$OD) δ 8.39 (s, 2H), 8.01 (s, 1H), 7.92 (s, 1H), 7.57-7.50 (m, 2H), 4.05-3.89 (m, 3H), 3.67-3.60 (m, 1H), 3.46-3.37 (m, 2H), 3.24-3.14 (m, 1H), 2.36 (s, 3H), 2.16 (s, 3H), 2.12-2.04 (m, 1H), 1.97-1.87 (m, 1H), 1.34 (d, J=6.4 Hz, 3H). MS (ES+) m/e 352.1 (M+H)+.

Example 26

N-(2-(3-ethyl-1,4-diazepan-1-yl)-5,6-dimethylpyrimidin-4-yl)-1H-indazol-5-amine

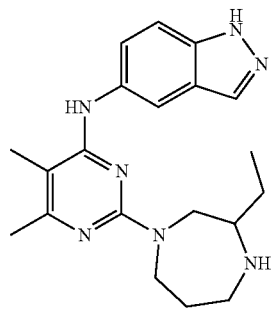 [SMILES: CCC1CN(c2nc(C)c(C)c(Nc3ccc4[nH]ncc4c3)n2)CCCN1]

The reaction was conducted following general protocol A. The reaction time of the first step was 96 hours and the crude material was further used without additional purification. The final residue was purified by reverse phase preparative HPLC to afford N-(2-(3-ethyl-1,4-diazepan-1-yl)-5,6-dimethylpyrimidin-4-yl)-1H-indazol-5-amine as a green solid (4%). $^1$H NMR (400 MHz, CD$_3$OD) δ 7.97 (d, J=0.8 Hz, 1H), 7.93 (d, J=1.2 Hz, 1H), 7.56 (dd, J=8.8, 2.0 Hz, 1H), 7.48 (d, J=8.8 Hz, 1H), 4.30-4.17 (m, 2H), 3.37-3.35 (m, 1H), 3.16-3.09 (m, 1H), 2.98-2.92 (m, 1H), 2.77 (m, 1H), 2.65-2.53 (m, 1H), 2.31 (s, 3H), 2.13 (s, 3H), 2.05 (m, 1H), 1.89-1.75 (m, 1H), 1.40-1.32 (m, 2H), 0.87-0.70 (m, 3H). MS (ES+) m/e 366.1 (M+H)+.

Example 27

N-(5,6-dimethyl-2-(2-methylpiperazin-1-yl)pyrimidin-4-yl)-1H-indazol-5-amine

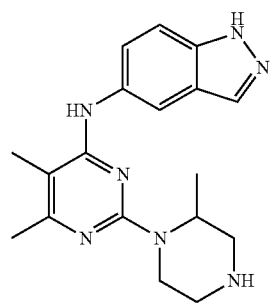

The reaction was conducted following general protocol A. The reaction time of the first step was 48 hours and the crude material was further used without additional purification. The final residue was purified by reverse phase preparative HPLC to afford N-(5,6-dimethyl-2-(2-methylpiperazin-1-yl)pyrimidin-4-yl)-1H-indazol-5-amine as a white solid (2%). $^1$H NMR (400 MHz, CD$_3$OD) δ 7.96 (d, J=0.8 Hz, 1H), 7.91 (d, J=1.2 Hz, 1H), 7.57 (dd, J=8.8, 2.0 Hz, 1H), 7.46 (d, J=8.8 Hz, 1H), 4.69-4.67 (m, 1H), 4.29-4.27 (m, 1H), 3.03-2.94 (m, 2H), 2.93-2.80 (m, 2H), 2.73-2.63 (m, 1H), 2.29 (s, 3H), 2.12 (s, 3H), 1.20 (d, J=6.8 Hz, 3H). MS (ES+) m/e 338.0 (M+H)⁺.

Example 28

N-(5,6-dimethyl-2-(6-methyl-1,4-diazepan-1-yl)pyrimidin-4-yl)-1H-indazol-5-amine

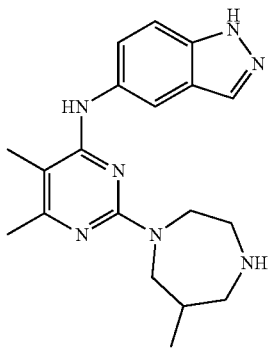 [SMILES: Cc1nc(N2CCNCC(C)C2)nc(Nc2ccc3[nH]ncc3c2)c1C]

The reaction was conducted following general protocol A. The reaction time of the first step was 24 hours and the crude material was further used without additional purification. The final residue was purified by reverse phase preparative HPLC to afford N-(5,6-dimethyl-2-(6-methyl-1,4-diazepan-1-yl)pyrimidin-4-yl)-1H-indazol-5-amine as a white solid (11%). ¹H NMR (400 MHz, CD₃OD) δ 7.99 (s, 1H), 7.97 (s, 1H), 7.59 (dd, J=8.8, 2.0 Hz, 1H), 748 (d, J=8.8 Hz, 1H), 4.19-4.08 (m, 2H), 3.51-3.48 (m, 1H), 3.22-3.15 (m, 1H), 3.03-2.86 (m, 3H), 2.60-2.55 (m, 1H), 2.31 (s, 3H), 2.14 (s, 3H), 2.10-2.03 (m, 1H), 0.88 (d, J=6.8 Hz, 3H). MS (ES+) m/e 352.1 (M+H)⁺.

Example 29

N-(2-(3,8-diazabicyclo[3.2.1]octan-8-yl)-5,6-dimethylpyrimidin-4-yl)-1H-indazol-5-amine

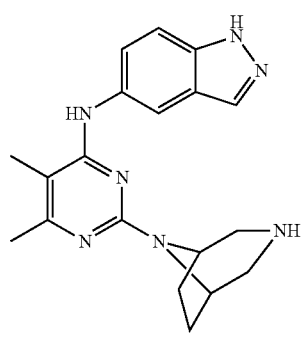 [SMILES: Cc1nc(N2C3CCC2CNC3)nc(Nc2ccc3[nH]ncc3c2)c1C]

The reaction was conducted following general protocol A. The reaction time of the first step was 16 hours and the crude material was further used without additional purification. The final residue was purified by reverse phase preparative HPLC to afford N-(2-(3,8-diazabicyclo[3.2.1]octan-8-yl)-5,6-dimethylpyrimidin-4-yl)-1H-indazol-5-amine as a white solid (15%). ¹H NMR (400 MHz, DMSO-d₆) δ 13.18 (brs, 1H), 12.09 (brs, 1H), 9.72 (brs, 1H), 9.44 (brs, 1H), 9.01 (brs, 1H), 8.11 (s, 1H), 7.84 (s, 1H), 7.56 (d, J=8.8 Hz, 1H), 7.49 (d, J=8.8, 1.6 Hz, 1H), 4.65 (s, 2H), 3.26-3.19 (m, 4H), 2.40 (s, 3H), 2.16 (s, 3H), 2.07-1.99 (m, 4H). MS (ES+) m/e 350.1 (M+H)⁺.

Example 30

N-(5-methoxy-2-(piperazin-1-yl)pyrimidin-4-yl)-1H-indazol-5-amine

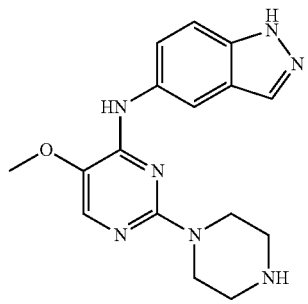 [SMILES: COc1cnc(N2CCNCC2)nc1Nc1ccc2[nH]ncc2c1]

The reaction was conducted following general protocol A. The reaction time of the first step was 64 hours and the crude material was further used without additional purification. The final residue was purified by reverse phase preparative HPLC to afford N-(5-methoxy-2-(piperazin-1-yl)pyrimidin-4-yl)-1H-indazol-5-amine as a yellow solid (20%). ¹H NMR (400 MHz, CD₃OD) δ 8.38 (s, 2H), 8.05 (d, J=1.2 Hz, 1H), 8.01 (s, 1H), 7.66 (s, 1H), 7.59 (dd, J=8.8, 2.0 Hz, 1H), 7.51 (d, J=9.2 Hz, 1H), 3.91 (s, 3H), 3.88 (t, J=5.2 Hz, 4H), 3.24 (t, J=5.2 Hz, 4H). MS (ES+) m/e 325.7 (M+H)⁺.

Example 31

N-(5-methoxy-2-(3-methylpiperazin-1-yl)pyrimidin-4-yl)-1H-indazol-5-amine

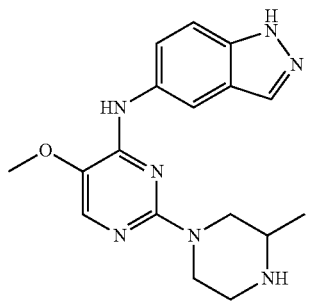

The reaction was conducted following general protocol A. The reaction time of the first step was 64 hours and the crude material was further used without additional purification. The final residue was purified by reverse phase preparative HPLC to afford N-(5-methoxy-2-(3-methylpiperazin-1-yl)pyrimidin-4-yl)-1H-indazol-5-amine as a white solid (28%). ¹H NMR (400 MHz, CD₃OD) δ 8.36 (s, 2H), 8.06 (d, J=1.6 Hz, 1H), 8.01 (d, J=1.2 Hz, 1H), 7.66 (s, 1H), 7.58 (dd, J=8.8, 2.0 Hz, 1H), 7.51 (d, J=9.2 Hz, 1H), 4.56 (dd, J=14.0, 2.8 Hz, 2H), 3.91 (s, 3H), 3.43-3.36 (m, 1H), 3.35-3.32 (m, 1H), 3.25-3.06 (m, 2H), 2.99-2.93 (m, 1H), 1.33 (d, J=6.8 Hz, 3H). MS (ES+) m/e 339.8 (M+H)⁺.

Example 32

N-(2-(3-isopropyl-1,4-diazepan-1-yl)-5-methoxypyrimidin-4-yl)-1H-indazol-5-amine

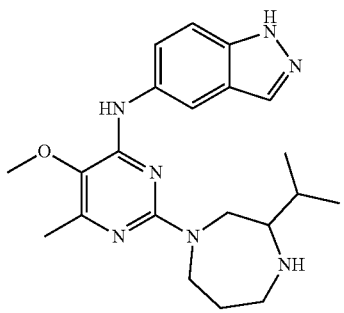 [SMILES: COc1c(C)nc(N2CCCNC(C(C)C)C2)nc1Nc1ccc2[nH]ncc2c1]

The reaction was conducted following general protocol C. The residue was purified by reverse phase preparative HPLC to afford N-(2-(3-isopropyl-1,4-diazepan-1-yl)-5-methoxypyrimidin-4-yl)-1H-indazol-5-amine as a light-yellow oil (9%). $^1$H NMR (400 MHz, CD$_3$OD) δ 8.50 (s, 2H), 8.05 (s, 1H), 8.01 (s, 1H), 7.66 (s, 1H), 7.57-7.52 (m, 2H), 4.32-4.28 (m, 1H), 4.14-4.10 (m, 1H), 3.92 (s, 3H), 3.56-3.47 (m, 3H), 3.25-3.19 (m, 1H), 3.07-3.02 (m, 1H), 2.20-1.84 (m, 3H), 0.89 (t, J=6.4 Hz, 6H). MS (ES+) m/e 382.1 (M+H)$^+$.

Example 33

N-(2-morpholinopyrimidin-4-yl)-1H-indazol-5-amine

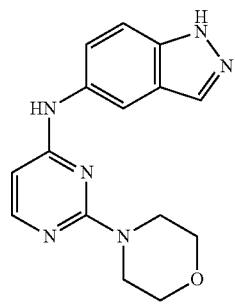 [SMILES: c1cc(Nc2ccc3[nH]ncc3c2)nc(N2CCOCC2)n1]

The reaction was conducted following general protocol C. The residue was purified by reverse phase preparative HPLC to afford N-(2-morpholinopyrimidin-4-yl)-1H-indazol-5-amine as a white solid (37%). $^1$H NMR (300 MHz, DMSO-d$_6$) δ 12.95 (s, 1H), 9.21 (s, 1H), 8.00 (dd, J=3.0, 1.8 Hz, 2H), 7.92 (d, J=5.7 Hz, 1H), 7.54-7.39 (m, 2H), 6.05 (d, J=5.8 Hz, 1H). MS (ES+) m/e 297 (M+H)$^+$.

Example 34

N-(2-(piperazin-1-yl)pyrimidin-4-yl)-1H-indazol-5-amine

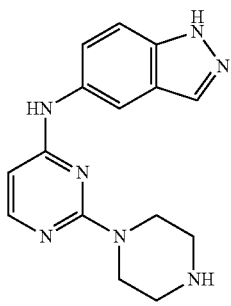 [SMILES: c1cc(Nc2ccc3[nH]ncc3c2)nc(N2CCNCC2)n1]

The reaction was conducted following general protocol A. The reaction time of the first step was 16 hours and the crude material was further used without additional purification. The final residue was purified by reverse phase preparative HPLC to afford N-(2-(piperazin-1-yl)pyrimidin-4-yl)-1H-indazol-5-amine as a white solid (67%). $^1$H NMR (300 MHz, DMSO-d$_6$) δ 12.96 (s, 1H), 9.15 (s, 1H), 8.01 (d, J=6.0 Hz, 2H), 7.89 (d, J=5.7 Hz, 1H), 7.54-7.40 (m, 2H), 6.00 (d, J=5.7 Hz, 1H), 3.65 (t, J=5.0 Hz, 4H), 2.76 (t, J=5.1 Hz, 4H). MS (ES+) m/e 296 (M+H)$^+$.

Example 35

N-(2-(1,4-diazepan-1-yl)pyrimidin-4-yl)-1H-indazol-5-amine

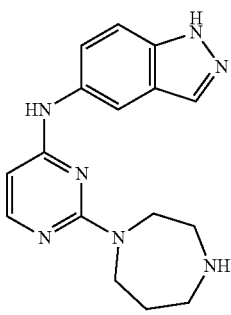 [SMILES: c1cc(Nc2ccc3[nH]ncc3c2)nc(N2CCCNCC2)n1]

The reaction was conducted following general protocol A. The reaction time of the first step was 16 hours and the crude material was further used without additional purification. The final residue was purified by reverse phase preparative HPLC to afford N-(2-(1,4-diazepan-1-yl)pyrimidin-4-yl)-1H-indazol-5-amine as a white solid (67%). $^1$H NMR (500 MHz, DMSO-d6) δ 12.91 (s, 1H), 9.10 (s, 1H), 8.18 (s, 1H), 7.96 (s, 1H), 7.87 (d, J=5.7 Hz, 1H), 7.46 (s, 2H), 5.97 (d, J=5.7 Hz, 1H), 3.75 (dt, J=23.6, 5.8 Hz, 5H), 2.93-2.80 (m, 2H), 2.69 (t, J=5.8 Hz, 2H), 1.79 (s, 2H). MS (ES$^+$) m/e 310 (M+H)$^+$.

Example 36

N-(2-(4-methoxypiperidin-1-yl)pyrimidin-4-yl)-1H-indazol-5-amine

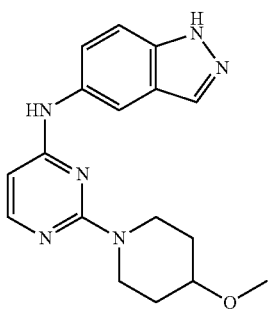 [SMILES: COC1CCN(c2nccc(Nc3ccc4[nH]ncc4c3)n2)CC1]

The reaction was conducted following general protocol C. The residue was purified by reverse phase preparative HPLC to afford N-(2-(4-methoxypiperidin-1-yl)pyrimidin-4-yl)-1H-indazol-5-amine a white solid (39%). $^1$H NMR (300 MHz, DMSO-$d_6$) δ 12.95 (s, 1H), 9.15 (s, 1H), 8.06-7.96 (m, 2H), 7.89 (d, J=5.7 Hz, 1H), 7.55-7.38 (m, 2H), 5.99 (d, J=5.7 Hz, 1H), 4.26-4.11 (m, 2H), 3.42 (m, 2H), 3.28 (s, 3H), 3.25-3.23 (m, 1H), 1.88 (m 2H), 1.38 (m, 2H). MS (ES$^+$) m/e 325 (M+H)$^+$.

Example 37

2-(3,8-diazabicyclo[3.2.1]octan-8-yl)-N-(4-(pyridin-4-yl)phenyl)-7,8-dihydro-5H-pyrano[4,3-d]pyrimidin-4-amine

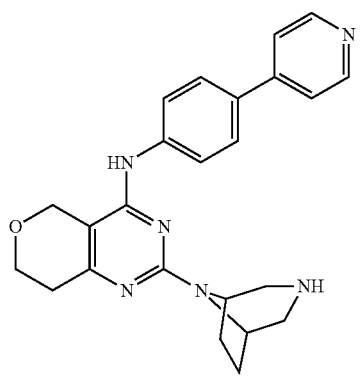 [SMILES: c1cc(-c2ccc(Nc3nc(N4C5CCC4CNC5)nc4c3COCC4)cc2)ccn1]

The reaction was conducted following general protocol G. The final residue was purified by reverse phase preparative HPLC to afford 2-(3,8-diazabicyclo[3.2.1]octan-8-yl)-N-(4-(pyridin-4-yl)phenyl)-7,8-dihydro-5H-pyrano[4,3-d]pyrimidin-4-amine as a yellow solid (65%). $^1$H NMR (400 MHz, DMSO-$d_6$) δ 9.21 (brs, 1H), 8.90 (brs, 1H), 8.82 (d, J=6.0 Hz, 2H), 8.15 (d, J=5.6 Hz, 2H), 8.02 (d, J=8.4 Hz, 2H), 7.87 (d, J=8.8 Hz, 2H), 4.70 (s, 2H), 4.64 (s, 2H), 3.94 (t, J=5.6 Hz, 2H), 3.21 (m, 4H), 2.72-2.67 (m, 2H), 2.11-2.02 (m, 4H). MS (ES+) m/e 361.1 (M+H).

Example 38

N-(4-(1H-pyrazol-4-yl)phenyl)-2-(piperazin-1-yl)pyrimidin-4-amine

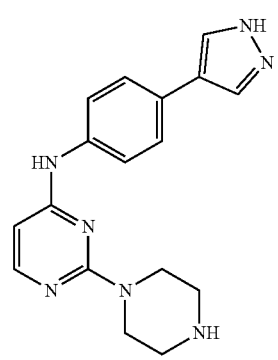 [SMILES: c1cc(Nc2ccc(-c3cn[nH]c3)cc2)nc(N2CCNCC2)n1]

The reaction was conducted following general protocol A. Intermediated was purified via reverse phase preparatory HPLC. The final residue was purified by reverse phase preparatory HPLC to afford N-(4-(1H-pyrazol-4-yl)phenyl)-2-(piperazin-1-yl)pyrimidin-4-amine as a white solid (41%). MS (ES+) m/e 322.1 (M+H).

Example 39

2-(3,8-diazabicyclo[3.2.1]octan-3-yl)-N-(1H-indazol-5-yl)-5,7-dihydrofuro[3,4-d]pyrimidin-4-amine

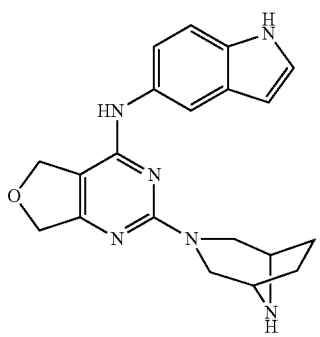 [SMILES: c1cc2cc(Nc3nc(N4CC5CCC(C4)N5)nc4c3COC4)ccc2[nH]1]

The reaction was conducted following general protocol A. The final residue was purified by reverse phase preparative HPLC to afford 2-(3,8-diazabicyclo[3.2.1]octan-3-yl)-N-(1H-indazol-5-yl)-5,7-dihydrofuro[3,4-d]pyrimidin-4-amine as an off-white solid (23%). $^1$H NMR (400 MHz, DMSO-$d_6$) δ 13.01 (s, 1H), 9.01-8.89 (m, 2H), 8.88 (m, 1H), 8.04 (s, 1H), 7.97 (s, 1H), 7.51-7.49 (m, 2H), 4.86 (m, 2H), 4.71 (m, 2H), 4.36 (d, J=13.6 Hz, 2H), 4.14 (m, 2H), 3.22 (d, J=13.2 Hz, 2H), 1.94-1.91 (m, 2H), 1.77 (d, J=7.6 Hz, 2H). MS (ES+) m/e 364.1 (M+H).

Example 40

2-(piperazin-1-yl)-N-(4-(pyridin-3-yl)phenyl)pyrimidin-4-amine

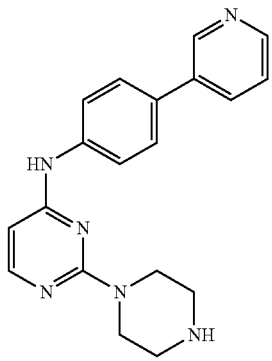 [SMILES: c1cncc(-c2ccc(Nc3ccnc(N4CCNCC4)n3)cc2)c1]

The reaction was conducted following general protocol G. The final residue was purified by reverse phase preparative HPLC to afford 2-(piperazin-1-yl)-N-(4-(pyridin-3-yl)phenyl)pyrimidin-4-amine as a white solid (87%). $^1$H NMR (400 MHz, DMSO-$d_6$) δ 11.68 (s, 1H), 9.80 (s, 2H), 9.24 (s, 1H), 8.88-8.77 (m, 2H), 8.06 (dd, J=8.0, 5.6 Hz, 1H), 8.01-7.87 (m, 5H), 6.71 (d, J=7.2 Hz, 1H), 4.11 (s, 4H), 3.28 (s, 4H). MS (ES+) m/e 330.0 (M+H).

Example 41

N-(4-(1H-1,2,3-triazol-5-yl)phenyl)-2-(piperazin-1-yl)pyrimidin-4-amine

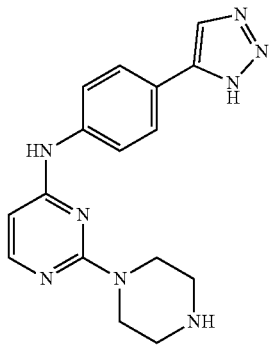 [SMILES: c1cc(Nc2ccc(-c3cnn[nH]3)cc2)nc(N2CCNCC2)n1]

To a mixture of compound tert-butyl 4-(4-((4-bromophenyl)amino)pyrimidin-2-yl)piperazine-1-carboxylate (998.96 mg, 2.30 mmol) and ethynyl(trimethyl)silane (6.78 g, 69.00 mmol) in DMF (10 mL) was added TEA (9.31 g, 92.00 mmol), CuI (43.85 mg) and Pd(PPh$_3$)$_2$Cl$_2$ (161.61 mg) in one portion at 20° C. under N$_2$. Then the reaction was heated to 100° C. and stirred for 16 hours. TLC (petroleum ether/EtOAc=1:1) showed the reaction was completed. The mixture was cooled to room temperature. Water (50 mL) was added and the mixture was extracted with EtOAc (40 mL×3). The combined organic phase was washed with brine (50 mL×3), dried over anhydrous Na$_2$SO$_4$, filtered and concentrated in vacuum. The residue was purified by silica gel chromatography (petroleum ether/EtOAc=3:1) to afford compound tert-butyl 4-(4-((4-((trimethylsilyl)ethynyl)phenyl)amino)pyrimidin-2-yl)piperazine-1-carboxylate (800.00 mg, 77%) as a yellow solid.

A mixture of compound tert-butyl 4-(4-((4-((trimethylsilyl)ethynyl)phenyl)amino)pyrimidin-2-yl)piperazine-1-carboxylate (1.70 g, 3.76 mmol) and K$_2$CO$_3$ (1.04 g, 7.52 mmol) in MeOH (5 mL) was stirred at 80° C. for 10 hours. TLC (petroleum ether/EtOAc=1:1) showed the reaction was completed. The reaction was cooled to room temperature. Water (50 mL) was added and the mixture was extracted with EtOAc (100 mL×3). The combined organic phase was washed with brine (50 mL), dried over anhydrous Na$_2$SO$_4$, filtered and concentrated in vacuum. The residue was purified by silica gel chromatography (petroleum ether/ethyl acetate=4/1 to 2/1) to afford compound tert-butyl 4-(4-((4-ethynylphenyl)amino)pyrimidin-2-yl)piperazine-1-carboxylate (1.40 g, 98%) as a yellow solid.

To a mixture of compound tert-butyl 4-(4-((4-ethynylphenyl)amino)pyrimidin-2-yl)piperazine-1- (500.00 mg, 1.32 mmol) and sodium ascorbate (261.50 mg, 1.32 mmol), CuSO$_4$ (42.14 mg, 264.00 umol) in and n-BuOH (5 mL) and H$_2$O (0.5 mL) was added NaN$_3$ (257.44 mg, 3.96 mmol) in one portion at under N$_2$. Then the mixture was stirred at 20° C. for 16 hours. LCMS showed the reaction was completed. The residue was poured into water (50 mL) and the mixture was extracted with EtOAc (40 mL×3). The combined organic phase was washed with saturated brine (20 mL), dried over anhydrous Na$_2$SO$_4$, filtered and concentrated in vacuum to give compound tert-butyl 4-(4-((4-(1H-1,2,3-triazol-5-yl)phenyl)amino)pyrimidin-2-yl)piperazine-1-carboxylate (400 mg, crude). The residue was used for the next step without purification.

A mixture of compound tert-butyl 4-(4-((4-(1H-1,2,3-triazol-5-yl)phenyl)amino)pyrimidin-2-yl)piperazine-1-carboxylate (400.00 mg, crude) in HCl/EtOAc (3 mL) was stirred at 23° C. for 3 hours. TLC (petroleum ether/EtOAc=1:1) showed the reaction was completed. The mixture was concentrated in vacuum. The residue was purified by pre-HPLC (base) to afford N-(4-(1H-1,2,3-triazol-5-yl)phenyl)-2-(piperazin-1-yl)pyrimidin-4-amine (100.0 mg, 24% yield, two steps) as white solid. $^1$H NMR: (400 MHz, DMSO-$d_6$) δ 9.36 (s, 1H), 8.23 (s, 1H), 7.93 (d, J=6.0 Hz, 1H), 7.79 (d, J=8.4 Hz, 2H), 7.72 (d, J=8.8 Hz, 2H), 6.04 (d, J=5.52 Hz, 1H), 3.63 (brs, 4H), 2.73 (brs, 4H). MS (ES+) m/e 323.1 (M+H).

Example 42

N-(4-(1H-tetrazol-5-yl)phenyl)-2-(piperazin-1-yl)pyrimidin-4-amine

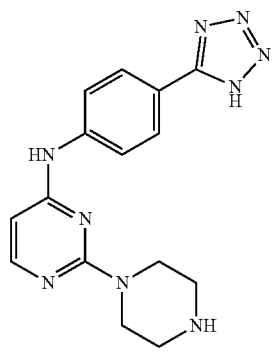 [SMILES: c1cc(Nc2ccc(-c3nnn[nH]3)cc2)nc(N2CCNCC2)n1]

To a mixture of compound tert-butyl 4-(4-((4-cyanophenyl)amino)pyrimidin-2-yl)piperazine-1-carboxylate (500.00 mg, 1.31 mmol) and NH$_4$Cl (70.30 mg, 1.31 mmol) in DMF (20 mL) was added NaN$_3$ (255.49 mg, 3.93 mmol). The reaction was stirred at 120° C. for 16 hrs. The reaction was diluted with H$_2$O (20 mL) and extracted with CH$_2$Cl$_2$ (30 mL×3). The organic layer was dried over Na$_2$SO$_4$, filtered and the filtrate was concentrated to afford compound tert-butyl 4-(4-((4-(1H-tetrazol-5-yl)phenyl)amino)pyrimidin-2-yl)piperazine-1-carboxylate (650.00 mg, crude) as brown oil. MS (ES+) m/e 424.2 (M+H).

To a solution of compound tert-butyl 4-(4-((4-(1H-tetrazol-5-yl)phenyl)amino)pyrimidin-2-yl)piperazine-1-carboxylate (650.00 mg, 1.53 mmol) in CH$_2$Cl$_2$ (10 mL) was added HCl/EtOAc (10 mL). The reaction was stirred at 25° C. for 16 hrs. The reaction was concentrated and purified by pre-HPLC (base) to afford N-(4-(1H-tetrazol-5-yl)phenyl)-2-(piperazin-1-yl)pyrimidin-4-amine (62.00 mg, 15%, two steps) as a white solid. $^1$H NMR: (400 MHz, DMSO-d$_6$) δ 7.91 (d, J=8.4 Hz, 2H), 7.88 (d, J=5.6 Hz, 1H), 7.64 (d, J=8.8 Hz, 2H), 6.04 (d, J=5.6 Hz, 1H), 3.61 (t, J=4.4 Hz, 4H), 2.71 (t, J=4.8 Hz, 4H). MS (ES+) m/e 324.1 (M+H).

Example 43

2-(3-methyl-1,4-diazepan-1-yl)-N-(4-(pyridin-4-yl)phenyl)pyrimidin-4-amine

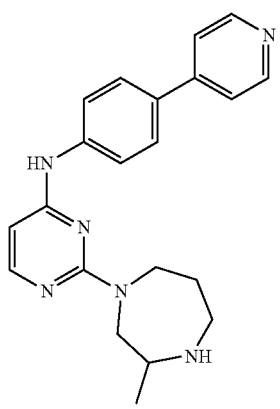 [SMILES: CC1CN(c2nccc(Nc3ccc(-c4ccncc4)cc3)n2)CCCN1]

The reaction was conducted following general protocol G. The final residue was purified by reverse phase preparative HPLC to afford 2-(3-methyl-1,4-diazepan-1-yl)-N-(4-(pyridin-4-yl)phenyl)pyrimidin-4-amine as a white solid (80%). $^1$H NMR (400 MHz, Methanol-d4) δ 8.57 (d, J=6.0 Hz, 2H), 8.32 (s, 2H), 7.99 (d, J=5.6 Hz, 1H), 7.84-7.78 (m, 4H), 7.74 (d, J=6.0 Hz, 2H), 6.20 (d, J=5.6 Hz, 1H), 4.48-4.40 (m, 2H), 3.67-3.66 (m, 1H), 3.50-3.44 (m, 3H), 3.11-3.05 (m, 1H), 2.34-2.16 (m, 2H), 1.41 (d, J=6.8 Hz, 3H). MS (ES+) m/e 361.2 (M+H).

Example 44

N-(4-(1H-pyrazol-4-phenyl)-2-(1,4-diazepan-1-yl)pyrimidin-4-amine

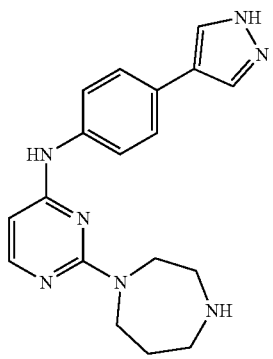 [SMILES: c1cc(Nc2ccc(-c3cn[nH]c3)cc2)nc(N2CCCNCC2)n1]

The reaction was conducted following general protocol A. Intermediated was purified via reverse phase preparatory HPLC. The final residue was purified by reverse phase preparatory HPLC to afford N-(4-(1H-pyrazol-4-yl)phenyl)-2-(1,4-diazepan-1-yl)pyrimidin-4-amine as a beige solid (28%). MS (ES+) m/e 336.1 (M+H).

Example 45

2-(5-methyl-1,4-diazepan-1-yl)-N-(4-(pyridin-4-yl)phenyl)pyrimidin-4-amine

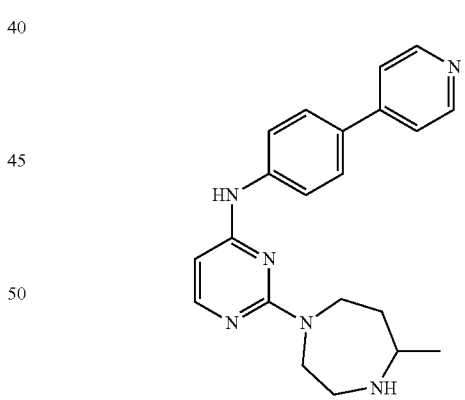

The reaction was conducted following general protocol G. The final residue was purified by reverse phase preparative HPLC to afford 2-(5-methyl-1,4-diazepan-1-yl)-N-(4-(pyridin-4-yl)phenyl)pyrimidin-4-amine as a yellow solid (47%). $^1$H NMR (400 MHz, Methanol-d4) δ 8.57 (d, J=6.0 Hz, 2H), 8.32 (s, 3H), 7.99 (d, J=5.6 Hz, 1H), 7.86-7.78 (m, 4H), 7.75 (d, J=5.6 Hz, 2H), 6.20 (d, J=5.6 Hz, 1H), 4.19-4.10 (m, 3H), 3.78-3.77 (m, 1H), 3.63-3.49 (m, 2H), 3.40-3.35 (m, 1H), 2.24-2.18 (m, 1H), 2.07-1.98 (m, 1H), 1.40 (d, J=6.8 Hz, 3H). MS (ES+) m/e 361.1 (M+H).

Example 46

2-(3,8-diazabicyclo[3.2.1]octan-8-yl)-N-(1H-indazol-5-yl)-7,8-dihydro-5H-pyrano[4,3-d]pyrimidin-4-amine

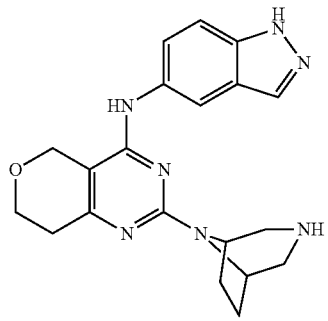 [SMILES: c1cc2[nH]ncc2cc1Nc1nc(N2C3CCC2CNC3)nc2c1COCC2]

The reaction was conducted following general protocol A. The reaction time of the first step was 16 hours and the crude material was further used without additional purification. The final residue was purified by reverse phase preparative HPLC to afford 2-(3,8-diazabicyclo[3.2.1]octan-8-yl)-N-(1H-indazol-5-yl)-7,8-dihydro-5H-pyrano[4,3-d]pyrimidin-4-amine as a yellow solid (33%). $^1$H NMR (400 MHz, DMSO-$d_6$) δ 13.11 (brs, 1H), 9.37 (s, 1H), 8.98 (s, 1H), 8.10 (s, 1H), 7.85 (s, 1H), 7.56-7.48 (m, 2H), 4.63-4.61 (m, 2H), 3.96-3.93 (m, 2H), 3.25-3.19 (m, 4H), 2.74 (m, 2H), 2.05-2.00 (m, 4H). MS (ES+) m/e 378.1 (M+H).

Example 47

N-(2-(5-isopropyl-1,4-diazepan-1-yl)-5-methoxypyrimidin-4-yl)-1H-indazol-5-amine

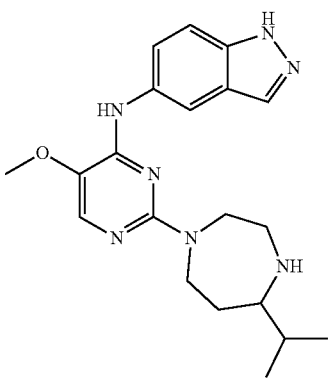 [SMILES: COc1cnc(N2CCNC(C(C)C)CC2)nc1Nc1ccc2[nH]ncc2c1]

The reaction was conducted following general protocol C. The residue was purified by reverse phase preparative HPLC to afford N-(2-(5-isopropyl-1,4-diazepan-1-yl)-5-methoxypyrimidin-4-yl)-1H-indazol-5-amine as a white solid (29%). $^1$H NMR (400 MHz, CD$_3$OD) δ 8.55 (s, 1H), 8.15 (d, J=1.2 Hz, 1H), 8.01 (d, J=0.8 Hz, 1H), 7.66 (s, 1H), 7.62 (dd, J=9.2, 2.0 Hz, 1H), 7.52 (d, J=8.8 Hz, 1H), 4.62 (m, 1H), 4.15-4.05 (m, 1H), 4.02-3.96 (m, 1H), 3.92 (s, 3H), 3.90-3.83 (m, 1H), 3.73-3.65 (m, 1H), 3.47-3.39 (m, 1H), 3.26-3.13 (m, 2H), 2.22-2.10 (m, 1H), 2.09-1.99 (m, 1H), 1.88-1.78 (m, 1H), 1.00 (t, J=6.8 Hz, 6H). MS (ES+) m/e 381.9 (M+H)$^+$.

Example 48

N-(5-methoxy-2-(3-phenyl-1,4-diazepan-1-yl)pyrimidin-4-yl)-1H-indazol-5-amine

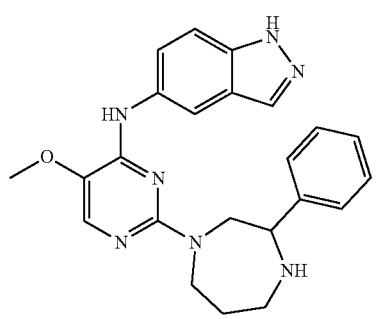 [SMILES: COc1cnc(N2CCCNC(c3ccccc3)C2)nc1Nc1ccc2[nH]ncc2c1]

The reaction was conducted following general protocol C. The residue was purified by reverse phase preparative HPLC to afford N-(5-methoxy-2-(3-phenyl-1,4-diazepan-1-yl)pyrimidin-4-yl)-1H-indazol-5-amine as a white solid (33%). $^1$H NMR (400 MHz, CD$_3$OD) δ 8.52 (s, 1H), 8.02 (s, 1H), 7.70 (s, 1H), 7.68 (s, 1H), 7.53 (dd, J=8.8, 2.0 Hz, 1H), 7.38 (t, J=7.6 Hz, 1H), 7.33 (d, J=8.8 Hz, 1H), 7.27 (t, J=7.2 Hz, 2H), 7.16-7.23 (m, 2H), 4.58-4.53 (m, 1H), 4.42-4.34 (m, 2H), 3.93 (s, 3H), 3.71-3.65 (m, 1H), 3.53-3.46 (m, 2H), 3.04-2.97 (m, 1H), 2.39-2.31 (m, 1H), 2.23-3.14 (m, 1H). MS (ES+) m/e 416.1 (M+H)$^+$.

Example 49

N-(2-(3-ethylpiperazin-1-yl)-5-methoxypyrimidin-4-yl)-1H-indazol-5-amine

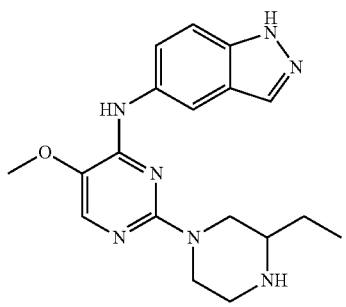 [SMILES: CCC1CN(c2ncc(OC)c(Nc3ccc4[nH]ncc4c3)n2)CCN1]

The reaction was conducted following general protocol C. The residue was purified by reverse phase preparative HPLC to afford N-(2-(3-ethylpiperazin-1-yl)-5-methoxypyrimidin-4-yl)-1H-indazol-5-amine as a white solid (33%). $^1$H NMR (400 MHz, CD$_3$OD) δ 8.40 (s, 2H), 8.09 (dd, J=2.0, 0.8 Hz, 1H), 8.01 (d, J=1.2 Hz, 1H), 7.69 (s, 1H), 7.59 (dd, J=8.8, 1.6 Hz, 1H), 7.53 (d, J=8.8 Hz, 1H), 4.74-4.70 (m, 1H), 4.62-4.53 (m, 1H), 3.94 (s, 3H), 3.43-3.37 (m, 1H), 3.26-3.18 (m, 1H), 3.17-3.09 (m, 2H), 2.97-2.90 (m, 1H), 1.78-1.59 (m, 2H), 1.04 (t, J=7.2 Hz, 3H). MS (ES+) m/e 354.1 (M+H)$^+$.

Example 50

N-(5-methoxy-2-(5-phenyl-1,4-diazepan-1-yl)pyrimidin-4-yl)-1H-indazol-5-amine

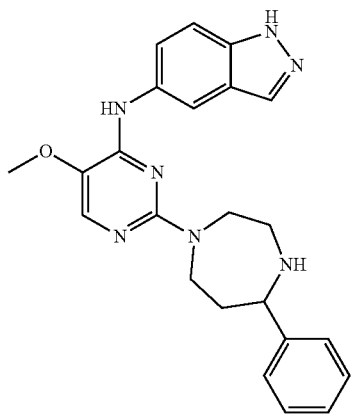 [SMILES: COc1cnc(N2CCNC(c3ccccc3)CC2)nc1Nc1ccc2[nH]ncc2c1]

The reaction was conducted following general protocol C. The residue was purified by reverse phase preparative HPLC to afford N-(5-methoxy-2-(5-phenyl-1,4-diazepan-1-yl)pyrimidin-4-yl)-1H-indazol-5-amine as a white solid (13%). $^1$H NMR (400 MHz, CD$_3$OD) δ 8.44 (s, 2H), 8.15 (d, J=1.2 Hz, 1H), 7.97 (d, J=0.8 Hz, 1H), 7.69 (s, 1H), 7.64 (dd, J=8.8, 2.0 Hz, 1H), 7.51 (d, J=8.8 Hz, 1H), 7.48-7.41 (m, 5H), 4.44-4.41 (m, 1H), 4.23-4.03 (m, 3H), 3.95 (s, 3H), 3.80-3.73 (m, 1H), 3.59-3.49 (m, 1H), 3.42-3.36 (m, 1H), 2.46-2.36 (m, 1H), 2.33-2.24 (m, 1H). MS (ES+) m/e 416.1 (M+H)$^+$.

Example 51

N-(2-(3-isopropylpiperazin-1-yl)-5-methoxypyrimidin-4-yl)-1H-indazol-5-amine

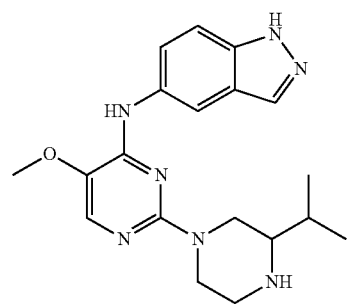 [SMILES: COc1cnc(N2CCNC(C(C)C)C2)nc1Nc1ccc2[nH]ncc2c1]

The reaction was conducted following general protocol C. The residue was purified by reverse phase preparative HPLC to afford N-(2-(3-isopropylpiperazin-1-yl)-5-methoxypyrimidin-4-yl)-1H-indazol-5-amine as a white solid (12%). $^1$H NMR (400 MHz, CD$_3$OD) δ 8.46 (s, 2H), 8.10 (d, J=1.2 Hz, 1H), 8.00 (d, J=0.8 Hz, 1H), 7.69 (s, 1H), 7.59 (dd, J=8.8, 1.6 Hz, 1H), 7.52 (d, J=8.8 Hz, 1H), 4.81 (m, 1H), 4.65-4.59 (m, 1H), 3.93 (s, 3H), 3.43-3.37 (m, 1H), 3.19-3.11 (m, 2H), 2.96-2.87 (m, 2H), 1.93-1.85 (m, 1H), 1.09-1.04 (m, 6H). MS (ES+) m/e 368.1 (M+H)$^+$.

Example 52

N-(2-(3,5-dimethylpiperazin-1-yl)-5-methoxypyrimidin-4-yl)-1H-indazol-5-amine

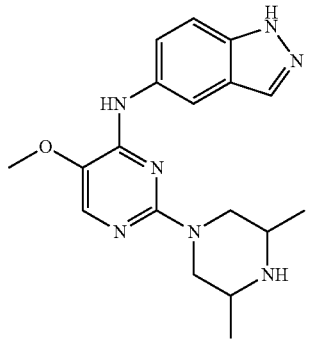

The reaction was conducted following general protocol A. The reaction time of the first step was 100 hours and the crude material was further used without additional purification. The final residue was purified by reverse phase preparative HPLC to afford N-(2-(3,5-dimethylpiperazin-1-yl)-5-methoxypyrimidin-4-yl)-1H-indazol-5-amine as a white solid (15%). $^1$H NMR (400 MHz, CD$_3$OD) δ 8.52 (s, 2H), 8.10 (d, J=1.2 Hz, 1H), 8.02 (s, 1H), 7.68 (s, 1H), 7.60 (dd, J=8.8, 1.6 Hz, 1H), 7.53 (d, J=8.8 Hz, 1H), 4.70-4.66 (m, 2H), 3.93 (s, 3H), 3.32-3.25 (m, 2H), 2.82-2.76 (m, 2H), 1.34 (d, J=6.4 Hz, 6H). MS (ES+) m/e 354.1 (M+H)$^+$.

Example 53

N-(5-methoxy-2-(5-methyl-1,4-diazepan-1-yl)pyrimidin-4-yl)-1H-indazol-5-amine

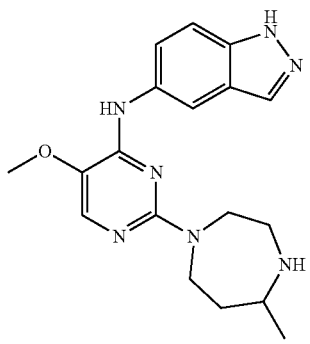 [SMILES: COc1cnc(N2CCNC(C)CC2)nc1Nc1ccc2[nH]ncc2c1]

The reaction was conducted following general protocol A. The reaction time of the first step was 52 hours and the crude material was further used without additional purification. The final residue was purified by reverse phase preparative HPLC to afford N-(5-methoxy-2-(5-methyl-1,4-diazepan-1-yl)pyrimidin-4-yl)-1H-indazol-5-amine as a white solid (7%). $^1$H NMR (400 MHz, CD$_3$OD) δ 8.45 (brs, 2H), 8.15 (d, J=1.2 Hz, 1H), 8.02 (s, 1H), 7.66 (s, 1H), 7.62 (dd, J=8.8, 1.6 Hz, 1H), 7.53 (d, J=9.2 Hz, 1H), 4.02-3.98 (m, 3H), 3.92 (s, 3H), 3.70-3.60 (m, 1H), 3.50-3.45 (m, 2H), 3.28-3.27 (m, 1H), 2.16-2.12 (m, 1H), 1.98-1.94 (m, 1H), 1.37 (d, J=6.8 Hz, 3H). MS (ES+) m/e 354.1 (M+H)$^+$.

Example 54

N-(2-(5-ethyl-1,4-diazepan-1-yl)-5-methoxypyrimidin-4-yl)-1H-indazol-5-amine

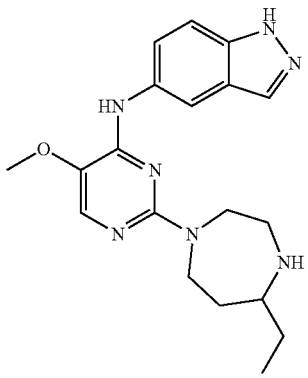 [SMILES: CCC1CCN(c2ncc(OC)c(Nc3ccc4[nH]ncc4c3)n2)CCN1]

The reaction was conducted following general protocol A. The reaction time of the first step was 80 hours and the crude material was further used without additional purification. The final residue was purified by reverse phase preparative HPLC to afford N-(2-(5-ethyl-1,4-diazepan-1-yl)-5-methoxypyrimidin-4-yl)-1H-indazol-5-amine as a yellow solid (8%). $^1$H NMR (400 MHz, CD$_3$OD) δ 8.41 (s, 2H), 8.13 (d, J=1.2 Hz, 1H), 8.00 (s, 1H), 7.64 (s, 1H), 7.60 (dd, J=9.2, 2.0 Hz, 1H), 7.51 (d, J=9.2 Hz, 1H), 4.08-3.92 (m, 3H), 3.90 (s, 3H), 3.69-3.62 (m, 1H), 3.48-3.43 (m, 1H), 3.28-3.22 (m, 2H), 2.20 (m, 1H), 1.94-1.84 (m, 1H), 1.80-1.55 (m, 2H), 1.01 (t, J=7.6 Hz, 3H). MS (ES+) m/e 368.1 (M+H)$^+$.

Example 55

N-(5-methoxy-2-(3-methyl-1,4-diazepan-1-yl)pyrimidin-4-yl)-1H-indazol-5-amine

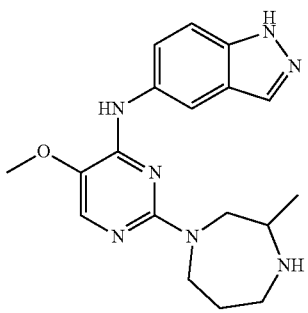

The reaction was conducted following general protocol A. The reaction time of the first step was 96 hours and the crude material was further used without additional purification. The final residue was purified by reverse phase preparative HPLC to afford N-(5-methoxy-2-(3-methyl-1,4-diazepan-1-yl)pyrimidin-4-yl)-1H-indazol-5-amine as a yellow solid (6%). $^1$H NMR (400 MHz, CD$_3$OD) δ 8.10 (s, 1H), 7.97 (s, 1H), 7.64 (d, J=8.8 Hz, 1H), 7.54 (d, J=8.8, 1.6 Hz, 1H), 7.46 (s, 1H), 4.14-4.11 (m, 1H), 4.01 (s, 3H), 3.82 (m, 1H), 3.63-3.43 (m, 4H), 3.23-3.13 (m, 1H), 2.38-2.18 (m, 2H), 1.07 (d, J=4.0 Hz, 3H). MS (ES+) m/e 354.1 (M+H)$^+$.

Example 56

N-(5-methoxy-2-(6-methyl-1,4-diazepan-1-yl)pyrimidin-4-yl)-1H-indazol-5-amine

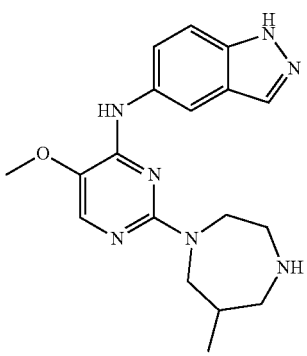 [SMILES: COc1cnc(N2CCNCC(C)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-methoxy-2-(6-methyl-1,4-diazepan-1-yl)pyrimidin-4-yl)-1H-indazol-5-amine as a yellow solid (13%). $^1$H NMR (400 MHz, CD$_3$OD) δ 8.13 (s, 1H), 8.00 (d, J=1.2 Hz, 1H), 7.66-7.58 (m, 2H), 7.45 (s, 1H), 4.07-3.97 (m, 5H), 3.95-3.84 (m, 1H), 3.59-3.46 (m, 1H), 3.37 (s, 1H), 3.31-3.19 (m, 2H), 3.10-3.04 (m, 1H), 2.37 (m, 1H), 1.01 (d, J=4.8 Hz, 3H). MS (ES+) m/e 354.2 (M+H)$^+$.

Example 57

N-(2-(5-methyl-1,4-diazepan-1-yl)pyrimidin-4-yl)-1H-indazol-5-amine

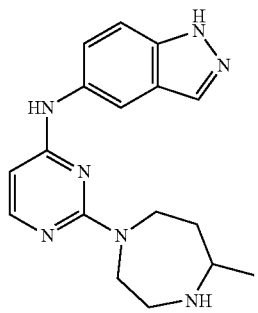 [SMILES: CC1CCN(c2nccc(Nc3ccc4[nH]ncc4c3)n2)CCN1]

The reaction was conducted following general protocol A. The reaction time of the first step was 16 hours and the crude material was further used without additional purification. The final residue was purified by reverse phase preparative HPLC to afford N-(2-(5-methyl-1,4-diazepan-1-yl)pyrimidin-4-yl)-1H-indazol-5-amine as a white solid (16%). $^1$H NMR (400 MHz, DMSO-d$_6$) δ 12.71 (s, 1H), 8.79 (s, 1H), 8.07 (s, 1H), 7.93 (s, 1H), 7.87 (d, J=5.6 Hz, 1H), 7.49-7.44 (m, 2H), 5.96 (d, J=5.6 Hz, 1H), 3.94-3.89 (m, 2H), 3.69-3.50 (m, 2H), 3.10-3.07 (m, 1H), 2.82-2.75 (m, 1H), 2.73-

2.63 (m, 1H), 1.97-1.87 (m, 1H), 1.47-1.35 (m, 1H), 1.03 (d, J=6.4 Hz, 3H). MS (ES+) m/e 324.1 (M+H)+.

Example 58

N-(2-(3-ethylpiperazin-1-yl)pyrimidin-4-yl)-1H-indazol-5-amine

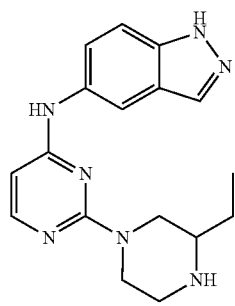 [SMILES: CCC1CN(c2nccc(Nc3ccc4[nH]ncc4c3)n2)CCN1]

The reaction was conducted following general protocol A. The reaction time of the first step was 16 hours and the crude material was further used without additional purification. The final residue was purified by reverse phase preparative HPLC to afford N-(2-(3-ethylpiperazin-1-yl)pyrimidin-4-yl)-1H-indazol-5-amine as a yellow gum (11%). $^1$H NMR (400 MHz, DMSO-$d_6$) δ 9.29 (s, 1H), 8.30 (s, 2H), 8.08 (s, 1H), 7.96 (s, 1H), 7.92 (d, J=5.6 Hz, 1H), 7.50-7.43 (m, 2H), 6.06 (d, J=5.6 Hz, 1H), 4.67-4.64 (m, 1H), 4.54-4.51 (m, 1H), 3.16-3.13 (m, 1H), 3.05-3.02 (m, 1H), 2.84-2.74 (m, 3H), 1.59-1.48 (m, 2H), 0.98 (t, J=7.6 Hz, 3H). MS (ES+) m/e 324.1 (M+H)+.

Example 59

N-(2-(3-isopropylpiperazin-1-yl)pyrimidin-4-yl)-1H-indazol-5-amine

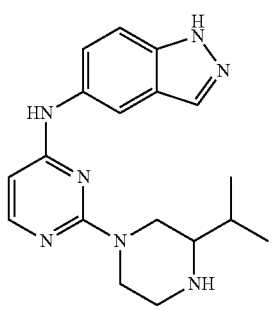 [SMILES: CC(C)C1CN(c2nccc(Nc3ccc4[nH]ncc4c3)n2)CCN1]

The reaction was conducted following general protocol A. The reaction time of the first step was 16 hours and the crude material was further used without additional purification. The final residue was purified by reverse phase preparative HPLC to afford N-(2-(3-isopropylpiperazin-1-yl)pyrimidin-4-yl)-1H-indazol-5-amine as a white solid (12%). $^1$H NMR (400 MHz, DMSO-$d_6$) δ 12.98 (brs, 1H), 9.23 (s, 1H), 8.29 (s, 2H), 8.12 (s, 1H), 7.92-7.89 (m, 2H), 7.49-7.43 (m, 2H), 6.02 (d, J=5.6 Hz, 1H), 4.67 (d, J=12.0 Hz, 1H), 4.50 (d, J=12.0 Hz, 1H), 3.07-3.04 (m, 1H), 2.87 (m, 1H), 2.71-2.68 (m, 1H), 2.65-2.59 (m, 1H), 2.43-2.41 (m, 1H), 1.69-1.66 (m, 1H), 0.99 (d, J=6.8 Hz, 6H). MS (ES+) m/e 338.1 (M+H)+.

Example 60

N-(2-(5-ethyl-1,4-diazepan-1-yl)pyrimidin-4-yl)-1H-indazol-5-amine

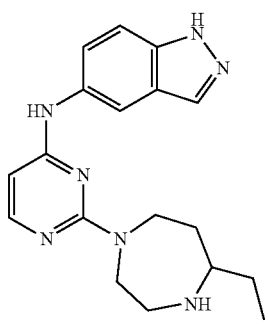 [SMILES: CCC1CCN(c2nccc(Nc3ccc4[nH]ncc4c3)n2)CCN1]

The reaction was conducted following general protocol A. The reaction time of the first step was 32 hours and the crude material was further used without additional purification. The final residue was purified by reverse phase preparative HPLC to afford N-(2-(5-ethyl-1,4-diazepan-1-yl)pyrimidin-4-yl)-1H-indazol-5-amine as a light brown solid (34%). $^1$H NMR (400 MHz, CD$_3$OD) δ 8.36 (s, 2H), 8.06 (s, 1H), 8.02 (s, 1H), 7.91 (d, J=6.0 Hz, 1H), 7.56-7.47 (m, 2H), 6.14 (d, J=6.0 Hz, 1H), 4.16-3.99 (m, 3H), 3.77-3.69 (m, 1H), 3.57-3.49 (m, 1H), 3.32-3.27 (m, 2H), 2.27-2.23 (m, 1H), 1.99-1.93 (m, 1H), 1.83-1.64 (m, 2H), 1.05 (t, J=7.6 Hz, 3H). MS (ES+) m/e 337.9 (M+H)+.

Example 61

N-(2-(5-isopropyl-1,4-diazepan-1-yl)pyrimidin-4-yl)-1H-indazol-5-amine

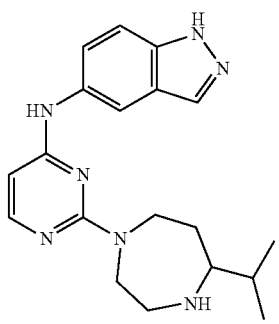 [SMILES: CC(C)C1CCN(c2nccc(Nc3ccc4[nH]ncc4c3)n2)CCN1]

The reaction was conducted following general protocol C. The residue was purified by reverse phase preparative HPLC to afford N-(2-(5-isopropyl-1,4-diazepan-1-yl)pyrimidin-4-yl)-1H-indazol-5-amine as a yellow solid (18%). $^1$H NMR (400 MHz, CD$_3$OD) δ 8.41 (s, 2H), 8.03 (s, 1H), 8.00 (s, 1H), 7.89 (d, J=6.0 Hz, 1H), 7.53-7.45 (m, 2H), 6.11 (d, J=6.0 Hz, 1H), 4.20-4.03 (m, 2H), 4.0-3.93 (m, 1H), 3.76-3.69 (m, 1H), 3.53-3.45 (m, 1H), 3.29-3.21 (m, 2H), 2.22-

1.99 (m, 2H), 1.94-1.83 (m, 1H), 1.01 (dd, J=8.8, 7.2 Hz, 6H). MS (ES+) m/e 352.1 (M+H)+.

Example 62

N-(2-(3-ethyl-1,4-diazepan-1-yl)pyrimidin-4-yl)-1H-indazol-5-amine

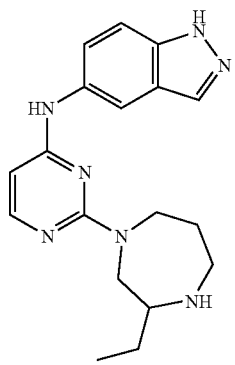 [SMILES: CCC1CN(c2nccc(Nc3ccc4[nH]ncc4c3)n2)CCCN1]

The reaction was conducted following general protocol A. The reaction time of the first step was 15 hours and the crude material was further used without additional purification. The final residue was purified by reverse phase preparative HPLC to afford N-(2-(3-ethyl-1,4-diazepan-1-yl)pyrimidin-4-yl)-1H-indazol-5-amine as a yellow solid (15%). $^1$H NMR (400 MHz, CD$_3$OD) δ 8.43 (s 2H), 7.98 (s, 2H), 7.89 (d, J=6.0 Hz, 1H), 7.51 (d, J=8.8 Hz, 1H), 7.45 (d, J=8.8, 1.6 Hz, 1H), 6.10 (d, J=6.0 Hz, 1H), 4.44 (dd, J=14.4, 2.4 Hz, 1H), 4.35-4.25 (m, 1H), 3.48-3.38 (m, 4H), 3.09-2.99 (m, 1H), 2.22-2.11 (m, 2H), 1.67-1.63 (m, 2H), 0.93 (m, 3H). MS (ES+) m/e 338.1 (M+H)+.

Example 63

N-(2-(5-phenyl-1,4-diazepan-1-yl)pyrimidin-4-yl)-1H-indazol-5-amine

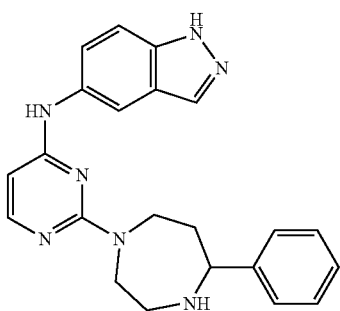 [SMILES: c1ccc(C2CCN(c3nccc(Nc4ccc5[nH]ncc5c4)n3)CCN2)cc1]

The reaction was conducted following general protocol C. The residue was purified by reverse phase preparative HPLC to afford N-(2-(5-phenyl-1,4-diazepan-1-yl)pyrimidin-4-yl)-1H-indazol-5-amine as a yellow solid (10%). $^1$H NMR (400 MHz, CD$_3$OD) δ 8.36 (s, 2H), 8.05 (s, 1H), 7.97 (s, 1H), 7.92 (d, J=6.0 Hz, 1H), 7.52-7.41 (m, 7H), 6.15 (d, J=6.0 Hz, 1H), 4.46 (dd, J=11.2, 2.0 Hz, 1H), 4.31-4.22 (m, 1H), 4.17-4.14 (m, 2H), 3.84-3.77 (m, 1H), 3.62-3.56 (m, 1H), 3.41-3.38 (m, 1H), 2.49-2.39 (m, 1H), 2.34-2.24 (m, 1H). MS (ES+) m/e 386.1 (M+H)+.

Example 64

N-(2-(3-phenyl-1,4-diazepan-1-yl)pyrimidin-4-yl)-1H-indazol-5-amine

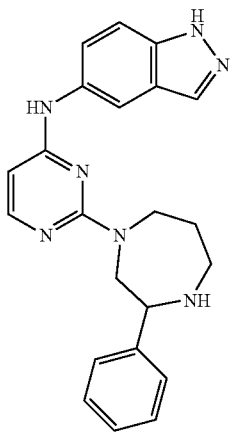 [SMILES: c1ccc(C2CN(c3nccc(Nc4ccc5[nH]ncc5c4)n3)CCCN2)cc1]

The reaction was conducted following general protocol C. The residue was purified by reverse phase preparative HPLC to afford N-(2-(3-phenyl-1,4-diazepan-1-yl)pyrimidin-4-yl)-1H-indazol-5-amine as a yellow solid (39%). $^1$H NMR (400 MHz, CD$_3$OD) δ 8.33 (m, 2H), 7.92 (d, J=6.0 Hz, 2H), 7.64 (s, 1H), 7.45-7.32 (m, 7H), 6.15 (d, J=6.0 Hz, 1H), 4.65 (d, J=14.4 Hz, 1H), 4.55-4.39 (m, 2H), 3.85-3.79 (m, 1H), 3.56-3.51 (m, 2H), 3.16-3.10 (m, 1H), 2.44-2.33 (m, 1H), 2.31-2.18 (m, 1H). MS (ES+) m/e 386.1 (M+H)+.

Example 65

N-(2-(3-isopropyl-1,4-diazepan-1-yl)pyrimidin-4-yl)-1H-indazol-5-amine

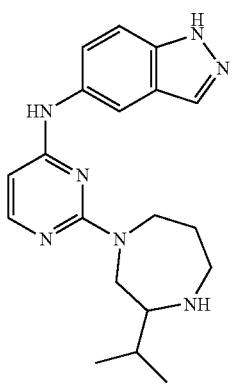 [SMILES: CC(C)C1CN(c2nccc(Nc3ccc4[nH]ncc4c3)n2)CCCN1]

The reaction was conducted following general protocol C. The residue was purified by reverse phase preparative HPLC to afford N-(2-(3-isopropyl-1,4-diazepan-1-yl)pyrimidin-4-yl)-1H-indazol-5-amine as a yellow solid (11%). $^1$H NMR (400 MHz, DMSO-d$_6$, T=80° C.) δ 10.75 (s, 1H), 9.24 (s, 2H), 8.04 (d, J=0.8 Hz, 1H), 7.97 (s, 1H), 7.84 (d, J=7.2 Hz, 1H), 7.57 (d, J=9.2 Hz, 1H), 7.49 (d, J=8.8 Hz, 1H), 6.50 (d, J=6.4 Hz, 1H), 4.25-4.18 (m, 1H), 4.02-3.95 (m, 1H), 3.78-3.64 (m, 1H), 3.42-3.41 (m, 1H), 3.34-3.31 (m, 2H), 3.10 (m, 1H), 2.18 (d, J=4.8 Hz, 2H), 2.05 (m, 1H), 0.99-0.75 (m, 6H). MS (ES+) m/e 351.8 (M+H)$^+$.

Example 66

N-(2-(4,7-diazaspiro[2.5]octan-7-yl)pyrimidin-4-yl)-1H-indazol-5-amine

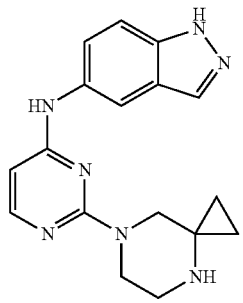 [SMILES: c1cc(Nc2ccc3[nH]ncc3c2)nc(N2CCNC3(CC3)C2)n1]

The reaction was conducted following general protocol A. The reaction time of the first step was 16 hours and the crude material was further used without additional purification. The final residue was purified by reverse phase preparative HPLC to afford N-(2-(4,7-diazaspiro[2.5]octan-7-yl)pyrimidin-4-yl)-1H-indazol-5-amine as a white solid (47%). $^1$H NMR (400 MHz, CD$_3$OD) δ 8.10 (d, J=0.8 Hz, 1H), 7.94 (s, 1H), 7.85 (d, J=7.2 Hz, 1H), 7.63 (d, J=8.8 Hz, 1H), 7.48 (d, J=9.2 Hz, 1H), 6.40 (d, J=7.2 Hz, 1H), 4.10 (t, J=5.2 Hz, 2H), 3.93 (s, 2H), 3.51 (t, J=5.2 Hz, 2H), 1.17 (t, J=7.2 Hz, 2H), 1.03 (t, J=6.4 Hz, 2H). MS (ES+) m/e 322.1 (M+H)$^+$.

Example 67

N-(2-(2,5-diazabicyclo[2.2.2]octan-2-yl)pyrimidin-4-yl)-1H-indazol-5-amine

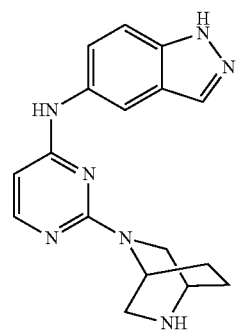 [SMILES: c1cc(Nc2ccc3[nH]ncc3c2)nc(N2CC3CCC2CN3)n1]

The reaction was conducted following general protocol A. The reaction time of the first step was 16 hours and the crude material was further used without additional purification. The final residue was purified by reverse phase preparative HPLC to afford N-(2-(2,5-diazabicyclo[2.2.2]octan-2-yl)pyrimidin-4-yl)-1H-indazol-5-amine as a yellow solid (18%). $^1$H NMR (400 MHz, CD$_3$OD) δ 8.10 (s, 1H), 8.02 (s, 1H), 7.83 (d, J=7.2 Hz, 1H), 7.63-7.48 (m, 2H), 6.40 (d, J=7.2 Hz, 1H), 4.84-4.77 (m, 1H), 4.04-3.97 (m, 2H), 3.87-3.84 (m, 1H), 3.66-3.48 (m, 2H), 2.27-2.18 (m, 2H), 2.12-2.02 (m, 2H). MS (ES+) m/e 322.1 (M+H)$^+$.

Example 68

N-(2-(2,5-dimethylpiperazin-1-yl)pyrimidin-4-yl)-1H-indazol-5-amine

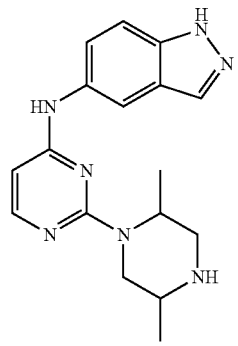 [SMILES: CC1CN(c2nccc(Nc3ccc4[nH]ncc4c3)n2)C(C)CN1]

The reaction was conducted following general protocol A. The reaction time of the first step was 16 hours and the crude material was further used without additional purification. The final residue was purified by reverse phase preparative HPLC to afford N-(2-(2,5-dimethylpiperazin-1-yl)pyrimidin-4-yl)-1H-indazol-5-amine as a white solid (18%). $^1$H NMR (400 MHz, CD$_3$OD) δ 8.10 (d, J=0.8 Hz, 1H), 7.98 (s, 1H), 7.85 (d, J=7.2 Hz, 1H), 7.63 (d, J=8.8 Hz, 1H), 7.50 (d, J=7.6 Hz, 1H), 6.41 (d, J=7.2 Hz, 1H), 4.76 (m, 1H), 4.24 (d, J=14.4 Hz, 1H), 3.89 (m, 1H), 3.73-6.69 (m, 1H), 3.64-3.59 (m, 1H), 3.28-3.24 (m, 1H), 1.46 (d, J=6.8 Hz, 3H), 1.42 (d, J=6.8 Hz, 3H). MS (ES+) m/e 324.0 (M+H)$^+$.

Example 69

N-(2-(2-propylpiperazin-1-yl)pyrimidin-4-yl)-1H-indazol-5-amine

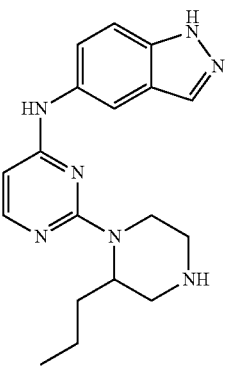 [SMILES: CCCC1CNCCN1c1nccc(Nc2ccc3[nH]ncc3c2)n1]

The reaction was conducted following general protocol A. The reaction time of the first step was 48 hours and the crude material was further used without additional purification. The final residue was purified by reverse phase preparative HPLC to afford N-(2-(2-propylpiperazin-1-yl)pyrimidin-4-yl)-1H-indazol-5-amine as a white solid (15%). $^1$H NMR (400 MHz, CD$_3$OD) δ 8.09 (s, 1H), 7.96 (s, 1H), 7.85 (d, J=7.2 Hz, 1H), 7.62 (d, J=8.8 Hz, 1H), 7.49 (d, J=8.8 Hz, 1H), 6.39 (d, J=7.2 Hz, 1H), 4.80 (m, 1H), 4.44-4.40 (m, 1H), 3.58-3.46 (m, 3H), 3.35 (m, 1H), 3.27-3.23 (m, 1H), 1.82 (q, J=8.0 Hz, 2H), 1.46-1.24 (m, 2H), 0.93 (t, J=7.2 Hz, 3H). MS (ES+) m/e 338.1 (M+H)+.

Example 70

N-(2-(2,7-diazaspiro[3.5]nonan-7-yl)pyrimidin-4-yl)-1H-indazol-5-amine

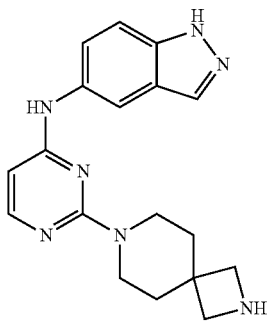 [SMILES: c1cc(Nc2ccc3[nH]ncc3c2)nc(N2CCC3(CC2)CNC3)n1]

The reaction was conducted following general protocol A. The reaction time of the first step was 16 hours and the crude material was further used without additional purification. The final residue was purified by reverse phase preparative HPLC to afford N-(2-(2,7-diazaspiro[3.5]nonan-7-yl)pyrimidin-4-yl)-1H-indazol-5-amine as a off-white solid (33%). $^1$H NMR (400 MHz, DMSO-$d_6$) δ 13.19 (brs, 1H), 10.56 (brs, 1H), 8.94 (brs, 2H), 8.08 (s, 1H), 8.01 (s, 1H), 7.88 (d, J=5.8 Hz, 1H), 7.59 (d, J=8.8 Hz, 1H), 7.48 (d, J=8.8 Hz, 1H), 6.30 (d, J=6.0 Hz, 1H), 3.81-3.78 (m, 4H), 3.67 (m, 4H), 1.88-1.85 (m, 4H). MS (ES+) m/e 336.1 (M+H)+.

Example 71

N-(2-(2,6-diazaspiro[3.4]octan-6-yl)pyrimidin-4-yl)-1H-indazol-5-amine

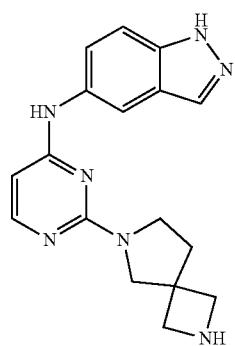 [SMILES: c1cc(Nc2ccc3[nH]ncc3c2)nc(N2CCC3(CNC3)C2)n1]

The reaction was conducted following general protocol A. The reaction time of the first step was 16 hours and the crude material was further used without additional purification. The final residue was purified by reverse phase preparative HPLC to afford N-(2-(2,6-diazaspiro[3.4]octan-6-yl)pyrimidin-4-yl)-1H-indazol-5-amine as a light brown solid (21%). $^1$H NMR (400 MHz, CD$_3$OD) δ 8.21 (s, 1H), 8.11 (s, 1H), 7.76 (d, J=7.2 Hz, 1H), 7.61 (m, 2H), 6.36 (d, J=6.8 Hz, 1H), 4.25-4.23 (m, 2H), 4.13-4.10 (m, 2H), 3.94-3.68 (m, 4H), 2.46 (m, 2H). MS (ES+) m/e 322.1 (M+H)+.

Example 72

N-(2-(1-oxa-4,9-diazaspiro[5.5]undecan-9-yl)pyrimidin-4-yl)-1H-indazol-5-amine

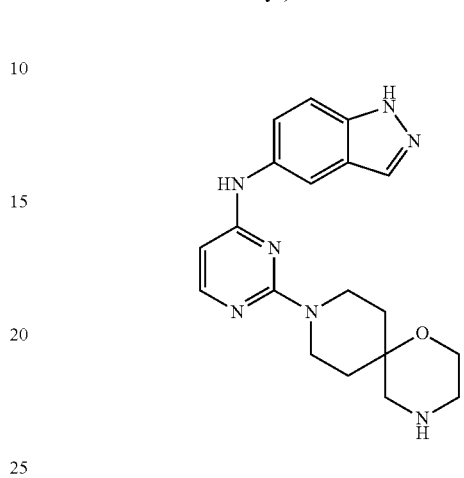

The reaction was conducted following general protocol A. The reaction time of the first step was 16 hours and the crude material was further used without additional purification. The final residue was purified by reverse phase preparative HPLC to afford N-(2-(1-oxa-4,9-diazaspiro[5.5]undecan-9-yl)pyrimidin-4-yl)-1H-indazol-5-amine as off-white solid (15%). $^1$H NMR (400 MHz, DMSO-$d_6$) δ 13.17 (brs, 1H), 10.54 (brs, 1H), 9.01 (s, 2H), 8.09 (s, 1H), 8.05 (s, 1H), 7.89 (d, J=6.0 Hz, 1H), 7.58 (d, J=8.8 Hz, 1H), 7.48 (m, 1H), 6.28 (m, 1H), 4.09 (m, 2H), 4.04-4.02 (m, 2H), 3.33 (m, 2H), 3.09-3.04 (m, 4H), 2.03-2.00 (m, 2H), 1.69-1.64 (m, 2H). MS (ES+) m/e 366.1 (M+H)+.

Example 73

N-(2-(2,7-diazaspiro[4.5]decan-2-yl)pyrimidin-4-yl)-1H-indazol-5-amine

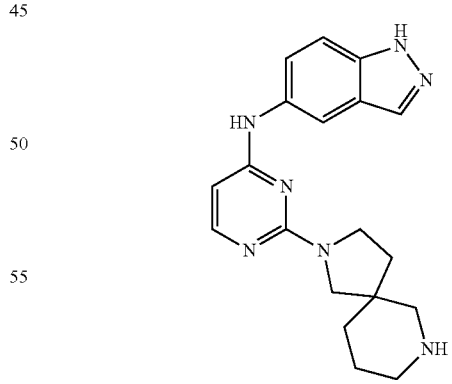

The reaction was conducted following general protocol A. The reaction time of the first step was 16 hours and the crude material was further used without additional purification. The final residue was purified by reverse phase preparative HPLC to afford N-(2-(2,7-diazaspiro[4.5]decan-2-yl)pyrimidin-4-yl)-1H-indazol-5-amine as a light brown solid (17%). $^1$H NMR (400 MHz, DMSO-$d_6$) δ 13.18 (brs, 1H), 10.72 (brs, 1H), 8.87-8.80 (m, 2H), 8.31 (m, 1H), 8.10 (s, 1H), 7.89 (d, J=7.2 Hz, 1H), 7.58 (s, 1H), 6.36 (m, 1H), 3.76 (m, 1H), 3.61 (m, 3H), 3.10-3.07 (m, 4H), 2.14 (m, 1H), 1.95 (m, 1H), 1.76-1.69 (m, 4H). MS (ES+) m/e 350.1 (M+H)$^+$.

Example 74

N-(2-(2,7-diazaspiro[4.5]decan-7-yl)pyrimidin-4-yl)-1H-indazol-5-amine

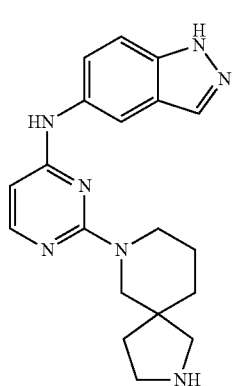 [SMILES: c1cc(Nc2ccc3[nH]ncc3c2)nc(N2CCCC3(CCNC3)C2)n1]

The reaction was conducted following general protocol A. The reaction time of the first step was 16 hours and the crude material was further used without additional purification. The final residue was purified by reverse phase preparative HPLC to afford N-(2-(2,7-diazaspiro[4.5]decan-7-yl)pyrimidin-4-yl)-1H-indazol-5-amine as a light brown solid (34%). $^1$H NMR (400 MHz, D$_2$O) δ 8.07 (s, 1H), 7.80 (brs, 1H), 7.57 (d, J=8.8 Hz, 1H), 7.50 (d, J=8.8 Hz, 1H), 7.42-7.40 (m, 1H), 6.16 (d, J=7.2 Hz, 1H), 3.62-3.54 (m, 2H), 3.34-3.31 (m, 2H), 3.07 (m, 1H), 2.94-2.88 (m, 2H), 2.67 (m, 1H), 1.75-1.60 (m, 6H). MS (ES+) m/e 350.1 (M+H)$^+$.

Example 75

N-(2-(2,6-diazaspiro[3.4]octan-2-yl)pyrimidin-4-yl)-1H-indazol-5-amine

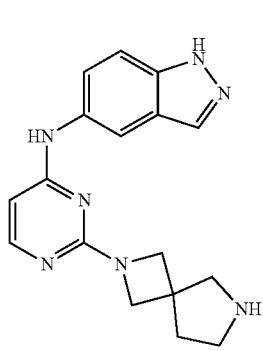 [SMILES: c1cc(Nc2ccc3[nH]ncc3c2)nc(N2CC3(CCNC3)C2)n1]

The reaction was conducted following general protocol A. The reaction time of the first step was 16 hours and the crude material was further used without additional purification. The final residue was purified by reverse phase preparative HPLC to afford N-(2-(2,6-diazaspiro[3.4]octan-2-yl)pyrimidin-4-yl)-1H-indazol-5-amine as a light brown solid (18%). $^1$H NMR (400 MHz, CD$_3$OD) δ 8.22 (m, 1H), 8.07 (s, 1H), 7.76 (d, J=7.2 Hz, 1H), 7.60-7.55 (m, 2H), 6.35 (d, J=6.4 Hz, 1H), 4.37 (d, J=9.6 Hz, 2H), 4.31 (d, J=9.6 Hz, 2H), 3.60 (s, 2H), 3.42 (t, J=7.6 Hz, 2H), 2.42 (t, J=7.6 Hz, 2H). MS (ES+) m/e 322.1 (M+H)$^+$.

Example 76

N-(2-(2,7-diazaspiro[3.5]nonan-2-yl)pyrimidin-4-yl)-1H-indazol-5-amine

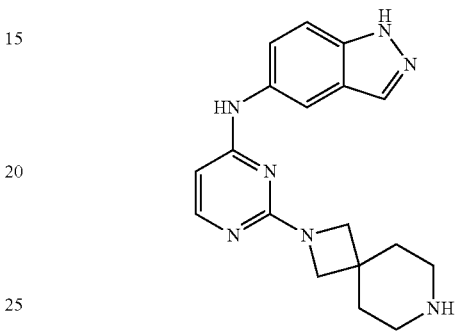

The reaction was conducted following general protocol A. The reaction time of the first step was 16 hours and the crude material was further used without additional purification. The final residue was purified by reverse phase preparative HPLC to afford N-(2-(2,7-diazaspiro[3.5]nonan-2-yl)pyrimidin-4-yl)-1H-indazol-5-amine as off-white solid (41%). $^1$H NMR (400 MHz, DMSO-d$_6$) δ 13.17 (brs, 1H), 10.66 (brs, 1H), 8.63 (s, 2H), 8.19 (brs, 1H), 8.11 (s, 1H), 7.88 (d, J=6.8 Hz, 1H), 7.59-7.54 (m, 2H), 6.33 (m, 1H), 3.99 (s, 4H), 3.09 (m, 4H), 1.97 (m, 4H). MS (ES+) m/e 336.1 (M+H)$^+$.

Example 77

N-(2-(2,6-diazaspiro[3.3]heptan-2-yl)pyrimidin-4-yl)-1H-indazol-5-amine

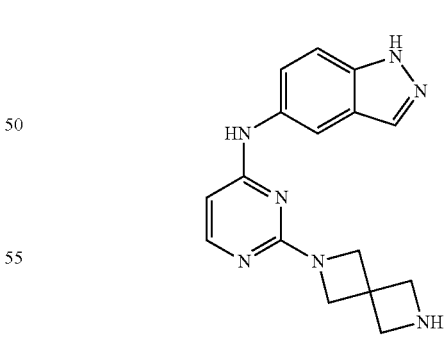

The reaction was conducted following general protocol A. The reaction time of the first step was 16 hours and the crude material was further used without additional purification. The final residue was purified by reverse phase preparative HPLC to afford N-(2-(2,7-diazaspiro[3.5]nonan-2-yl)pyrimidin-4-yl)-1H-indazol-5-amine as off-white solid (45%). $^1$H NMR (400 MHz, DMSO-d$_6$) δ 13.22 (brs, 1H), 10.73 (s, 1H), 8.76 (s, 2H), 8.20 (brs, 1H), 8.07 (s, 1H), 7.89 (d, J=7.2

Hz, 1H), 7.59-7.52 (m, 2H), 6.34 (m, 1H), 4.38 (s, 4H), 4.21-4.18 (m, 4H). MS (ES+) m/e 308.1 (M+H)⁺.

Example 78

N-(2-(3,6-diazabicyclo[3.2.1]octan-3-yl)pyrimidin-4-yl)-1H-indazol-5-amine

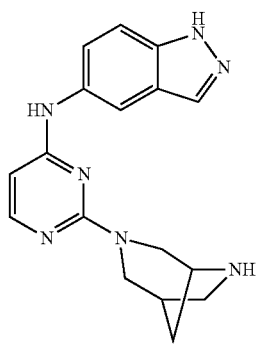 [SMILES: c1cc(Nc2ccc3[nH]ncc3c2)nc(N2CC3CNC(C3)C2)n1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.2.1]octan-3-yl)pyrimidin-4-yl)-1H-indazol-5-amine as a light brown solid (12%). ¹H NMR (400 MHz, CD₃OD) δ 8.12 (s, 1H), 8.07 (s, 1H), 7.82 (d, J=7.2 Hz, 1H), 7.64-7.57 (m, 2H), 6.46 (m, 1H), 4.42-4.39 (m, 1H), 4.30 (m, 1H), 4.14 (m, 1H), 3.46-3.37 (m, 4H), 2.94 (m, 1H), 2.20-2.12 (m, 2H). MS (ES+) m/e 322.1 (M+H)⁺.

Example 79

N-(2-(3,7-diazabicyclo[3.3.1]nonan-3-yl)pyrimidin-4-yl)-1H-indazol-5-amine

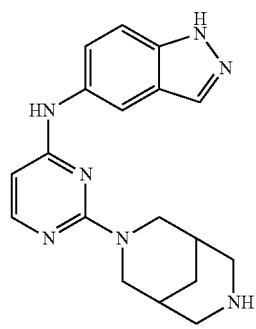 [SMILES: c1cc(Nc2ccc3[nH]ncc3c2)nc(N2CC3CNCC(C3)C2)n1]

The reaction was conducted following general protocol A. The reaction time of the first step was 16 hours and the crude material was further used without additional purification. The final residue was purified by reverse phase preparative HPLC to afford N-(2-(3,7-diazabicyclo[3.3.1]nonan-3-yl)pyrimidin-4-yl)-1H-indazol-5-amine as a light brown solid (19%). ¹H NMR (400 MHz, CD₃OD) δ 8.11 (s, 1H), 8.08 (s, 1H), 7.82 (d, J=7.2 Hz, 1H), 7.64-7.62 (m, 2H), 6.43 (m, 1H), 4.40-4.37 (m, 2H), 3.54-3.45 (m, 4H), 3.37-3.34 (m, 2H), 2.43 (m, 2H), 2.13-2.02 (m, 2H). MS (ES+) m/e 336.1 (M+H)⁺.

Example 80

N-(2-(octahydro-5H-pyrrolo[3,2-c]pyridin-5-yl)pyrimidin-4-yl)-1H-indazol-5-amine

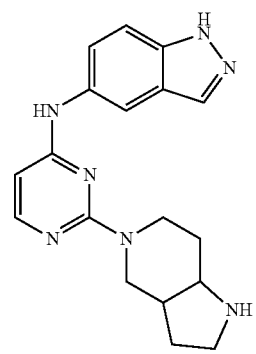 [SMILES: c1cc(Nc2ccc3[nH]ncc3c2)nc(N2CCC3NCCC3C2)n1]

The reaction was conducted following general protocol A. The reaction time of the first step was 16 hours and the crude material was further used without additional purification. The final residue was purified by reverse phase preparative HPLC to afford N-(2-(octahydro-5H-pyrrolo[3,2-c]pyridin-5-yl)pyrimidin-4-yl)-1H-indazol-5-amine as a light brown solid (18%). ¹H NMR (400 MHz, CD₃OD) δ 8.10 (s, 1H), 8.05 (s, 1H), 7.79 (d, J=7.2 Hz, 1H), 7.64-7.53 (m, 2H), 6.37 (d, J=6.8 Hz, 1H), 4.06-3.90 (m, 2H), 3.92-3.90 (m, 2H), 3.54-3.45 (m, 2H), 3.38-3.35 (m, 1H), 2.77-2.70 (m, 1H), 2.27-2.21 (m, 2H), 2.05-1.84 (m, 2H). MS (ES+) m/e 336.1 (M+H)⁺.

Example 81

N-(2-((1S,5 S)-3,6-diazabicyclo[3.2.0]heptan-3-yl)pyrimidin-4-yl)-1H-indazol-5-amine

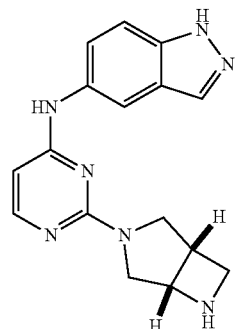

The reaction was conducted following general protocol A. The reaction time of the first step was 16 hours and the crude material was further used without additional purification. The final residue was purified by reverse phase preparative HPLC to afford N-(2-((1S,5S)-3,6-diazabicyclo[3.2.0]heptan-3-yl)pyrimidin-4-yl)-1H-indazol-5-amine as a light brown solid (11%). ¹H NMR (400 MHz, CD₃OD) δ 8.18 (s, 1H), 8.11 (s, 1H), 7.85 (d, J=7.2 Hz, 1H), 7.63-7.58 (m, 2H), 6.46 (d, J=6.8 Hz, 1H), 5.13-5.10 (m, 1H), 4.56-4.52 (m, 1H), 4.32-4.27 (m, 1H), 4.17 (m, 1H), 3.82-3.73 (m, 2H), 3.64-3.61 (m, 2H). MS (ES+) m/e 308.1 (M+H)⁺.

Example 82

N-(2-((1R,6S)-3,7-diazabicyclo[4.2.0]octan-3-yl)pyrimidin-4-yl)-1H-indazol-5-amine

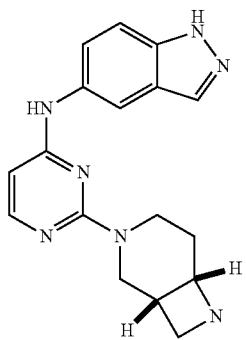 [SMILES: c1cc(Nc2ccc3[nH]ncc3c2)nc(N2CC[C@@H]3NC[C@@H]3C2)n1]

The reaction was conducted following general protocol A. The reaction time of the first step was 16 hours and the crude material was further used without additional purification. The final residue was purified by reverse phase preparative HPLC to afford N-(2-((1R,6S)-3,7-diazabicyclo[4.2.0]octan-3-yl)pyrimidin-4-yl)-1H-indazol-5-amine as a light brown solid (9%). ¹H NMR (400 MHz, CD₃OD) δ 8.09 (m, 2H), 7.82 (d, J=7.2 Hz, 1H), 7.63-7.56 (m, 1H), 6.42 (m, 1H), 4.80-4.78 (m, 1H), 4.21-4.16 (m, 2H), 4.04-3.89 (m, 3H), 3.73-3.69 (m, 1H), 3.38 (m, 1H), 2.46-2.37 (m, 2H). MS (ES+) m/e 322.1 (M+H)⁺.

Example 83

N-(2-(3-(azetidin-3-yl)pyrrolidin-1-yl)pyrimidin-4-yl)-1H-indazol-5-amine

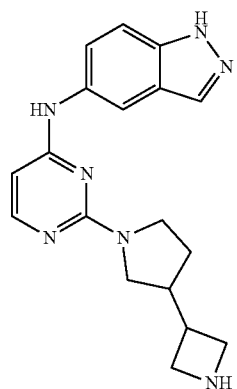 [SMILES: c1cc(Nc2ccc3[nH]ncc3c2)nc(N2CCC(C3CNC3)C2)n1]

The reaction was conducted following general protocol A. The reaction time of the first step was 16 hours and the crude material was further used without additional purification. The final residue was purified by reverse phase preparative HPLC to afford N-(2-(3-(azetidin-3-yl)pyrrolidin-1-yl)pyrimidin-4-yl)-1H-indazol-5-amine as a light brown solid (13%). ¹H NMR (400 MHz, CD₃OD) δ 8.27 (s, 1H), 8.08 (s, 1H), 7.54 (d, J=7.2 Hz, 1H), 7.59 (m, 2H), 6.35 (d, J=6.4 Hz, 1H), 4.23-4.18 (m, 2H), 4.01-3.88 (m, 3H), 3.74-3.60 (m, 2H), 3.18-3.16 (m, 1H), 3.05-3.03 (m, 1H), 2.84-2.75 (m, 1H), 2.32-2.25 (m, 1H), 1.85-1.75 (m, 1H). MS (ES+) m/e 336.1 (M+H)⁺.

Example 84

N-(2-(octahydro-2H-pyrazino[1,2-a]pyrazin-2-yl)pyrimidin-4-yl)-1H-indazol-5-amine

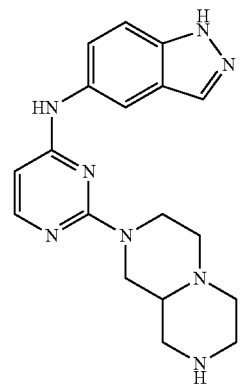 [SMILES: c1cc(Nc2ccc3[nH]ncc3c2)nc(N2CCN3CCNCC3C2)n1]

The reaction was conducted following general protocol A. The reaction time of the first step was 16 hours and the crude material was further used without additional purification. The final residue was purified by reverse phase preparative HPLC to afford N-(2-(octahydro-2H-pyrazino[1,2-a]pyrazin-2-yl)pyrimidin-4-yl)-1H-indazol-5-amine as a light brown solid (13%). ¹H NMR (400 MHz, CD₃OD) δ 8.11 (s, 1H), 8.05 (s, 1H), 7.80 (d, J=7.2 Hz, 1H), 7.64-7.54 (m, 2H), 6.38 (m, 1H), 4.35 (m, 2H), 3.44-3.38 (m, 2H), 3.25-3.19 (m, 2H), 3.10-2.90 (m, 4H), 2.53-2.40 (m, 3H). MS (ES+) m/e 351.1 (M+H)⁺.

Example 85

N-(2-(octahydropyrrolo[3,4-d]azepin-6(1H)-yl)pyrimidin-4-yl)-1H-indazol-5-amine

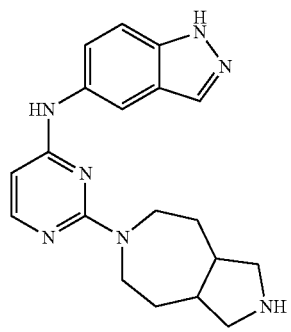 [SMILES: c1cc(Nc2ccc3[nH]ncc3c2)nc(N2CCC3CNCC3CC2)n1]

The reaction was conducted following general protocol A. The reaction time of the first step was 16 hours and the crude material was further used without additional purification. The final residue was purified by reverse phase preparative HPLC to afford N-(2-(octahydropyrrolo[3,4-d]azepin-6(1H)-yl)pyrimidin-4-yl)-1H-indazol-5-amine as a light brown solid (22%). ¹H NMR (400 MHz, CD₃OD) δ 8.09 (m, 2H), 7.77 (d, J=7.2 Hz, 1H), 7.62-7.60 (m, 1H), 7.53 (m, 1H), 6.37 (d, J=6.4 Hz, 1H), 4.05 (m, 2H), 3.62-3.50 (m, 4H), 3.09-3.05 (m, 2H), 2.71 (m, 2H), 2.07-2.04 (m, 2H), 1.95-1.87 (m, 2H). MS (ES+) m/e 350.1 (M+H)⁺.

Example 86

N-(2-([3,3'-bipiperidin]-1-yl)pyrimidin-4-yl)-1H-indazol-5-amine

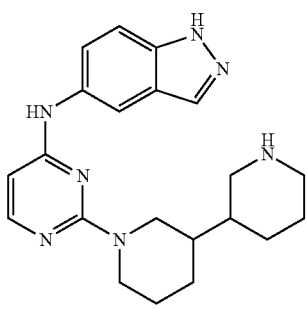 [SMILES: c1cc(Nc2ccc3[nH]ncc3c2)nc(N2CCCC(C3CCCNC3)C2)n1]

The reaction was conducted following general protocol A. The reaction time of the first step was 16 hours and the crude material was further used without additional purification. The final residue was purified by reverse phase preparative HPLC to afford N-(2-([3,3'-bipiperidin]-1-yl)pyrimidin-4-yl)-1H-indazol-5-amine as a light brown solid (31%). ¹H NMR (400 MHz, CD₃OD) δ 8.10 (s, 1H), 8.04 (brs, 1H), 7.75 (d, J=7.2 Hz, 1H), 7.62 (d, J=9.2 Hz, 1H), 7.48 (d, J=8.0 Hz, 1H), 6.32 (d, J=7.2 Hz, 1H), 4.58 (m, 1H), 4.12-4.08 (m, 1H), 3.43-3.40 (m, 1H), 3.29-3.18 (m, 2H), 2.91-2.63 (m, 3H), 1.97-1.87 (m, 3H), 1.61-1.35 (m, 6H), 0.97-0.86 (m, 1H). MS (ES+) m/e 378.1 (M+H)⁺.

Example 87

N-(2-(spiro[indoline-3,4'-piperidin]-1-yl)pyrimidin-4-yl)-1H-indazol-5-amine

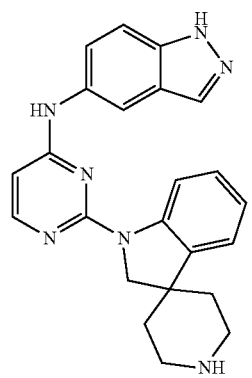 [SMILES: c1ccc2c(c1)N(c1nccc(Nc3ccc4[nH]ncc4c3)n1)CC21CCNCC1]

The reaction was conducted following general protocol D. The reaction time of the first step was 16 hours and the crude material was further used without additional purification. The final residue was purified by reverse phase preparative HPLC to afford N-(2-(spiro[indoline-3,4'-piperidin]-1-yl)pyrimidin-4-yl)-1H-indazol-5-amine as a yellow solid (37%). ¹H NMR (400 MHz, DMSO-d₆) δ 13.11 (brs, 1H), 9.81 (brs, 1H), 8.73-8.71 (m, 1H), 8.49-8.47 (m, 1H), 8.18-8.07 (m, 4H), 7.59 (d, J=8.8 Hz, 1H), 7.41 (dd, J=8.8, 1.6 Hz, 1H), 7.18-7.15 (m, 1H), 6.98 (m, 2H), 6.33 (d, J=6.0 Hz, 1H), 4.19 (s, 2H), 3.42-3.34 (m, 2H), 3.08-2.99 (m, 2H), 2.06-2.00 (m, 2H), 1.87-1.84 (m, 2H). MS (ES+) m/e 398.2 (M+H)⁺.

Example 88

N-(2-(3-(piperidin-4-yl)indolin-1-yl)pyrimidin-4-yl)-1H-indazol-5-amine

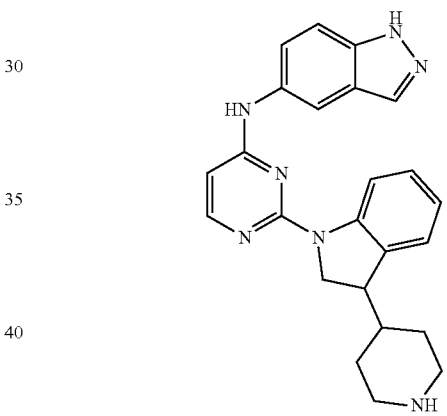

The reaction was conducted following general protocol D. The reaction time of the first step was 16 hours and the crude material was further used without additional purification. The final residue was purified by reverse phase preparative HPLC to afford N-(2-(3-(piperidin-4-yl)indolin-1-yl)pyrimidin-4-yl)-1H-indazol-5-amine as a yellow solid (43%). ¹H NMR (400 MHz, DMSO-d₆) δ 13.12 (brs, 1H), 10.03 (brs, 1H), 8.52-8.50 (m, 1H), 8.15-8.07 (m, 5H), 7.61 (d, J=8.4 Hz, 1H), 7.44 (d, J=7.6 Hz, 1H), 7.27-7.25 (m, 1H), 6.97-6.95 (m, 2H), 4.19-4.14 (m, 1H), 4.06-4.03 (m, 1H), 3.47 (m, 1H), 3.46-3.45 (m, 2H), 3.32-3.23 (m, 2H), 1.97 (m, 1H), 1.84-1.81 (m, 2H), 1.44-1.39 (m, 2H). MS (ES+) m/e 412.1 (M+H)⁺.

Example 89

N-(2-(3-(piperidin-3-yl)indolin-1-yl)pyrimidin-4-yl)-1H-indazol-5-amine

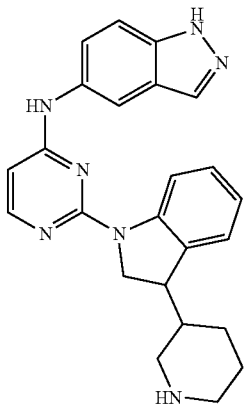 [SMILES: c1ccc2c(c1)C(C1CCCNC1)CN2c1nccc(Nc2ccc3[nH]ncc3c2)n1]

The reaction was conducted following general protocol D. The reaction time of the first step was 16 hours and the crude material was further used without additional purification. The final residue was purified by reverse phase preparative HPLC to afford N-(2-(3-(piperidin-3-yl)indolin-1-yl)pyrimidin-4-yl)-1H-indazol-5-amine as a yellow solid (38%). $^1$H NMR (400 MHz, DMSO-$d_6$) δ 13.16 (brs, 1H), 10.18 (brs, 1H), 8.77-8.62 (m, 1H), 8.38-8.29 (m, 1H), 8.08-8.06 (m, 4H), 7.62 (d, J=8.8 Hz, 1H), 7.44-7.42 (m, 1H), 7.27-7.22 (m, 1H), 7.01-6.94 (m, 2H), 6.39-6.37 (m, 1H), 4.13-4.12 (m, 2H), 3.53-3.49 (m, 1H), 3.46-3.32 (m, 1H), 3.24-3.21 (m, 1H), 2.78-2.67 (m, 2H), 2.06-2.05 (m, 1H), 1.78-1.75 (m, 1H), 1.55-1.29 (m, 3H). MS (ES+) m/e 412.1 (M+H)$^+$.

Example 90

N-(5-chloro-2-(3-methyl-1,4-diazepan-1-yl)pyrimidin-4-yl)-1H-indazol-5-amine

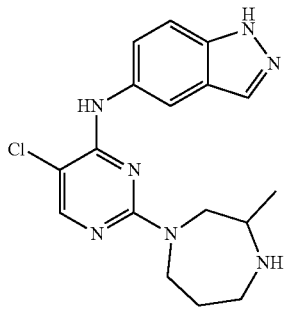 [SMILES: CC1CN(c2ncc(Cl)c(Nc3ccc4[nH]ncc4c3)n2)CCCN1]

The reaction was conducted following general protocol A. The reaction time of the first step was 16 hours and the crude material was further used without additional purification. The final residue was purified by reverse phase preparative HPLC to afford N-(5-chloro-2-(3-methyl-1,4-diazepan-1-yl)pyrimidin-4-yl)-1H-indazol-5-amine as a yellow solid (21%). $^1$H NMR (400 MHz, CD$_3$OD) δ 8.54 (s, 1H), 8.04 (s, 1H), 7.98 (s, 1H), 7.94 (s, 1H), 7.57-7.52 (m, 2H), 4.60 (m, 1H), 4.27-4.19 (m, 2H), 3.39-3.36 (m, 2H), 3.27-3.21 (m, 2H), 2.97-2.91 (m, 1H), 2.17-2.16 (m, 1H), 2.04-1.99 (m, 1H), 1.11 (m, 3H). MS (ES+) m/e 358.0 (M+H)$^+$.

Example 91

N-(5-methyl-2-(3-methylpiperazin-1-yl)pyrimidin-4-yl)-1H-indazol-5-amine

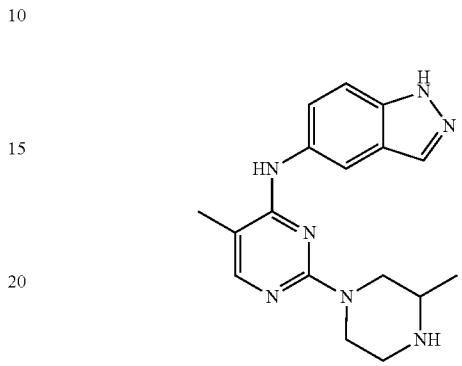

The reaction was conducted following general protocol A. The reaction time of the first step was 48 hours and the crude material was further used without additional purification. The final residue was purified by reverse phase preparative HPLC to afford N-(5-methyl-2-(3-methylpiperazin-1-yl)pyrimidin-4-yl)-1H-indazol-5-amine as a yellow solid (26%). $^1$H NMR (400 MHz, DMSO-$d_6$) δ 12.96 (brs, 1H), 8.28 (s, 3H), 7.99 (d, J=0.8 Hz, 1H), 7.97 (d, J=1.6 Hz, 1H), 7.78 (d, J=0.8 Hz, 1H), 7.57 (dd, J=8.8, 2.0 Hz, 1H), 7.47 (d, J=8.8 Hz, 1H), 4.40-4.34 (m, 2H), 3.06-3.03 (m, 1H), 2.94-2.82 (m, 2H), 2.78-2.67 (m, 1H), 2.59-2.56 (m, 1H), 2.07 (s, 3H), 1.08 (d, J=6.4 Hz, 3H). MS (ES+) m/e 324.1 (M+H)$^+$.

Example 92

N-(2-(3-isopropyl-1,4-diazepan-1-yl)-5-methylpyrimidin-4-yl)-1H-indazol-5-amine

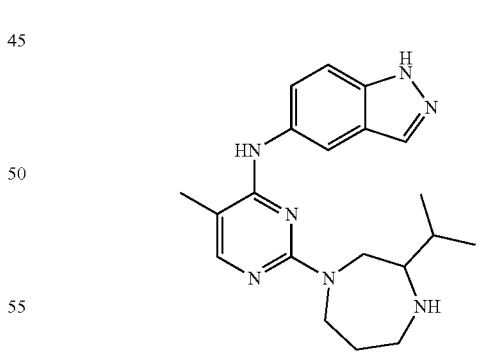

The reaction was conducted following general protocol C. The residue was purified by reverse phase preparative HPLC to afford N-(2-(3-isopropyl-1,4-diazepan-1-yl)-5-methylpyrimidin-4-yl)-1H-indazol-5-amine as a yellow oil (7%). $^1$H NMR (400 MHz, CD$_3$OD) δ 8.43 (s, 2H), 8.00 (s, 1H), 7.86 (s, 1H), 7.75 (s, 1H), 7.53-7.47 (m, 2H), 4.24-4.19 (m, 1H), 4.09-4.05 (m, 1H), 3.51-3.38 (m, 3H), 3.14-3.08 (m, 1H), 3.03-2.96 (m, 1H), 2.13-1.75 (m, 6H), 0.75 (m, 6H). MS (ES+) m/e 365.9 (M+H)$^+$.

Example 93

N-(2-(5-isopropyl-1,4-diazepan-1-yl)-5-methylpyrimidin-4-yl)-1H-indazol-5-amine

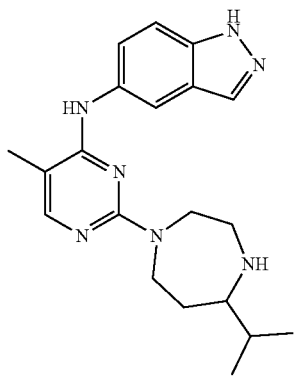 [SMILES: Cc1cnc(N2CCNC(C(C)C)CC2)nc1Nc1ccc2[nH]ncc2c1]

The reaction was conducted following general protocol C. The residue was purified by reverse phase preparative HPLC to afford N-(2-(5-isopropyl-1,4-diazepan-1-yl)-5-methylpyrimidin-4-yl)-1H-indazol-5-amine as a white solid (17%). $^1$H NMR (400 MHz, CD$_3$OD) δ 8.53 (s, 1H), 8.02 (d, J=0.8 Hz, 1H), 7.96 (d, J=1.2 Hz, 1H), 7.78 (d, J=0.8 Hz, 1H), 7.59 (dd, J=8.8, 2.0 Hz, 1H), 7.52 (d, J=8.8 Hz, 1H), 4.09-4.00 (m, 1H), 3.99-3.91 (m, 1H), 3.86-3.80 (m, 1H), 3.68-3.61 (m, 1H), 3.40-3.35 (m, 1H), 3.21-3.15 (m, 2H), 2.15 (s, 3H), 2.07-2.03 (m, 2H), 1.85-1.75 (m, 1H), 0.99 (t, J=6.8 Hz, 6H). MS (ES+) m/e 365.9 (M+H)$^+$.

Example 94

N-(5-methyl-2-(5-phenyl-1,4-diazepan-1-yl)pyrimidin-4-yl)-1H-indazol-5-amine

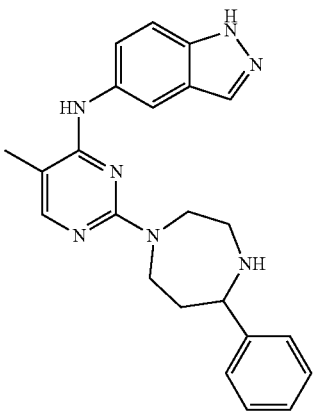 [SMILES: Cc1cnc(N2CCNC(c3ccccc3)CC2)nc1Nc1ccc2[nH]ncc2c1]

The reaction was conducted following general protocol C. The residue was purified by reverse phase preparative HPLC to afford N-(5-methyl-2-(5-phenyl-1,4-diazepan-1-yl)pyrimidin-4-yl)-1H-indazol-5-amine as a white solid (31%). $^1$H NMR (400 MHz, CD$_3$OD) δ 8.44 (s, 2H), 7.98 (s, 1H), 7.97 (s, 1H), 7.80 (d, J=0.8 Hz, 1H), 7.61 (dd, J=8.8, 1.6 Hz, 1H), 7.51 (d, J=8.8 Hz, 1H), 7.46-7.40 (m, 5H), 4.39-4.35 (m, 1H), 4.16-4.00 (m, 3H), 3.75-3.68 (m, 1H), 3.51-3.43 (m, 1H), 3.32-3.25 (m, 1H), 2.41-2.30 (m, 1H), 2.25-2.20 (m, 1H), 2.19 (s, 3H). MS (ES+) m/e 400.2 (M+H)$^+$.

Example 95

N-(5-methyl-2-(piperazin-1-yl)pyrimidin-4-yl)-1H-indazol-5-amine

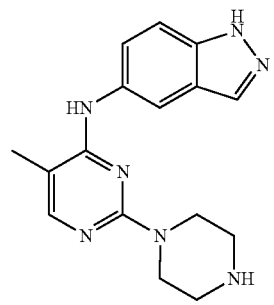

The reaction was conducted following general protocol A. The reaction time of the first step was 48 hours and the crude material was further used without additional purification. The final residue was purified by reverse phase preparative HPLC to afford N-(5-methyl-2-(piperazin-1-yl)pyrimidin-4-yl)-1H-indazol-5-amine as an off-white solid (14%). $^1$H NMR (400 MHz, DMSO-d$_6$) δ 8.17 (s, 1H), 7.89 (s, 1H), 7.73 (s, 1H), 7.64 (d, J=8.8 Hz, 1H), 7.57 (d, J=9.2 Hz, 1H), 3.90 (t, J=4.8 Hz, 4H), 3.34 (s, 4H), 2.25 (s, 3H). MS (ES+) m/e 310.1 (M+H)$^+$.

Example 96

N-(2-(5-ethyl-1,4-diazepan-1-yl)-5-methylpyrimidin-4-yl)-1H-indazol-5-amine

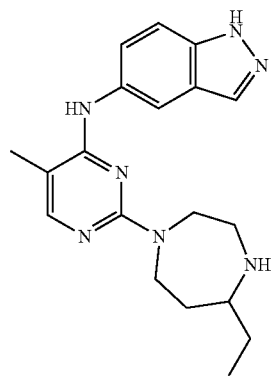 [SMILES: CCC1CCN(c2ncc(C)c(Nc3ccc4[nH]ncc4c3)n2)CCN1]

The reaction was conducted following general protocol A. The reaction time of the first step was 48 hours and the crude material was further used without additional purification. The final residue was purified by reverse phase preparative HPLC to afford N-(2-(5-ethyl-1,4-diazepan-1-yl)-5-methylpyrimidin-4-yl)-1H-indazol-5-amine as a yellow solid (25%). $^1$H NMR (400 MHz, CD$_3$OD) δ 8.36 (s, 2H), 8.01 (d, J=0.8 Hz, 1H), 7.98-7.91 (m, 1H), 7.75 (d, J=0.8 Hz, 1H), 7.58-7.50 (m, 2H), 4.03-3.82 (m, 3H), 3.64-3.57 (m, 1H), 3.43-3.36 (m, 1H), 3.27-3.15 (m, 2H), 2.20-2.10 (m, 4H), 1.90-1.80 (m, 1H), 1.77-1.58 (m, 2H), 0.99 (t, J=7.6 Hz, 3H). MS (ES+) m/e 352.1 (M+H)+.

Example 97

N-(5-methyl-2-(2-methylpiperazin-1-yl)pyrimidin-4-yl)-1H-indazol-5-amine

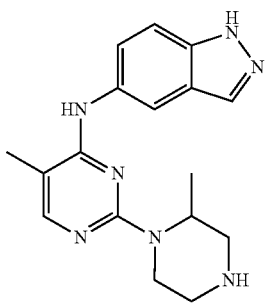 [SMILES: Cc1cnc(N2CCNCC2C)nc1Nc1ccc2[nH]ncc2c1]

The reaction was conducted following general protocol A. The reaction time of the first step was 96 hours and the crude material was further used without additional purification. The final residue was purified by reverse phase preparative HPLC to afford N-(5-methyl-2-(2-methylpiperazin-1-yl)pyrimidin-4-yl)-1H-indazol-5-amine as an yellow solid (21%). $^1$H NMR (400 MHz, CD$_3$OD) δ 8.35 (s, 2H), 8.02-7.98 (m, 1H), 7.90 (d, J=1.2 Hz, 1H), 7.78 (s, 1H), 7.57-7.49 (m, 2H), 4.93 (m, 1H), 4.53-4.49 (m, 1H), 3.36 (m, 1H), 3.29-3.25 (m, 1H), 3.25-3.16 (m, 2H), 3.06-2.97 (m, 1H), 2.15 (s, 3H), 1.28 (d, J=7.2 Hz, 3H). MS (ES+) m/e 324.1 (M+H)+.

Example 98

N-(2-(3,5-dimethylpiperazin-1-yl)-5-methylpyrimidin-4-yl)-1H-indazol-5-amine

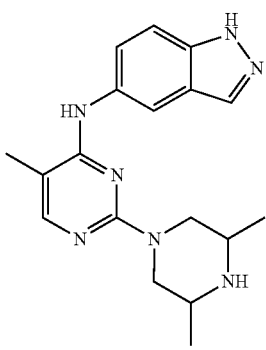

The reaction was conducted following general protocol A. The reaction time of the first step was 50 hours and the crude material was further used without additional purification. The final residue was purified by reverse phase preparative HPLC to afford N-(2-(3,5-dimethylpiperazin-1-yl)-5-methylpyrimidin-4-yl)-1H-indazol-5-amine as an yellow solid (11%). $^1$H NMR (400 MHz, CD$_3$OD) δ 8.52 (s, 2H), 8.02 (s, 1H), 7.94 (s, 1H), 7.80 (s, 1H), 7.58-7.52 (m, 2H), 4.69 (d, J=2.4 Hz, 1H), 4.65 (d, J=2.0 Hz, 1H), 3.27-3.21 (m, 2H), 2.78-2.72 (m, 2H), 2.15 (s, 3H), 1.29 (d, J=6.4 Hz, 6H). MS (ES+) m/e 337.8 (M+H)+.

Example 99

N-(2-(3-ethylpiperazin-1-yl)-5-methylpyrimidin-4-yl)-1H-indazol-5-amine

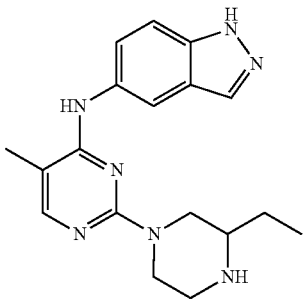 [SMILES: CCC1CN(c2ncc(C)c(Nc3ccc4[nH]ncc4c3)n2)CCN1]

The reaction was conducted following general protocol A. The reaction time of the first step was 48 hours and the crude material was further used without additional purification. The final residue was purified by reverse phase preparative HPLC to afford N-(2-(3-ethylpiperazin-1-yl)-5-methylpyrimidin-4-yl)-1H-indazol-5-amine as an yellow oil (21%). $^1$H NMR (400 MHz, CD$_3$OD) δ 8.34 (s, 2H), 8.01 (s, 1H), 7.91 (dd, J=2.0, 0.8 Hz, 1H), 7.80 (d, J=1.2 Hz, 1H), 7.58-7.51 (m, 2H), 4.69-4.67 (m, 1H), 4.56-4.53 (m, 1H), 3.39-3.37 (m, 1H), 3.29-3.20 (m, 1H), 3.13-3.03 (m, 2H), 2.96-2.90 (m, 1H), 2.16 (s, 3H), 1.70-1.60 (m, 2H), 0.95 (t, J=7.2 Hz, 3H). MS (ES+) m/e 338.1 (M+H)+.

Example 100

N-(5-methyl-2-(5-methyl-1,4-diazepan-1-yl)pyrimidin-4-yl)-1H-indazol-5-amine

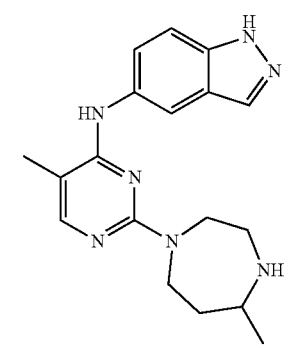 [SMILES: Cc1cnc(N2CCNC(C)CC2)nc1Nc1ccc2[nH]ncc2c1]

The reaction was conducted following general protocol A. The reaction time of the first step was 36 hours and the crude material was further used without additional purification. The final residue was purified by reverse phase preparative HPLC to afford N-(5-methyl-2-(5-methyl-1,4-diazepan-1-yl)pyrimidin-4-yl)-1H-indazol-5-amine as an yellow solid (25%). $^1$H NMR (400 MHz, CD$_3$OD) δ 8.39 (brs, 2H), 8.02 (s, 1H), 7.97 (d, J=1.2 Hz, 1H), 7.77 (s, 1H), 7.59 (dd, J=8.8, 1.6 Hz, 1H), 7.53 (d, J=8.8 Hz, 1H), 4.02-3.93 (m, 3H), 3.62 (m, 1H), 3.43-3.38 (m, 2H), 3.21 (m, 1H), 2.16 (s, 3H), 2.11-2.07 (m, 1H), 1.94-1.90 (m, 1H), 1.35 (d, J=6.8 Hz, 1H). MS (ES+) m/e 338.1 (M+H)+.

Example 101

N-(2-(3-isopropylpiperazin-1-yl)-5-methylpyrimidin-4-yl)-1H-indazol-5-amine

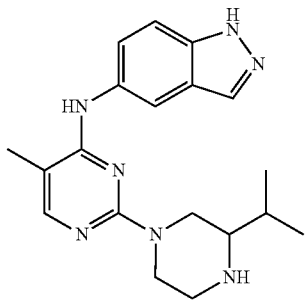 [SMILES: Cc1cnc(N2CCNC(C(C)C)C2)nc1Nc1ccc2[nH]ncc2c1]

The reaction was conducted following general protocol A. The reaction time of the first step was 56 hours and the crude material was further used without additional purification. The final residue was purified by reverse phase preparative HPLC to afford N-(2-(3-isopropylpiperazin-1-yl)-5-methylpyrimidin-4-yl)-1H-indazol-5-amine as an yellow solid (43%). $^1$H NMR (400 MHz, CD$_3$OD) δ 8.42 (brs, 2H), 8.01 (s, 1H), 7.91 (s, 1H), 7.81 (s, 1H), 7.57-7.51 (m, 2H), 4.80-4.76 (m, 1H), 4.62-4.59 (m, 1H), 3.39 (m, 1H), 3.18-3.14 (m, 2H), 2.92-2.83 (m, 2H), 2.16 (s, 3H), 1.88-1.82 (m, 1H), 1.02 (d, J=6.8 Hz, 3H), 0.95 (d, J=6.8 Hz, 3H). MS (ES+) m/e 352.1 (M+H)$^+$.

Example 102

N-(5-methyl-2-(3-methyl-1,4-diazepan-1-yl)pyrimidin-4-yl)-1H-indazol-5-amine

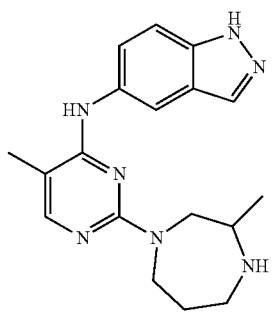

The reaction was conducted following general protocol A. The reaction time of the first step was 96 hours and the crude material was further used without additional purification. The final residue was purified by reverse phase preparative HPLC to afford N-(5-methyl-2-(3-methyl-1,4-diazepan-1-yl)pyrimidin-4-yl)-1H-indazol-5-amine as an yellow oil (31%). $^1$H NMR (400 MHz, CD$_3$OD) δ 8.38 (s, 2H), 8.03 (s, 1H), 7.93 (s, 1H), 7.77 (s, 1H), 7.55 (s, 2H), 4.23-4.18 (m, 2H), 3.45-3.38 (m, 3H), 3.30-3.23 (m, 1H), 3.04-2.94 (m, 1H), 2.22-2.09 (m, 5H), 1.10 (d, J=5.6 Hz, 3H). MS (ES+) m/e 338.1 (M+H)$^+$.

Example 103

N-(5-methyl-2-(3-phenyl-1,4-diazepan-1-yl)pyrimidin-4-yl)-1H-indazol-5-amine

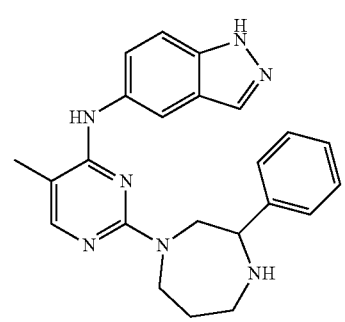 [SMILES: Cc1cnc(N2CCCNC(c3ccccc3)C2)nc1Nc1ccc2[nH]ncc2c1]

The reaction was conducted following general protocol C. The residue was purified by reverse phase preparative HPLC to afford N-(5-methyl-2-(3-phenyl-1,4-diazepan-1-yl)pyrimidin-4-yl)-1H-indazol-5-amine as a white solid (11%). $^1$H NMR (400 MHz, CD3OD) δ 7.96 (s, 1H), 7.80 (s, 1H), 7.74 (d, J=0.8 Hz, 1H), 7.56 (d, J=8.8 Hz, 1H), 7.38 (d, J=8.4 Hz, 1H), 7.27-6.87 (m, 5H), 4.46-4.43 (m, 1H), 4.25-4.23 (m, 1H), 3.84 (m, 1H), 3.46-3.39 (m, 1H), 3.22-3.15 (m, 2H), 2.62-2.53 (m, 1H), 2.15 (m, 4H), 1.96-1.86 (m, 1H). MS (ES+) m/e 400.2 (M+H)$^+$.

Example 104 (KL-01047)

N-(5-methyl-2-(2-methyl-1,4-diazepan-1-yl)pyrimidin-4-yl)-1H-indazol-5-amine

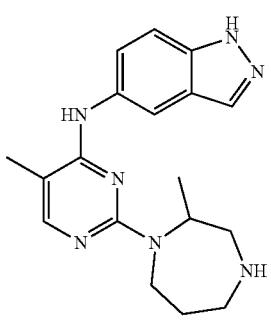 [SMILES: Cc1cnc(N2CCCNCC2C)nc1Nc1ccc2[nH]ncc2c1]

The reaction was conducted following general protocol B. The reaction time of the first step was 48 hours and the crude material was further used without additional purification. The final residue was purified by reverse phase preparative HPLC to afford N-(5-methyl-2-(2-methyl-1,4-diazepan-1-yl)pyrimidin-4-yl)-1H-indazol-5-amine as an white solid (3%). $^1$H NMR (400 MHz, CD$_3$OD) δ 8.11 (s, 1H), 7.99 (s, 1H), 7.72 (s, 1H), 7.64 (d, J=8.8 Hz, 1H), 7.49 (d, J=9.2 Hz, 1H), 4.62 (m, 1H), 4.25-4.22 (m, 1H), 3.35-3.34 (m, 1H), 3.19-3.16 (m, 2H), 2.74-2.68 (m, 2H), 2.13 (s, 3H), 1.82-1.74 (m, 2H), 1.10 (d, J=6.4 Hz, 3H). MS (ES+) m/e 338.1 (M+H)$^+$.

Example 105 (KL-01048)

N-(2-(2-ethyl-1,4-diazepan-1-yl)-5-methylpyrimidin-4-yl)-1H-indazol-5-amine

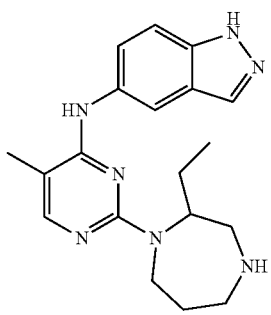 [SMILES: CCC1CNCCCN1c1ncc(C)c(Nc2ccc3[nH]ncc3c2)n1]

The reaction was conducted following general protocol B. The reaction time of the first step was 64 hours and the crude material was further used without additional purification. The final residue was purified by reverse phase preparative HPLC to afford N-(2-(2-ethyl-1,4-diazepan-1-yl)-5-methylpyrimidin-4-yl)-1H-indazol-5-amine as an white solid (3%). $^1$H NMR (400 MHz, CD$_3$OD) δ 8.04 (s, 1H), 7.96 (d, J=0.8 Hz, 1H), 7.69 (s, 1H), 7.61 (dd, J=8.8, 2.0 Hz, 1H), 7.47 (d, J=8.8 Hz, 1H), 4.51 (m, 1H), 4.20-4.16 (m, 1H), 3.40-3.34 (m, 1H), 3.16-3.04 (m, 2H), 2.68-2.54 (m, 2H), 2.11 (s, 3H), 1.80 (m, 1H), 1.66-1.45 (m, 3H), 0.81 (m, 3H). MS (ES+) m/e 352.1 (M+H)$^+$.

Example 106

N-(2-(3-ethyl-1,4-diazepan-1-yl)-5-methylpyrimidin-4-yl)-1H-indazol-5-amine

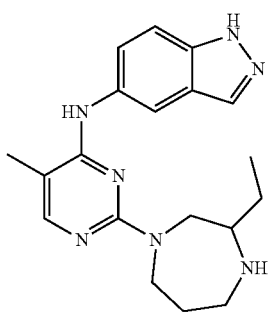 [SMILES: CCC1CN(c2ncc(C)c(Nc3ccc4[nH]ncc4c3)n2)CCCN1]

The reaction was conducted following general protocol A. The reaction time of the first step was 16 hours and the crude material was further used without additional purification. The final residue was purified by reverse phase preparative HPLC to afford N-(2-(3-ethyl-1,4-diazepan-1-yl)-5-methylpyrimidin-4-yl)-1H-indazol-5-amine as an yellow solid (8%). $^1$H NMR (400 MHz, CD$_3$OD) δ 8.11 (s, 1H), 7.83 (d, J=1.2 Hz, 1H), 7.71 (d, J=0.8 Hz, 1H), 7.65 (d, J=8.8 Hz, 1H), 7.45 (dd, J=8.8, 1.6 Hz 1H), 4.16-4.14 (m 1H), 3.75 (m, 1H), 3.60-3.54 (m, 1H), 3.53-3.46 (m, 1H), 3.41-3.39 (m, 1H), 3.19-3.15 (m, 2H), 2.26 (m, 5H), 1.34-1.20 (m, 2H), 0.42 (m, 3H). MS (ES+) m/e 352.2 (M+H)$^+$.

Example 107

N-(2-(3,8-diazabicyclo[3.2.1]octan-8-yl)-5-methylpyrimidin-4-yl)-1H-indazol-5-amine

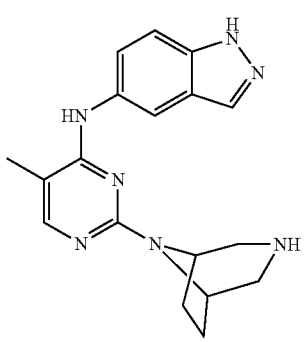 [SMILES: Cc1cnc(N2C3CCC2CNC3)nc1Nc1ccc2[nH]ncc2c1]

The reaction was conducted following general protocol A. The reaction time of the first step was 32 hours and the crude material was further used without additional purification. The final residue was purified by reverse phase preparative HPLC to afford N-(2-(3-ethyl-1,4-diazepan-1-yl)-5-methylpyrimidin-4-yl)-1H-indazol-5-amine as an white solid (2%). $^1$H NMR (400 MHz, DMSO-d$_6$) δ 13.11 (brs, 1H), 9.11 (brs, 1H), 8.83 (brs, 1H), 8.08 (s, 1H), 7.91 (s, 1H), 7.89 (s, 1H), 7.53 (s, 2H), 4.56 (s, 2H), 3.19 (m, 4H), 2.16 (s, 3H), 2.11-1.92 (m, 4H). MS (ES+) m/e 336.1 (M+H)$^+$.

Example 108

N-(6-methyl-2-(5-phenyl-1,4-diazepan-1-yl)pyrimidin-4-yl)-1H-indazol-5-amine

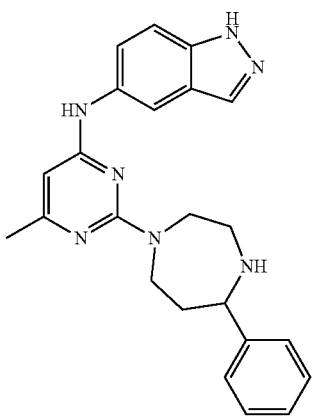 [SMILES: Cc1cc(Nc2ccc3[nH]ncc3c2)nc(N2CCNC(c3ccccc3)CC2)n1]

The reaction was conducted following general protocol C. The residue was purified by reverse phase preparative HPLC to afford N-(6-methyl-2-(5-phenyl-1,4-diazepan-1-yl)pyrimidin-4-yl)-1H-indazol-5-amine as a yellow solid (24%). $^1$H NMR (400 MHz, CD$_3$OD) δ 8.45 (s, 2H), 8.05 (s, 1H), 7.97 (s, 1H), 7.50-7.41 (m, 7H), 6.04 (s, 1H), 4.45-4.42 (m, 1H), 4.27-4.17 (m, 3H), 3.85 (m, 1H), 3.59 (m, 1H), 3.41-3.40 (m, 1H), 2.47-2.42 (m, 1H), 2.31-2.27 (m, 4H). MS (ES+) m/e 400.2 (M+H)$^+$.

Example 109

N-(2-(5-ethyl-1,4-diazepan-1-yl)-6-methylpyrimidin-4-yl)-1H-indazol-5-amine

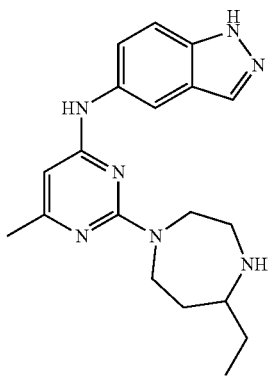 [SMILES: CCC1CCN(c2nc(C)cc(Nc3ccc4[nH]ncc4c3)n2)CCN1]

The reaction was conducted following general protocol A. The reaction time of the first step was 32 hours and the crude material was further used without additional purification. The final residue was purified by reverse phase preparative HPLC to afford N-(2-(5-ethyl-1,4-diazepan-1-yl)-6-methylpyrimidin-4-yl)-1H-indazol-5-amine as a yellow solid (40%). $^1$H NMR (400 MHz, CD$_3$OD) δ 8.36 (s, 2H), 8.02 (s, 1H), 7.99 (s, 1H), 7.52-7.44 (m, 2H), 5.99 (s, 1H), 4.14-4.04 (m, 3H), 3.78-3.71 (m, 1H), 3.57-3.46 (m, 1H), 3.33 (m, 1H), 3.29-3.23 (m, 1H), 2.28-2.17 (m, 4H), 1.99-1.89 (m, 1H), 1.82-1.61 (m, 2H), 1.03 (t, J=7.6 Hz, 3H). MS (ES+) m/e 352.1 (M+H)$^+$.

Example 110

N-(2-(3-isopropyl-1,4-diazepan-1-yl)-6-methylpyrimidin-4-yl)-1H-indazol-5-amine

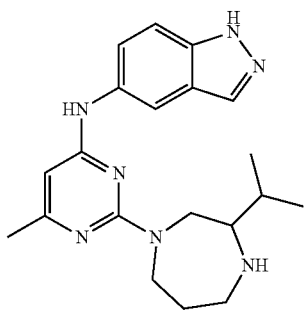 [SMILES: Cc1cc(Nc2ccc3[nH]ncc3c2)nc(N2CCCNC(C(C)C)C2)n1]

The reaction was conducted following general protocol C. The residue was purified by reverse phase preparative HPLC to afford N-(2-(3-isopropyl-1,4-diazepan-1-yl)-6-methylpyrimidin-4-yl)-1H-indazol-5-amine as a yellow gum (14%). $^1$H NMR (400 MHz, CD$_3$OD) δ 8.45 (brs, 2H), 8.01-7.99 (m, 2H), 7.53-7.443 (m, 2H), 5.98 (s, 1H), 4.47-4.43 (m, 1H), 4.28 (m, 1H), 3.61-3.50 (m, 3H), 3.29-3.27 (m, 1H), 3.07 (m, 1H), 2.24-2.13 (m, 5H), 2.00-1.99 (m, 1H), 1.02 (m, 6H). MS (ES+) m/e 366.1 (M+H)$^+$.

Example 111

N-(2-(5-isopropyl-1,4-diazepan-1-yl)-6-methylpyrimidin-4-yl)-1H-indazol-5-amine

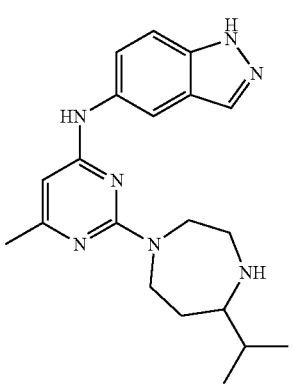 [SMILES: Cc1cc(Nc2ccc3[nH]ncc3c2)nc(N2CCNC(C(C)C)CC2)n1]

The reaction was conducted following general protocol C. The residue was purified by reverse phase preparative HPLC to afford N-(2-(5-isopropyl-1,4-diazepan-1-yl)-6-methylpyrimidin-4-yl)-1H-indazol-5-amine as a yellow solid (7%). $^1$H NMR (400 MHz, CD$_3$OD) δ 8.48 (s, 2H), 8.04 (s, 1H), 8.00 (s, 1H), 7.56-7.46 (m, 2H), 5.99 (s, 1H), 4.22 (m, 1H), 4.18-4.12 (m, 1H), 4.09-4.01 (m, 1H), 3.78-3.70 (m, 1H), 3.50-3.49 (m, 1H), 3.30-3.23 (m, 2H), 2.24-2.16 (m, 4H), 2.08-2.05 (m, 1H), 1.91-1.88 (m, 1H), 1.05-1.01 (m, 6H). MS (ES+) m/e 366.1 (M+H)$^+$.

Example 112

N-(6-methyl-2-(3-phenyl-1,4-diazepan-1-yl)pyrimidin-4-yl)-1H-indazol-5-amine

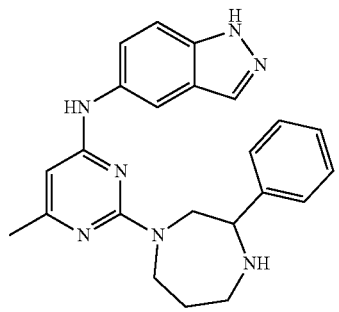 [SMILES: Cc1cc(Nc2ccc3[nH]ncc3c2)nc(N2CCCNC(c3ccccc3)C2)n1]

The reaction was conducted following general protocol C. The residue was purified by reverse phase preparative HPLC to afford N-(6-methyl-2-(3-phenyl-1,4-diazepan-1-yl)pyrimidin-4-yl)-1H-indazol-5-amine as a yellow solid (7%). $^1$H NMR (400 MHz, CD$_3$OD) δ 8.49 (s, 2H), 7.97 (s, 1H), 7.65 (brs, 1H), 7.46-7.33 (m, 7H), 6.02 (s, 1H), 4.70-4.66 (m, 1H), 4.54 (m, 1H), 4.48-4.44 (m, 1H), 3.81-3.74 (m, 1H), 3.54-3.50 (m, 2H), 3.10-3.07 (m, 1H), 2.38-2.37 (m, 1H), 2.26-2.25 (m, 4H). MS (ES+) m/e 400.1 (M+H)$^+$.

Example 113

N-(2-(3,5-dimethylpiperazin-1-yl)-6-methylpyrimidin-4-yl)-1H-indazol-5-amine

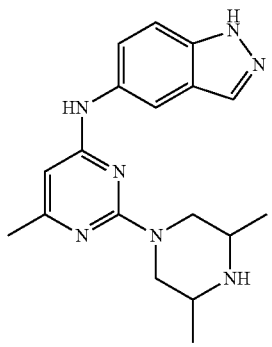

The reaction was conducted following general protocol A. The reaction time of the first step was 50 hours and the crude material was further used without additional purification. The final residue was purified by reverse phase preparative HPLC to afford N-(2-(3,5-dimethylpiperazin-1-yl)-6-methylpyrimidin-4-yl)-1H-indazol-5-amine as an yellow oil (37%). $^1$H NMR (400 MHz, CD$_3$OD) δ 8.39 (brs, 2H), 8.01 (s, 1H), 7.97 (s, 1H), 7.53 (d, J=8.8 Hz, 1H), 7.45 (d, J=8.8, 2.0 Hz, 1H), 6.01 (s, 1H), 4.95-4.94 (m, 2H), 3.37-3.36 (m, 2H), 2.88-2.82 (m, 2H), 2.24 (s, 3H), 1.38 (d, J=6.4 Hz, 6H). MS (ES+) m/e 338.1 (M+H)$^+$.

Example 114

N-(2-(3-ethylpiperazin-1-yl)-6-methylpyrimidin-4-yl)-1H-indazol-5-amine

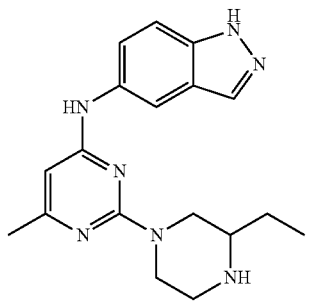 [SMILES: CCC1CN(c2nc(C)cc(Nc3ccc4[nH]ncc4c3)n2)CCN1]

The reaction was conducted following general protocol A. The reaction time of the first step was 36 hours and the crude material was further used without additional purification. The final residue was purified by reverse phase preparative HPLC to afford N-(2-(3-ethylpiperazin-1-yl)-6-methylpyrimidin-4-yl)-1H-indazol-5-amine as an yellow solid (9%). $^1$H NMR (400 MHz, CD$_3$OD) δ 8.43 (brs, 2H), 7.99 (s, 2H), 7.53-7.46 (m, 2H), 6.01 (s, 1H), 4.80-4.77 (m, 2H), 3.43-3.40 (m, 1H), 3.28 (m, 1H), 3.17-3.13 (m, 2H), 3.04-3.01 (m, 1H), 2.24 (s, 3H), 1.75-1.68 (m, 2H), 1.09 (t, J=7.6 Hz, 3H). MS (ES+) m/e 338.1 (M+H)$^+$.

Example 115

N-(2-(3-isopropylpiperazin-1-yl)-6-methylpyrimidin-4-yl)-1H-indazol-5-amine

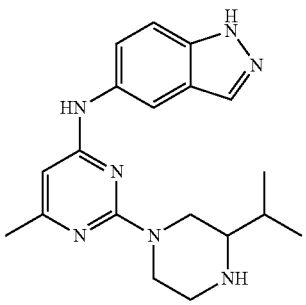 [SMILES: Cc1cc(Nc2ccc3[nH]ncc3c2)nc(N2CCNC(C(C)C)C2)n1]

The reaction was conducted following general protocol A. The reaction time of the first step was 36 hours and the crude material was further used without additional purification. The final residue was purified by reverse phase preparative HPLC to afford N-(2-(3-isopropylpiperazin-1-yl)-6-methylpyrimidin-4-yl)-1H-indazol-5-amine as an yellow solid (30%). $^1$H NMR (400 MHz, CD$_3$OD) δ 8.46 (brs, 2H), 8.01 (s, 1H), 7.98 (s, 1H), 7.53-7.46 (m, 2H), 6.01 (s, 1H), 5.02-4.97 (m, 1H), 4.83 (m, 1H), 3.43-3.40 (m, 1H), 3.21-3.13 (m, 2H), 2.99-2.96 (m, 2H), 2.24 (s, 3H), 1.96-1.91 (m, 1H), 1.13-1.10 (m, 6H). MS (ES+) m/e 352.1 (M+H)$^+$.

Example 116

N-(6-methyl-2-(5-methyl-1,4-diazepan-1-yl)pyrimidin-4-yl)-1H-indazol-5-amine

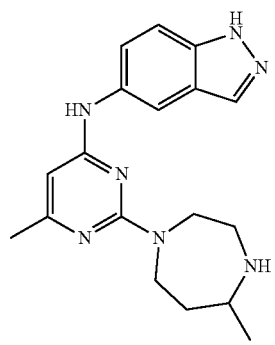 [SMILES: Cc1cc(Nc2ccc3[nH]ncc3c2)nc(N2CCNC(C)CC2)n1]

The reaction was conducted following general protocol A. The reaction time of the first step was 36 hours and the crude material was further used without additional purification. The final residue was purified by reverse phase preparative HPLC to afford N-(6-methyl-2-(5-methyl-1,4-diazepan-1-yl)pyrimidin-4-yl)-1H-indazol-5-amine as an yellow solid (8%). $^1$H NMR (400 MHz, CD$_3$OD) δ 8.10 (s, 1H), 8.00 (brs, 1H), 7.63-7.61 (m, 1H), 7.51 (m, 1H), 6.23 (s, 1H), 4.13-4.03 (m, 3H), 3.76-3.70 (m, 1H), 3.69 (m, 2H), 3.57 (m, 1H), 2.43 (s, 3H), 2.19 (m, 2H), 1.43 (d, J=6.4 Hz, 3H). MS (ES+) m/e 338.1 (M+H)$^+$.

Example 117

N-(6-methyl-2-(2-methyl-1,4-diazepan-1-yl)pyrimidin-4-yl)-1H-indazol-5-amine

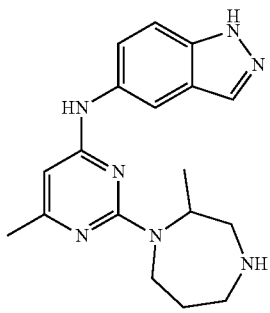 [SMILES: Cc1cc(Nc2ccc3[nH]ncc3c2)nc(N2CCCNCC2C)n1]

The reaction was conducted following general protocol B. The reaction time of the first step was 48 hours and the crude material was further used without additional purification. The final residue was purified by reverse phase preparative HPLC to afford N-(6-methyl-2-(2-methyl-1,4-diazepan-1-yl)pyrimidin-4-yl)-1H-indazol-5-amine as an white solid (6%). $^1$H NMR (400 MHz, CD$_3$OD) δ 8.17 (s, 1H), 7.94 (s, 1H), 7.50-7.44 (m, 2H), 5.88 (s, 1H), 4.59 (m, 1H), 4.45-4.42 (m, 1H), 3.41-3.36 (m, 1H), 3.17-3.13 (m, 2H), 2.76-2.70 (m, 2H), 2.20 (s, 3H), 1.94-1.76 (m, 2H), 1.15 (d, J=5.6 Hz, 3H). MS (ES+) m/e 338.0 (M+H)$^+$.

Example 118

N-(6-methyl-2-(6-methyl-1,4-diazepan-1-yl)pyrimidin-4-yl)-1H-indazol-5-amine

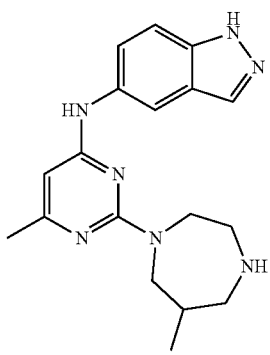 [SMILES: Cc1cc(Nc2ccc3[nH]ncc3c2)nc(N2CCNCC(C)C2)n1]

The reaction was conducted following general protocol A. The reaction time of the first step was 16 hours and the crude material was further used without additional purification. The final residue was purified by reverse phase preparative HPLC to afford N-(6-methyl-2-(6-methyl-1,4-diazepan-1-yl)pyrimidin-4-yl)-1H-indazol-5-amine as an white solid (4%). $^1$H NMR (400 MHz, CD$_3$OD) δ 8.09 (s, 1H), 7.98 (m, 1H), 7.62-7.61 (m, 1H), 7.50 (m, 1H), 6.23 (s, 1H), 4.17 (m, 2H), 3.97 (m, 1H), 3.62 (m, 1H), 3.39-3.36 (m, 1H), 3.27-3.15 (m, 2H), 3.10 (m, 1H), 2.42 (m, 4H), 1.06 (m, 3H). MS (ES+) m/e 338.1 (M+H)$^+$.

Example 119

N-(2-(3,8-diazabicyclo[3.2.1]octan-3-yl)-6-methylpyrimidin-4-yl)-1H-indazol-5-amine

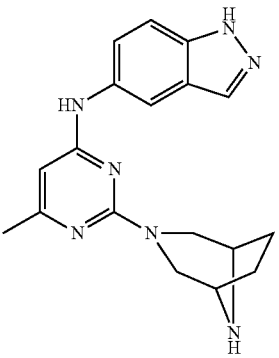 [SMILES: Cc1cc(Nc2ccc3[nH]ncc3c2)nc(N2CC3CCC(C2)N3)n1]

The reaction was conducted following general protocol A. The reaction time of the first step was 16 hours and the crude material was further used without additional purification. The final residue was purified by reverse phase preparative HPLC to afford N-(2-(3,8-diazabicyclo[3.2.1]octan-3-yl)-6-methylpyrimidin-4-yl)-1H-indazol-5-amine an white solid (18%). $^1$H NMR (400 MHz, DMSO-d$_6$) δ 13.06 (brs, 1H), 10.32 (s, 1H), 9.31-9.10 (m, 2H), 8.08 (s, 1H), 7.94 (s, 1H), 7.56 (d, J=8.8 Hz, 1H), 7.45 (d, J=8.8 Hz, 1H), 6.17 (s, 1H), 4.32-4.22 (m, 4H), 3.40 (d, J=14.0 Hz, 2H), 2.30 (s, 3H), 1.96-1.95 (m, 2H), 1.86-1.84 (m, 2H). MS (ES+) m/e 336.1 (M+H)$^+$.

Example 120

N-(2-(3,6-diazabicyclo[3.1.1]heptan-3-yl)-6-methylpyrimidin-4-yl)-1H-indazol-5-amine

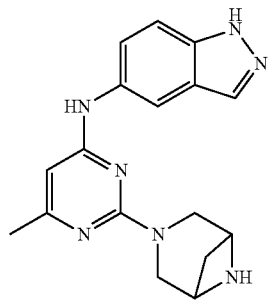 [SMILES: Cc1cc(Nc2ccc3[nH]ncc3c2)nc(N2CC3CC(C2)N3)n1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.1.1]heptan-3-yl)-6-methylpyrimidin-4-yl)-1H-indazol-5-amine an white solid (13%). $^1$H NMR (400 MHz, DMSO-d$_6$) δ 13.07 (brs, 1H), 10.55 (s, 1H), 9.71 (s, 1H), 8.29 (s, 1H), 8.13-8.02 (m, 2H), 7.56-7.49 (m, 2H), 6.41 (s, 1H), 4.50 (d, J=5.2 Hz, 2H), 4.18-3.90 (m, 4H), 2.94-2.86 (m, 1H), 2.37 (s, 3H), 1.88-1.84 (m, 1H). MS (ES+) m/e 322.1 (M+H)$^+$.

Example 121

N-(6-methyl-2-(2,7-diazaspiro[3.5]nonan-7-yl)pyrimidin-4-yl)-1H-indazol-5-amine

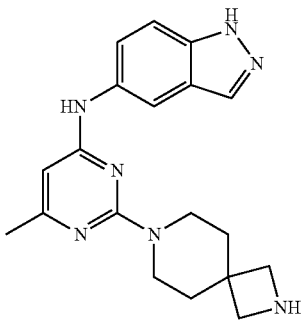 [SMILES: Cc1cc(Nc2ccc3[nH]ncc3c2)nc(N2CCC3(CC2)CNC3)n1]

The reaction was conducted following general protocol A. The reaction time of the first step was 16 hours and the crude material was further used without additional purification. The final residue was purified by reverse phase preparative HPLC to afford N-(6-methyl-2-(2,7-diazaspiro[3.5]nonan-7-yl)pyrimidin-4-yl)-1H-indazol-5-amine as an off-white solid (23%). $^1$H NMR (400 MHz, DMSO-$d_6$) δ 13.13 (brs, 1H), 11.78 (brs, 1H), 10.61 (brs, 1H), 8.80 (brs, 2H), 8.06-8.01 (m, 2H), 7.58-7.47 (m, 2H), 6.10 (s, 1H), 3.80-3.70 (m, 8H), 2.29 (s, 3H), 1.85 (m, 4H). MS (ES+) m/e 350.1 (M+H)$^+$.

Example 122

N-(6-methyl-2-(2,6-diazaspiro[3.4]octan-6-yl)pyrimidin-4-yl)-1H-indazol-5-amine

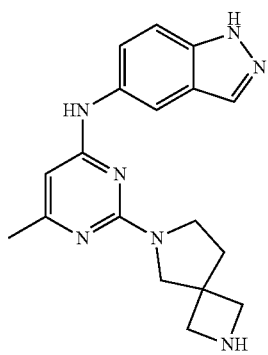 [SMILES: Cc1cc(Nc2ccc3[nH]ncc3c2)nc(N2CCC3(CNC3)C2)n1]

The reaction was conducted following general protocol A. The reaction time of the first step was 16 hours and the crude material was further used without additional purification. The final residue was purified by reverse phase preparative HPLC to afford N-(6-methyl-2-(2,6-diazaspiro[3.4]octan-6-yl)pyrimidin-4-yl)-1H-indazol-5-amine as an off-white solid (31%). $^1$H NMR (400 MHz, DMSO-$d_6$) δ 13.16 (brs, 1H), 11.91 (brs, 1H), 10.61 (brs, 1H), 9.09-8.97 (m, 2H), 8.22-8.12 (m, 2H), 7.57 (s, 2H), 6.17 (s, 1H), 4.07 (m, 2H), 3.95 (m, 2H), 3.84 (m, 2H), 3.62 (m, 2H), 2.32 (m, 5H). MS (ES+) m/e 336.1 (M+H)$^+$.

Example 123

N-(6-methyl-2-(1-oxa-4,9-diazaspiro[5.5]undecan-9-yl)pyrimidin-4-yl)-1H-indazol-5-amine

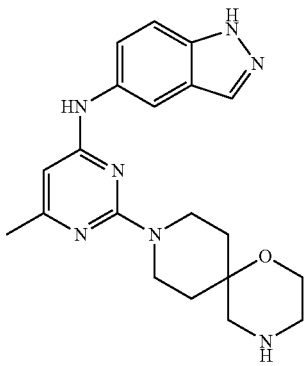 [SMILES: Cc1cc(Nc2ccc3[nH]ncc3c2)nc(N2CCC3(CC2)CNCCO3)n1]

The reaction was conducted following general protocol A. The reaction time of the first step was 16 hours and the crude material was further used without additional purification. The final residue was purified by reverse phase preparative HPLC to afford N-(6-methyl-2-(1-oxa-4,9-diazaspiro[5.5]undecan-9-yl)pyrimidin-4-yl)-1H-indazol-5-amine as an brown (38%). $^1$H NMR (400 MHz, DMSO-$d_6$) δ 13.17 (brs, 1H), 11.84 (brs, 1H), 10.58 (brs, 1H), 9.12 (s, 2H), 8.08 (s, 1H), 8.02 (s, 1H), 7.58-7.48 (m, 2H), 6.13 (m, 1H), 4.17-4.15 (m, 2H), 3.85 (m, 2H), 3.40-3.33 (m, 2H), 3.09-3.05 (m, 4H), 2.34 (s, 3H), 2.03-2.00 (m, 2H), 1.69-1.64 (m, 2H). MS (ES+) m/e 380.1 (M+H)$^+$.

Example 124

N-(6-methyl-2-(2,7-diazaspiro[4.5]decan-2-yl)pyrimidin-4-yl)-1H-indazol-5-amine

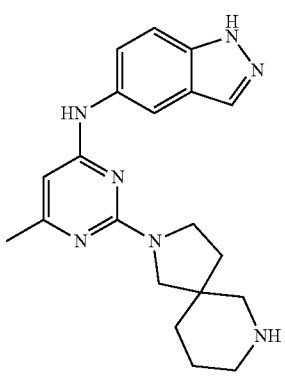 [SMILES: Cc1cc(Nc2ccc3[nH]ncc3c2)nc(N2CCC3(CCCNC3)C2)n1]

The reaction was conducted following general protocol A. The reaction time of the first step was 16 hours and the crude material was further used without additional purification. The final residue was purified by reverse phase preparative HPLC to afford N-(6-methyl-2-(2,7-diazaspiro[4.5]decan-2-yl)pyrimidin-4-yl)-1H-indazol-5-amine as an off-white solid (41%). $^1$H NMR (400 MHz, DMSO-$d_6$) δ 13.12 (brs, 1H), 11.77 (brs, 1H), 10.63 (brs, 1H), 7.80 (m, 2H), 8.27 (brs, 1H), 8.08 (s, 1H), 7.56 (m, 2H), 6.18 (m, 1H), 3.68 (m, 4H), 3.06 (m, 4H), 2.33 (s, 3H), 2.13 (m, 1H), 1.93 (m, 1H), 1.69 (m, 4H). MS (ES+) m/e 364.1 (M+H)+.

Example 125

N-(6-methyl-2-(2,7-diazaspiro[4.5]decan-7-yl)pyrimidin-4-yl)-1H-indazol-5-amine

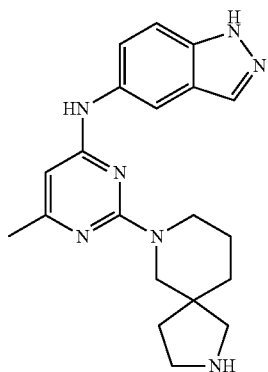 [SMILES: Cc1cc(Nc2ccc3[nH]ncc3c2)nc(N2CCCC3(CCNC3)C2)n1]

The reaction was conducted following general protocol A. The reaction time of the first step was 16 hours and the crude material was further used without additional purification. The final residue was purified by reverse phase preparative HPLC to afford N-(6-methyl-2-(2,7-diazaspiro[4.5]decan-7-yl)pyrimidin-4-yl)-1H-indazol-5-amine as an off-white solid (41%). $^1$H NMR (400 MHz, DMSO-d$_6$) δ 13.11 (brs, 1H), 11.68 (brs, 1H), 10.62 (brs, 1H), 8.92 (brs, 2H), 8.09-8.01 (m, 2H), 7.57-7.47 (m, 2H), 6.18-6.07 (m, 1H), 3.74 (m, 4H), 3.32 (m, 2H), 3.03-2.98 (m, 2H), 2.28 (s, 3H), 1.87-1.84 (m, 1H), 1.72-1.65 (m, 5H). MS (ES+) m/e 364.1 (M+H)+.

Example 126

N-(6-methyl-2-(2,6-diazaspiro[3.4]octan-2-yl)pyrimidin-4-yl)-1H-indazol-5-amine

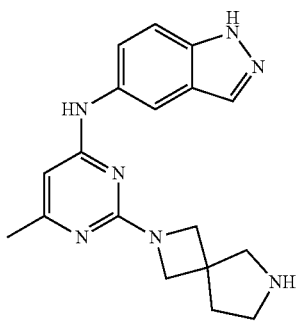 [SMILES: Cc1cc(Nc2ccc3[nH]ncc3c2)nc(N2CC3(CCNC3)C2)n1]

The reaction was conducted following general protocol A. The reaction time of the first step was 16 hours and the crude material was further used without additional purification. The final residue was purified by reverse phase preparative HPLC to afford N-(6-methyl-2-(2,6-diazaspiro[3.4]octan-2-yl)pyrimidin-4-yl)-1H-indazol-5-amine as an off-white solid (18%). $^1$H NMR (400 MHz, D$_2$O) δ 8.04 (s, 2H), 7.57-7.51 (m, 1H), 7.37-7.35 (m, 1H), 5.88 (s, 1H), 4.08-4.05 (m, 4H), 3.49 (s, 2H), 3.33 (t, J=7.2 Hz, 2H), 2.28 (m, 2H), 2.14 (s, 3H). MS (ES+) m/e 336.1 (M+H)+.

Example 127

N-(6-methyl-2-(2,7-diazaspiro[3.5]nonan-2-yl)pyrimidin-4-yl)-1H-indazol-5-amine

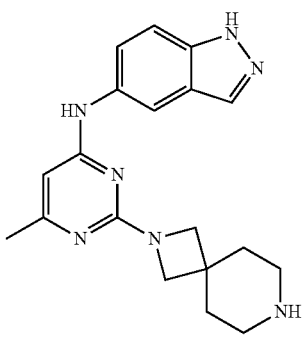 [SMILES: Cc1cc(Nc2ccc3[nH]ncc3c2)nc(N2CC3(CCNCC3)C2)n1]

The reaction was conducted following general protocol A. The reaction time of the first step was 16 hours and the crude material was further used without additional purification. The final residue was purified by reverse phase preparative HPLC to afford N-(6-methyl-2-(2,7-diazaspiro[3.5]nonan-2-yl)pyrimidin-4-yl)-1H-indazol-5-amine as an off-white solid (11%). H NMR (400 MHz, DMSO-d$_6$) δ 13.16 (brs, 1H), 12.24 (brs, 1H), 10.59 (brs, 1H), 8.63 (s, 2H), 8.19 (brs, 1H), 8.11 (s, 1H), 7.56-7.49 (m, 2H), 6.15 (brs, 1H), 4.00 (s, 4H), 3.08 (m, 4H), 2.30 (s, 3H), 1.97 (m, 4H). MS (ES+) m/e 350.1 (M+H)+.

Example 128

N-(6-methyl-2-(2,6-diazaspiro[3.3]heptan-2-yl)pyrimidin-4-yl)-1H-indazol-5-amine

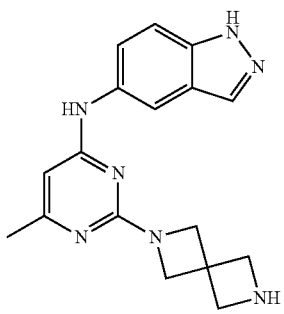 [SMILES: Cc1cc(Nc2ccc3[nH]ncc3c2)nc(N2CC3(CNC3)C2)n1]

The reaction was conducted following general protocol A. The reaction time of the first step was 16 hours and the crude material was further used without additional purification. The final residue was purified by reverse phase preparative HPLC to afford N-(6-methyl-2-(2,6-diazaspiro[3.3]heptan-2-yl)pyrimidin-4-yl)-1H-indazol-5-amine as an off-white solid (34%). $^1$H NMR (400 MHz, DMSO-d$_6$) δ 13.16 (brs, 1H), 12.37 (brs, 1H), 10.61 (brs, 1H), 8.68 (s, 2H), 8.19 (brs, 1H), 8.06 (brs, 1H), 7.58-7.52 (m, 2H), 6.15 (s, 1H), 4.37 (s, 4H), 4.21-4.18 (m, 4H), 2.29 (s, 3H). MS (ES+) m/e 322.1 (M+H)+.

Example 129

N-(2-(3,6-diazabicyclo[3.2.1]octan-3-yl)-6-methylpyrimidin-4-yl)-1H-indazol-5-amine

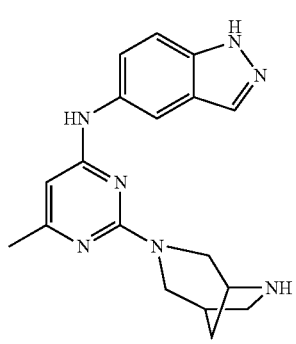 [SMILES: Cc1cc(Nc2ccc3[nH]ncc3c2)nc(N2CC3CNC(C3)C2)n1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.2.1]octan-3-yl)-6-methylpyrimidin-4-yl)-1H-indazol-5-amine as an off-white solid (9%). $^1$H NMR (400 MHz, CD$_3$OD) δ 8.11 (s, 1H), 8.02 (s, 1H), 7.63-7.54 (m, 2H), 6.26 (brs, 1H), 4.49-4.46 (m, 1H), 4.28 (m, 2H), 3.44-3.40 (m, 4H), 2.93 (m, 1H), 2.43 (s, 3H), 2.20-2.12 (m, 2H). MS (ES+) m/e 336.1 (M+H)$^+$.

Example 130

N-(2-(3,7-diazabicyclo[3.3.1]nonan-3-yl)-6-methylpyrimidin-4-yl)-1H-indazol-5-amine

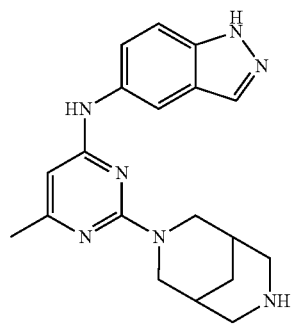 [SMILES: Cc1cc(Nc2ccc3[nH]ncc3c2)nc(N2CC3CNCC(C3)C2)n1]

The reaction was conducted following general protocol A. The reaction time of the first step was 16 hours and the crude material was further used without additional purification. The final residue was purified by reverse phase preparative HPLC to afford N-(2-(3,7-diazabicyclo[3.3.1]nonan-3-yl)-6-methylpyrimidin-4-yl)-1H-indazol-5-amine as an off-white solid (4%). $^1$H NMR (400 MHz, CD$_3$OD) δ 8.10 (s, 1H), 8.06 (s, 1H), 7.61 (m, 2H), 6.25 (brs, 1H), 4.49-4.46 (m, 2H), 3.55-3.44 (m, 4H), 3.37 (m, 2H), 2.42 (m, 5H), 2.13-2.02 (m, 2H). MS (ES+) m/e 350.1 (M+H)$^+$.

Example 131

N-(6-methyl-2-(octahydro-5H-pyrrolo[3,2-c]pyridin-5-yl)pyrimidin-4-yl)-1H-indazol-5-amine

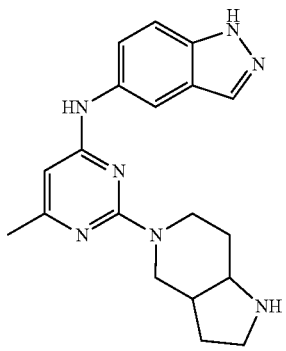 [SMILES: Cc1cc(Nc2ccc3[nH]ncc3c2)nc(N2CCC3NCCC3C2)n1]

The reaction was conducted following general protocol A. The reaction time of the first step was 16 hours and the crude material was further used without additional purification. The final residue was purified by reverse phase preparative HPLC to afford N-(6-methyl-2-(octahydro-5H-pyrrolo[3,2-c]pyridin-5-yl)pyrimidin-4-yl)-1H-indazol-5-amine as an off-white solid (7%). $^1$H NMR (400 MHz, CD$_3$OD) δ 8.09 (s, 1H), 8.02 (brs, 1H), 7.63-7.52 (m, 2H), 6.18 (brs, 1H), 4.12-4.08 (m, 1H), 3.99-3.94 (m, 3H), 3.57-3.51 (m, 2H), 3.39-3.37 (m, 1H), 2.76-2.71 (m, 1H), 2.41 (s, 3H), 2.26-2.22 (m, 2H), 2.05-2.00 (m, 1H), 1.93-1.87 (m, 1H). MS (ES+) m/e 350.1 (M+H)$^+$.

Example 132

N-(6-methyl-2-(octahydropyrrolo[3,4-d]azepin-6(1H)-yl)pyrimidin-4-yl)-1H-indazol-5-amine

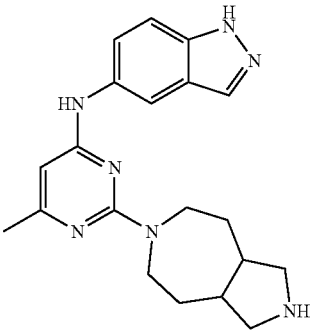 [SMILES: Cc1cc(Nc2ccc3[nH]ncc3c2)nc(N2CCC3CNCC3CC2)n1]

The reaction was conducted following general protocol A. The reaction time of the first step was 16 hours and the crude material was further used without additional purification. The final residue was purified by reverse phase preparative HPLC to afford N-(6-methyl-2-(octahydropyrrolo[3,4-d]azepin-6(1H)-yl)pyrimidin-4-yl)-1H-indazol-5-amine an off-white solid (13%). $^1$H NMR (400 MHz, CD$_3$OD) δ 8.09 (m, 2H), 7.59-7.54 (m, 2H), 6.19 (s, 1H), 4.08 (m, 2H), 3.66-3.60 (m, 2H), 3.54-3.50 (m, 2H), 3.09-3.04 (m, 2H), 2.70 (m, 2H), 2.42 (s, 3H), 2.03 (m, 2H), 1.93-1.91 (m, 2H). MS (ES+) m/e 364.1 (M+H)$^+$.

Example 133

N-(6-methyl-2-(octahydro-2H-pyrazino[1,2-a]pyrazin-2-yl)pyrimidin-4-yl)-1H-indazol-5-amine

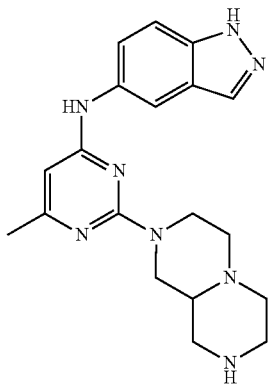 [SMILES: Cc1cc(Nc2ccc3[nH]ncc3c2)nc(N2CCN3CCNCC3C2)n1]

The reaction was conducted following general protocol A. The reaction time of the first step was 16 hours and the crude material was further used without additional purification. The final residue was purified by reverse phase preparative HPLC to afford N-(6-methyl-2-(octahydro-2H-pyrazino[1,2-a]pyrazin-2-yl)pyrimidin-4-yl)-1H-indazol-5-amine a light brown solid (11%). $^1$H NMR (400 MHz, CD$_3$OD) δ 8.10 (s, 1H), 8.02 (brs, 1H), 7.63-7.53 (m, 2H), 6.20 (s, 1H), 4.44 (m, 2H), 3.44-3.41 (m, 1H), 3.25-3.20 (m, 3H), 3.09-3.06 (m, 1H), 3.03-3.00 (m, 1H), 2.96-2.90 (m, 2H), 2.54-2.41 (m, 6H). MS (ES+) m/e 365.1 (M+H)$^+$.

Example 134

N-(2-(3,6-diazabicyclo[3.2.0]heptan-3-yl)-6-methylpyrimidin-4-yl)-1H-indazol-5-amine

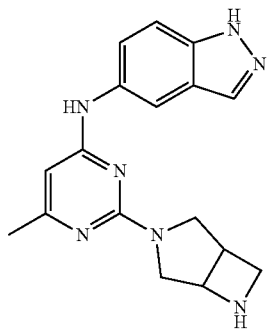 [SMILES: Cc1cc(Nc2ccc3[nH]ncc3c2)nc(N2CC3CNC3C2)n1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.2.0]heptan-3-yl)-6-methylpyrimidin-4-yl)-1H-indazol-5-amine a light brown solid (19%). $^1$H NMR (400 MHz, CD$_3$OD) δ 8.15 (s, 1H), 8.10 (s, 1H), 7.60 (m, 2H), 6.27 (s, 1H), 5.13-5.10 (m, 1H), 4.62-4.59 (m, 1H), 4.29-4.26 (m, 2H), 3.82-3.72 (m, 2H), 3.64-3.62 (m, 2H), 2.45 (s, 3H). MS (ES+) m/e 322.1 (M+H)$^+$.

Example 135

N-(2-(3,7-diazabicyclo[4.2.0]octan-3-yl)-6-methylpyrimidin-4-yl)-1H-indazol-5-amine The reaction was conducted following general protocol A. The reaction time of the first step was 16 hours and the crude material was further used without additional purification. The final residue was purified by reverse phase preparative HPLC to afford N-(2-(3,7-diazabicyclo[4.2.0]octan-3-yl)-6-methylpyrimidin-4-yl)-1H-indazol-5-amine a light brown solid (21%). $^1$H NMR (400 MHz, CD$_3$OD) δ 8.09 (m, 2H), 7.59 (m, 2H), 6.23 (s, 1H), 4.80-4.77 (m, 1H), 4.18-4.05 (m, 3H), 3.97-3.92 (m, 2H), 3.75-3.71 (m, 1H), 3.38-3.37 (m, 1H), 2.44-2.40 (m, 5H). MS (ES+) m/e 336.1 (M+H)$^+$.

Example 136

N-(2-([3,3'-bipiperidin]-1-yl)-6-methylpyrimidin-4-yl)-1H-indazol-5-amine

The reaction was conducted following general protocol A. The reaction time of the first step was 16 hours and the crude material was further used without additional purification. The final residue was purified by reverse phase preparative HPLC to afford N-(2-([3,3'-bipiperidin]-1-yl)-6-methylpyrimidin-4-yl)-1H-indazol-5-amine a light brown solid (6%). $^1$H NMR (400 MHz, CD$_3$OD) δ 8.09 (s, 1H), 8.01 (s, 1H), 7.61 (d, J=8.4 Hz, 1H), 7.47 (d, J=8.0 Hz, 1H), 6.15 (s, 1H), 4.63-4.60 (m, 1H), 4.22-4.20 (m, 1H), 3.42-3.39 (m, 1H), 3.27-3.19 (m, 2H), 2.88 (m, 1H), 2.75 (m, 1H), 2.62-2.60 (m, 1H), 2.40 (s, 3H), 1.96-1.86 (m, 2H), 1.73 (m, 1H), 1.61-1.55 (m, 4H), 1.39-1.32 (m, 2H), 0.92 (m, 1H). MS (ES+) m/e 392.1 (M+H)$^+$.

Example 137

N-(6-methyl-2-(3-(piperidin-4-yl)indolin-1-yl)pyrimidin-4-yl)-1H-indazol-5-amine

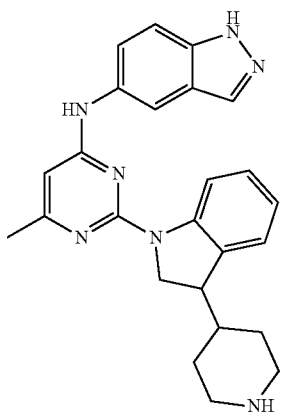 [SMILES: Cc1cc(Nc2ccc3[nH]ncc3c2)nc(N2CC(C3CCNCC3)c3ccccc32)n1]

The reaction was conducted following general protocol D. The reaction time of the first step was 16 hours and the crude material was further used without additional purification. The final residue was purified by reverse phase preparative HPLC to afford N-(6-methyl-2-(3-(piperidin-4-yl)indolin-1-yl)pyrimidin-4-yl)-1H-indazol-5-amine as a yellow solid (44%). $^1$H NMR (400 MHz, DMSO-d$_6$) δ 13.13 (brs, 1H), 9.93 (brs, 1H), 8.54-8.51 (m, 1H), 8.19 (m, 2H), 8.07 (m, 2H), 7.60 (d, J=8.8 Hz, 1H), 7.42 (d, J=8.0 Hz, 1H), 7.26-7.24 (m, 1H), 6.96 (m, 2H), 6.20 (s, 1H), 4.21-4.18 (m, 1H), 4.10-4.07 (m, 1H), 3.46-3.44 (m, 1H), 3.32-3.24 (m, 2H), 2.85-2.80 (m, 2H), 2.33 (s, 3H), 1.96 (m, 1H), 1.83-1.80 (m, 1H), 1.44 (m, 3H). MS (ES+) m/e 426.1 (M+H)$^+$.

Example 138

N-(6-methyl-2-(spiro[indoline-3,4'-piperidin]-1-yl)pyrimidin-4-yl)-1H-indazol-5-amine

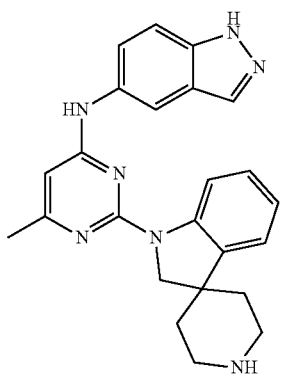 [SMILES: Cc1cc(Nc2ccc3[nH]ncc3c2)nc(N2CC3(CCNCC3)c3ccccc32)n1]

The reaction was conducted following general protocol D. The reaction time of the first step was 16 hours and the crude material was further used without additional purification. The final residue was purified by reverse phase preparative HPLC to afford N-(6-methyl-2-(spiro[indoline-3,4'-piperidin]-1-yl)pyrimidin-4-yl)-1H-indazol-5-amine as a yellow solid (39%). $^1$H NMR (400 MHz, DMSO-d$_6$) δ 13.21 (brs, 1H), 9.97 (brs, 1H), 8.82 (m, 1H), 8.59-8.57 (m, 1H), 8.12-8.08 (m, 3H), 7.60 (d, J=8.8 Hz, 1H), 7.40 (dd, J=8.8, 1.6 Hz, 1H), 7.19-7.17 (m, 1H), 7.02-6.99 (m, 2H), 6.23 (s, 1H), 4.22 (s, 2H), 3.43-3.40 (m, 2H), 3.08-3.02 (m, 2H), 2.35 (s, 3H), 2.07-2.01 (m, 2H), 1.87-1.84 (m, 2H). MS (ES+) m/e 412.1 (M+H)$^+$.

Example 139

N-(6-methyl-2-(3-(piperidin-3-yl)indolin-1-yl)pyrimidin-4-yl)-1H-indazol-5-amine

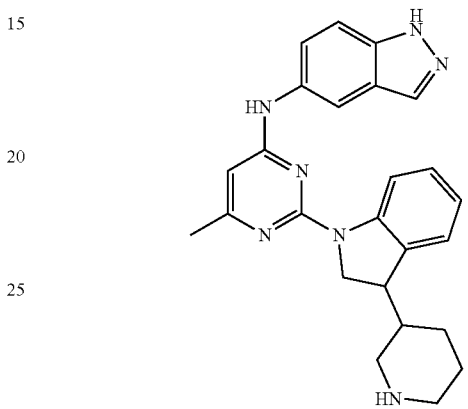

The reaction was conducted following general protocol D. The reaction time of the first step was 16 hours and the crude material was further used without additional purification. The final residue was purified by reverse phase preparative HPLC to afford N-(6-methyl-2-(3-(piperidin-3-yl)indolin-1-yl)pyrimidin-4-yl)-1H-indazol-5-amine as a yellow solid (28%). $^1$H NMR (400 MHz, DMSO-d$_6$) δ 13.13 (brs, 1H), 9.89 (brs, 1H), 8.73-8.59 (m, 1H), 8.35-8.32 (m, 1H), 8.18 (m, 1H), 8.12-8.04 (m, 2H), 7.59 (d, J=8.8 Hz, 1H), 7.41 (d, J=8.8 Hz, 1H), 7.26-7.21 (m, 1H), 6.97 (m, 2H), 6.20 (s, 1H), 4.19-4.12 (m, 2H), 3.49-3.48 (m, 1H), 3.34-3.31 (m, 1H), 3.24-3.21 (m, 1H), 2.80-2.77 (m, 2H), 2.34 (s, 3H), 1.79-1.75 (m, 1H), 1.48-1.44 (m, 1H), 1.32-1.29 (m, 3H). MS (ES+) m/e 412.1 (M+H)$^+$.

Example 140

N-(5-fluoro-2-(3-methylpiperazin-1-yl)pyrimidin-4-yl)-1H-indazol-5-amine

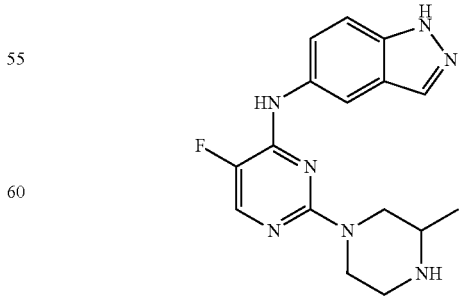

The reaction was conducted following general protocol A. The reaction time of the first step was 16 hours and the crude material was further used without additional purification. The final residue was purified by reverse phase preparative HPLC to afford N-(5-fluoro-2-(3-methylpiperazin-1-yl)pyrimidin-4-yl)-1H-indazol-5-amine a white solid (41%). $^1$H NMR (400 MHz, DMSO-d$_6$) δ 13.03 (brs, 1H), 9.29 (s, 1H), 8.30 (s, 2H), 8.07 (d, J=1.2 Hz, 1H), 8.00 (d, J=0.8 Hz, 1H), 7.99 (d, J=3.6 Hz, 1H), 7.60 (dd, J=8.8, 2.0 Hz, 1H), 7.49 (d, J=9.2 Hz, 1H), 4.33 (t, J=10.8 Hz, 2H), 3.01 (d, J=12.0 Hz, 1H), 2.91-2.77 (m, 2H), 2.74-2.67 (m, 1H), 2.59-2.52 (m, 1H), 1.06 (d, J=6.4 Hz, 3H). MS (ES+) m/e 328.1 (M+H)$^+$.

Example 141

N-(5-fluoro-2-(3-phenyl-1,4-diazepan-1-yl)pyrimidin-4-yl)-1H-indazol-5-amine

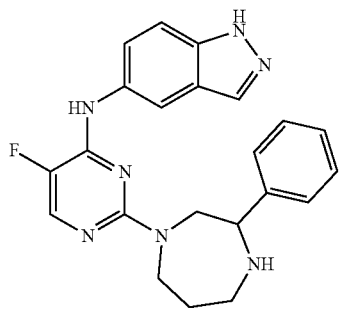 [SMILES: Fc1cnc(N2CCCNC(c3ccccc3)C2)nc1Nc1ccc2[nH]ncc2c1]

The reaction was conducted following general protocol C. The residue was purified by reverse phase preparative HPLC to afford N-(5-fluoro-2-(3-phenyl-1,4-diazepan-1-yl)pyrimidin-4-yl)-1H-indazol-5-amine as a yellow solid (29%). $^1$H NMR (400 MHz, CD$_3$OD) δ 8.47 (s, 2H), 7.95 (s, 1H), 7.91 (d, J=3.6 Hz, 1H), 7.72 (s, 1H), 7.51 (d, J=9.2 Hz, 1H), 7.40-7.17 (m, 6H), 4.51 (dd, J=15.2, 2.8 Hz, 1H), 4.43-4.37 (m, 2H), 3.70 (dd, J=15.2, 10.8 Hz, 1H), 3.53-3.42 (m, 2H), 3.08-2.98 (m, 1H), 2.39-2.27 (m, 1H), 2.25-2.12 (m, 1H). MS (ES+) m/e 404.1 (M+H)$^+$.

Example 142

N-(5-fluoro-2-(5-phenyl-1,4-diazepan-1-yl)pyrimidin-4-yl)-1H-indazol-5-amine

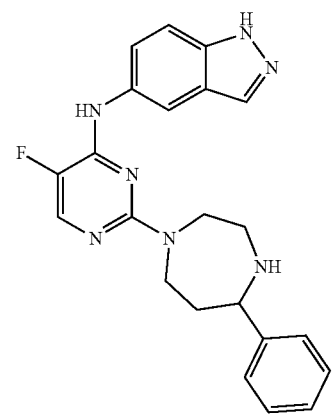 [SMILES: Fc1cnc(N2CCNC(c3ccccc3)CC2)nc1Nc1ccc2[nH]ncc2c1]

The reaction was conducted following general protocol C. The residue was purified by reverse phase preparative HPLC to afford N-(5-fluoro-2-(5-phenyl-1,4-diazepan-1-yl)pyrimidin-4-yl)-1H-indazol-5-amine as a yellow solid (19%). $^1$H NMR (400 MHz, CD$_3$OD) 8.43 (s, 2H), 8.08 (d, J=1.2 Hz, 1H), 7.96 (s, 1H), 7.92 (d, J=4.0 Hz, 1H), 7.61 (dd, J=9.2, 2.0 Hz, 1H), 7.50 (d, J=8.8 Hz, 1H), 7.46-7.38 (m, 5H), 4.42 (dd, J=11.2, 2.4, Hz 1H), 4.20-4.17 (m, 1H), 4.14-4.04 (m, 2H), 3.79-3.71 (m, 1H), 3.56-3.47 (m, 1H), 3.36 (m, 1H), 2.42-2.32 (m, 1H), 2.27-2.22 (m, 1H). MS (ES+) m/e 404.0 (M+H)$^+$.

Example 143

N-(2-(2-ethylpiperazin-1-yl)-5-fluoropyrimidin-4-yl)-1H-indazol-5-amine

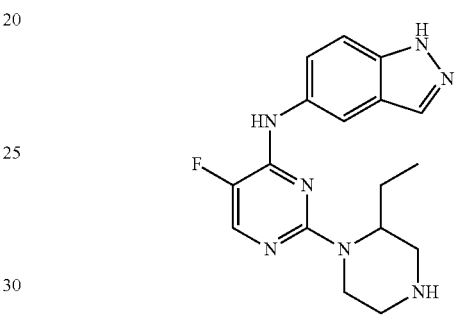

The reaction was conducted following general protocol A. The reaction time of the first step was 16 hours and the crude material was further used without additional purification. The final residue was purified by reverse phase preparative HPLC to afford N-(2-(2-ethylpiperazin-1-yl)-5-fluoropyrimidin-4-yl)-1H-indazol-5-amine a white solid (5%). $^1$H NMR (400 MHz, DMSO-d$_6$) δ 9.46 (s, 1H), 8.91 (s, 1H), 8.68 (s, 1H), 8.08-8.04 (m, 2H), 8.01 (s, 1H), 7.62-7.57 (m, 1H), 7.52-7.47 (m, 1H), 4.57 (d, J=13.6 Hz, 1H), 4.46 (d, J=12.80 Hz, 1H), 3.34 (d, J=12.4 Hz, 1H), 3.24-2.86 (m, 4H), 1.68-1.50 (m, 2H), 0.94 (t, J=7.6 Hz, 3H). MS (ES+) m/e 342.2 (M+H)$^+$.

Example 144

N-(5-fluoro-2-(3-isopropyl-1,4-diazepan-1-yl)pyrimidin-4-yl)-1H-indazol-5-amine

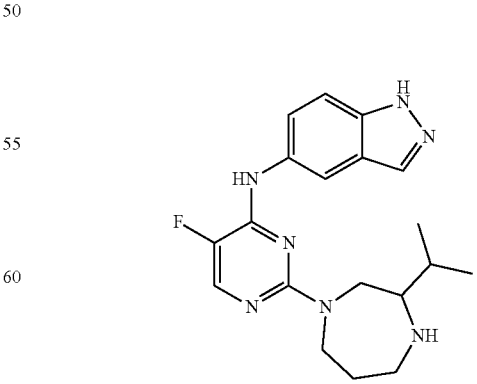

The reaction was conducted following general protocol C. The residue was purified by reverse phase preparative HPLC to afford N-(5-fluoro-2-(3-isopropyl-1,4-diazepan-1-yl)pyrimidin-4-yl)-1H-indazol-5-amine as a yellow solid (5%). ¹H NMR (400 MHz, DMSO-d₆) δ 9.41 (s, 1H), 8.53 (s, 1H), 8.32 (s, 1H), 8.08-7.95 (m, 3H), 7.62-7.47 (m, 2H), 4.14 (m, 1H), 4.00 (m, 1H), 3.61 (m, 1H), 3.53-3.51 (m, 2H), 3.19 (m, 1H), 2.99 (m, 1H), 2.04 (m, 3H), 0.79 (m, 6H). MS (ES+) m/e 369.9 (M+H)⁺.

Example 145

N-(5-fluoro-2-(5-isopropyl-1,4-diazepan-1-yl)pyrimidin-4-yl)-1H-indazol-5-amine

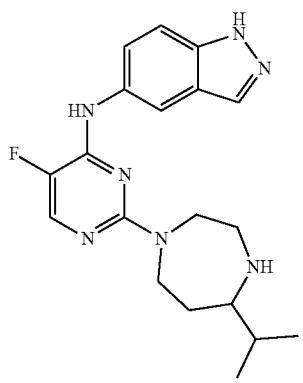 [SMILES: CC(C)C1CCN(c2ncc(F)c(Nc3ccc4[nH]ncc4c3)n2)CCN1]

The reaction was conducted following general protocol C. The residue was purified by reverse phase preparative HPLC to afford N-(5-fluoro-2-(5-isopropyl-1,4-diazepan-1-yl)pyrimidin-4-yl)-1H-indazol-5-amine as a yellow solid (5%). ¹H NMR (400 MHz, CD₃OD) δ 8.52 (s, 1H), 8.06 (d, J=1.2 Hz, 1H), 8.01 (d, J=0.8 Hz, 1H), 7.88 (d, J=4.0 Hz, 1H), 7.59 (dd, J=9.2, 2.0 Hz, 1H), 7.52 (d, J=9.2 Hz, 1H), 4.15-3.95 (m, 2H), 3.92-3.85 (m, 1H), 3.71-3.64 (m, 1H), 3.48-3.38 (m, 1H), 3.25-3.14 (m, 2H), 2.16-1.98 (m, 2H), 1.85-1.80 (m, 1H), 0.99 (t, J=7.2 Hz, 6H). MS (ES+) m/e 370.1 (M+H)⁺.

Example 146

N-(2-(5-ethyl-1,4-diazepan-1-yl)-5-fluoropyrimidin-4-yl)-1H-indazol-5-amine

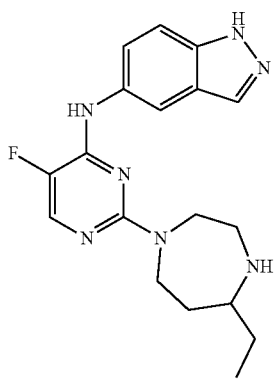 [SMILES: CCC1CCN(c2ncc(F)c(Nc3ccc4[nH]ncc4c3)n2)CCN1]

The reaction was conducted following general protocol C. The residue was purified by reverse phase preparative HPLC to afford N-(2-(5-ethyl-1,4-diazepan-1-yl)-5-fluoropyrimidin-4-yl)-1H-indazol-5-amine as a yellow solid (28%). ¹H NMR (400 MHz, CD₃OD) δ 8.51 (s, 1H), 8.07 (d, J=1.2 Hz, 1H), 8.01 (d, J=0.8 Hz, 1H), 7.88 (d, J=4.0 Hz, 1H), 7.59 (dd, J=8.8, 1.6 Hz, 1H), 7.52 (d, J=9.2 Hz, 1H), 4.08-3.89 (m, 3H), 3.69-3.62 (m, 1H), 3.48-3.40 (m, 1H), 3.27-3.20 (m, 2H), 2.22-2.12 (m, 1H), 1.92-1.82 (m, 1H), 1.78-1.60 (m, 2H), 1.01 (t, J=7.6 Hz, 3H). MS (ES+) m/e 356.1 (M+H)⁺.

Example 147

N-(5-fluoro-2-(3-isopropylpiperazin-1-yl)pyrimidin-4-yl)-1H-indazol-5-amine

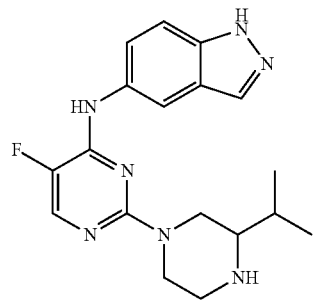 [SMILES: CC(C)C1CN(c2ncc(F)c(Nc3ccc4[nH]ncc4c3)n2)CCN1]

The reaction was conducted following general protocol A. The reaction time of the first step was 48 hours and the crude material was further used without additional purification. The final residue was purified by reverse phase preparative HPLC to afford N-(5-fluoro-2-(3-isopropylpiperazin-1-yl)pyrimidin-4-yl)-1H-indazol-5-amine a yellow solid (3%). ¹H NMR (400 MHz, CD₃OD) δ 8.49 (s, 2H), 8.03 (d, J=1.2 Hz, 1H), 7.99 (d, J=0.8 Hz, 1H), 7.90 (d, J=3.6 Hz, 1H), 7.56 (dd, J=9.2, 2.0 Hz, 1H), 7.51 (d, J=8.8 Hz, 1H), 4.82-4.80 (m, 1H), 4.66-4.63 (m, 1H), 3.37-3.34 (m, 1H), 3.11-3.04 (m, 2H), 2.91-2.88 (m, 2H), 1.91-1.80 (m, 1H), 1.06-1.00 (m, 6H). MS (ES+) m/e 356.1 (M+H)⁺.

Example 148

N-(2-(3-ethyl-1,4-diazepan-1-yl)-5-fluoropyrimidin-4-yl)-1H-indazol-5-amine

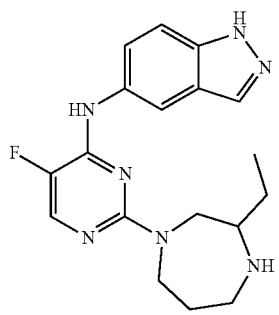 [SMILES: CCC1CN(c2ncc(F)c(Nc3ccc4[nH]ncc4c3)n2)CCCN1]

The reaction was conducted following general protocol A. The reaction time of the first step was 48 hours and the crude material was further used without additional purification. The final residue was purified by reverse phase preparative HPLC to afford N-(2-(3-ethyl-1,4-diazepan-1-yl)-5-fluoropyrimidin-4-yl)-1H-indazol-5-amine a yellow solid (4%). ¹H NMR (400 MHz, CD₃OD) δ 8.50 (s, 2H), 8.00 (s, 2H), 7.88 (d, J=4.0 Hz, 1H), 7.56-7.51 (m, 2H), 4.35-4.22 (m, 2H), 3.45-3.38 (m, 3H), 3.04-3.02 (m, 1H), 3.01-2.98 (m, 1H), 2.20-2.18 (m, 1H), 2.17-2.06 (m, 1H), 1.58-1.54 (m, 2H), 0.81 (m, 3H). MS (ES+) m/e 356.1 (M+H)⁺.

Example 149

N-(2-(3-ethylpiperazin-1-yl)-5-fluoropyrimidin-4-yl)-1H-indazol-5-amine

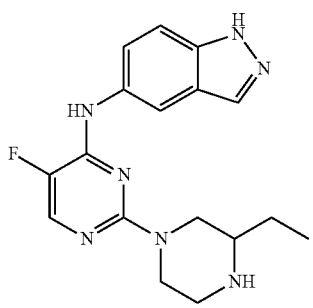 [SMILES: CCC1CN(c2ncc(F)c(Nc3ccc4[nH]ncc4c3)n2)CCN1]

The reaction was conducted following general protocol A. The reaction time of the first step was 32 hours and the crude material was further used without additional purification. The final residue was purified by reverse phase preparative HPLC to afford N-(2-(3-ethylpiperazin-1-yl)-5-fluoropyrimidin-4-yl)-1H-indazol-5-amine a yellow solid (22%). ¹H NMR (400 MHz, CD₃OD) δ 8.51 (s, 1H), 8.02 (s, 1H), 8.00 (s, 1H), 7.90 (d, J=3.6 Hz, 1H), 7.57 (dd, J=8.8, 1.6 Hz, 1H), 7.52 (d, J=8.8 Hz, 1H), 4.73 (d, J=12.4 Hz, 1H), 4.61 (d, J=14.0 Hz, 1H), 3.41-3.35 (m, 1H), 3.28-3.18 (m, 1H), 3.15-3.05 (m, 2H), 2.96-2.92 (m, 1H), 1.71-1.58 (m, 2H), 1.00 (t, J=7.6 Hz, 3H). MS (ES+) m/e 342.1 (M+H)⁺.

Example 150

N-(2-(3,5-dimethylpiperazin-1-yl)-5-fluoropyrimidin-4-yl)-1H-indazol-5-amine

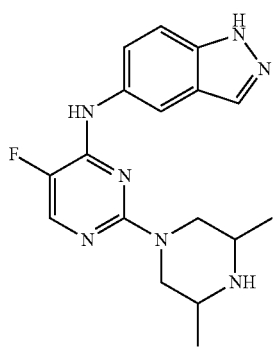

The reaction was conducted following general protocol A. The reaction time of the first step was 50 hours and the crude material was further used without additional purification. The final residue was purified by reverse phase preparative HPLC to afford N-(2-(3,5-dimethylpiperazin-1-yl)-5-fluoropyrimidin-4-yl)-1H-indazol-5-amine a white solid (14%). ¹H NMR (400 MHz, CD₃OD) δ 8.53 (s, 2H), 8.05-8.03 (m, 2H), 7.92 (d, J=4.0 Hz, 1H), 7.61-7.53 (m, 2H), 4.73-4.70 (m, 2H), 3.31-3.26 (m, 2H), 2.82-2.75 (m, 2H), 1.32 (d, J=6.4 Hz, 6H). MS (ES+) m/e 342.1 (M+H)⁺.

Example 151

N-(5-fluoro-2-(3-methyl-1,4-diazepan-1-yl)pyrimidin-4-yl)-1H-indazol-5-amine

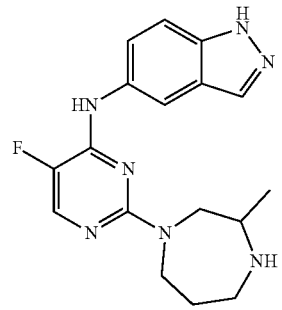 [SMILES: CC1CN(c2ncc(F)c(Nc3ccc4[nH]ncc4c3)n2)CCCN1]

The reaction was conducted following general protocol A. The reaction time of the first step was 16 hours and the crude material was further used without additional purification. The final residue was purified by reverse phase preparative HPLC to afford N-(5-fluoro-2-(3-methyl-1,4-diazepan-1-yl)pyrimidin-4-yl)-1H-indazol-5-amine as a yellow solid (10%). ¹H NMR (400 MHz, CD₃OD) δ 8.49 (s, 2H), 8.05 (s, 1H), 8.01 (s, 1H), 7.88 (d, J=4.0 Hz, 1H), 7.59-7.51 (m, 2H), 4.30-4.25 (m, 2H), 3.53-3.43 (m, 1H), 3.41-3.33 (m, 3H), 3.05-2.95 (m, 1H), 2.22-2.08 (m, 2H), 1.21 (d, J=6.4 Hz, 3H). MS (ES+) m/e 342.1 (M+H)⁺.

Example 152

N-(5-fluoro-2-(5-methyl-1,4-diazepan-1-yl)pyrimidin-4-yl)-1H-indazol-5-amine

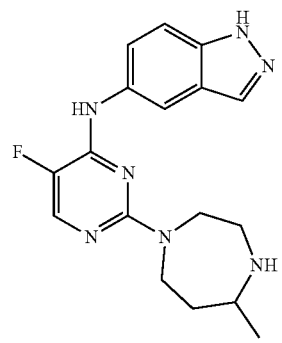 [SMILES: CC1CCN(c2ncc(F)c(Nc3ccc4[nH]ncc4c3)n2)CCN1]

The reaction was conducted following general protocol A. The reaction time of the first step was 52 hours and the crude material was further used without additional purification. The final residue was purified by reverse phase preparative HPLC to afford N-(5-fluoro-2-(5-methyl-1,4-diazepan-1-yl)pyrimidin-4-yl)-1H-indazol-5-amine as a yellow solid (8%). ¹H NMR (400 MHz, CD₃OD) δ 8.07 (s, 1H), 8.05 (s, 1H), 8.00 (d, J=4.8 Hz, 1H), 7.60 (m, 2H), 4.05-3.96 (m, 3H), 3.66 (m, 1H), 3.51-3.48 (m, 2H), 3.25 (m, 1H), 2.17-2.13 (m, 1H), 2.06-2.01 (m, 1H), 1.39 (d, J=6.8 Hz, 3H). MS (ES+) m/e 342.1 (M+H)$^+$.

Example 153

N-(5-fluoro-2-(4,7-diazaspiro[2.5]octan-7-yl)pyrimidin-4-yl)-1H-indazol-5-amine

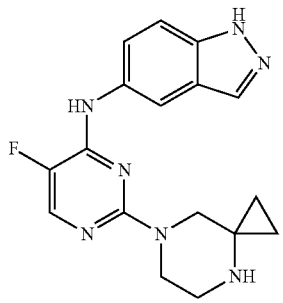 [SMILES: Fc1cnc(N2CCNC3(CC3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(4,7-diazaspiro[2.5]octan-7-yl)pyrimidin-4-yl)-1H-indazol-5-amine as white solid (40%). $^1$H NMR (400 MHz, CD$_3$OD) δ 8.05 (d, J=1.2 Hz, 1H), 8.00 (s, 1H), 7.83 (d, J=4.0 Hz, 1H), 7.60 (dd, J=8.8, 2.0 Hz, 1H), 7.51 (d, J=8.8 Hz, 1H), 3.73-3.71 (m, 2H), 3.58 (s, 2H), 2.94-2.92 (m, 2H), 0.61-0.59 (m, 4H). MS (ES+) m/e 340.2 (M+H)$^+$.

Example 154

N-(2-(2,5-diazabicyclo[2.2.2]octan-2-yl)-5-fluoropyrimidin-4-yl)-1H-indazol-5-amine

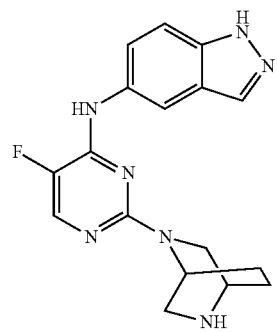 [SMILES: Fc1cnc(N2CC3CCC2CN3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(2,5-diazabicyclo[2.2.2]octan-2-yl)-5-fluoropyrimidin-4-yl)-1H-indazol-5-amine as white solid (16%). $^1$H NMR (400 MHz, CD$_3$OD) δ 8.07 (s, 2H), 8.01-8.00 (m, 1H), 7.62-7.56 (m, 2H), 4.73 (s, 1H), 3.96-3.91 (m, 2H), 3.79-3.76 (m, 1H), 3.55-3.45 (m, 2H), 2.20-2.12 (m, 2H), 2.03-1.99 (m, 2H). MS (ES+) m/e 340.1 (M+H)$^+$.

Example 155

N-(2-(2,5-dimethylpiperazin-1-yl)-5-fluoropyrimidin-4-yl)-1H-indazol-5-amine

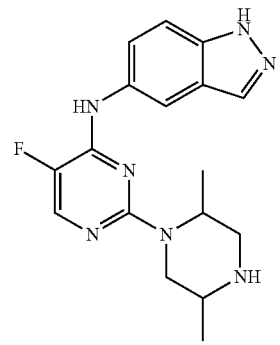 [SMILES: CC1CN(c2ncc(F)c(Nc3ccc4[nH]ncc4c3)n2)C(C)CN1]

The reaction was conducted following general protocol A. The reaction time of the first step was 16 hours and the crude material was further used without additional purification. The final residue was purified by reverse phase preparative HPLC to afford N-(2-(2,5-dimethylpiperazin-1-yl)-5-fluoropyrimidin-4-yl)-1H-indazol-5-amine as yellow solid (20%). $^1$H NMR (400 MHz, CD$_3$OD) δ 8.06 (s, 1H), 8.02 (t, J=1.2 Hz, 1H), 7.98 (d, J=4.4 Hz, 1H), 7.58 (d, J=1.2 Hz, 2H), 4.85-4.81 (m, 1H), 4.34-4.30 (m, 1H), 3.81-3.73 (m, 1H), 3.57-3.49 (m, 2H), 3.17-3.12 (m, 1H), 1.37 (t, J=7.6 Hz, 6H). MS (ES+) m/e 342.2 (M+H)$^+$.

Example 156

(1-(4-((1H-indazol-5-yl)amino)-5-fluoropyrimidin-2-yl)piperazin-2-yl)methanol

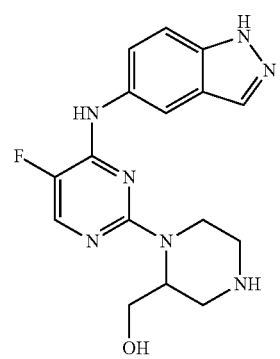 [SMILES: OCC1CNCCN1c1ncc(F)c(Nc2ccc3[nH]ncc3c2)n1]

The reaction was conducted following general protocol A. The reaction time of the first step was 16 hours and the crude material was further used without additional purification. The final residue was purified by reverse phase preparative HPLC to afford (1-(4-((1H-indazol-5-yl)amino)-5-fluoropyrimidin-2-yl)piperazin-2-yl)methanol as white solid (5%). $^1$H NMR (400 MHz, CD$_3$OD) δ 8.12 (d, J=1.6 Hz, 1H), 8.02 (s, 1H), 7.86 (d, J=3.6 Hz, 1H), 7.63 (dd, J=8.8, 2.0 Hz, 1H), 7.52 (d, J=8.8 Hz, 1H), 4.59-4.55 (m, 1H), 4.32 (m, 1H), 3.96-3.92 (m, 1H), 3.74-3.70 (m, 1H), 3.30-3.27 (m, 1H), 3.10 (m, 2H), 2.87-2.84 (m, 1H), 2.83-2.73 (m, 1H). MS (ES+) m/e 344.1 (M+H)$^+$.

Example 157

N-(2-(3,6-diazabicyclo[3.1.1]heptan-3-yl)-5-fluoro-pyrimidin-4-yl)-1H-indazol-5-amine

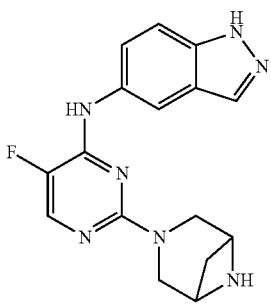 [SMILES: Fc1cnc(N2CC3CC(C2)N3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.1.1]heptan-3-yl)-5-fluoropyrimidin-4-yl)-1H-indazol-5-amine as white solid (11%). $^1$H NMR (400 MHz, CD$_3$OD) δ 8.24 (d, J=1.2 Hz, 1H), 8.00 (s, 1H), 7.86 (d, J=4.0 Hz, 1H), 7.70 (dd, J=9.2, 2.0 Hz, 1H), 7.50 (d, J=8.8 Hz, 1H), 3.85-3.72 (m, 6H), 2.71-2.70 (m, 1H), 1.61 (d, J=9.2 Hz, 1H). MS (ES+) m/e 326.1 (M+H)$^+$.

Example 158

N-(5-fluoro-2-(2,7-diazaspiro[3.5]nonan-7-yl)pyrimidin-4-yl)-1H-indazol-5-amine

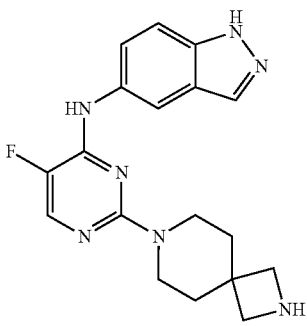 [SMILES: Fc1cnc(N2CCC3(CC2)CNC3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(2,7-diazaspiro[3.5]nonan-7-yl)pyrimidin-4-yl)-1H-indazol-5-amine as off-white solid (70%). $^1$H NMR (400 MHz, DMSO-d$_6$) δ 13.04 (brs, 1H), 9.56 (s, 1H), 8.78 (brs, 2H), 8.05-8.03 (m, 3H), 7.60 (d, J=8.8, 1.6 Hz, 1H), 7.52 (d, J=8.8 Hz, 1H), 3.76-3.73 (m, 4H), 3.60-3.58 (m, 4H), 1.78-1.75 (m, 4H). MS (ES+) m/e 354.1 (M+H)$^+$.

Example 159

N-(5-fluoro-2-(2,6-diazaspiro[3.4]octan-6-yl)pyrimidin-4-yl)-1H-indazol-5-amine

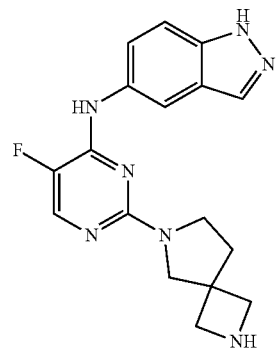 [SMILES: Fc1cnc(N2CCC3(CNC3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(2,6-diazaspiro[3.4]octan-6-yl)pyrimidin-4-yl)-1H-indazol-5-amine as off-white solid (51%). $^1$H NMR (400 MHz, DMSO-d$_6$) δ 13.14 (brs, 1H), 10.00 (brs, 1H), 8.96 (brs, 1H), 8.81 (brs, 1H), 8.23 (s, 1H), 8.15 (d, J=4.8 Hz, 1H), 8.10 (s, 1H), 7.69 (dd, J=8.8, 1.6 Hz, 1H), 7.55 (d, J=9.2 Hz, 1H), 4.04-4.00 (m, 2H), 3.93-3.92 (m, 2H), 3.70 (m, 2H), 3.52-3.49 (m, 2H), 2.26-2.22 (m, 2H). MS (ES+) m/e 340.1 (M+H)$^+$.

Example 160

N-(5-fluoro-2-(1-oxa-4,9-diazaspiro[5.5]undecan-9-yl)pyrimidin-4-yl)-1H-indazol-5-amine

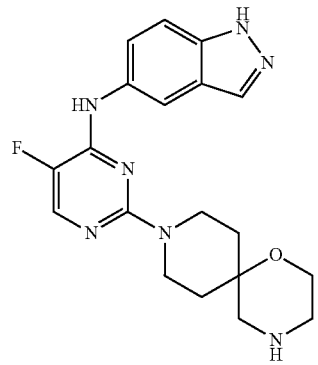 [SMILES: Fc1cnc(N2CCC3(CC2)CNCCO3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(1-oxa-4,9-diazaspiro[5.5]undecan-9-yl)pyrimidin-4-yl)-1H-indazol-5-amine as off-white solid (42%). $^1$H NMR (400 MHz, DMSO-d$_6$) δ 13.02 (brs, 1H), 9.53 (brs, 1H), 8.94 (brs, 2H), 8.07-8.03 (m, 3H), 7.60 (dd, J=9.2, 2.0 Hz, 1H), 7.51 (d, J=8.8 Hz, 1H), 4.09-4.06 (m, 2H), 3.84-3.81 (m, 2H), 3.28-3.23 (m, 2H), 3.07-3.02 (m, 4H), 1.91-1.88 (m, 2H), 1.60-1.54 (m, 2H). MS (ES+) m/e 384.1 (M+H)+.

Example 161

N-(5-fluoro-2-(2,7-diazaspiro[4.5]decan-2-yl)pyrimidin-4-yl)-1H-indazol-5-amine

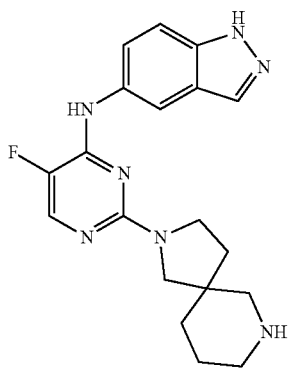 [SMILES: Fc1cnc(N2CCC3(CCCNC3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(2,7-diazaspiro[4.5]decan-2-yl)pyrimidin-4-yl)-1H-indazol-5-amine as white solid (11%). $^1$H NMR (400 MHz, CD$_3$OD) δ 8.16 (s, 1H), 8.10 (s, 1H), 8.00 (d, J=5.2 Hz, 1H), 7.66 (dd, J=9.2, 2.0 Hz, 1H), 7.60 (d, J=8.8 Hz, 1H), 3.72-3.70 (m, 2H), 3.61-3.58 (m, 1H), 3.49-3.47 (m, 1H), 3.20-3.15 (m, 4H), 2.12-2.09 (m, 2H), 1.91-1.79 (m, 4H). MS (ES+) m/e 368.1 (M+H)+.

Example 162

N-(5-fluoro-2-(2,7-diazaspiro[4.5]decan-7-yl)pyrimidin-4-yl)-1H-indazol-5-amine

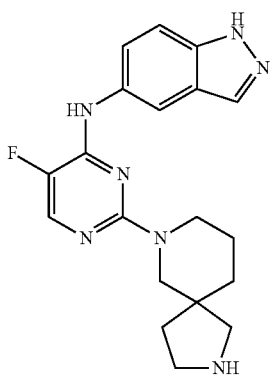 [SMILES: Fc1cnc(N2CCCC3(CCNC3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(2,7-diazaspiro[4.5]decan-7-yl)pyrimidin-4-yl)-1H-indazol-5-amine as a light brown solid (37%). $^1$H NMR (400 MHz, DMSO-d$_6$) δ 13.04 (brs, 1H), 9.45 (s, 1H), 8.83 (s, 2H), 8.08 (d, J=1.2 Hz, 1H), 8.05 (s, 1H), 8.01 (d, J=4.0 Hz, 1H), 7.61 (dd, J=9.2, 2.0 Hz, 1H), 7.53 (d, J=9.2 Hz, 1H), 3.65-3.56 (m, 2H), 3.30-3.29 (m, 2H), 3.28-3.18 (m, 2H), 2.98-2.95 (m, 2H), 1.84-1.82 (m, 1H), 1.70-1.57 (m, 5H). MS (ES+) m/e 368.1 (M+H)+.

Example 163

N-(5-fluoro-2-(2,6-diazaspiro[3.4]octan-2-yl)pyrimidin-4-yl)-1H-indazol-5-amine

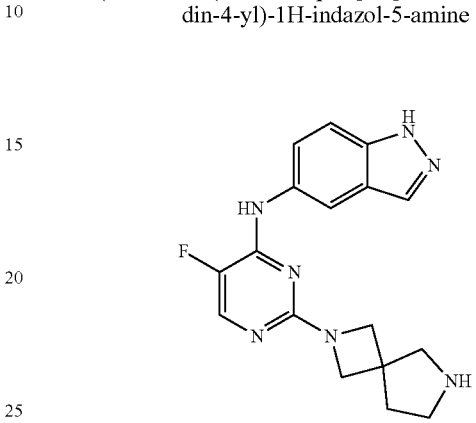

The reaction was conducted following general protocol A. The reaction time of the first step was 16 hours and the crude material was further used without additional purification. The final residue was purified by reverse phase preparative HPLC to afford N-(5-fluoro-2-(2,6-diazaspiro[3.4]octan-2-yl)pyrimidin-4-yl)-1H-indazol-5-amine as an off-white solid (31%). $^1$H NMR (400 MHz, DMSO-d$_6$) δ 13.11 (brs, 1H), 9.96 (s, 1H), 8.90 (s, 2H), 8.18 (d, J=1.2 Hz, 1H), 8.14 (d, J=4.8 Hz, 1H), 8.04 (s, 1H), 7.64 (dd, J=9.2, 2.0 Hz, 1H), 7.52 (d, J=8.8 Hz, 1H), 4.07 (d, J=8.8 Hz, 2H), 3.99 (d, J=8.8 Hz, 2H), 3.41-3.38 (m, 2H), 3.25-3.21 (m, 2H), 2.20 (t, J=7.2 Hz, 2H). MS (ES+) m/e 340.1 (M+H)+.

Example 164

N-(5-fluoro-2-(2,7-diazaspiro[3.5]nonan-2-yl)pyrimidin-4-yl)-1H-indazol-5-amine

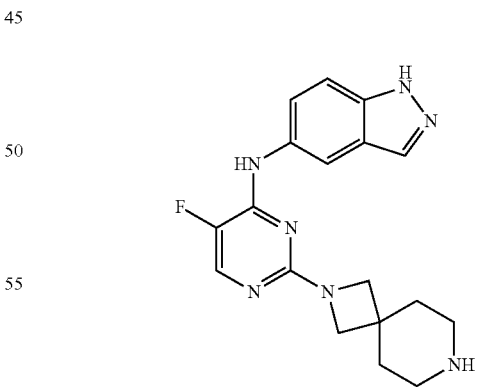

The reaction was conducted following general protocol A. The reaction time of the first step was 16 hours and the crude material was further used without additional purification. The final residue was purified by reverse phase preparative HPLC to afford N-(5-fluoro-2-(2,7-diazaspiro[3.5]nonan-2-yl)pyrimidin-4-yl)-1H-indazol-5-amine as an off-white solid (24%). $^1$H NMR (400 MHz, DMSO-d$_6$) δ 13.08 (brs, 1H), 9.82 (brs, 1H), 8.48 (brs, 2H), 8.19 (d, J=1.6 Hz, 1H), 8.11 (d, J=4.4 Hz, 1H), 8.07 (s, 1H), 7.65 (dd, J=8.8, 2.0 Hz, 1H), 7.52 (d, J=8.8 Hz, 1H), 3.82 (s, 4H), 3.07 (m, 4H), 1.93-1.91 (m, 4H). MS (ES+) m/e 354.1 (M+H)⁺.

Example 165

N-(5-fluoro-2-(2,6-diazaspiro[3.3]heptan-2-yl)pyrimidin-4-yl)-1H-indazol-5-amine

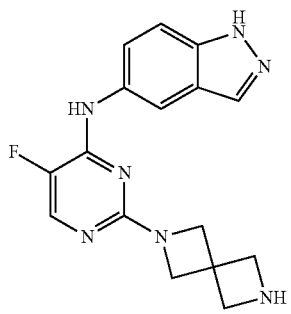 [SMILES: Fc1cnc(N2CC3(CNC3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(2,6-diazaspiro[3.3]heptan-2-yl)pyrimidin-4-yl)-1H-indazol-5-amine as an off-white solid (29%). ¹H NMR (400 MHz, DMSO-d₆) δ 13.11 (brs, 1H), 9.89 (s, 1H), 8.61 (brs, 2H), 8.20 (d, J=1.2 Hz, 1H), 8.12 (d, J=4.4 Hz, 1H), 8.04 (s, 1H), 7.63 (dd, J=9.2, 2.0 Hz, 1H), 7.52 (d, J=8.8 Hz, 1H), 4.20-4.14 (m, 8H). MS (ES+) m/e 326.1 (M+H)⁺.

Example 166

N-(2-(3,6-diazabicyclo[3.2.1]octan-3-yl)-5-fluoropyrimidin-4-yl)-1H-indazol-5-amine

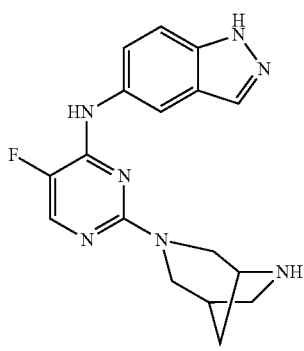 [SMILES: Fc1cnc(N2CC3CNC(C3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.2.1]octan-3-yl)-5-fluoropyrimidin-4-yl)-1H-indazol-5-amine as an off-white solid (34%). ¹H NMR (400 MHz, D₂O) δ 8.08 (s, 1H), 7.91-7.90 (m, 1H), 7.77 (d, J=5.2 Hz, 1H), 7.59 (d, J=8.8 Hz, 1H), 7.50 (dd, J=8.8, 2.0 Hz, 1H), 4.13-4.09 (m, 2H), 3.88-3.85 (m, 1H), 3.30-3.20 (m, 4H), 2.80 (m, 1H), 1.99 (m, 2H). MS (ES+) m/e 340.1 (M+H)⁺.

Example 167

N-(2-(3,7-diazabicyclo[3.3.1]nonan-3-yl)-5-fluoropyrimidin-4-yl)-1H-indazol-5-amine

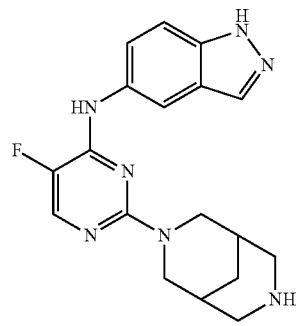 [SMILES: Fc1cnc(N2CC3CNCC(C3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,7-diazabicyclo[3.3.1]nonan-3-yl)-5-fluoropyrimidin-4-yl)-1H-indazol-5-amine as an off-white solid (7%). ¹H NMR (400 MHz, CD₃OD) δ 8.11 (s, 1H), 8.07-8.05 (m, 2H), 7.67-7.61 (m, 2H), 4.35-4.32 (m, 2H), 3.51-3.48 (m, 2H), 3.39-3.36 (m, 2H), 3.29 (m, 2H), 2.36 (m, 2H), 2.09-1.97 (m, 2H). MS (ES+) m/e 354.1 (M+H)⁺.

Example 168

N-(5-fluoro-2-(octahydro-5H-pyrrolo[3,2-c]pyridin-5-yl)pyrimidin-4-yl)-1H-indazol-5-amine

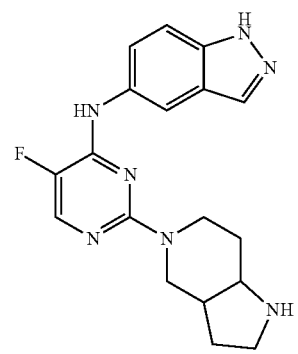 [SMILES: Fc1cnc(N2CCC3NCCC3C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(octahydro-5H-pyrrolo[3,2-c]pyridin-5-yl)pyrimidin-4-yl)-1H-indazol-5-amine as an light brown solid (4%). ¹H NMR (400 MHz, CD₃OD) δ 8.09 (s, 1H), 8.04 (s, 1H), 8.00 (d, J=8.8 Hz, 1H), 7.63-7.58 (m, 2H), 4.00-3.86 (m, 3H), 3.81-3.80 (m, 1H), 3.45-3.44 (m, 2H), 3.31-3.29 (m, 1H), 2.67-2.65 (m, 1H), 2.19-2.15 (m, 2H), 1.95-1.86 (m, 2H). MS (ES+) m/e 354.1 (M+H)⁺.

Example 169

N-(5-fluoro-2-(octahydropyrrolo[3,4-d]azepin-6(1H)-yl)pyrimidin-4-yl)-1H-indazol-5-amine

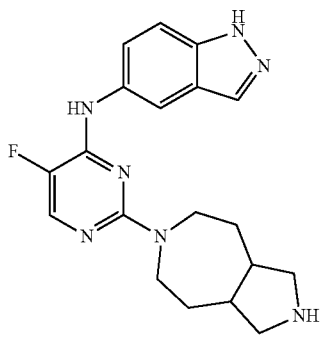 [SMILES: Fc1cnc(N2CCC3CNCC3CC2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(octahydropyrrolo[3,4-d]azepin-6(1H)-yl)pyrimidin-4-yl)-1H-indazol-5-amine as an light brown solid (11%). $^1$H NMR (400 MHz, CD$_3$OD) δ 8.09-8.08 (m, 2H), 7.89 (d, J=8.8 Hz, 1H), 7.61-7.60 (m, 2H), 4.02-3.98 (m, 2H), 3.56-3.47 (m, 4H), 3.06-3.01 (m, 2H), 2.68-2.65 (m, 2H), 2.01-1.97 (m, 2H), 1.89-1.84 (m, 2H). MS (ES+) m/e 368.1 (M+H)$^+$.

Example 170

N-(2-(3,7-diazabicyclo[4.2.0]octan-3-yl)-5-fluoropyrimidin-4-yl)-1H-indazol-5-amine

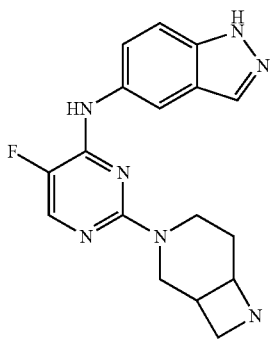 [SMILES: Fc1cnc(N2CCC3NCC3C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,7-diazabicyclo[4.2.0]octan-3-yl)-5-fluoropyrimidin-4-yl)-1H-indazol-5-amine as an light brown solid (7%). $^1$H NMR (400 MHz, CD$_3$OD) δ 8.08-8.03 (m, 3H), 7.64-7.59 (m, 2H), 4.76-4.74 (m, 1H), 4.17-4.06 (m, 2H), 3.93-3.91 (m, 2H), 3.82 (m, 1H), 3.65-3.60 (m, 1H), 3.37 (m, 1H), 2.43-2.32 (m, 2H). MS (ES+) m/e 340.1 (M+H)$^+$.

Example 171

N-(2-([3,3'-bipiperidin]-1-yl)-5-fluoropyrimidin-4-yl)-1H-indazol-5-amine

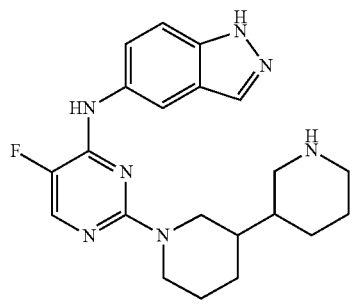 [SMILES: Fc1cnc(N2CCCC(C3CCCNC3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-([3,3'-bipiperidin]-1-yl)-5-fluoropyrimidin-4-yl)-1H-indazol-5-amine as an light brown solid (13%). $^1$H NMR (400 MHz, CD$_3$OD) δ 8.11 (s, 1H), 8.02-8.01 (m, 1H), 7.96 (d, J=5.2 Hz, 1H), 7.63 (d, J=8.8 Hz, 1H), 7.54 (dd, J=8.0, 1.6 Hz, 1H), 4.46-4.43 (m, 1H), 4.08-4.05 (m, 1H), 3.40-3.37 (m, 1H), 3.27 (m, 1H), 3.19-3.13 (m, 1H), 2.87-2.72 (m, 2H), 2.62-2.56 (m, 1H), 1.93-1.82 (m, 2H), 1.69-1.49 (m, 5H), 1.35-1.29 (m, 2H), 0.90-0.87 (m, 1H). MS (ES+) m/e 396.1 (M+H)$^+$.

Example 172

N-(2-(3-(azetidin-3-yl)pyrrolidin-1-yl)-5-fluoropyrimidin-4-yl)-1H-indazol-5-amine

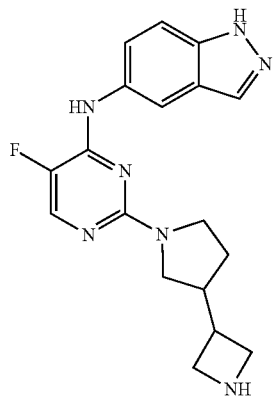 [SMILES: Fc1cnc(N2CCC(C3CNC3)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3-(azetidin-3-yl)pyrrolidin-1-yl)-5-fluoropyrimidin-4-yl)-1H-indazol-5-amine as an light brown solid (18%). $^1$H NMR (400 MHz, CD$_3$OD) δ 8.16 (s, 1H), 8.09 (s, 1H), 8.00 (d, J=5.6 Hz, 1H), 7.66 (dd, J=9.2, 2.0 Hz, 1H), 7.60 (d, J=8.8 Hz, 1H), 4.20-4.13 (m, 2H), 3.98-3.91 (m, 2H), 3.77-3.58 (m, 3H), 3.19-3.15 (m, 1H), 3.03-2.97 (m, 1H), 2.76 (m, 1H), 2.25 (m, 1H), 1.76 (m, 1H). MS (ES+) m/e 354.1 (M+H)⁺.

Example 173

N-(5-fluoro-2-(octahydro-2H-pyrazino[1,2-a]pyrazin-2-yl)pyrimidin-4-yl)-1H-indazol-5-amine

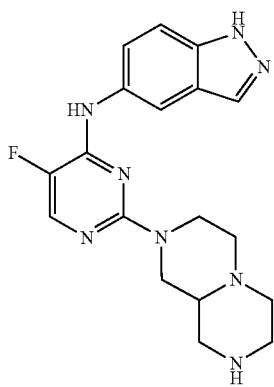 [SMILES: Fc1cnc(N2CCN3CCNCC3C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(octahydro-2H-pyrazino[1,2-a]pyrazin-2-yl)pyrimidin-4-yl)-1H-indazol-5-amine as a light brown solid (19%). ¹H NMR (400 MHz, CD₃OD) δ 8.10 (s, 1H), 8.03-8.01 (m, 2H), 7.63-7.57 (m, 2H), 4.33-4.29 (m, 2H), 3.43-3.21 (m, 1H), 3.27-3.17 (m, 3H), 3.08-3.05 (m, 1H), 2.98-2.96 (m, 1H), 2.90-2.84 (m, 2H), 2.52-2.34 (m, 3H). MS (ES+) m/e 369.1 (M+H)⁺.

Example 174

N-(2-(3,6-diazabicyclo[3.2.0]heptan-3-yl)-5-fluoropyrimidin-4-yl)-1H-indazol-5-amine

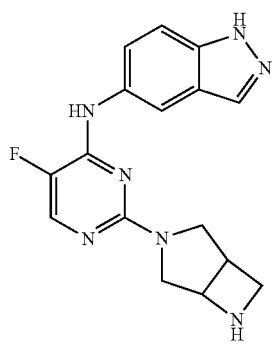 [SMILES: Fc1cnc(N2CC3CNC3C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.2.0]heptan-3-yl)-5-fluoropyrimidin-4-yl)-1H-indazol-5-amine as a light brown solid (19%). ¹H NMR (400 MHz, CD₃OD) δ 8.16 (s, 1H), 8.06 (s, 1H), 8.03 (d, J=7.2 Hz, 1H), 7.64 (dd, J=8.8, 2.0 Hz, 1H), 7.56 (d, J=9.2 Hz, 1H), 5.03-5.00 (m, 1H), 4.39 (d, J=14.0 Hz, 1H), 4.25-4.20 (m, 1H), 4.08 (d, J=11.6 Hz, 1H), 3.74-3.70 (m, 1H), 3.56-3.52 (m, 2H), 3.46-3.41 (m, 2H). MS (ES+) m/e 326.3 (M+H)⁺.

Example 175

N-(5-fluoro-2-(3-(piperidin-4-yl)indolin-1-yl)pyrimidin-4-yl)-1H-indazol-5-amine

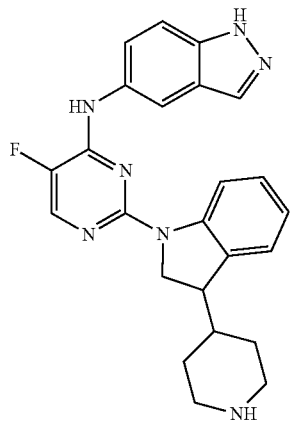 [SMILES: Fc1cnc(N2CC(C3CCNCC3)c3ccccc32)nc1Nc1ccc2[nH]ncc2c1]

The reaction was conducted following general protocol D. The reaction time of the first step was 16 hours and the crude material was further used without additional purification. The final residue was purified by reverse phase preparative HPLC to afford N-(5-fluoro-2-(3-(piperidin-4-yl)indolin-1-yl)pyrimidin-4-yl)-1H-indazol-5-amine as a yellow solid (31%). ¹H NMR (400 MHz, DMSO-d₆) δ 13.10 (brs, 1H), 9.55 (s, 1H), 8.44-8.41 (m, 1H), 8.20-8.16 (m, 2H), 8.07-8.05 (m, 3H), 7.61-7.56 (m, 2H), 7.20-7.18 (m, 1H), 6.88-6.84 (m, 2H), 4.11-4.02 (m, 2H), 3.38-3.21 (m, 3H), 2.84-2.79 (m, 2H), 1.94 (m, 1H), 1.81-1.80 (m, 1H), 1.46-1.40 (m, 3H). MS (ES+) m/e 430.1 (M+H)⁺.

Example 176

N-(5-fluoro-2-(spiro[indoline-3,4'-piperidin]-1-yl)pyrimidin-4-yl)-1H-indazol-5-amine

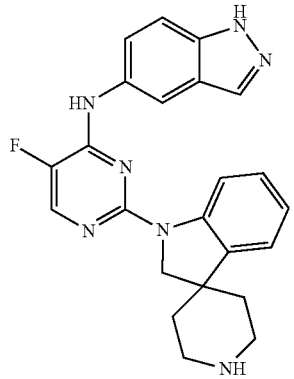 [SMILES: Fc1cnc(N2CC3(CCNCC3)c3ccccc32)nc1Nc1ccc2[nH]ncc2c1]

The reaction was conducted following general protocol D. The reaction time of the first step was 16 hours and the crude material was further used without additional purification. The final residue was purified by reverse phase preparative HPLC to afford N-(5-fluoro-2-(spiro[indoline-3,4'-piperidin]-1-yl)pyrimidin-4-yl)-1H-indazol-5-amine as a yellow solid (29%). ¹H NMR (400 MHz, DMSO-d₆) δ 13.13 (brs, 1H), 9.58 (s, 1H), 8.72-8.69 (m, 1H), 8.49-8.46 (m, 1H), 8.21-8.20 (m, 2H), 8.09 (s, 1H), 8.00 (m, 1H), 7.60-7.54 (m, 2H), 7.12-7.10 (m, 1H), 6.91-6.87 (m, 2H), 4.14 (s, 2H), 3.38-3.35 (m, 2H), 3.11-3.02 (m, 2H), 2.03-1.97 (m, 2H), 1.83-1.79 (m, 2H). MS (ES+) m/e 416.1 (M+H)⁺.

Example 177

N-(5-fluoro-2-(3-(piperidin-3-yl)indolin-1-yl)pyrimidin-4-yl)-1H-indazol-5-amine

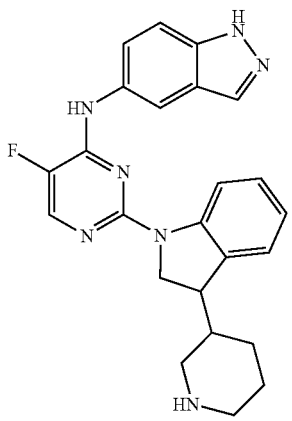 [SMILES: Fc1cnc(N2CC(C3CCCNC3)c3ccccc32)nc1Nc1ccc2[nH]ncc2c1]

The reaction was conducted following general protocol D. The reaction time of the first step was 16 hours and the crude material was further used without additional purification. The final residue was purified by reverse phase preparative HPLC to afford N-(5-fluoro-2-(3-(piperidin-3-yl)indolin-1-yl)pyrimidin-4-yl)-1H-indazol-5-amine as a yellow solid (23%). ¹H NMR (400 MHz, DMSO-d₆) δ 13.11 (brs, 1H), 9.55 (s, 1H), 8.61-8.58 (m, 1H), 8.24-8.15 (m, 3H), 8.07-8.02 (m, 2H), 7.58 (s, 2H), 7.20-7.15 (m, 1H), 6.88-6.87 (m, 2H), 4.08-4.06 (m, 2H), 3.43-3.40 (m, 1H), 3.29-3.18 (m, 2H), 2.82-2.79 (m, 2H), 2.02-2.01 (m, 1H), 1.79-1.77 (m, 1H), 1.53-1.27 (m, 3H). MS (ES+) m/e 430.1 (M+H)⁺.

Example 178

N-(5-chloro-2-(piperazin-1-yl)pyrimidin-4-yl)-1H-indazol-5-amine

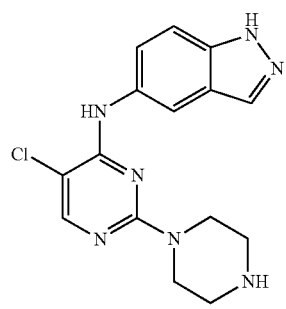 [SMILES: Clc1cnc(N2CCNCC2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-chloro-2-(piperazin-1-yl)pyrimidin-4-yl)-1H-indazol-5-amine as a yellow solid (48%). ¹H NMR (400 MHz, DMSO-d₆) δ 13.04 (s, 1H), 8.79 (s, 1H), 8.29 (s, 1H), 8.05-8.01 (m, 2H), 7.89 (d, J=1.2 Hz, 1H), 7.45 (dd, J=8.8, 2.0 Hz, 1H), 7.49 (d, J=8.8 Hz, 1H), 3.60 (t, J=4.8 Hz, 4H), 2.80 (t, J=4.8 Hz, 4H). MS (ES+) m/e 330.0 (M+H)⁺.

Example 179

N-(5-chloro-2-(2-methylpiperazin-1-yl)pyrimidin-4-yl)-1H-indazol-5-amine

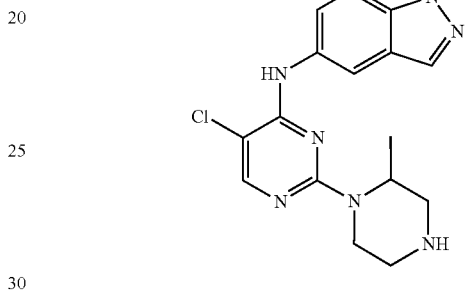

The reaction was conducted following general protocol A. The reaction time of the first step was 32 hours and the crude material was further used without additional purification. The final residue was purified by reverse phase preparative HPLC to afford N-(5-chloro-2-(2-methylpiperazin-1-yl)pyrimidin-4-yl)-1H-indazol-5-amine as a white solid (11%). ¹H NMR (400 MHz, DMSO-d₆) δ 13.05 (brs, 1H), 8.75 (s, 1H), 8.30 (s, 2H), 8.01 (s, 2H), 7.93 (d, J=1.6 Hz, 1H), 7.55 (dd, J=9.2, 2.0 Hz, 1H), 7.48 (d, J=8.8 Hz, 1H), 4.51 (m, 1H), 4.17-4.14 (m, 1H), 2.94-2.87 (m, 2H), 2.81-2.70 (m, 2H), 2.56 (m, 1H), 1.15 (d, J=6.8 Hz, 3H). MS (ES+) m/e 344.0 (M+H)⁺.

Example 180

N-(5-chloro-2-(3-methylpiperazin-1-yl)pyrimidin-4-yl)-1H-indazol-5-amine

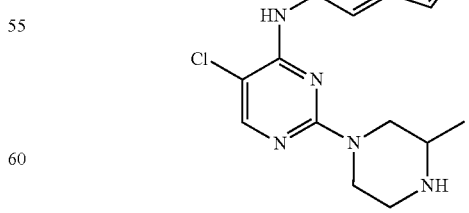

The reaction was conducted following general protocol A. The reaction time of the first step was 16 hours and the crude material was further used without additional purification. The final residue was purified by reverse phase preparative HPLC to afford N-(5-chloro-2-(3-methylpiperazin-1-yl)pyrimidin-4-yl)-1H-indazol-5-amine as a yellow solid (23%). $^1$H NMR (400 MHz, DMSO-d$_6$) δ 13.00 (brs, 1H), 8.80 (s, 1H), 8.28 (s, 2H), 8.02 (s, 2H), 7.92 (s, 1H), 7.54 (d, J=8.8 Hz, 1H), 7.49 (d, J=9.2 Hz, 1H), 4.31 (t, J=12.0 Hz, 2H), 2.99-2.54 (m, 5H), 1.03 (d, J=6.0 Hz, 3H). MS (ES+) m/e 344.1 (M+H)$^+$.

Example 181

N-(5-chloro-2-(3-isopropyl-1,4-diazepan-1-yl)pyrimidin-4-yl)-1H-indazol-5-amine

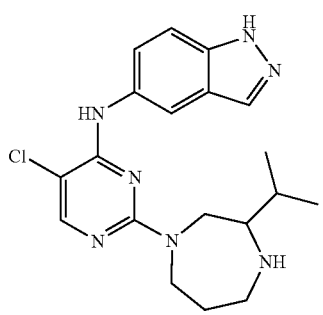 [SMILES: CC(C)C1CN(c2ncc(Cl)c(Nc3ccc4[nH]ncc4c3)n2)CCCN1]

The reaction was conducted following general protocol C. The residue was purified by reverse phase preparative HPLC to afford N-(5-chloro-2-(3-isopropyl-1,4-diazepan-1-yl)pyrimidin-4-yl)-1H-indazol-5-amine as a yellow solid (16%). $^1$H NMR (400 MHz, CD$_3$OD) δ 8.54 (s, 1H), 8.04 (s, 1H), 7.98 (s, 1H), 7.89 (s, 1H), 7.56-7.54 (d, J=8.8 Hz, 1H), 7.51-7.48 (d, J=8.8 Hz, 1H), 4.24-4.14 (m, 2H), 3.49-3.39 (m, 3H), 3.01-3.00 (m, 2H), 2.12-2.05 (m, 2H), 1.77 (m, 1H), 0.78 (m, 6H). MS (ES+) m/e 386.1 (M+H)$^+$.

Example 182

N-(5-chloro-2-(5-isopropyl-1,4-diazepan-1-yl)pyrimidin-4-yl)-1H-indazol-5-amine

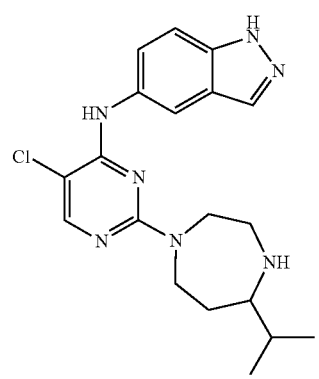 [SMILES: CC(C)C1CCN(c2ncc(Cl)c(Nc3ccc4[nH]ncc4c3)n2)CCN1]

The reaction was conducted following general protocol C. The residue was purified by reverse phase preparative HPLC to afford N-(5-chloro-2-(5-isopropyl-1,4-diazepan-1-yl)pyrimidin-4-yl)-1H-indazol-5-amine as a yellow solid (31%). $^1$H NMR (400 MHz, CD$_3$OD) δ 8.55 (s, 1H), 8.04 (s, 1H), 7.99 (s, 1H), 7.95 (s, 1H), 7.58-7.52 (m, 2H), 4.05-4.00 (m, 2H), 3.98-3.95 (m, 1H), 3.67-3.64 (m, 1H), 3.35 (m, 1H), 3.17-3.13 (m, 2H), 2.05-2.01 (m, 2H), 1.80 (m, 1H), 1.00-0.97 (t, J=7.2 Hz, 6H). MS (ES+) m/e 386.1 (M+H)$^+$.

Example 183

N-(5-chloro-2-(3-phenyl-1,4-diazepan-1-yl)pyrimidin-4-yl)-1H-indazol-5-amine

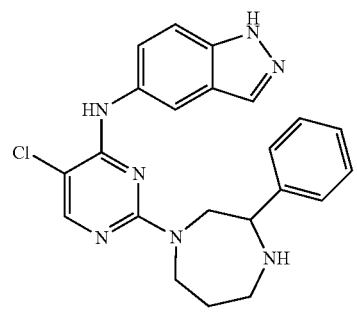 [SMILES: Clc1cnc(N2CCCNC(c3ccccc3)C2)nc1Nc1ccc2[nH]ncc2c1]

The reaction was conducted following general protocol C. The residue was purified by reverse phase preparative HPLC to afford N-(5-chloro-2-(3-phenyl-1,4-diazepan-1-yl)pyrimidin-4-yl)-1H-indazol-5-amine as a yellow solid (36%). $^1$H NMR (400 MHz, CD$_3$OD) δ 8.52 (s, 1H), 8.01 (s, 1H), 7.91-7.78 (m, 2H), 7.49-6.93 (m, 7H), 4.45-4.42 (m, 3H), 3.57-3.46 (m, 1H), 3.45-3.41 (m, 2H), 3.00-2.94 (m, 1H), 2.27-2.26 (m, 1H), 2.16-2.14 (m, 1H). MS (ES+) m/e 420.1 (M+H)$^+$.

Example 184

N-(5-chloro-2-(5-phenyl-1,4-diazepan-1-yl)pyrimidin-4-yl)-1H-indazol-5-amine

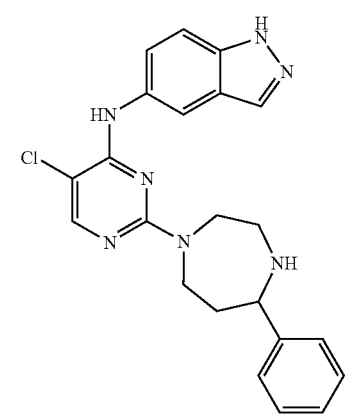 [SMILES: Clc1cnc(N2CCNC(c3ccccc3)CC2)nc1Nc1ccc2[nH]ncc2c1]

The reaction was conducted following general protocol C. The residue was purified by reverse phase preparative HPLC to afford N-(5-chloro-2-(5-phenyl-1,4-diazepan-1-yl)pyrimidin-4-yl)-1H-indazol-5-amine as a yellow solid (48%). $^1$H NMR (400 MHz, CD$_3$OD) δ 8.54 (s, 1H), 7.99-7.97 (m, 3H), 7.60 (dd, J=8.8, 1.6 Hz, 1H), 7.51 (d, J=9.2 Hz, 1H), 7.41-7.31 (m, 5H), 4.09-4.01 (m, 3H), 3.87 (m, 1H), 3.76-3.74 (m, 1H), 3.35 (m, 1H), 3.18-3.15 (m, 1H), 2.18-2.13 (m, 2H). MS (ES+) m/e 420.1 (M+H)$^+$.

Example 185

N-(5-chloro-2-(3-isopropylpiperazin-1-yl)pyrimidin-4-yl)-1H-indazol-5-amine

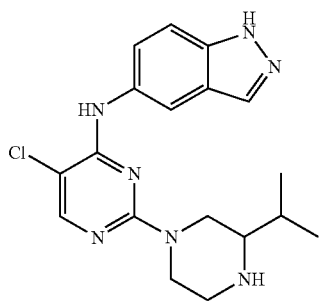 [SMILES: CC(C)C1CN(c2ncc(Cl)c(Nc3ccc4[nH]ncc4c3)n2)CCN1]

The reaction was conducted following general protocol C. The residue was purified by reverse phase preparative HPLC to afford N-(5-chloro-2-(3-isopropylpiperazin-1-yl)pyrimidin-4-yl)-1H-indazol-5-amine as a yellow solid (32%). $^1$H NMR (400 MHz, CD$_3$OD) δ 8.52 (s, 1H), 8.03 (s, 1H), 8.01 (s, 2H), 7.91 (s, 1H), 7.56-7.51 (m, 2H), 4.81-4.75 (m, 1H), 4.67-4.63 (m, 1H), 3.36 (m, 1H), 3.15-3.05 (m, 2H), 2.89-2.85 (m, 2H), 1.85-1.80 (m, 1H), 1.01 (d, J=6.8 Hz, 3H), 0.93 (d, J=6.4 Hz, 3H). MS (ES+) m/e 372.1 (M+H)$^+$.

Example 186

N-(5-chloro-2-(3-ethyl 4-diazepan-1-yl)pyrimidin-4-yl)-1H-indazol-5-amine

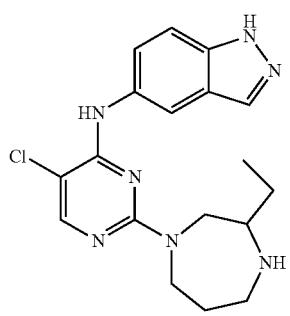 [SMILES: CCC1CN(c2ncc(Cl)c(Nc3ccc4[nH]ncc4c3)n2)CCCN1]

The reaction was conducted following general protocol C. The residue was purified by reverse phase preparative HPLC to afford N-(5-chloro-2-(3-ethyl-1,4-diazepan-1-yl)pyrimidin-4-yl)-1H-indazol-5-amine as a yellow solid (18%). $^1$H NMR (400 MHz, CD$_3$OD) δ8.45 (brs, 2H), 8.04 (s, 1H), 7.99 (s, 1H), 7.89 (s, 1H), 7.57-7.50 (m, 2H), 4.25-4.22 (m, 2H), 3.42-3.36 (m, 3H), 3.18 (m, 1H), 3.03-3.00 (m, 1H), 2.16-2.14 (m, 1H), 2.07-2.05 (m, 1H), 1.50-1.48 (m, 2H), 0.70-0.65 (m, 3H). MS (ES+) m/e 372.2 (M+H)$^+$.

Example 187

N-(5-chloro-2-(2-ethylpiperazin-1-yl)pyrimidin-4-yl)-1H-indazol-5-amine

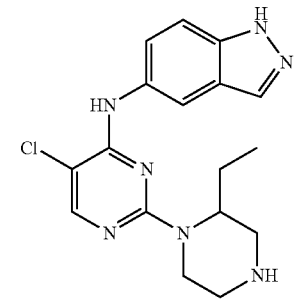 [SMILES: CCC1CNCCN1c1ncc(Cl)c(Nc2ccc3[nH]ncc3c2)n1]

The reaction was conducted following general protocol A. The reaction time of the first step was 48 hours and the crude material was further used without additional purification. The final residue was purified by reverse phase preparative HPLC to afford N-(5-chloro-2-(2-ethylpiperazin-1-yl)pyrimidin-4-yl)-1H-indazol-5-amine as a yellow solid (19%). $^1$H NMR (400 MHz, CD$_3$OD) δ 8.53 (s, 1H), 8.04 (s, 1H), 8.00 (s, 1H), 7.90 (s, 1H), 7.57-7.54 (m, 2H), 4.75-4.64 (m, 2H), 3.34 (m, 1H), 3.33 (m, 1H), 3.28-3.20 (m, 1H), 3.12-3.09 (m, 1H), 2.99-2.98 (m, 1H), 1.80-1.71 (m, 2H), 0.89 (t, J=7.6 Hz, 3H). MS (ES+) m/e 358.0 (M+H)$^+$.

Example 188

N-(5-chloro-2-(5-ethyl-1,4-diazepan-1-yl)pyrimidin-4-yl)-1H-indazol-5-amine

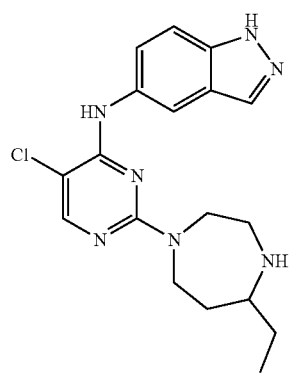 [SMILES: CCC1CCN(c2ncc(Cl)c(Nc3ccc4[nH]ncc4c3)n2)CCN1]

The reaction was conducted following general protocol A. The reaction time of the first step was 48 hours and the crude material was further used without additional purification. The final residue was purified by reverse phase preparative HPLC to afford N-(5-chloro-2-(5-ethyl-1,4-diazepan-1-yl)pyrimidin-4-yl)-1H-indazol-5-amine as an off-white solid (19%). $^1$H NMR (400 MHz, CD3OD) δ 8.53 (s, 1H), 8.04 (s, 1H), 8.00 (s, 1H), 7.96 (s, 1H), 7.59-7.53 (m, 2H), 4.06-3.94 (m, 3H), 3.65-3.58 (m, 1H), 3.42-3.35 (m, 1H), 3.25-3.13 (m, 2H), 2.18-2.07 (m, 1H), 1.91-1.58 (m, 3H), 0.99 (t, J=7.6 Hz, 3H). MS (ES+) m/e 371.8 (M+H)$^+$.

Example 189

N-(5-chloro-2-(3,5-dimethylpiperazin-1-yl)pyrimidin-4-yl)-1H-indazol-5-amine

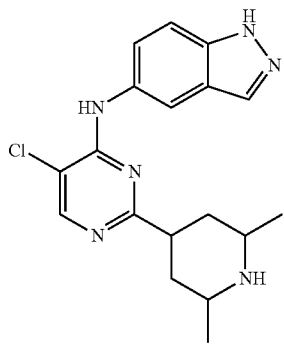 [SMILES: CC1CC(c2ncc(Cl)c(Nc3ccc4[nH]ncc4c3)n2)CC(C)N1]

The reaction was conducted following general protocol A. The reaction time of the first step was 48 hours and the crude material was further used without additional purification. The final residue was purified by reverse phase preparative HPLC to afford N-(5-chloro-2-(3,5-dimethylpiperazin-1-yl)pyrimidin-4-yl)-1H-indazol-5-amine as a white solid (41%). $^1$H NMR (400 MHz, DMSO-$d_6$) δ 13.02 (brs, 1H), 8.78 (s, 1H), 8.29 (s, 2H), 8.00 (m, 2H), 7.96 (d, J=1.2 Hz, 1H), 7.55 (dd, J=8.8, 1.6 Hz, 1H), 7.49 (d, J=8.8 Hz, 1H), 4.36-4.34 (m, 2H), 2.72-2.68 (m, 2H), 2.36-2.30 (m, 2H), 0.99 (d, J=6.4 Hz, 6H). MS (ES+) m/e 358.0 (M+H)$^+$.

Example 190

N-(5-chloro-2-(3-ethylpiperazin-1-yl)pyrimidin-4-yl)-1H-indazol-5-amine

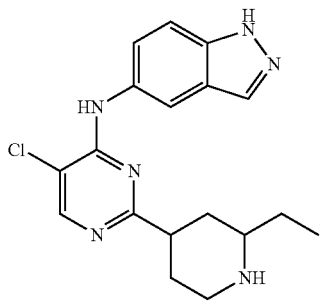 [SMILES: CCC1CC(c2ncc(Cl)c(Nc3ccc4[nH]ncc4c3)n2)CCN1]

The reaction was conducted following general protocol A. The reaction time of the first step was 36 hours and the crude material was further used without additional purification. The final residue was purified by reverse phase preparative HPLC to afford N-(5-chloro-2-(3-ethylpiperazin-1-yl)pyrimidin-4-yl)-1H-indazol-5-amine as a yellow solid (22%). $^1$H NMR (400 MHz, CD$_3$OD) δ 8.52 (s, 1H), 8.03 (s, 1H), 8.01 (s, 1H), 7.91 (s, 1H), 7.55 (s, 2H), 4.69-4.66 (m, 1H), 4.60-4.56 (m, 1H), 3.30 (m, 1H), 3.21-3.20 (m, 1H), 3.05-3.01 (m, 2H), 2.92-2.89 (m, 1H), 1.65-1.55 (m, 2H), 0.94 (t, J=7.6 Hz, 3H). MS (ES+) m/e 358.1 (M+H)$^+$.

Example 191

N-(5-chloro-2-(5-methyl-1,4-diazepan-1-yl)pyrimidin-4-yl)-1H-indazol-5-amine

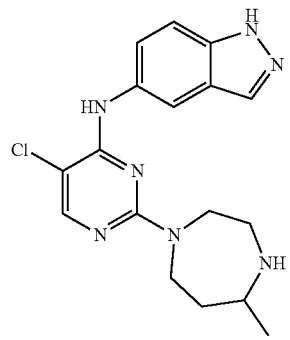 [SMILES: CC1CCN(c2ncc(Cl)c(Nc3ccc4[nH]ncc4c3)n2)CCN1]

The reaction was conducted following general protocol A. The reaction time of the first step was 36 hours and the crude material was further used without additional purification. The final residue was purified by reverse phase preparative HPLC to afford N-(5-chloro-2-(5-methyl-1,4-diazepan-1-yl)pyrimidin-4-yl)-1H-indazol-5-amine amine as a yellow solid (26%). $^1$H NMR (400 MHz, CD$_3$OD) δ 8.48 (brs, 2H), 8.04 (s, 1H), 8.00 (s, 1H), 7.97 (s, 1H), 7.56-7.55 (m, 2H), 4.04-3.94 (m, 3H), 3.62 (m, 1H), 3.45-3.41 (m, 2H), 3.23-3.21 (m, 1H), 2.10-2.06 (m, 1H), 1.93-1.87 (m, 1H), 1.35 (d, J=6.8 Hz, 3H). MS (ES+) m/e 358.0 (M+H)$^+$.

Example 192

N-(2-(3,8-diazabicyclo[3.2.1]octan-8-yl)-5-chloropyrimidin-4-yl)-1H-indazol-5-amine

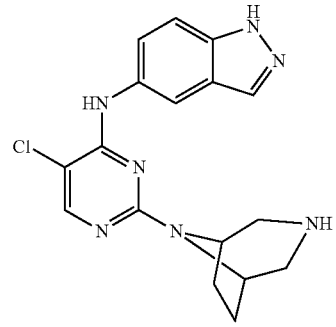 [SMILES: Clc1cnc(N2C3CCC2CNC3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,8-diazabicyclo[3.2.1]octan-8-yl)-5-chloropyrimidin-4-yl)-1H-indazol-5-amine as a light yellow solid (71%). $^1$H NMR (400 MHz, DMSO-$d_6$) δ 13.00 (brs, 1H), 8.83 (s, 1H), 8.24 (s, 1H), 8.06 (s, 1H), 8.03 (s, 1H), 7.94-7.93 (d, J=1.6 Hz, 1H), 7.58-7.48 (m, 2H), 4.39 (s, 2H), 2.97 (d, J=12.0 Hz, 2H), 2.78 (d, J=12.0 Hz, 2H), 1.94-1.92 (m, 4H). MS (ES+) m/e 356.0 (M+H)$^+$.

Example 193

N-(5-chloro-2-(6-methyl-1,4-diazepan-1-yl)pyrimidin-4-yl)-1H-indazol-5-amine

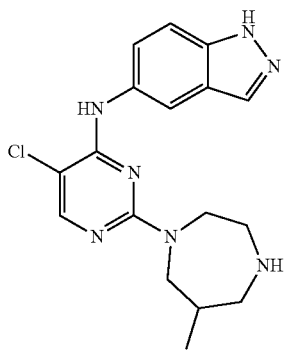 [SMILES: CC1CNCCN(c2ncc(Cl)c(Nc3ccc4[nH]ncc4c3)n2)C1]

The reaction was conducted following general protocol A. The reaction time of the first step was 16 hours and the crude material was further used without additional purification. The final residue was purified by reverse phase preparative HPLC to afford N-(5-chloro-2-(6-methyl-1,4-diazepan-1-yl)pyrimidin-4-yl)-1H-indazol-5-amine as a yellow solid (44%). $^1$H NMR (400 MHz, CD$_3$OD) δ 8.51 (s, 1H), 8.04 (s, 1H), 8.00 (s, 1H), 7.97 (s, 1H), 7.55-7.53 (m, 2H), 4.25-4.21 (m, 2H), 3.72-3.65 (m, 1H), 3.54-3.41 (m, 1H), 3.27-3.15 (m, 2H), 3.11-3.05 (m, 1H), 3.01-2.95 (m, 1H), 2.27-2.14 (m, 1H), 0.96 (d, J=5.6 Hz, 3H). MS (ES+) m/e 358.0 (M+H)$^+$.

Example 194

N-(2-(2,5-diazabicyclo[2.2.1]heptan-2-yl)-5-chloropyrimidin-4-yl)-1H-indazol-5-amine

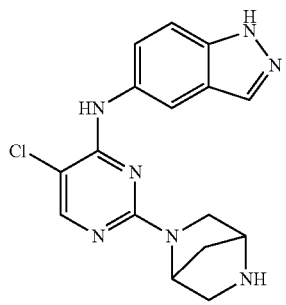 [SMILES: Clc1cnc(N2CC3CC2CN3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(2,5-diazabicyclo[2.2.1]heptan-2-yl)-5-chloropyrimidin-4-yl)-1H-indazol-5-amine as a white solid (31%). $^1$H NMR (400 MHz, CD$_3$CN) δ 8.82 (s, 1H), 8.27 (s, 2H), 8.10 (s, 1H), 8.08 (s, 1H), 8.02 (s, 1H), 7.61 (d, J=8.8 Hz, 1H), 7.55 (d, J=8.8 Hz, 1H), 4.89 (s, 1H), 4.49 (s, 1H), 3.77 (m, 1H), 3.65 (m, 1H), 3.51-3.45 (m, 1H), 3.39-3.37 (m, 1H), 2.18-2.13 (m, 1H), 2.08-2.04 (m, 1H). MS (ES+) m/e 342.1 (M+H)$^+$.

Example 195

N-(2-(3,8-diazabicyclo[3.2.1]octan-3-yl)-5-chloropyrimidin-4-yl)-1H-indazol-5-amine

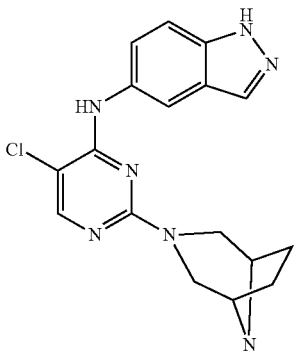 [SMILES: Clc1cnc(N2CC3CCC(C2)N3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,8-diazabicyclo[3.2.1]octan-3-yl)-5-chloropyrimidin-4-yl)-1H-indazol-5-amine as a white solid (35%). $^1$H NMR (400 MHz, DMSO-d$_6$) δ 9.06-8.79 (m, 3H), 8.07 (s, 1H), 8.04 (s, 1H), 7.89 (d, J=1.2 Hz, 1H), 7.57-7.48 (m, 2H), 4.26-4.22 (m, 2H), 4.09 (s, 2H), 3.17 (d, J=13.6 Hz, 2H), 1.95-1.84 (m, 2H), 1.73-1.71 (m, 2H). MS (ES+) m/e 356.1 (M+H)$^+$.

Example 196

N-(5-methyl-2-(6-methyl-1,4-diazepan-1-yl)pyrimidin-4-yl)-1H-indazol-5-amine

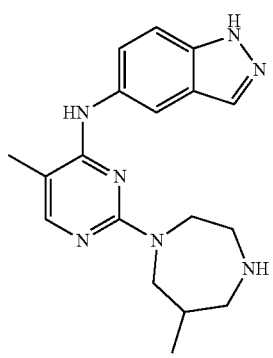 [SMILES: Cc1cnc(N2CCNCC(C)C2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-methyl-2-(6-methyl-1,4-diazepan-1-yl)pyrimidin-4-yl)-1H-indazol-5-amine as a white solid (26%). $^1$H NMR (400 MHz, CD$_3$OD) δ 8.16 (d, J=0.8 Hz, 1H), 7.92 (d, J=1.2 Hz, 1H), 7.71 (d, J=1.2 Hz, 1H), 7.65 (d, J=8.8 Hz, 1H), 7.57 (d, J=8.8, 1.6 Hz, 1H), 4.04-3.91 (m, 2H), 3.88-3.78 (m, 1H), 3.34 (m, 2H), 3.28-3.13 (m, 2H), 3.06 (m, 1H), 2.33-2.27 (m, 4H), 0.97 (m, 3H). MS (ES+) m/e 338.2 (M+H)$^+$.

Example 197

N-(5,6-dimethyl-2-(piperazin-1-yl)pyrimidin-4-yl)-1H-indazol-5-amine

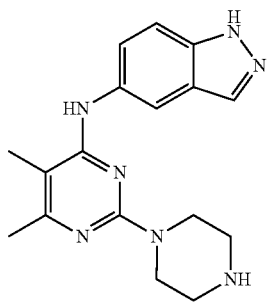 [SMILES: Cc1nc(N2CCNCC2)nc(Nc2ccc3[nH]ncc3c2)c1C]

The reaction was conducted following general protocol A. The reaction time of the first step was 32 hours and the crude material was further used without additional purification. The final residue was purified by reverse phase preparative HPLC to afford N-(5,6-dimethyl-2-(piperazin-1-yl)pyrimidin-4-yl)-1H-indazol-5-amine as a yellow solid (31%). $^1$H NMR (400 MHz, CD$_3$OD) δ 8.35 (s, 2H), 7.99 (s, 1H), 7.85 (d, J=0.8 Hz, 1H), 7.55-7.48 (m, 2H), 3.86 (t, J=5.2 Hz, 4H), 3.18 (t, J=5.2 Hz, 4H), 2.33 (s, 3H), 2.14 (s, 3H). MS (ES+) m/e 324.1 (M+H)$^+$.

Example 198

N-(2-(3,8-diazabicyclo[3.2.1]octan-8-yl)-5-methoxypyrimidin-4-yl)-1H-indazol-5-amine

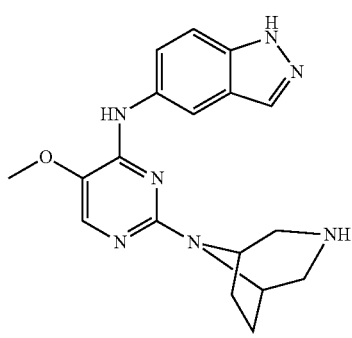 [SMILES: COc1cnc(N2C3CCC2CNC3)nc1Nc1ccc2[nH]ncc2c1]

The reaction was conducted following general protocol A. The reaction time of the first step was 16 hours and the crude material was further used without additional purification. The final residue was purified by the reverse phase preparative HPLC to afford N-(2-(3,8-diazabicyclo[3.2.1]octan-8-yl)-5-methoxypyrimidin-4-yl)-1H-indazol-5-amine as a yellow solid (32%). $^1$H NMR (400 MHz, DMSO-d$_6$) δ 13.08 (brs, 1H), 9.70 (brs, 1H), 9.13 (brs, 1H), 8.84 (brs, 1H), 8.08 (s, 1H), 8.04 (s, 1H), 7.74 (s, 1H), 7.62 (dd, J=8.8, 2.0 Hz, 1H), 7.52 (d, J=8.8 Hz, 1H), 4.60 (s, 2H), 3.91 (s, 3H), 3.21 (m, 4H), 2.10-2.00 (m, 4H). MS (ES+) m/e 352.1 (M+H)$^+$.

Example 199

N-(2-(3,6-diazabicyclo[3.1.1]heptan-3-yl)pyrimidin-4-yl)-1H-indazol-5-amine

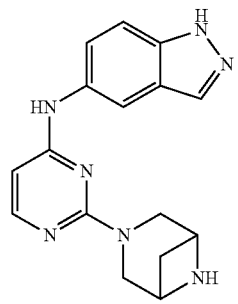 [SMILES: c1cc(Nc2ccc3[nH]ncc3c2)nc(N2CC3CC(C2)N3)n1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.1.1]heptan-3-yl)pyrimidin-4-yl)-1H-indazol-5-amine as a yellow solid (52%). $^1$H NMR (400 MHz, CD$_3$OD) δ 8.13 (s, 1H), 8.10 (s, 1H), 7.89 (d, J=7.2 Hz, 1H), 7.65-7.55 (m, 2H), 6.49 (d, J=7.2 Hz, 1H), 4.61 (d, J=5.6 Hz, 2H), 4.17 (m, 4H), 3.16-3.10 (m, 1H), 2.05-2.02 (m, 1H). MS (ES+) m/e 308.1 (M+H)$^+$.

Example 200

N-(2-(3,6-diazabicyclo[3.1.1]heptan-6-yl)pyrimidin-4-yl)-1H-indazol-5-amine

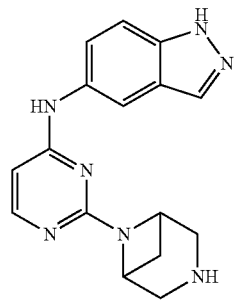 [SMILES: c1cc(Nc2ccc3[nH]ncc3c2)nc(N2C3CNCC2C3)n1]

The reaction was conducted following general protocol A. The reaction time of the first step was 32 hours and the crude material was further used without additional purification. The final residue was purified by reverse phase preparative HPLC to afford N-(2-(3,6-diazabicyclo[3.1.1]heptan-6-yl)pyrimidin-4-yl)-1H-indazol-5-amine as a yellow solid (38%). $^1$H NMR (400 MHz, CD$_3$OD) δ 8.27 (s, 1H), 8.10-7.94 (m, 3H), 7.56-7.44 (m, 2H), 6.26 (d, J=6.0 Hz, 1H), 4.51 (d, J=6.0 Hz, 2H), 3.92-3.89 (m, 2H), 3.41-3.38 (m, 2H), 3.02-2.93 (m, 1H), 1.92-1.90 (m, 1H). MS (ES+) m/e 308.1 (M+H)$^+$.

Example 201

N-(2-(2,5-diazabicyclo[2.2.1]heptan-2-yl)pyrimidin-4-yl)-1H-indazol-5-amine

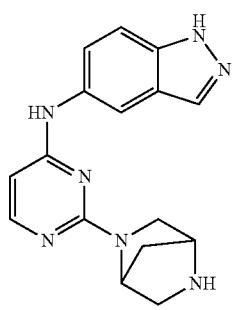 [SMILES: c1cc(Nc2ccc3[nH]ncc3c2)nc(N2CC3CC2CN3)n1]

The reaction was conducted following general protocol A. The reaction time of the first step was 32 hours and the crude material was further used without additional purification. The final residue was purified by reverse phase preparative HPLC to afford N-(2-(2,5-diazabicyclo[2.2.1]heptan-2-yl)pyrimidin-4-yl)-1H-indazol-5-amine as a white solid (38%). $^1$H NMR (400 MHz, CD$_3$OD) δ 8.11 (s, 1H), 8.10 (s, 1H), 7.82 (d, J=7.2 Hz, 1H), 7.66-7.50 (m, 2H), 6.41 (d, J=6.4 Hz, 1H), 5.11 (s, 1H), 4.66 (s, 1H), 3.89-3.80 (m, 2H), 3.58-3.47 (m, 2H), 2.36 (d, J=11.2 Hz, 1H), 2.17 (d, J=11.2 Hz, 1H). MS (ES+) m/e 308.1 (M+H)$^+$.

Example 202

N-(2-(2,8-diazaspiro[4.5]decan-2-yl)pyrimidin-4-yl)-1H-indazol-5-amine

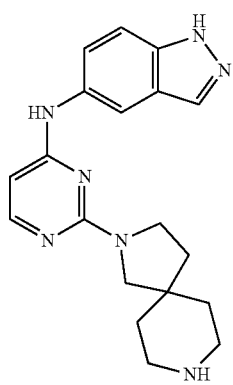 [SMILES: c1cc(Nc2ccc3[nH]ncc3c2)nc(N2CCC3(CCNCC3)C2)n1]

The reaction was conducted following general protocol A. The reaction time of the first step was 16 hours and the crude material was further used without additional purification. The final residue was purified by reverse phase preparative HPLC to afford N-(2-(2,8-diazaspiro[4.5]decan-2-yl)pyrimidin-4-yl)-1H-indazol-5-amine as a white solid (69%). MS (ES+) m/e 349.1 (M+H)$^+$.

Example 203

N-(2-(3-methyl-1,4-diazepan-1-yl)pyrimidin-4-yl)-1H-indazol-5-amine

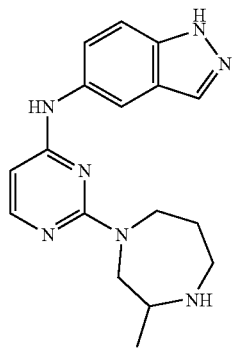 [SMILES: CC1CN(c2nccc(Nc3ccc4[nH]ncc4c3)n2)CCCN1]

The reaction was conducted following general protocol A. The reaction time of the first step was 16 hours and the crude material was further used without additional purification. The final residue was purified by reverse phase preparative HPLC to afford N-(2-(3-methyl-1,4-diazepan-1-yl)pyrimidin-4-yl)-1H-indazol-5-amine as a white solid (29%). $^1$H NMR (400 MHz, CD$_3$OD) δ 8.12 (s, 1H), 7.96 (s, 1H), 7.83 (d, J=6.0 Hz, 1H), 7.49 (s, 2H), 6.02 (d, J=6.0 Hz, 1H), 4.36-4.24 (m, 2H), 3.43-3.36 (m, 1H), 3.15-3.11 (m, 2H), 3.03-2.96 (m, 1H), 2.67-2.61 (m, 1H), 2.13-2.11 (m, 1H), 1.92-1.85 (m, 1H), 1.16 (d, J=6.4 Hz, 3H). MS (ES+) m/e 323.9 (M+H).

Example 204

N-(6-methyl-2-(3-methylpiperazin-1-yl)pyrimidin-4-yl)-1H-indazol-5-amine

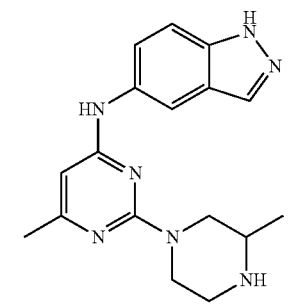

The reaction was conducted following general protocol A. The reaction time of the first step was 16 hours and the crude material was further used without additional purification. The final residue was purified by reverse phase preparative HPLC to afford N-(6-methyl-2-(3-methylpiperazin-1-yl)pyrimidin-4-yl)-1H-indazol-5-amine as a yellow solid (56%). $^1$H NMR (400 MHz, DMSO-d$_6$) δ 12.90 (brs, 1H), 9.11 (s, 1H), 8.27 (s, 2H), 7.98 (s, 2H), 7.48 (d, J=8.8 Hz, 1H), 7.41 (d, J=8.8 Hz, 1H), 5.91 (s, 1H), 4.54 (d, J=13.2 Hz, 2H), 3.15 (d, J=10.0 Hz, 1H), 3.00 (m, 2H), 2.88-2.67 (m, 2H), 2.13 (s, 3H), 1.16 (d, J=5.6 Hz, 3H). MS (ES+) m/e 324.1 (M+H).

Example 205

N-(6-methyl-2-(piperazin-1-yl)pyrimidin-4-yl)-1H-indazol-5-amine

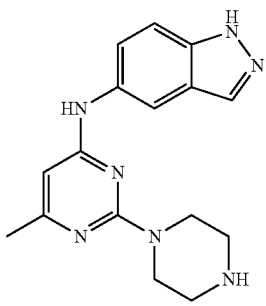 [SMILES: Cc1cc(Nc2ccc3[nH]ncc3c2)nc(N2CCNCC2)n1]

The reaction was conducted following general protocol A. The reaction time of the first step was 32 hours and the crude material was further used without additional purification. The final residue was purified by reverse phase preparative HPLC to afford N-(6-methyl-2-(piperazin-1-yl)pyrimidin-4-yl)-1H-indazol-5-amine as a yellow solid (46%). $^1$H NMR (400 MHz, CD$_3$OD) δ 8.35 (s, 2H), 8.00 (s, 1H), 7.94 (s, 1H), 7.51 (d, J=8.8 Hz, 1H), 7.45 (dd, J=8.8, 1.6 Hz, 1H), 6.00 (s, 1H), 4.03 (t, J=4.8 Hz, 4H), 3.25 (d, J=5.2 Hz, 4H), 2.22 (s, 3H). MS (ES+) m/e 310.1 (M+H).

Example 206

N-(2-(3-ethyl-1,4-diazepan-1-yl)-6-methylpyrimidin-4-yl)-1H-indazol-5-amine

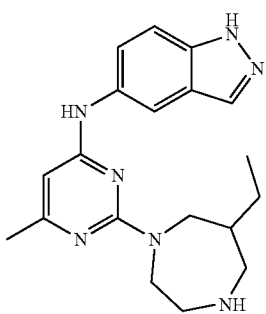 [SMILES: CCC1CNCCN(c2nc(C)cc(Nc3ccc4[nH]ncc4c3)n2)C1]

The reaction was conducted following general protocol A. The reaction time of the first step was 36 hours and the crude material was further used without additional purification. The final residue was purified by reverse phase preparative HPLC to afford N-(2-(3-ethyl-1,4-diazepan-1-yl)-6-methylpyrimidin-4-yl)-1H-indazol-5-amine as a yellow solid (13%). $^1$H NMR (400 MHz, CD$_3$OD) δ 8.38 (s, 2H), 7.99 (m, 2H), 7.53-7.44 (m, 2H), 5.99 (s, 1H), 4.51-4.47 (m, 1H), 4.36-4.34 (m, 1H), 3.47-3.42 (m, 3H), 3.37-3.36 (m, 1H), 3.05-3.02 (m, 1H), 2.27-2.24 (m, 4H), 2.14-2.13 (m, 1H), 1.68-1.65 (m, 2H), 0.99-0.97 (m, 3H). MS (ES+) m/e 352.1 (M+H).

Example 207

N-(6-methyl-2-(2-methylpiperazin-1-yl)pyrimidin-4-yl)-1H-indazol-5-amine

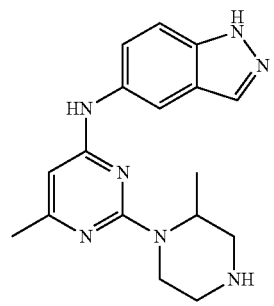

The reaction was conducted following general protocol A. The reaction time of the first step was 64 hours and the crude material was further used without additional purification. The final residue was purified by reverse phase preparative HPLC to afford N-(6-methyl-2-(2-methylpiperazin-1-yl)pyrimidin-4-yl)-1H-indazol-5-amine as a yellow solid (12%). $^1$H NMR (400 MHz, CD$_3$OD) δ 12.59 (s, 1H), 11.14 (s, 1H), 9.85 (s, 1H), 9.54 (s, 1H), 8.10 (s, 1H), 8.04 (s, 1H), 7.57 (s, 2H), 6.36 (s, 1H), 4.94 (m, 1H), 4.63-4.60 (m, 1H), 3.52-3.46 (m, 1H), 3.3-3.05 (m, 4H), 2.42 (s, 3H), 1.42 (d, J=6.8 Hz, 3H). MS (ES+) m/e 324.2 (M+H).

Example 208

N-(6-methyl-2-(3-methyl-1,4-diazepan-1-yl)pyrimidin-4-yl)-1H-indazol-5-amine

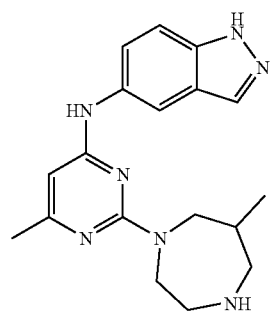

The reaction was conducted following general protocol A. The reaction time of the first step was 16 hours and the crude material was further used without additional purification. The final residue was purified by reverse phase preparative HPLC to afford N-(6-methyl-2-(3-methyl-1,4-diazepan-1-yl)pyrimidin-4-yl)-1H-indazol-5-amine as a yellow solid (37%). $^1$H NMR (400 MHz, CD$_3$OD) δ 8.10 (s, 1H), 7.95 (brs, 1H), 7.64-7.62 (d, J=8.8 Hz, 1H), 7.48 (m, 1H), 6.24 (s, 1H), 4.26 (m, 1H), 3.95 (m, 1H), 3.67-3.51 (m, 4H), 3.24-3.22 (m, 1H), 2.43 (s, 3H), 2.31 (m, 2H), 1.15 (m, 3H). MS (ES+) m/e 338.1 (M+H).

Example 209

N-(2-(3,8-diazabicyclo[3.2.1]octan-8-yl)-6-methylpyrimidin-4-yl)-1H-indazol-5-amine

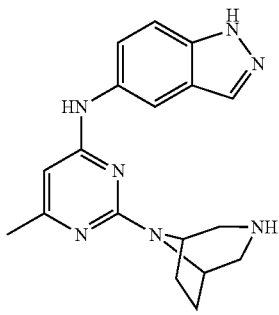 [SMILES: Cc1cc(Nc2ccc3[nH]ncc3c2)nc(N2C3CCC2CNC3)n1]

The reaction was conducted following general protocol A. The reaction time of the first step was 16 hours and the crude material was further used without additional purification. The final residue was purified by reverse phase preparative HPLC to afford N-(2-(3,8-diazabicyclo[3.2.1]octan-8-yl)-6-methylpyrimidin-4-yl)-1H-indazol-5-amine as a yellow solid (37%). $^1$H NMR (400 MHz, DMSO-$d_6$) δ 12.96 (brs, 1H), 9.09 (s, 1H), 8.26 (s, 2H), 8.02 (s, 1H), 8.00 (s, 1H), 7.49-7.42 (m, 2H), 5.91 (s, 1H), 4.58 (s, 2H), 2.98 (d, J=12.0 Hz, 2H), 2.80 (d, J=12.0 Hz, 2H), 2.14 (s, 3H), 1.98-1.91 (m, 4H). MS (ES+) m/e 336.1 (M+H).

Example 210

N-(2-(hexahydropyrrolo[3,4-c]pyrrol-2(1H)-yl)pyrimidin-4-yl)-1H-indazol-5-amine

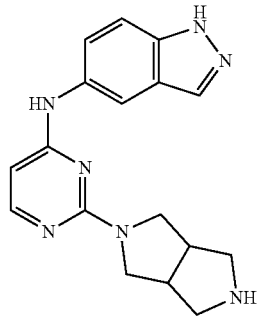 [SMILES: c1cc(Nc2ccc3[nH]ncc3c2)nc(N2CC3CNCC3C2)n1]

The reaction was conducted following general protocol A. The reaction time of the first step was 16 hours and the crude material was further used without additional purification. The final residue was purified by reverse phase preparative HPLC to afford N-(2-(hexahydropyrrolo[3,4-c]pyrrol-2 (1H)-yl)pyrimidin-4-yl)-1H-indazol-5-amine as a white solid (55%). MS (ES+) m/e 322.1 (M+H)$^+$.

Example 211

N-(2-(2,5-diazabicyclo[2.2.1]heptan-2-yl)-6-methylpyrimidin-4-yl)-1H-indazol-5-amine

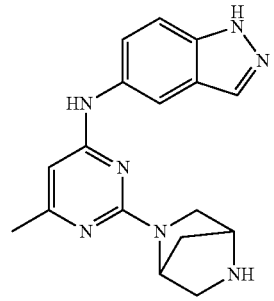 [SMILES: Cc1cc(Nc2ccc3[nH]ncc3c2)nc(N2CC3CC2CN3)n1]

The reaction was conducted following general protocol A. The reaction time of the first step was 16 hours and the crude material was further used without additional purification. The final residue was purified by reverse phase preparative HPLC to afford N-(2-(2,5-diazabicyclo[2.2.1]heptan-2-yl)-6-methylpyrimidin-4-yl)-1H-indazol-5-amine as a yellow solid (11%). $^1$H NMR (400 MHz, CD$_3$OD) δ 8.08 (s, 1H), 8.04 (s, 1H), 7.65-7.41 (m, 2H), 6.20 (s, 1H), 5.14 (s, 1H), 4.63 (s, 1H), 3.90-3.81 (m, 2H), 3.60-3.54 (m, 1H), 3.49-3.43 (m, 1H), 2.39 (s, 3H), 2.34-2.31 (m, 1H), 2.18-2.11 (m, 1H). MS (ES+) m/e 338.1 (M+H).

Example 212

N-(6-methyl-2-(4,7-diazaspiro[2.5]octan-7-yl)pyrimidin-4-yl)-1H-indazol-5-amine

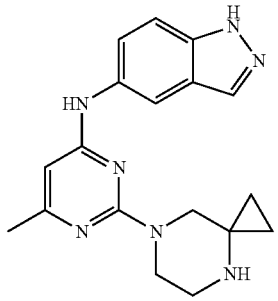 [SMILES: Cc1cc(Nc2ccc3[nH]ncc3c2)nc(N2CCNC3(CC3)C2)n1]

The reaction was conducted following general protocol A. The reaction time of the first step was 16 hours and the crude material was further used without additional purification. The final residue was purified by reverse phase preparative HPLC to afford N-(6-methyl-2-(4,7-diazaspiro[2.5]octan-7-yl)pyrimidin-4-yl)-1H-indazol-5-amine as a white solid (9%). $^1$H NMR (400 MHz, DMSO-$d_6$) δ 13.04 (brs, 1H), 9.90 (s, 1H), 9.37 (s, 2H), 8.05 (s, 1H), 7.92 (s, 1H), 7.53 (d, J=8.8 Hz, 1H), 7.40 (d, J=8.4 Hz, 1H), 6.09 (s, 1H), 4.00 (m, 2H), 3.87 (s, 2H), 3.34 (m, 2H), 2.24 (s, 3H), 1.07-1.01 (m, 2H), 0.95-0.88 (m, 2H). MS (ES+) m/e 336.1 (M+H).

Example 213

N-(2-(3,6-diazabicyclo[3.1.1]heptan-6-yl)-6-methylpyrimidin-4-yl)-1H-indazol-5-amine

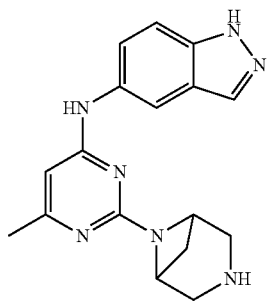 [SMILES: Cc1cc(Nc2ccc3[nH]ncc3c2)nc(N2C3CNCC2C3)n1]

The reaction was conducted following general protocol A. The reaction time of the first step was 32 hours and the crude material was further used without additional purification. The final residue was purified by reverse phase preparative HPLC to afford N-(2-(3,6-diazabicyclo[3.1.1]heptan-6-yl)-6-methylpyrimidin-4-yl)-1H-indazol-5-amine as a white solid (10%). $^1$H NMR (400 MHz, CD3OD) δ 8.08 (s, 1H), 8.01 (s, 1H), 7.66-7.39 (m, 2H), 6.23 (s, 1H), 4.76 (d, J=6.0 Hz, 2H), 3.89 (d, J=12.8 Hz, 2H), 3.59 (d, J=13.2 Hz, 2H), 3.16-3.04 (m, 1H), 2.38 (s, 3H), 2.00 (d, J=10.0 Hz, 1H). MS (ES+) m/e 322.1 (M+H).

Example 214

N-(5-fluoro-2-(piperazin-1-yl)pyrimidin-4-yl)-1H-indazol-5-amine

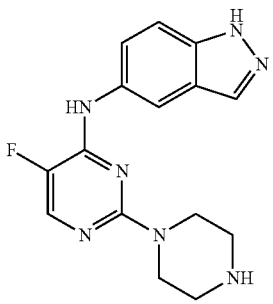 [SMILES: Fc1cnc(N2CCNCC2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(5-fluoro-2-(piperazin-1-yl)pyrimidin-4-yl)-1H-indazol-5-amine as a yellow solid (29%). $^1$H NMR (400 MHz, CD$_3$OD) δ 8.44 (s, 2H), 8.02 (s, 1H), 8.00 (s, 1H), 7.91 (d, J=3.6 Hz, 1H), 7.59-7.50 (m, 2H), 3.91 (t, J=5.2 Hz, 4H), 3.22 (t, J=5.2 Hz, 4H). MS (ES+) m/e 313.7 (M+H).

Example 215

N-(2-(1,4-diazepan-1-yl)-5-fluoropyrimidin-4-yl)-1H-indazol-5-amine

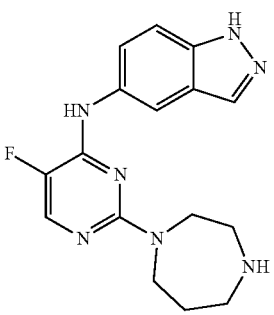 [SMILES: Fc1cnc(N2CCCNCC2)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(1,4-diazepan-1-yl)-5-fluoropyrimidin-4-yl)-1H-indazol-5-amine as a yellow solid (28%). $^1$H NMR (400 MHz, CD$_3$OD) δ 8.39 (s, 2H), 8.07 (d, J=1.2 Hz, 1H), 8.01 (d, J=0.8 Hz, 1H), 7.88 (d, J=4.0 Hz, 1H), 7.61-7.49 (m, 2H), 3.97 (t, J=5.2 Hz, 2H), 3.85 (t, J=6.0 Hz, 2H), 3.35-3.32 (m, 2H), 3.28-3.25 (m, 2H), 2.13-2.07 (m, 2H). MS (ES+) m/e 327.7 (M+H).

Example 216

N-(5-fluoro-2-(2-methylpiperazin-1-yl)pyrimidin-4-yl)-1H-indazol-5-amine

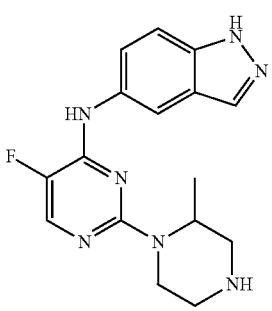

The reaction was conducted following general protocol A. The reaction time of the first step was 64 hours and the crude material was further used without additional purification. The final residue was purified by reverse phase preparative HPLC to afford N-(5-fluoro-2-(2-methylpiperazin-1-yl)pyrimidin-4-yl)-1H-indazol-5-amine as a white solid (3%). $^1$H NMR (400 MHz, CD$_3$OD) δ 8.51 (s, 2H), 8.01 (m, 2H), 7.90 (d, J=3.6 Hz, 1H), 7.58 (dd, J=9.2, 2.0 Hz, 1H), 7.52 (d, J=8.8 Hz, 1H), 4.53 (m, 2H), 3.35 (m, 1H), 3.27-3.19 (m, 3H), 3.05-3.01 (m, 1H), 1.30 (d, J=7.2 Hz, 3H). MS (ES+) m/e 328.1 (M+H).

Example 217

N-(2-(3,8-diazabicyclo[3.2.1]octan-3-yl)-5-fluoropyrimidin-4-yl)-1H-indazol-5-amine

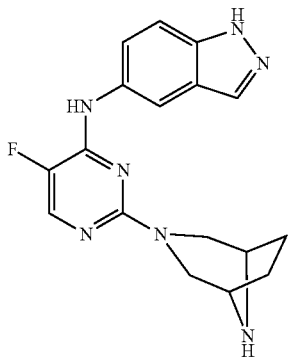 [SMILES: Fc1cnc(N2CC3CCC(C2)N3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,8-diazabicyclo[3.2.1]octan-3-yl)-5-fluoropyrimidin-4-yl)-1H-indazol-5-amine as off-white solid 9%). $^{1}$H NMR (400 MHz, CD$_{3}$OD) δ 8.49 (s, 1H), 8.05 (s, 2H), 7.91 (d, J=3.6 Hz, 1H), 7.60 (dd, J=8.8, 2.0 Hz, 1H), 7.54 (d, J=8.8 Hz, 1H), 4.45-4.42 (m, 2H), 4.13 (m, 2H), 3.26-2.23 (m, 2H), 2.09-1.97 (m, 4H). MS (ES+) m/e 340.0 (M+H).

Example 218

N-(5-fluoro-2-(6-methyl-1,4-diazepan-1-yl)pyrimidin-4-yl)-1H-indazol-5-amine

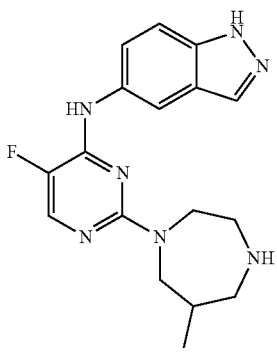 [SMILES: CC1CNCCN(c2ncc(F)c(Nc3ccc4[nH]ncc4c3)n2)C1]

The reaction was conducted following general protocol A. The reaction time of the first step was 16 hours and the crude material was further used without additional purification. The final residue was purified by reverse phase preparative HPLC to afford N-(5-fluoro-2-(6-methyl-1,4-diazepan-1-yl) pyrimidin-4-yl)-1H-indazol-5-amine as yellow solid (46%). $^{1}$H NMR (400 MHz, CD$_{3}$OD) δ 8.52 (s, 2H), 8.11 (d, J=1.2 Hz, 1H), 8.02 (d, J=0.8 Hz, 1H), 7.90 (d, J=3.6 Hz, 1H), 7.61 (dd, J=8.8, 2.0 Hz, 1H), 7.54 (d, J=8.8 Hz, 1H), 4.32-4.22 (m, 2H), 3.76-3.69 (m, 1H), 3.57-3.50 (m, 1H), 3.29-3.19 (m, 2H), 3.15-3.09 (m, 1H), 3.04-2.98 (m, 1H), 2.32-2.21 (m, 1H), 1.03 (d, J=6.8 Hz, 3H). MS (ES+) m/e 342.0 (M+H).

Example 219

N-(2-(2,5-diazabicyclo[2.2.1]heptan-2-yl)-5-fluoropyrimidin-4-yl)-1H-indazol-5-amine

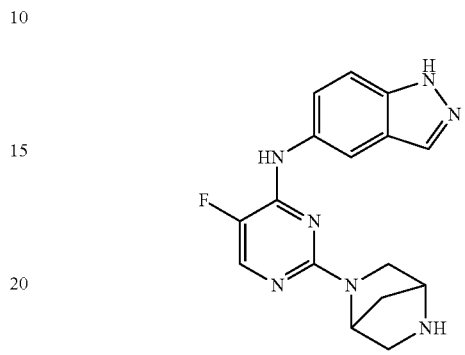

The reaction was conducted following general protocol A. The reaction time of the first step was 16 hours and the crude material was further used without additional purification. The final residue was purified by reverse phase preparative HPLC to afford N-(2-(2,5-diazabicyclo[2.2.1]heptan-2-yl)-5-fluoropyrimidin-4-yl)-1H-indazol-5-amine as a white solid (33%). $^{1}$H NMR (400 MHz, CD$_{3}$OD) δ 8.19 (s, 1H), 8.02 (d, J=0.8 Hz, 1H), 7.83 (d, J=4.0 Hz, 1H), 7.66 (dd, J=8.8 Hz, 2.0 Hz, 1H), 7.52 (d, J=8.8 Hz, 1H), 4.76 (s, 1H), 3.94 (s, 1H), 3.63-3.56 (m, 1H), 3.55-3.48 (m, 1H), 3.12-3.06 (m, 2H), 2.01-1.98 (m, 1H), 1.85-1.82 (m, 1H). MS (ES+) m/e 326.3 (M+H).

Example 220

N-(2-(3,6-diazabicyclo[3.1.1]heptan-6-yl)-5-fluoropyrimidin-4-yl)-1H-indazol-5-amine

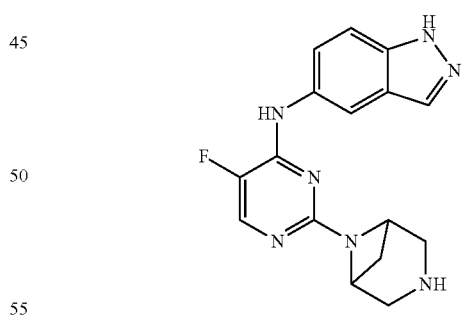

The reaction was conducted following general protocol A. The reaction time of the first step was 16 hours and the crude material was further used without additional purification. The final residue was purified by reverse phase preparative HPLC to afford N-(2-(3,6-diazabicyclo[3.1.1]heptan-6-yl)-5-fluoropyrimidin-4-yl)-1H-indazol-5-amine as a yellow solid (20%). $^{1}$H NMR (400 MHz, CD$_{3}$OD) δ 8.13 (d, J=1.6 Hz, 1H), 8.02-7.98 (m, 1H), 7.86 (d, J=4.2 Hz, 1H), 7.65-7.59 (m, 1H), 7.53-7.48 (m, 1H), 4.27 (d, J=6.0 Hz, 2H), 3.58-3.55 (m, 2H), 2.89-2.86 (m, 2H), 2.74-2.67 (m, 1H), 1.79 (d, J=8.4 Hz, 1H). MS (ES+) m/e 326.2 (M+H).

Example 221

N-(2-(3,8-diazabicyclo[3.2.1]octan-8-yl)-5-fluoropyrimidin-4-yl)-1H-indazol-5-amine

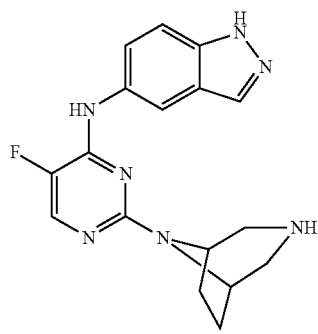 [SMILES: Fc1cnc(N2C3CCC2CNC3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,8-diazabicyclo[3.2.1]octan-8-yl)-5-fluoropyrimidin-4-yl)-1H-indazol-5-amine as a white solid (5%). $^1$H NMR (400 MHz, DMSO-$d_6$) δ 9.61 (s, 1H), 9.07 (s, 1H), 8.86 (s, 1H), 8.17-8.00 (m, 3H), 7.61 (dd, J=8.8, 1.6 Hz, 1H), 7.51 (d, J=8.8 Hz, 1H), 4.57 (s, 2H), 3.16 (m, 4H), 2.13-1.93 (m, 4H). MS (ES+) m/e 340.1 (M+H).

Example 222

N-(2-(3,6-diazabicyclo[3.1.1]heptan-6-yl)-5-chloropyrimidin-4-yl)-1H-indazol-5-amine

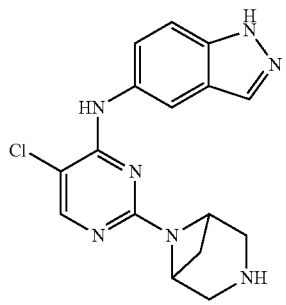 [SMILES: Clc1cnc(N2C3CNCC2C3)nc1Nc1ccc2[nH]ncc2c1]

The reaction was conducted following general protocol A. The reaction time of the first step was 16 hours and the crude material was further used without additional purification. The final residue was purified by reverse phase preparative HPLC to afford N-(2-(3,6-diazabicyclo[3.1.1]heptan-6-yl)-5-chloropyrimidin-4-yl)-1H-indazol-5-amine as a white solid (5%). $^1$H NMR (400 MHz, DMSO-$d_6$) δ 13.02 (brs, 1H), 9.17 (s, 1H), 9.06 (s, 1H), 8.39 (m, 1H), 8.16 (s, 1H), 8.06 (s, 1H), 7.97 (s, 1H), 7.55-7.48 (m, 2H), 4.24 (m, 2H), 3.65-3.62 (m, 2H), 3.31-3.26 (m, 2H), 2.74-2.68 (m, 1H), 1.82-1.80 (m, 1H). MS (ES+) m/e 342.0 (M+H).

Example 223

8-(4-((1H-indazol-5-yl)amino)pyrimidin-2-yl)-8-azabicyclo[3.2.1]octan-3-ol

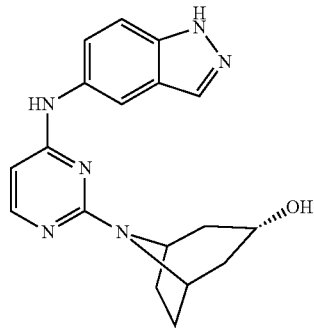

The reaction was conducted following general protocol C. The reaction was stirred for 48 hours at 110° C. Residue was purified by reverse phase preparative HPLC to afford 8-(4-((1H-indazol-5-yl)amino)pyrimidin-2-yl)-8-azabicyclo[3.2.1]octan-3-ol as a white solid (5%). $^1$H NMR (400 MHz, DMSO-$d_6$) δ 12.94 (brs, 1H), 9.13 (s, 1H), 8.10 (s, 1H), 7.98 (s, 1H), 7.88 (d, J=6.0 Hz, 1H), 7.49-7.44 (m, 2H), 5.98 (d, J=6.0 Hz, 1H), 4.58 (s, 1H), 4.58 (s, 1H), 4.51 (s, 2H), 3.89 (s, 1H), 2.28-1.64 (m, 8H). MS (ES+) m/e 337.1 (M+H).

Example 224

N-(2-(3-phenylpiperazin-1-yl)pyrimidin-4-yl)-1H-indazol-5-amine

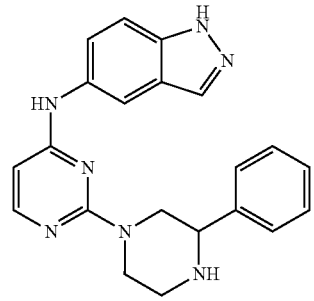 [SMILES: c1ccc(C2CN(c3nccc(Nc4ccc5[nH]ncc5c4)n3)CCN2)cc1]

The reaction was conducted following general protocol C. The reaction was stirred for 16 hours. Residue was purified by reverse phase preparative HPLC to afford N-(2-(3-phenylpiperazin-1-yl)pyrimidin-4-yl)-1H-indazol-5-amine as a white solid (17%). $^1$H NMR (400 MHz, DMSO-$d_6$) δ 12.96 (brs, 1H), 9.20 (s, 1H), 8.10 (s, 1H), 7.91 (d, J=6.0 Hz, 1H), 7.82 (s, 1H), 7.48-7.29 (m, 7H), 6.02 (d, J=5.6 Hz, 1H), 4.64 (d, J=12.0 Hz, 1H), 4.57 (d, J=12.0 Hz, 1H), 3.70 (d, J=8.0 Hz, 1H), 3.06 (d, J=11.2 Hz, 1H), 2.91-2.67 (m, 4H). MS (ES+) m/e 372.1 (M+H).

Example 225

N-(2-(3-methylpiperazin-1-yl)pyrimidin-4-yl)-1H-indazol-5-amine

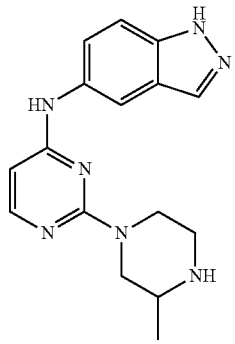 [SMILES: CC1CN(c2nccc(Nc3ccc4[nH]ncc4c3)n2)CCN1]

The reaction was conducted following general protocol A. The reaction time of the first step was 16 hours and the crude material was further used without additional purification. The final residue was purified by reverse phase preparative HPLC to afford N-(2-(3-methylpiperazin-1-yl)pyrimidin-4-yl)-1H-indazol-5-amine as a yellow solid (10%). $^1$H NMR (400 MHz, DMSO-$d_6$) δ 13.0 (s, 1H), 9.15 (s, 1H), 8.05 (s, 1H), 7.98 (s, 1H), 7.88 (d, J=5.6 Hz, 1H), 7.48 (d, J=9.2 Hz, 1H), 7.43 (d, J=9.2 Hz, 1H), 5.98 (d, J=5.6 Hz, 1H), 4.45 (t, J=11.2 Hz, 2H), 2.91 (d, J=11.6 Hz, 2H), 2.78 (t, J=12.0 Hz, 1H), 2.64-2.57 (m, 2H), 2.42-2.37 (m, 1H), 1.01 (d, J=6.4 Hz, 3H). MS (ES+) m/e 310.2 (M+H).

Example 226

N-(2-(3,5-dimethylpiperazin-1-yl)pyrimidin-4-yl)-1H-indazol-5-amine

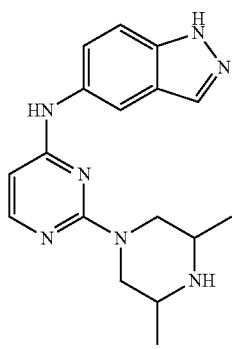 [SMILES: CC1CN(c2nccc(Nc3ccc4[nH]ncc4c3)n2)CC(C)N1]

The reaction was conducted following general protocol A. The reaction time of the first step was 16 hours and the crude material was further used without additional purification. The final residue was purified by reverse phase preparative HPLC to afford N-(2-(3,5-dimethylpiperazin-1-yl)pyrimidin-4-yl)-1H-indazol-5-amine as a yellow solid (10%). $^1$H NMR (400 MHz, DMSO-$d_6$) δ 9.15 (s, 1H), 8.06 (s, 1H), 7.95 (s, 1H), 7.87 (d, J=5.6 Hz, 1H), 7.48 (d, J=8.8 Hz, 1H), 7.42 (d, J=8.8 Hz, 1H), 5.97 (d, J=5.6 Hz, 1H), 4.51 (d, J=10.4 Hz, 2H), 2.70-2.64 (m, 2H), 2.30-2.27 (m, 2H), 2.21 (br.s, 1H), 1.02 (d, J=6.4 Hz, 6H). MS (ES+) m/e 324.2 (M+H).

Example 227

N-(2-(3,3-dimethylpiperazin-1-yl)pyrimidin-4-yl)-1H-indazol-5-amine

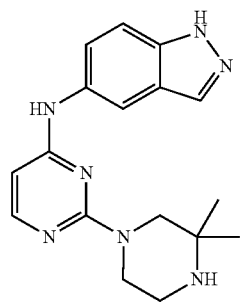 [SMILES: CC1(C)CN(c2nccc(Nc3ccc4[nH]ncc4c3)n2)CCN1]

The reaction was conducted following general protocol A. The reaction time of the first step was 16 hours and the crude material was further used without additional purification. The final residue was purified by reverse phase preparative HPLC to afford N-(2-(3,3-dimethylpiperazin-1-yl)pyrimidin-4-yl)-1H-indazol-5-amine as a white solid (35%). $^1$H NMR (400 MHz, DMSO-$d_6$) δ 13.0 (s, 1H), 9.12 (s, 1H), 8.06 (s, 1H), 7.97 (s, 1H), 7.86 (d, J=5.6 Hz, 1H), 7.48 (d, J=8.8 Hz, 1H), 7.42 (d, J=8.8 Hz, 1H), 5.95 (d, J=5.6 Hz, 1H), 3.65 (t, J=4.8 Hz, 2H), 3.47 (s, 2H), 2.77 (t, J=4.8 Hz, 2H), 1.88 (br.s, 1H), 1.04 (s, 6H). MS (ES+) m/e 324.1 (M+H).

Example 228

N-(2-(3,8-diazabicyclo[3.2.1]octan-8-yl)pyrimidin-4-yl)-1H-indazol-5-amine

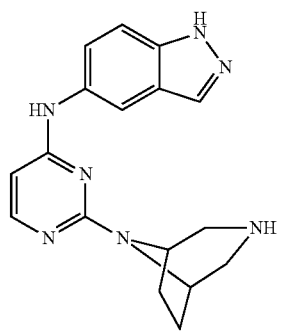 [SMILES: c1cc(Nc2ccc3[nH]ncc3c2)nc(N2C3CCC2CNC3)n1]

The reaction was conducted following general protocol A. The reaction time of the first step was 16 hours at 110° C. and the crude material was further used without additional purification. The final residue was purified by reverse phase preparative HPLC to afford N-(2-(3,8-diazabicyclo[3.2.1]octan-8-yl)pyrimidin-4-yl)-1H-indazol-5-amine as a white solid (12%). $^1$H NMR (400 MHz, CD$_3$OD) δ 8.04 (s, 1H), 8.00 (s, 1H), 7.86 (d, J=5.6 Hz, 1H), 7.51 (s, 2H), 6.06 (d, J=5.6 Hz, 1H), 4.59 (m, 2H), 3.11-3.07 (m, 2H), 2.74-2.71 (m, 2H), 2.09-2.02 (m, 4H). MS (ES+) m/e 322.1 (M+H).

Example 229

N-(2-(3,8-diazabicyclo[3.2.1]octan-3-yl)pyrimidin-4-yl)-1H-indazol-5-amine

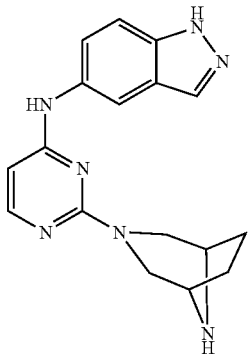 [SMILES: c1cc(Nc2ccc3[nH]ncc3c2)nc(N2CC3CCC(C2)N3)n1]

The reaction was conducted following general protocol A. The reaction time of the first step was 16 hours at 110° C. and the crude material was further used without additional purification. The final residue was purified by reverse phase preparative HPLC to afford N-(2-(3,8-diazabicyclo[3.2.1]octan-3-yl)pyrimidin-4-yl)-1H-indazol-5-amine as a white solid (16%). $^1$H NMR (400 MHz, DMSO-$d_6$) δ 12.95 (brs, 1H), 9.12 (s, 1H), 8.05 (s, 1H), 8.00 (s, 1H), 7.86 (d, J=5.2 Hz, 1H), 7.50-7.44 (m, 2H), 5.99 (d, J=6.0 Hz, 1H), 4.16 (d, J=11.2 Hz, 2H), 3.46 (s, 2H), 2.93 (d, J=12.0 Hz, 2H), 1.64-1.54 (m, 4H). MS (ES+) m/e 322.1 (M+H).

Example 230

(1-(4-((1H-indazol-5-yl)amino)pyrimidin-2-yl)piperazin-2-yl)methanol

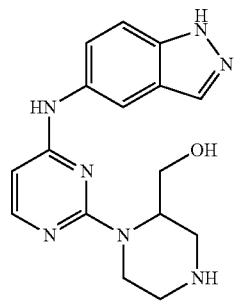 [SMILES: OCC1CNCCN1c1nccc(Nc2ccc3[nH]ncc3c2)n1]

The reaction was conducted following general protocol A. The reaction time of the first step was 48 hours at 110° C. and the crude material was further used without additional purification. The final residue was purified by reverse phase preparative HPLC to afford (1-(4-((1H-indazol-5-yl)amino)pyrimidin-2-yl)piperazin-2-yl)methanol as a white solid (4%). $^1$H NMR (400 MHz, CD$_3$OD) δ 8.05 (s, 1H), 8.01 (s, 1H), 7.87 (d, J=6.0 Hz, 1H), 7.54-7.46 (m, 2H), 6.05 (d, J=6.0 Hz, 1H), 4.68 (d, J=3.2 Hz, 1H), 4.45 (d, J=11.6 Hz, 1H), 3.97 (dd, J=10.4 Hz, 8.4 Hz, 1H), 3.76 (dd, J=10.4 Hz, 5.2 Hz, 1H), 3.20-3.04 (m, 2H), 2.90 (dd, J=12.8 Hz, 4.4 Hz, 1H), 2.78 (td, J=12.4 Hz, 3.6 Hz, 1H). MS (ES+) m/e 326.1 (M+H).

Example 231

(R)—N-(2-(3-aminopyrrolidin-1-yl)pyrimidin-4-yl)-1H-indazol-5-amine

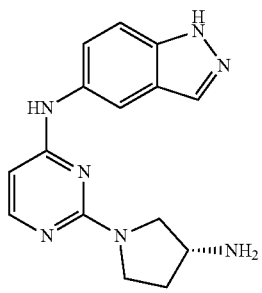 [SMILES: N[C@@H]1CCN(c2nccc(Nc3ccc4[nH]ncc4c3)n2)C1]

The reaction was conducted following general protocol A. The reaction time of the first step was 16 and the crude material was further used without additional purification. The final residue was purified by reverse phase preparative HPLC to afford (R)—N-(2-(3-aminopyrrolidin-1-yl)pyrimidin-4-yl)-1H-indazol-5-amine as a white solid (17%). $^1$H NMR (400 MHz, DMSO-$d_6$) δ 12.91 (brs, 1H), 9.17-9.04 (m, 1H), 8.26 (brs, 1H), 7.98 (s, 1H), 7.86 (d, J=5.6 Hz, 1H), 7.53-7.43 (m, 2H), 5.97 (d, J=5.6 Hz, 1H), 3.68-3.51 (m, 4H), 3.18 (brs, 1H), 2.09-1.97 (m, 1H), 1.74-1.63 (m, 1H). MS (ES+) m/e 296.1 (M+H).

Example 232

N-(2-(2-methylpiperazin-1-yl)pyrimidin-4-yl)-1H-indazol-5-amine

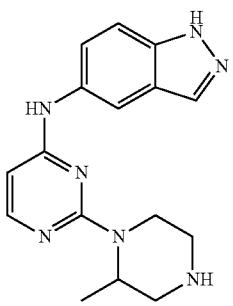 [SMILES: CC1CNCCN1c1nccc(Nc2ccc3[nH]ncc3c2)n1]

The reaction was conducted following general protocol E. Intermediate was purified via reverse phase preparative HPLC. The final residue was purified by reverse phase preparative HPLC (base) to afford N-(2-(2-methylpiperazin-1-yl)pyrimidin-4-yl)-1H-indazol-5-amine as a white solid (32%). $^1$H NMR (400 MHz, CD$_3$OD) δ 8.02 (s, 1H), 7.99 (s, 1H), 7.86 (d, J=5.6 Hz, 1H), 7.51 (s, 2H), 6.04 (d, J=5.6 Hz, 1H), 4.78-4.77 (m, 1H), 4.39-4.36 (m, 1H), 4.34-4.32 (m, 1H), 3.00-2.91 (m, 2H), 2.79-2.71 (m, 2H), 1.30 (d, J=6.8 Hz, 3H). MS (ES+) m/e 310.1 (M+H).

Example 233

N-(2-(3-((3-methoxybenzyl)amino)piperidin-1-yl)pyrimidin-4-yl)-1H-indazol-5-amine

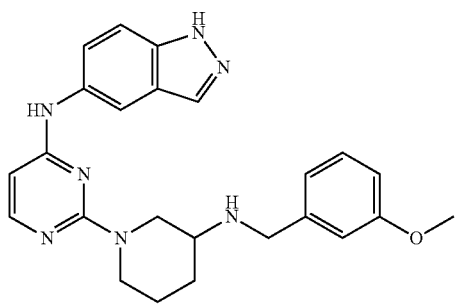 [SMILES: COc1cccc(CNC2CCCN(c3nccc(Nc4ccc5[nH]ncc5c4)n3)C2)c1]

The reaction was conducted following general protocol F. The final residue was purified by reverse phase preparative HPLC to afford N-(2-(3-((3-methoxybenzyl)amino)piperidin-1-yl)pyrimidin-4-yl)-1H-indazol-5-amine as a white solid (38%). $^1$H NMR (400 MHz, DMSO-d$_6$) δ 12.94 (s, 1H), 9.16 (s, 1H), 8.13 (s, 1H), 7.93 (s, 1H), 7.87 (d, J=5.6 Hz, 1H), 7.50-7.42 (m, 2H), 7.14 (t, J=7.6 Hz, 1H), 6.88-6.79 (m, 2H), 6.74 (d, J=8.4 Hz, 1H), 5.96 (d, J=6.0 Hz, 1H), 4.68 (d, J=11.2 Hz, 1H), 4.37 (d, J=12.8 Hz, 1H), 3.86-3.81 (m, 1H), 3.73-3.64 (m, 3H), 2.95 (t, J=10.4 Hz, 1H), 2.84-2.73 (m, 1H), 2.45 (m, 1H), 1.93 (m, 1H), 1.68 (m, 1H), 1.35-1.34 (m, 2H). MS (ES+) m/e 430.2 (M+H).

Example 234

N-(2-(3-(benzylamino)piperidin-1-yl)pyrimidin-4-yl)-1H-indazol-5-amine

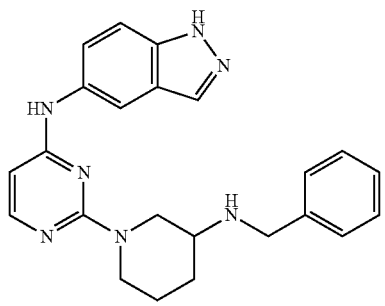 [SMILES: c1ccc(CNC2CCCN(c3nccc(Nc4ccc5[nH]ncc5c4)n3)C2)cc1]

The reaction was conducted following general protocol F. The final residue was purified by reverse phase preparative HPLC to afford N-(2-(3-(benzylamino)piperidin-1-yl)pyrimidin-4-yl)-1H-indazol-5-amine as a white solid (2%). $^1$H NMR (400 MHz, DMSO-d$_6$) δ 12.94 (s, 1H), 9.15 (s, 1H), 8.10 (s, 1H), 7.92 (s, 1H), 7.87 (d, J=5.6 Hz, 1H), 7.47 (s, 2H), 7.28-7.14 (m, 5H), 5.96 (d, J=5.6 Hz, 1H), 4.67 (d, J=10.4 Hz, 1H), 4.37 (d, J=12.4 Hz, 1H), 3.87-3.78 (m, 1H), 3.76-3.66 (m, 1H), 2.99-2.90 (m, 1H), 2.81-2.75 (m, 1H), 2.43 (m, 1H), 1.93 (m, 1H), 1.67 (m, 1H), 1.34-1.32 (m, 2H). MS (ES+) m/e 400.2 (M+H).

Example 235

N-(2-(2-ethylpiperazin-1-yl)pyrimidin-4-yl)-1H-indazol-5-amine

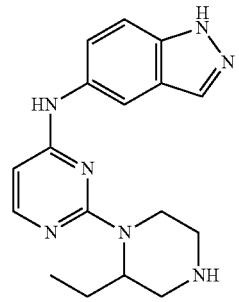 [SMILES: CCC1CNCCN1c1nccc(Nc2ccc3[nH]ncc3c2)n1]

The reaction was conducted following general protocol A. The final residue was purified by reverse phase preparative HPLC to afford N-(2-(2-ethylpiperazin-1-yl)pyrimidin-4-yl)-1H-indazol-5-amine as a white solid (42%). $^1$H NMR (400 MHz, DMSO-d$_6$) δ 12.95 (s, 1H), 9.14 (s, 1H), 8.10 (s, 1H), 7.96 (s, 1H), 7.87 (d, J=5.6 Hz, 1H), 7.49-7.42 (m, 2H), 5.96 (d, J=5.6 Hz, 1H), 4.44-4.37 (m, 2H), 2.94-2.86 (m, 3H), 2.67-2.63 (m, 1H), 2.52-2.51 (m, 1H), 1.87-1.85 (m, 1H), 1.58-1.55 (m, 1H), 0.88 (t, J=7.2 Hz, 3H). MS (ES+) m/e 324.2 (M+H).

Example 236

2-(7-benzyl-1,4-diazepan-1-yl)-N-(1H-indazol-5-yl)-5,7-dihydrofuro[3,4-d]pyrimidin-4-amine

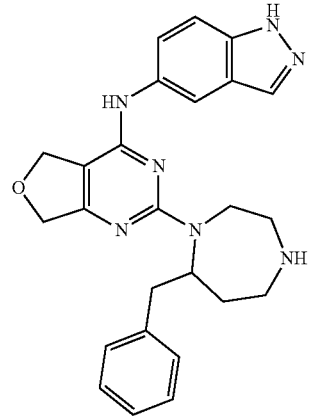 [SMILES: c1ccc(CC2CCNCCN2c2nc3c(c(Nc4ccc5[nH]ncc5c4)n2)COC3)cc1]

The reaction was conducted following general protocol B. The final residue was purified by reverse phase preparative HPLC to afford 2-(7-benzyl-1,4-diazepan-1-yl)-N-(1H-indazol-5-yl)-5,7-dihydrofuro[3,4-d]pyrimidin-4-amine as a white solid (63%). $^1$H NMR (400 MHz, DMSO-d$_6$) δ 12.75 (s, 1H), 8.46 (s, 1H), 7.98 (s, 1H), 7.95 (s, 1H), 7.53-7.46 (m, 2H), 7.19-7.01 (m, 5H), 4.88 (s, 2H), 4.83-4.73 (m, 1H), 4.68 (s, 2H), 4.25 (d, J=14 Hz, 1H), 2.94-2.86 (m, 4H), 2.72-2.69 (m, 2H), 2.37-2.27 (m, 1H), 1.95-1.85 (m, 1H), 1.65-1.56 (m, 1H). MS (ES+) m/e 442.3 (M+H).

Example 237

N-(2-(6-methyl-1,4-diazepan-1-yl)pyrimidin-4-yl)-1H-indazol-5-amine

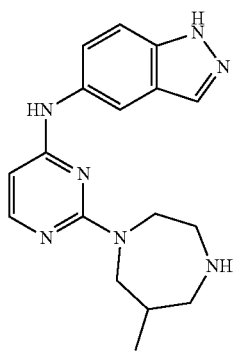 [SMILES: CC1CNCCN(c2nccc(Nc3ccc4[nH]ncc4c3)n2)C1]

The reaction was conducted following general protocol B. The final residue was purified by reverse phase preparative HPLC to afford N-(2-(6-methyl-1,4-diazepan-1-yl)pyrimidin-4-yl)-1H-indazol-5-amine as a white solid (25%). $^1$H NMR (400 MHz, Methanol-d4) δ 8.13 (s, 1H), 7.97 (s, 1H), 7.85 (d, J=5.6 Hz, 1H), 7.53-7.46 (m, 2H), 6.04 (d, J=6.0 Hz, 1H), 4.36-4.15 (m, 2H), 3.57-3.53 (m, 1H), 3.31-3.23 (m, 1H), 3.12-2.97 (m, 3H), 2.66 (dd, J=13.6 Hz, 9.2 Hz, 1H), 2.18-2.15 (m, 1H), 0.99 (d, J=6.8 Hz, 3H). MS (ES+) m/e 324.1 (M+H).

Example 238

N-(2-(2-methyl-1,4-diazepan-1-yl)pyrimidin-4-yl)-1H-indazol-5-amine

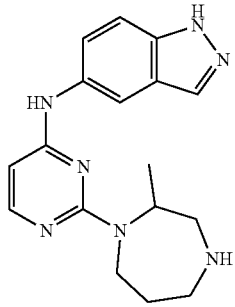 [SMILES: CC1CNCCCN1c1nccc(Nc2ccc3[nH]ncc3c2)n1]

The reaction was conducted following general protocol B. The final residue was purified by reverse phase preparative HPLC to afford N-(2-(2-methyl-1,4-diazepan-1-yl)pyrimidin-4-yl)-1H-indazol-5-amine as a white solid (12%). $^1$H NMR (400 MHz, Methanol-d4) δ 8.20 (s, 1H), 7.97 (s, 1H), 7.85 (d, J=6.0 Hz, 1H), 7.54-7.48 (m, 2H), 6.03 (d, J=6.0 Hz, 1H), 4.72 (m, 1H), 4.33 (m, 1H), 3.40 (dd, J=14.4 Hz, 6.0 Hz, 1H), 3.25-3.17 (m, 2H), 2.74-2.68 (m, 2H), 2.03-1.78 (m, 2H), 1.17 (d, J=6.0 Hz, 3H). MS (ES+) m/e 324.2 (M+H).

Example 239

2-(5-methyl-1,4-diazepan-1-yl)-N-(4-(pyridin-4-yl)phenyl)quinazolin-4-amine

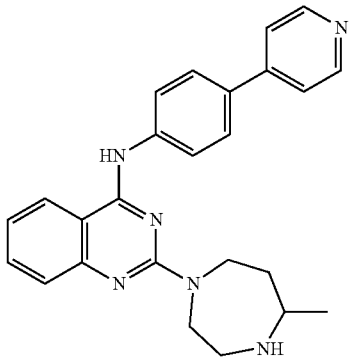 [SMILES: CC1CCN(c2nc(Nc3ccc(-c4ccncc4)cc3)c3ccccc3n2)CCN1]

The reaction was conducted following general protocol G. The final residue was purified by reverse phase preparative HPLC to afford 2-(5-methyl-1,4-diazepan-1-yl)-N-(4-(pyridin-4-yl)phenyl)quinazolin-4-amine as a yellow solid (56%). $^1$H NMR (400 MHz, Methanol-d$_4$) δ 8.60 (d, J=6.0 Hz, 2H), 8.41 (brs, 1H), 8.24 (d, J=7.2 Hz, 1H), 7.99 (d, J=8.8 Hz, 2H), 7.87 (d, J=8.8 Hz, 2H), 7.78 (d, J=6.4 Hz, 2H), 7.72-7.66 (m, 1H), 7.56 (d, J=8.0 Hz, 1H), 7.32-7.29 (m, 1H), 4.29-4.17 (m, 3H), 3.88-3.81 (m, 1H), 3.65-3.50 (m, 2H), 3.42-3.34 (m, 1H), 2.25-2.20 (m, 1H), 2.09-1.99 (m, 1H), 1.39 (d, J=6.4 Hz, 3H). MS (ES+) m/e 411.0 (M+H).

Example 240

N-(2-(7-methyl-1,4-diazepan-1-yl)pyrimidin-4-yl)-1H-indazol-5-amine

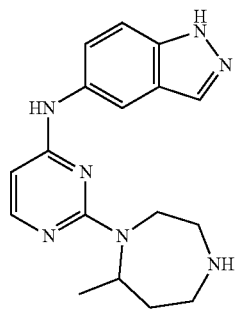 [SMILES: CC1CCNCCN1c1nccc(Nc2ccc3[nH]ncc3c2)n1]

The reaction was conducted following general protocol A. The final residue was purified by reverse phase preparative HPLC to afford N-(2-(7-methyl-1,4-diazepan-1-yl)pyrimidin-4-yl)-1H-indazol-5-amine as a white solid (27%). $^1$H NMR (400 MHz, DMSO-d$_6$) δ 12.97 (brs, 1H), 9.23 (s, 1H), 8.29 (s, 2H), 8.14 (brs, 1H), 8.00 (s, 1H), 7.90 (d, J=5.6 Hz, 1H), 7.49-7.43 (m, 2H), 6.03 (d, J=5.6 Hz, 1H), 3.98-3.93 (m, 2H), 3.81-3.78 (m, 1H), 3.68-3.66 (m, 1H), 3.29 (m, 1H), 3.11-3.05 (m, 2H), 1.99 (m, 1H), 1.75 (m, 1H), 1.17 (d, J=6.4 Hz, 3H). MS (ES+) m/e 324.2 (M+H).

Example 241

N-(2-(2-ethyl-1,4-diazepan-1-yl)pyrimidin-4-yl)-1H-indazol-5-amine

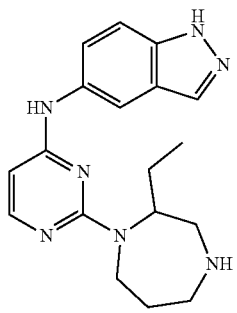 [SMILES: CCC1CNCCCN1c1nccc(Nc2ccc3[nH]ncc3c2)n1]

The reaction was conducted following general protocol B. The final residue was purified by reverse phase preparative HPLC to afford N-(2-(2-ethyl-1,4-diazepan-1-yl)pyrimidin-4-yl)-1H-indazol-5-amine as a white solid (30%). $^1$H NMR (400 MHz, Methanol-d4) δ 8.16 (brs, 1H), 7.96 (s, 1H), 7.83 (d, J=6.0 Hz, 1H), 7.52-7.46 (m, 2H), 6.01 (d, J=6.0 Hz, 1H), 4.75-4.67 (m, 1H), 4.22 (m, 1H), 3.50-3.45 (m, 1H), 3.19-3.14 (m, 2H), 2.71-2.67 (m, 2H), 1.89 (m, 1H), 1.76-1.72 (m, 2H), 1.58-1.51 (m, 1H), 0.94 (t, J=7.6 Hz, 3H). MS (ES+) m/e 338.2 (M+H).

Example 242

N-(2-(3-((3-methoxybenzyl)(methyl)amino)piperidin-1-yl)pyrimidin-4-yl)-1H-indazol-5-amine

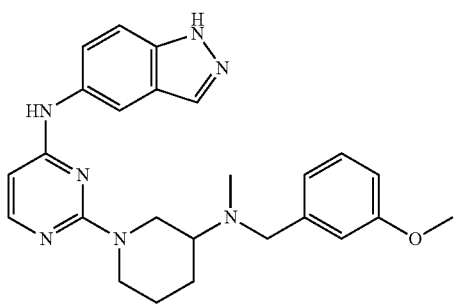 [SMILES: COc1cccc(CN(C)C2CCCN(c3nccc(Nc4ccc5[nH]ncc5c4)n3)C2)c1]

The reaction was conducted following general protocol F. The final residue was purified by reverse phase preparative HPLC to afford N-(2-(3-((3-methoxybenzyl)(methyl)amino)piperidin-1-yl)pyrimidin-4-yl)-1H-indazol-5-amine as a white solid (12%). $^1$H NMR (400 MHz, DMSO-d$_6$) δ 12.93 (s, 1H), 9.15 (s, 1H), 8.13 (brs, 1H), 7.91 (s, 1H), 7.88 (d, J=5.2 Hz, 1H), 7.47-7.45 (m, 2H), 7.18 (t, J=7.6 Hz, 1H), 6.87-6.84 (m, 2H), 6.77 (d, J=8.0 Hz, 1H), 5.97 (d, J=5.6 Hz, 1H), 4.82 (d, J=12.0 Hz, 1H), 4.56 (d, J=12.0 Hz, 1H), 3.68 (s, 3H), 3.66-3.56 (m, 2H), 2.88-2.76 (m, 2H), 2.47-2.44 (m, 1H), 2.21 (s, 3H), 1.93 (d, J=10.8 Hz, 1H), 1.75 (d, J=13.2 Hz, 1H), 1.60-1.56 (m, 1H), 1.38 (m, 1H). MS (ES+) m/e 444.4 (M+H).

Example 243

N-(4-(1H-pyrazol-4-yl)phenyl)-2-(3,8-diazabicyclo[3.2.1]octan-8-yl)-7,8-dihydro-5H-pyrano[4,3-d]pyrimidin-4-amine

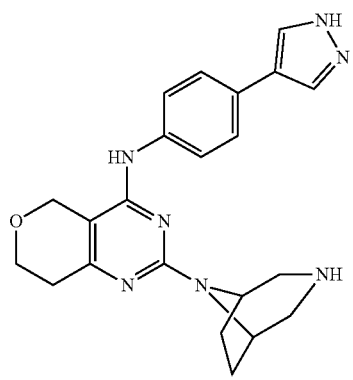 [SMILES: c1cc(-c2cn[nH]c2)ccc1Nc1nc(N2C3CCC2CNC3)nc2c1COCC2]

The reaction was conducted following general protocol A. Intermediate was purified via reverse phase preparatory HPLC. The final residue was purified by reverse phase preparative HPLC to afford -(4-(1H-pyrazol-4-yl)phenyl)-2-(3,8-diazabicyclo[3.2.1]octan-8-yl)-7,8-dihydro-5H-pyrano[4,3-d]pyrimidin-4-amine as a white solid (19%). $^1$H NMR (400 MHz, DMSO-d$_6$) δ 9.26 (brs, 1H), 8.94 (brs, 1H), 8.04 (s, 1H), 7.61 (d, J=8.4 Hz, 2H), 7.56 (d, J=8.4 Hz, 2H), 4.69 (s, 2H), 4.60 (s, 2H), 3.93 (t, J=5.6 Hz, 2H), 3.22 (m, 4H), 2.71 (m, 2H), 2.10-2.01 (m, 4H). MS (ES+) m/e 404.1 (M+H).

Example 244

N-(2-(3-((2-methoxyphenyl)amino)piperidin-1-yl)pyrimidin-4-yl)-1H-indazol-5-amine

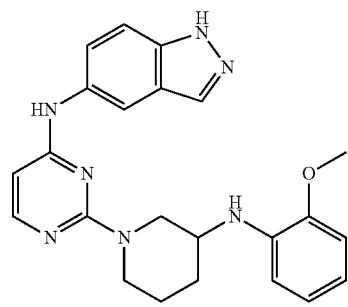 [SMILES: COc1ccccc1NC1CCCN(c2nccc(Nc3ccc4[nH]ncc4c3)n2)C1]

The reaction was conducted following general protocol F. The final residue was purified by reverse phase preparative HPLC to afford N-(2-(3-((2-methoxyphenyl)amino)piperidin-1-yl)pyrimidin-4-yl)-1H-indazol-5-amine as a white solid (6%). $^1$H NMR (400 MHz, Methanol-d$_4$) δ 8.31-8.66 (m, 1H), 7.98 (s, 1H), 7.79 (d, J=6.3 Hz, 1H), 7.70 (s, 1H), 7.34-7.49 (m, 2H), 6.82-6.80 (m, 1H), 6.73-6.70 (m, 1H), 6.57-6.54 (m, 2H), 6.12 (d, J=6.3 Hz, 1H), 4.50 (d, J=12.6 Hz, 1H), 4.11 (d, J=12.9 Hz, 1H), 3.80 (s, 3H), 3.51 (d, J=3.9 Hz, 1H), 3.36-3.43 (m, 1H), 3.21 (dd, J=12.9, 8.4 Hz, 1H), 2.12 (s, 1H), 1.88 (s, 1H), 1.70 (t, J=9.3 Hz, 2H). MS (ES+) m/e 416.3 (M+H).

Example 245

6-methyl-2-(5-methyl-1,4-diazepan-1-yl)-N-(4-(pyridin-4-yl)phenyl)pyrimidin-4-amine

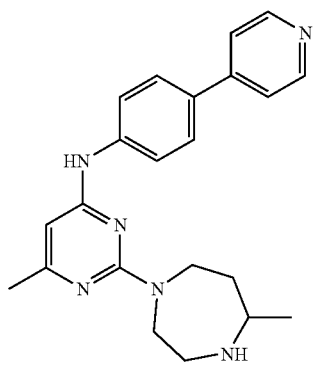 [SMILES: Cc1cc(Nc2ccc(-c3ccncc3)cc2)nc(N2CCNC(C)CC2)n1]

The reaction was conducted following general protocol G. The final residue was purified by reverse phase preparative HPLC to afford 6-methyl-2-(5-methyl-1,4-diazepan-1-yl)-N-(4-(pyridin-4-yl)phenyl)pyrimidin-4-amine as a yellow solid (50%). $^1$H NMR (400 MHz, Methanol-d4) δ 8.56 (d, J=6.0 Hz, 2H), 8.26 (s, 3H), 7.84-7.75 (m, 4H), 7.74 (d, J=6.0 Hz, 2H), 6.08 (s, 1H), 4.20-4.11 (m, 3H), 3.83-3.77 (m, 1H), 3.64-3.49 (m, 2H), 3.41-3.34 (m, 1H), 2.28 (s, 3H), 2.24-2.20 (m, 1H), 2.10-1.97 (m, 1H), 1.40 (d, J=6.4 Hz, 3H). MS (ES+) m/e 374.8 (M+H).

Example 246

(R)—N-(2-(3-((4-methoxyphenyl)amino)pyrrolidin-1-yl)pyrimidin-4-yl)-1H-indazol-5-amine

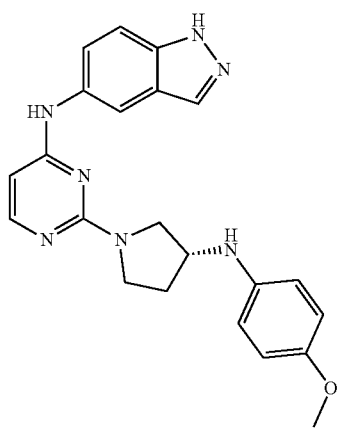 [SMILES: COc1ccc(N[C@@H]2CCN(c3nccc(Nc4ccc5[nH]ncc5c4)n3)C2)cc1]

The reaction was conducted following general protocol F. The final residue was purified by reverse phase preparative HPLC to afford (R)—N-(2-(3-((4-methoxyphenyl)amino)pyrrolidin-1-yl)pyrimidin-4-yl)-1H-indazol-5-amine as a white solid (13%). $^1$H NMR (400 MHz, DMSO-d$_6$) δ 12.91 (s, 1H), 9.13 (s, 1H), 8.28 (s, 1H), 7.92-7.86 (m, 2H), 7.46 (s, 2H), 6.75 (d, J=8.8 Hz, 2H), 6.61 (d, J=8.8 Hz, 2H), 5.99 (d, J=5.6 Hz, 1H), 5.42 (d, J=6.8 Hz, 1H), 4.02 (m, 1H), 3.83 (m, 1H), 3.65-3.63 (m, 5H), 3.44-3.42 (m, 1H), 2.26-2.23 (m, 1H), 1.93-1.91 (m, 1H). MS (ES+) m/e 402.1 (M+H).

Example 247

6-methyl-2-(3-methyl-1,4-diazepan-1-yl)-N-(4-(pyridin-4-yl)phenyl)pyrimidin-4-amine

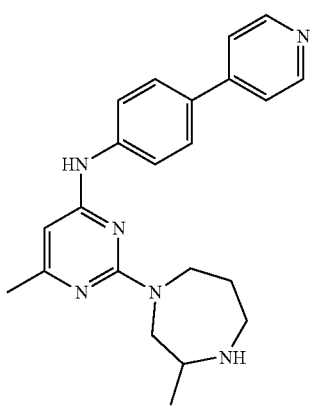 [SMILES: Cc1cc(Nc2ccc(-c3ccncc3)cc2)nc(N2CCCNC(C)C2)n1]

The reaction was conducted following general protocol G. The final residue was purified by reverse phase preparative HPLC to afford 6-methyl-2-(3-methyl-1,4-diazepan-1-yl)-N-(4-(pyridin-4-yl)phenyl)pyrimidin-4-amine as a yellow solid (56%). $^1$H NMR (400 MHz, Methanol-d$_4$) δ 8.56 (d, J=6.4 Hz, 2H), 8.36 (s, 2H), 7.82-7.76 (m, 4H), 7.73 (d, J=6.4 Hz, 2H), 6.07 (s, 1H), 4.52-4.46 (m, 2H), 3.71-3.68 (m, 1H), 3.50-3.42 (m, 3H), 3.09-3.06 (m, 1H), 2.34-2.15 (m, 5H), 1.41 (d, J=6.8 Hz, 3H). MS (ES+) m/e 374.8 (M+H).

Example 248

2-(3-ethyl-1,4-diazepan-1-yl)-N-(4-(pyridin-4-yl)phenyl)pyrimidin-4-amine

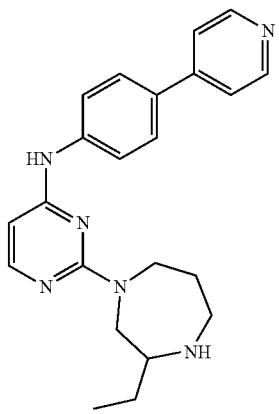 [SMILES: CCC1CN(c2nccc(Nc3ccc(-c4ccncc4)cc3)n2)CCCN1]

The reaction was conducted following general protocol G. The final residue was purified by reverse phase preparative HPLC to afford 2-(3-ethyl-1,4-diazepan-1-yl)-N-(4-(pyridin-4-yl)phenyl)pyrimidin-4-amine as a yellow solid (65%). $^1$H NMR (400 MHz, Methanol-d4) δ 8.55 (d, J=6.0 Hz, 2H), 8.32 (s, 2H), 7.97 (d, J=6.0 Hz, 1H), 7.81-7.75 (m, 4H), 7.71 (d, J=6.0 Hz, 2H), 6.17 (d, J=6.0 Hz, 1H), 4.52 (d, J=12.80 Hz, 1H), 4.41-4.31 (m, 1H), 3.56-3.40 (m, 4H), 3.14-3.04

(m, 1H), 2.28-2.14 (m, 2H), 1.79-1.74 (m, 2H), 1.09 (t, J=7.6 Hz, 3H). MS (ES+) m/e 375.2 (M+H).

Example 249

2-(5-ethyl-1,4-diazepan-1-yl)-N-(4-(pyridin-4-yl)phenyl)pyrimidin-4-amine

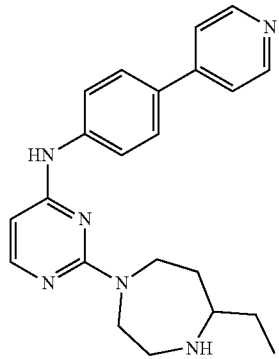 [SMILES: CCC1CCN(c2nccc(Nc3ccc(-c4ccncc4)cc3)n2)CCN1]

The reaction was conducted following general protocol G. The final residue was purified by reverse phase preparative HPLC to afford 2-(5-ethyl-1,4-diazepan-1-yl)-N-(4-(pyridin-4-yl)phenyl)pyrimidin-4-amine as a yellow solid (65%). $^1$H NMR (400 MHz, Methanol-d4) δ 8.56 (d, J=6.1 Hz, 2H), 8.36 (brs, 2H), 7.99 (d, J=5.8 Hz, 1H), 7.86-7.78 (m, 4H), 7.74 (d, J=6.3 Hz, 2H), 6.20 (d, J=5.9 Hz, 1H), 4.22-4.03 (m, 3H), 3.81-3.75 (m, 1H), 3.63-3.54 (m, 1H), 3.40-3.34 (m, 2H), 2.31-2.27 (m, 1H), 2.03-1.97 (m, 1H), 1.81-1.69 (m, 2H), 1.06 (t, J=7.5 Hz, 3H). MS (ES+) m/e 375.1 (M+H).

Example 250

2-(5-isopropyl-1,4-diazepan-1-yl)-N-(4-(pyridin-4-yl)phenyl)pyrimidin-4-amine

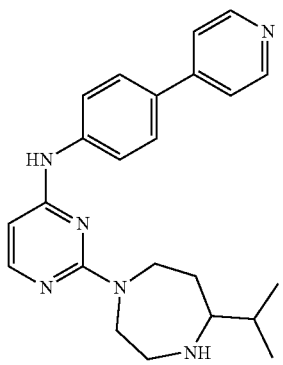 [SMILES: CC(C)C1CCN(c2nccc(Nc3ccc(-c4ccncc4)cc3)n2)CCN1]

The reaction was conducted following general protocol G. The final residue was purified by reverse phase preparative HPLC to afford 2-(5-isopropyl-1,4-diazepan-1-yl)-N-(4-(pyridin-4-yl)phenyl)pyrimidin-4-amine as a yellow solid (65%). $^1$H NMR (400 MHz, Methanol-d4) δ 8.55 (d, J=6.0 Hz, 2H), 8.33 (s, 2H), 7.97 (d, J=6.0 Hz, 1H), 7.82-7.76 (m, 4H), 7.72 (d, J=6.4 Hz, 2H), 6.18 (d, J=6.0 Hz, 1H), 4.26-4.08 (m, 2H), 4.06-4.0 (m, 1H), 3.81-3.71 (m, 1H), 3.60-3.51 (m, 1H), 3.29 (m, 2H), 2.23-2.19 (m, 1H), 2.14-2.03 (m, 1H), 1.95-1.86 (m, 1H), 1.05-1.00 (m, 6H). MS (ES+) m/e 389.2 (M+H).

Example 251

2-(3-isopropyl-1,4-diazepan-1-yl)-N-(4-(pyridin-4-yl)phenyl)pyrimidin-4-amine

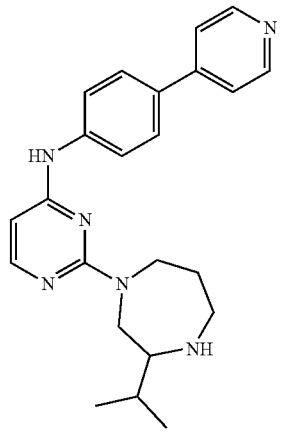 [SMILES: CC(C)C1CN(c2nccc(Nc3ccc(-c4ccncc4)cc3)n2)CCCN1]

The reaction was conducted following general protocol G. The final residue was purified by reverse phase preparative HPLC to afford 2-(3-isopropyl-1,4-diazepan-1-yl)-N-(4-(pyridin-4-yl)phenyl)pyrimidin-4-amine as a yellow solid (66%). $^1$H NMR (400 MHz, Methanol-d4) δ 8.55 (d, J=6.0 Hz, 2H), 8.30 (s, 2H), 7.97 (d, J=6.0 Hz, 1H), 7.80-7.72 (m, 4H), 7.71 (d, J=6.4 Hz, 2H), 6.17 (d, J=6.0 Hz, 1H), 4.45 (dd, J=15.2, 3.2 Hz, 1H), 4.31-4.20 (m, 1H), 3.68-3.62 (m, 2H), 3.49-3.48 (m, 1H), 3.41-3.38 (m, 1H), 3.12 (m, 1H), 2.25-2.08 (m, 3H), 1.11 (dd, J=6.8, 2.0 Hz, 6H). MS (ES+) m/e 389.2 (M+H).

Example 252

N-(4-(1H-pyrazol-4-yl)phenyl)-2-(3-methylpiperazin-1-yl)pyrimidin-4-amine

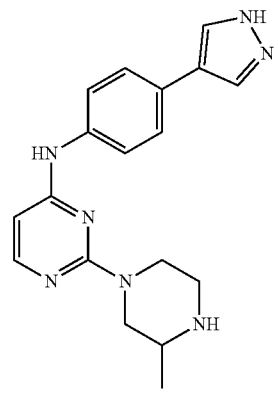 [SMILES: CC1CN(c2nccc(Nc3ccc(-c4cn[nH]c4)cc3)n2)CCN1]

The reaction was conducted following general protocol A. Intermediate was purified via reverse phase preparatory HPLC. The final residue was purified by reverse phase preparatory HPLC (base) to afford N-(4-(1H-pyrazol-4-yl)phenyl)-2-(3-methylpiperazin-1-yl)pyrimidin-4-amine as a white solid (24%). ¹H NMR (400 MHz, DMSO-d₆) δ 12.85 (s, 1H), 9.19 (s, 1H), 8.13-8.07 (m, 2H), 7.91 (d, J=5.6 Hz, 1H), 7.61 (d, J=8.8 Hz, 2H), 7.53 (d, J=8.8 Hz, 2H), 6.01 (d, J=5.6 Hz, 1H), 4.44 (t, J=9.6 Hz, 2H), 2.92 (d, J=11.67 Hz, 1H), 2.82-2.75 (m, 1H), 2.66-2.60 (m, 2H), 2.44-2.39 (m, 1H), 2.26 (brs, 1H), 1.02 (d, J=6.4 Hz, 3H). MS (ES+) m/e 336.2 (M+H).

Example 253

N-(4-(1H-pyrazol-4-yl)phenyl)-2-(2-methylpiperazin-1-yl)pyrimidin-4-amine

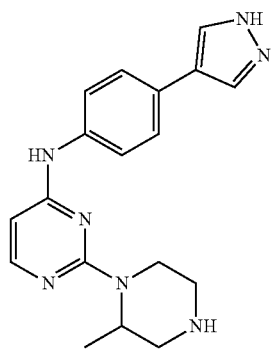 [SMILES: CC1CNCCN1c1nccc(Nc2ccc(-c3cn[nH]c3)cc2)n1]

The reaction was conducted following general protocol C. Intermediated was purified via reverse phase preparatory HPLC. The final residue was purified by reverse phase preparatory HPLC (base) to afford N-(4-(1H-pyrazol-4-yl)phenyl)-2-(3-methylpiperazin-1-yl)pyrimidin-4-amine as a white solid (10%). ¹H NMR (400 MHz, CD₃OD) δ 7.93 (s, 1H), 7.89 (d, J=5.6 Hz, 1H), 7.62 (d, J=8.8 Hz, 2H), 7.53 (d, J=8.8 Hz, 2H), 6.06 (d, J=5.6 Hz, 1H), 4.79-4.74 (m, 1H), 4.39-4.34 (m, 1H), 3.16-3.06 (m, 2H), 3.00-2.91 (m, 2H), 2.78-2.72 (m, 1H), 1.30 (d, J=6.8 Hz, 3H). MS (ES+) m/e 336.2 (M+H).

Example 254

(S)—N-(4-(1H-pyrazol-4-yl)phenyl)-2-(3-aminopyrrolidin-1-yl)pyrimidin-4-amine

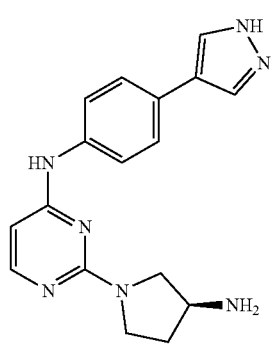 [SMILES: N[C@H]1CCN(c2nccc(Nc3ccc(-c4cn[nH]c4)cc3)n2)C1]

The reaction was conducted following general protocol A. Intermediated was purified via reverse phase preparatory HPLC. The final residue was purified by reverse phase preparatory HPLC (base) to afford (S)—N-(4-(1H-pyrazol-4-yl)phenyl)-2-(3-aminopyrrolidin-1-yl)pyrimidin-4-amine as a white solid (25%). ¹H NMR (400 MHz, CD₃OD) δ 7.92 (s, 1H), 7.83 (d, J=6.0 Hz, 1H), 7.74 (d, J=8.8 Hz, 2H), 7.53 (d, J=8.8 Hz, 2H), 6.04 (d, J=6.0 Hz, 1H), 3.86-3.72 (m, 2H), 3.71-3.57 (m, 2H), 3.39 (d, J=4.8 Hz, 1H), 2.31-2.20 (m, 1H), 1.92-1.84 (m, 1H). MS (ES+) m/e 322.1 (M+H).

Example 255

N-(4-(1H-pyrazol-4-yl)phenyl)-2-(3,3-dimethylpiperazin-1-yl)pyrimidin-4-amine

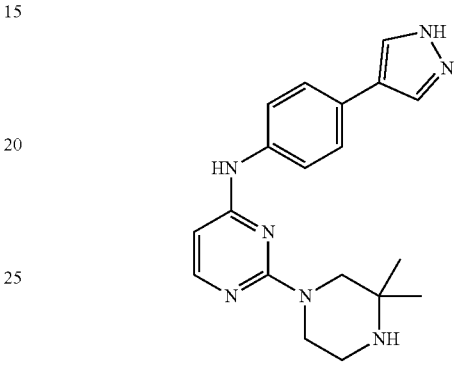

The reaction was conducted following general protocol A. Intermediate was purified via reverse phase preparatory HPLC. The final residue was purified by reverse phase preparatory HPLC (base) to afford N-(4-(1H-pyrazol-4-yl)phenyl)-2-(3,3-dimethylpiperazin-1-yl)pyrimidin-4-amine as a yellow solid (42%). ¹H NMR (400 MHz, DMSO-d₆) δ 12.77 (s, 1H), 9.18 (s, 1H), 7.99 (s, 2H), 7.89 (d, J=5.6 Hz, 1H), 7.62 (d, J=8.8 Hz, 2H), 7.54 (d, J=8.8 Hz, 2H), 5.98 (d, J=5.6 Hz, 1H), 3.64-3.62 (m, 2H), 3.47 (s, 2H), 2.78 (brs, 2H), 1.87 (brs, 1H), 1.04 (s, 6H). MS (ES+) m/e 322.1 (M+H).

Example 256

N-(4-(1H-pyrazol-4-yl)phenyl)-2-(3,5-dimethylpiperazin-1-yl)pyrimidin-4-amine

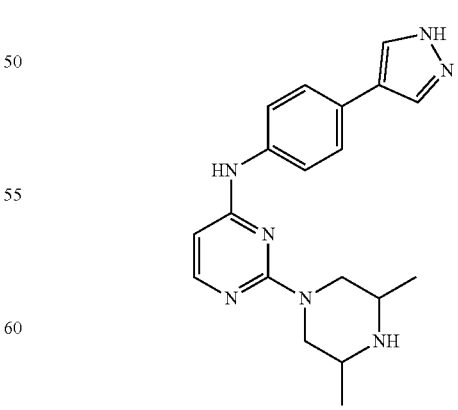

The reaction was conducted following general protocol A. Intermediate was purified via reverse phase preparatory HPLC. The final residue was purified by reverse phase preparatory HPLC (base) to afford N-(4-(1H-pyrazol-4-yl)phenyl)-2-(3,5-dimethylpiperazin-1-yl)pyrimidin-4-amine as a white solid (34%). $^1$H NMR (400 MHz, DMSO-d$_6$) δ 12.80 (s, 1H), 9.20 (s, 1H), 8.00 (s, 2H), 7.90 (d, J=5.6 Hz, 1H), 7.61 (d, J=8.8 Hz, 2H), 7.54 (d, J=8.8 Hz, 2H), 6.00 (d, J=5.6 Hz, 1H), 4.49 (d, J=10.4 Hz, 2H), 2.68 (brs, 2H), 2.31 (t, J=12.4 Hz, 2H), 2.20 (brs, 1H), 1.02 (d, J=6.4 Hz, 6H). MS (ES+) m/e 350.1 (M+H).

Example 257

N-(4-(1H-pyrazol-4-yl)phenyl)-2-(3,8-diazabicyclo[3.2.1]octan-8-yl)pyrimidin-4-amine

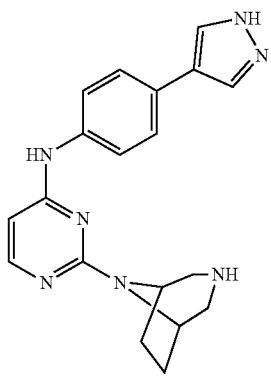 [SMILES: c1cc(Nc2ccc(-c3cn[nH]c3)cc2)nc(N2C3CCC2CNC3)n1]

The reaction was conducted following general protocol A. Intermediate was purified via reverse phase preparatory HPLC. The final residue was purified by reverse phase preparatory HPLC (base) to afford N-(4-(1H-pyrazol-4-yl)phenyl)-2-(3,8-diazabicyclo[3.2.1]octan-8-yl)pyrimidin-4-amine as a white solid (14%). $^1$H NMR (400 MHz, CD$_3$OD) δ 7.93 (s, 2H), 7.87 (d, J=6.0 Hz, 1H), 7.63 (d, J=8.8 Hz, 2H), 7.53 (d, J=8.8 Hz, 2H), 6.07 (d, J=5.6 Hz, 1H), 4.58 (s, 2H), 3.06 (d, J=12.8 Hz, 2H), 2.68 (d, J=12.8 Hz, 2H), 2.08-2.01 (m, 4H). MS (ES+) m/e 348.2 (M+H).

Example 258

N-(4-(1H-pyrazol-4-yl)phenyl)-2-(3,8-diazabicyclo[3.2.1]octan-3-yl)pyrimidin-4-amine

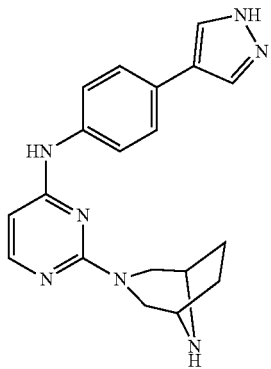 [SMILES: c1cc(Nc2ccc(-c3cn[nH]c3)cc2)nc(N2CC3CCC(C2)N3)n1]

The reaction was conducted following general protocol A. Intermediate was purified via reverse phase preparatory HPLC. The final residue was purified by reverse phase preparatory HPLC (base) to afford N-(4-(1H-pyrazol-4-yl)phenyl)-2-(3,8-diazabicyclo[3.2.1]octan-3-yl)pyrimidin-4-amine as a white solid (14%). $^1$H NMR (400 MHz, CD$_3$OD) δ 7.93 (s, 2H), 7.86 (d, J=6.0 Hz, 1H), 7.63 (d, J=8.8 Hz, 2H), 7.55 (d, J=8.4 Hz, 2H), 6.08 (d, J=5.6 Hz, 1H), 4.25 (d, J=12.4 Hz, 2H), 3.61 (s, 2H), 3.11 (d, J=12.4 Hz, 2H), 1.86-1.76 (m, 4H). MS (ES+) m/e 348.1 (M+H).

Example 259

8-(4-((4-(1H-pyrazol-4-yl)phenyl)amino)pyrimidin-2-yl)-8-azabicyclo[3.2.1]octan-3-ol

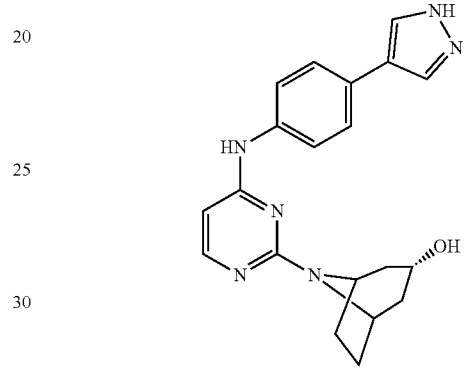

The reaction was conducted following general protocol A. Intermediate was purified via reverse phase preparatory HPLC. The final residue was purified by reverse phase preparative HPLC (base) to afford 8-(4-((4-(1H-pyrazol-4-yl)phenyl)amino)pyrimidin-2-yl)-8-azabicyclo[3.2.1]octan-3-ol as a white solid (61%). $^1$H NMR (400 MHz, CD3OD) δ 7.94 (brs, 1H), 7.84 (d, J=6.0 Hz, 1H), 7.67 (d, J=8.4 Hz, 2H), 7.54 (d, J=8.4 Hz, 2H), 6.04 (d, J=6.0 Hz, 1H), 4.61 (brs, 2H), 4.06 (brs, 1H), 2.40-2.31 (m, 2H), 2.21 (d, J=14.4 Hz, 2H), 2.04 (dd, J=9.6 Hz, 4.8 Hz, 2H), 1.78 (d, J=14.4 Hz, 2H). MS (ES+) m/e 363.1 (M+H).

Example 260

N-(4-(1H-pyrazol-4-yl)phenyl)-2-(3-phenylpiperazin-1-yl)pyrimidin-4-amine

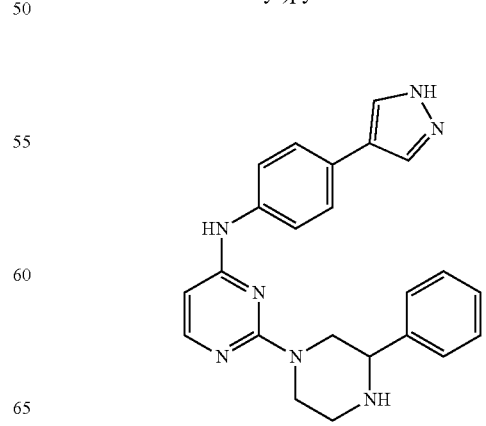

The reaction was conducted following general protocol A. Intermediate was purified via reverse phase preparatory HPLC. The final residue was purified by reverse phase preparative HPLC to afford N-(4-(1H-pyrazol-4-yl)phenyl)-2-(3-phenylpiperazin-1-yl)pyrimidin-4-amine as a yellow solid (15%). $^1$H NMR (400 MHz, DMSO-d$_6$) δ 12.87 (s, 1H), 9.25 (s, 1H), 8.11 (s, 1H), 7.93 (d, J=5.6 Hz, 1H), 7.86 (s, 1H), 7.62 (d, J=8.4 Hz, 2H), 7.52-7.46 (m, 4H), 7.40-7.30 (m, 3H), 6.04 (d, J=5.6 Hz, 1H), 4.63 (d, J=11.6 Hz, 1H), 4.56 (d, J=12.4 Hz, 1H), 3.70 (d, J=7.6 Hz, 1H), 3.06 (d, J=11.6 Hz, 1H), 2.95-2.65 (m, 4H). MS (ES+) m/e 398.1 (M+H).

Example 261

N-(4-(1H-pyrazol-4-yl)phenyl)-2-(1,4-diazepan-1-yl)-5-methylpyrimidin-4-amine

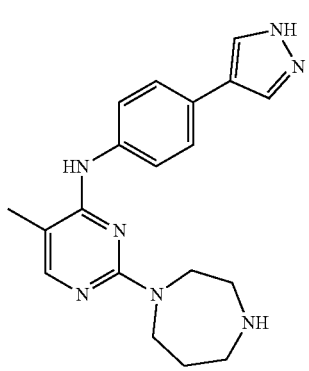 [SMILES: Cc1cnc(N2CCCNCC2)nc1Nc1ccc(-c2cn[nH]c2)cc1]

The reaction was conducted following general protocol A. Intermediate was purified via reverse phase preparatory HPLC. The final residue was purified by reverse phase preparative HPLC (base) to afford N-(4-(1H-pyrazol-4-yl)phenyl)-2-(1,4-diazepan-1-yl)-5-methylpyrimidin-4-amine as a white solid (16%). $^1$H NMR (400 MHz, DMSO-d$_6$) δ 8.30 (s, 2H), 8.18 (s, 1H), 8.00 (s, 2H), 7.80 (s, 1H), 7.72 (d, J=8.4 Hz, 2H), 7.54 (d, J=8.4 Hz, 2H), 3.84 (s, 2H), 3.75 (t, J=5.6 Hz, 2H), 3.11 (s, 2H), 2.99 (s, 2H), 2.07 (s, 3H), 1.95 (s, 2H). MS (ES+) m/e 350.2 (M+H).

Example 262

N-(4-(1H-pyrazol-4-yl)phenyl)-2-(1,4-diazepan-1-yl)-5,7-dihydrofuro[3,4-d]pyrimidin-4-amine

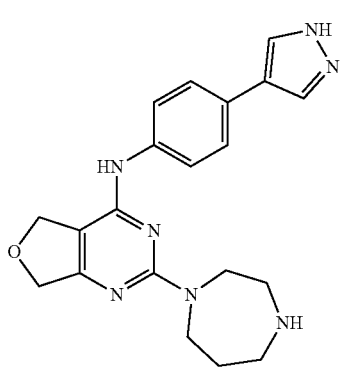 [SMILES: c1cc(-c2cn[nH]c2)ccc1Nc1nc(N2CCCNCC2)nc2c1COC2]

The reaction was conducted following general protocol A. Intermediate was purified via reverse phase preparatory HPLC. The final residue was purified by reverse phase preparative HPLC (base) to afford N-(4-(1H-pyrazol-4-yl)phenyl)-2-(1,4-diazepan-1-yl)-5,7-dihydrofuro[3,4-d]pyrimidin-4-amine as a yellow solid (35%). $^1$H NMR (400 MHz, CD$_3$OD) δ 7.93 (s, 2H), 7.70 (d, J=8.8 Hz, 2H), 7.53 (d, J=8.8 Hz, 2H), 4.99 (s, 2H), 4.79 (s, 2H), 3.87 (t, J=5.6 Hz, 4H), 3.04 (t, J=5.2 Hz, 2H), 2.87 (t, J=6.0 Hz, 2H), 1.98-1.95 (m, 2H). MS (ES+) m/e 378.2 (M+H).

Example 263

N-(4-(1H-pyrazol-4-yl)phenyl)-2-(1,4-diazepan-1-yl)-5,7-dihydrothieno[3,4-d]pyrimidin-4-amine

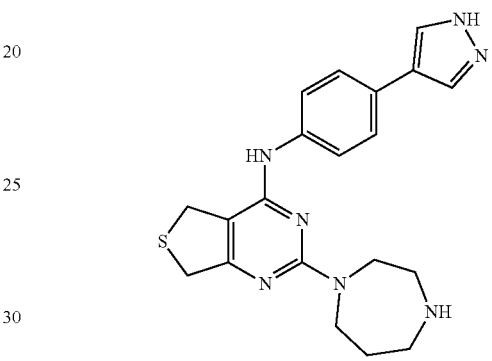

The reaction was conducted following general protocol A. Intermediate was purified via reverse phase preparatory HPLC. The final residue was purified by reverse phase preparative HPLC (base) to afford N-(4-(1H-pyrazol-4-yl)phenyl)-2-(1,4-diazepan-1-yl)-5,7-dihydrothieno[3,4-d]pyrimidin-4-amine as a yellow solid (40%). $^1$H NMR (400 MHz, CD$_3$OD) δ 8.60 (s, 2H), 7.81 (d, J=8.4 Hz, 2H), 7.70 (d, J=8.4 Hz, 2H), 4.36-4.35 (m, 2H), 4.19 (brs, 2H), 4.10 (t, J=4.8 Hz, 2H), 3.87 (brs, 2H), 3.45-3.42 (m, 4H), 2.34-2.28 (m, 2H). MS (ES+) m/e 394.1 (M+H).

Example 264

N-(4-(1H-pyrazol-4-yl)phenyl)-2-(1,4-diazepan-1-yl)thieno[3,2-d]pyrimidin-4-amine

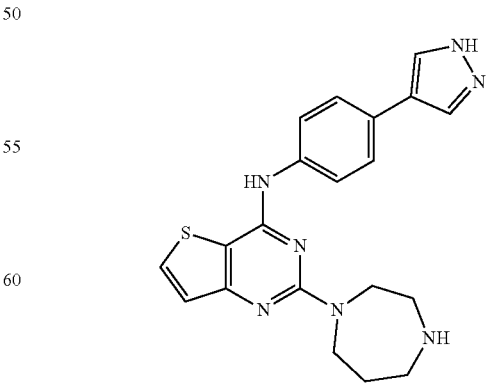

The reaction was conducted following general protocol A. Intermediate was purified via reverse phase preparatory HPLC. The final residue was purified by reverse phase preparative HPLC (base) to afford N-(4-(1H-pyrazol-4-yl)phenyl)-2-(1,4-diazepan-1-yl)thieno[3,2-d]pyrimidin-4-amine as a yellow solid (30%). $^1$H NMR (400 MHz, CD$_3$OD) δ 7.97 (s, 2H), 7.90 (d, J=5.6 Hz, 1H), 7.71 (d, J=8.4 Hz, 2H), 7.60 (d, J=8.8 Hz, 2H), 7.19 (d, J=5.2 Hz, 1H), 4.11 (t, J=5.6 Hz, 1H), 3.98 (t, J=6.0 Hz, 1H), 3.42 (t, J=5.2 Hz, 1H), 3.30-2.29 (m, 2H), 2.20-2.18 (m, 2H). MS (ES+) m/e 392.1 (M+H).

Example 265

N-(4-(1H-pyrazol-4-yl)phenyl)-2-(1,4-diazepan-1-yl)-6-methylpyrimidin-4-amine

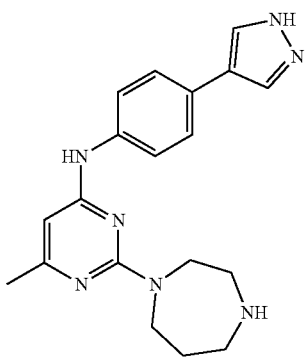 [SMILES: Cc1cc(Nc2ccc(-c3cn[nH]c3)cc2)nc(N2CCCNCC2)n1]

The reaction was conducted following general protocol A. Intermediate was purified via reverse phase preparative HPLC. The final residue was purified by reverse phase preparative HPLC (base) to afford N-(4-(1H-pyrazol-4-yl)phenyl)-2-(1,4-diazepan-1-yl)-6-methylpyrimidin-4-amine as a yellow solid (30%). $^1$H NMR (400 MHz, DMSO-d$_6$) δ 9.07 (d, J=16.8 Hz, 1H), 7.98 (s, 2H), 7.65 (t, J=8.0 Hz, 2H), 7.51 (dd, J=8.4, J=3.6 Hz, 2H), 5.87 (d, J=11.2 Hz, 1H), 3.69-3.82 (m, 4H), 3.30 (d, J=5.6 Hz, 2H), 2.84 (s, 1H), 2.66 (t, J=5.6 Hz, 1H), 2.12 (s, 3H), 1.77 (s, 2H). MS (ES+) m/e 350.2 (M+H).

Example 266

N-(4-(1H-pyrazol-4-yl)phenyl)-2-(1,4-diazepan-1-yl)-5,6-dimethylpyrimidin-4-amine

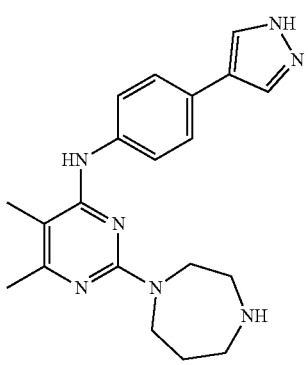 [SMILES: Cc1nc(N2CCCNCC2)nc(Nc2ccc(-c3cn[nH]c3)cc2)c1C]

The reaction was conducted following general protocol A. Intermediate was purified via reverse phase preparative HPLC. The final residue was purified by reverse phase preparative HPLC (base) to afford N-(4-(1H-pyrazol-4-yl)phenyl)-2-(1,4-diazepan-1-yl)-5,6-dimethylpyrimidin-4-amine as a white solid (4%). $^1$H NMR (400 MHz, CD$_3$OD) δ 7.93 (s, 2H), 7.66 (d, J=8.4 Hz, 2H), 7.52 (d, J=8.0 Hz, 2H), 3.80-3.89 (m, 4H), 3.05 (s, 2H), 2.91 (s, 2H), 2.31 (s, 3H), 2.12 (s, 3H), 1.96 (s, 2H). MS (ES+) m/e 364.1 (M+H).

Example 267

N-(4-(1H-pyrazol-4-yl)phenyl)-2-(1,4-diazepan-1-yl)-5-methoxypyrimidin-4-amine

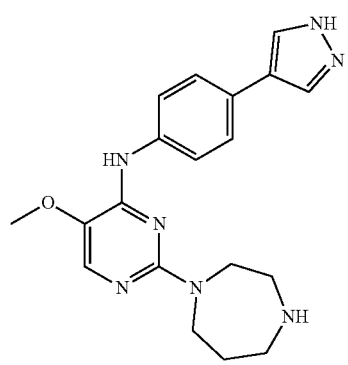 [SMILES: COc1cnc(N2CCCNCC2)nc1Nc1ccc(-c2cn[nH]c2)cc1]

The reaction was conducted following general protocol A. Intermediate was purified via reverse phase preparative HPLC. The final residue was purified by reverse phase preparative HPLC (base) to afford N-(4-(1H-pyrazol-4-yl)phenyl)-2-(1,4-diazepan-1-yl)-5-methoxypyrimidin-4-amine as a white solid (7%). $^1$H NMR (400 MHz, CD$_3$OD) δ 7.94 (s, 2H), 7.77 (d, J=8.8 Hz, 2H), 7.63 (s, 1H), 7.55 (d, J=8.8 Hz, 2H), 3.90 (s, 3H), 3.81-3.87 (m, 4H), 3.04-3.12 (m, 2H), 2.91-2.95 (m, 2H), 1.95-2.03 (m, 2H). MS (ES+) m/e 366.2 (M+H).

Example 268

N-(4-(1H-pyrazol-4-yl)phenyl)-2-(1,4-diazepan-1-yl)quinazolin-4-amine

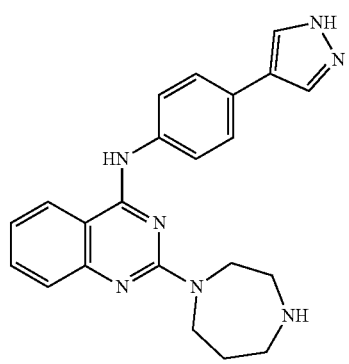 [SMILES: c1ccc2c(Nc3ccc(-c4cn[nH]c4)cc3)nc(N3CCCNCC3)nc2c1]

The reaction was conducted following general protocol A. Intermediate was purified via reverse phase preparative HPLC. The final residue was purified by reverse phase preparative HPLC (base) to afford N-(4-(1H-pyrazol-4-yl)phenyl)-2-(1,4-diazepan-1-yl)quinazolin-4-amine as a yellow solid 16%). $^1$H NMR (400 MHz, DMSO-d$_6$) δ 13.00 (brs, 1H), 11.12 (s, 1H), 9.56 (brs, 2H), 8.75 (d, J=8.4 Hz, 1H), 8.32-8.17 (m, 3H), 7.89 (t, J=8.0 Hz, 1H), 7.74 (m, 4H), 7.54 (t, J=7.6 Hz, 1H), 4.33 (m, 1H), 4.01-3.89 (m, 3H), 3.40-3.25 (m, 4H), 2.23-2.08 (m, 2H). MS (ES+) m/e 386.1 (M+H).

Example 269

N-(4-(1H-pyrazol-4-yl)phenyl)-2-(3-(3-methoxyphenyl)pyrrolidin-1-yl)pyrimidin-4-amine

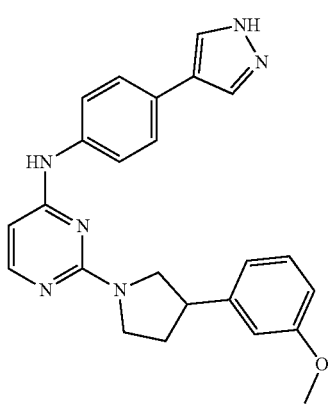 [SMILES: COc1cccc(C2CCN(c3nccc(Nc4ccc(-c5cn[nH]c5)cc4)n3)C2)c1]

The reaction was conducted following general protocol A. The final residue was purified by reverse phase preparative HPLC to afford N-(4-(1H-pyrazol-4-yl)phenyl)-2-(3-(3-methoxyphenyl)pyrrolidin-1-yl)pyrimidin-4-amine as a white solid (10%). $^1$H NMR (400 MHz, DMSO-d$_6$) δ 12.81 (s, 1H), 9.20 (s, 1H), 7.97 (s, 1H), 7.91 (d, J=5.6 Hz, 1H), 7.73 (s, 2H), 7.51 (d, J=7.2 Hz, 2H), 7.26 (t, J=7.6 Hz, 1H), 6.88-6.95 (m, 2H), 6.82 (d, J=8.4 Hz, 1H), 6.02 (d, J=5.6 Hz, 1H), 4.00 (s, 1H), 3.75 (s, 4H), 3.44-3.58 (m, 3H), 2.33 (s, 1H), 2.07 (t, J=9.6 Hz, 1H). MS (ES+) m/e 413.2 (M+H).

Example 270

N-(4-(1H-pyrazol-4-yl)phenyl)-2-(3-phenylpyrrolidin-1-yl)pyrimidin-4-amine

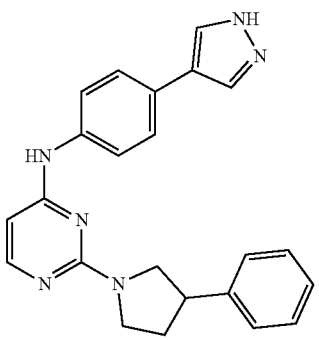 [SMILES: c1ccc(C2CCN(c3nccc(Nc4ccc(-c5cn[nH]c5)cc4)n3)C2)cc1]

The reaction was conducted following general protocol A. The final residue was purified by reverse phase preparative HPLC to afford N-(4-(1H-pyrazol-4-yl)phenyl)-2-(3-phenylpyrrolidin-1-yl)pyrimidin-4-amine as a yellow solid (33%). $^1$H NMR (400 MHz, DMSO-d$_6$) δ 12.82 (s, 1H), 9.21 (s, 1H), 8.09 (s, 1H), 7.91 (d, J=5.6 Hz, 1H), 7.85 (s, 1H), 7.73 (s, 2H), 7.52 (s, 2H), 7.35 (d, J=4.4 Hz, 4H), 7.25 (d, J=3.2 Hz, 1H), 6.02 (d, J=5.8 Hz, 1H), 4.01 (s, 1H), 3.77 (s, 1H), 3.42-3.62 (m, 3H), 2.33 (s, 1H), 2.07 (t, J=9.6 Hz, 1H). MS (ES+) m/e 383.1 (M+H).

Example 271

2-(5-phenyl-1,4-diazepan-1-yl)-N-(4-(pyridin-4-yl)phenyl)pyrimidin-4-amine

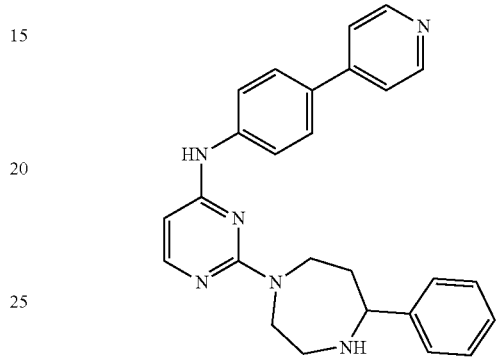

The reaction was conducted following general protocol G. The final residue was purified by reverse phase preparative HPLC to afford 2-(5-phenyl-1,4-diazepan-1-yl)-N-(4-(pyridin-4-yl)phenyl)pyrimidin-4-amine as a yellow solid (22%). $^1$H NMR (400 MHz, Methanol-d$_4$) δ 8.52 (d, J=6.4 Hz, 2H), 8.43 (s, 2H), 8.00 (d, J=6.0 Hz, 1H), 7.83 (d, J=8.8 Hz, 2H), 7.76 (d, J=8.8 Hz, 2H), 7.70 (d, J=6.4 Hz, 2H), 7.49-7.39 (m, 5H), 6.21 (d, J=6.0 Hz, 1H), 4.49-4.43 (m, 1H), 4.32-4.29 (m, 1H), 4.20 (m, 2H), 3.89-3.82 (m, 1H), 3.67-3.58 (m, 1H), 3.49-3.39 (m, 1H), 2.51-2.38 (m, 1H), 2.37-2.29 (m, 1H). MS (ES+) m/e 423.0 (M+H).

Example 272

2-(1,4-diazepan-1-yl)-N-(4-(pyridin-4-yl)phenyl)quinazolin-4-amine

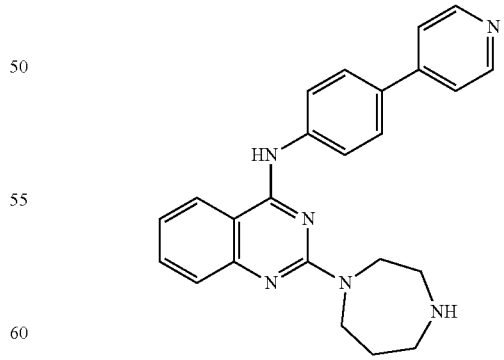

The reaction was conducted following general protocol G. The final residue was purified by reverse phase preparative HPLC to afford 2-(1,4-diazepan-1-yl)-N-(4-(pyridin-4-yl)phenyl)quinazolin-4-amine as a yellow solid (24%). MS (ES+) m/e 397 (M+H).

Example 273

2-(1,4-diazepan-1-yl)-N-(4-(pyridin-4-yl)phenyl)pyrimidin-4-amine

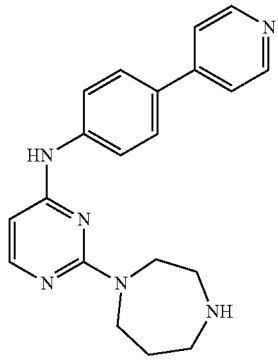 [SMILES: c1cc(-c2ccc(Nc3ccnc(N4CCCNCC4)n3)cc2)ccn1]

The reaction was conducted following general protocol G. The final residue was purified by reverse phase preparative HPLC to afford 2-(1,4-diazepan-1-yl)-N-(4-(pyridin-4-yl)phenyl)pyrimidin-4-amine as a yellow solid (29%). MS (ES+) m/e 447 (M+H).

Example 274

2-(3,8-diazabicyclo[3.2.1]octan-8-yl)-N-(1H-indazol-5-yl)thieno[2,3-d]pyrimidin-4-amine

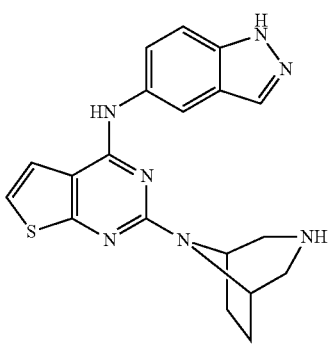 [SMILES: c1cc2c(Nc3ccc4[nH]ncc4c3)nc(N3C4CCC3CNC4)nc2s1]

The reaction was conducted following general protocol A. The final residue was purified by reverse phase preparative HPLC to afford 2-(3,8-diazabicyclo[3.2.1]octan-8-yl)-N-(1H-indazol-5-yl)thieno[2,3-d]pyrimidin-4-amine as a yellow solid (47%). $^1$H NMR (400 MHz, DMSO-d$_6$) δ δ 13.06 (s, 1H), 9.59 (s, 1H), 8.90-8.79 (m, 2H), 8.09 (s, 2H), 7.69 (d, J=6.0 Hz, 1H), 7.65-7.63 (m, 1H), 7.55 (d, J=8.8 Hz, 1H), 7.26 (d, J=6.0 Hz, 1H), 4.67 (s, 2H), 3.20-3.17 (m, 4H), 2.11-2.00 (m, 4H). MS (ES+) m/e 378.1 (M+H).

Example 275

2-(3,8-diazabicyclo[3.2.1]octan-8-yl)-N-(1H-indazol-5-yl)-6,7-dihydro-5H-pyrrolo[3,4-d]pyrimidin-4-amine

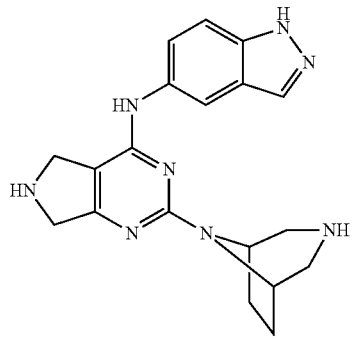 [SMILES: c1cc2[nH]ncc2cc1Nc1nc(N2C3CCC2CNC3)nc2c1CNC2]

The reaction was conducted following general protocol A. The final residue was purified by reverse phase preparative HPLC to afford 2-(3,8-diazabicyclo[3.2.1]octan-8-yl)-N-(1H-indazol-5-yl)-6,7-dihydro-5H-pyrrolo[3,4-d]pyrimidin-4-amine as an off-white solid (38%). $^1$H NMR (400 MHz, DMSO-d$_6$) δ δ 13.11 (s, 1H), 9.49 (s, 2H), 9.21 (s, 1H), 9.16-9.14 (m, 1H), 8.90 (s, 1H), 8.08 (s, 1H), 8.00 (s, 1H), 7.55-7.50 (m, 2H), 4.64 (s, 2H), 4.36-4.28 (m, 4H), 3.22-3.12 (m, 4H), 2.08-2.00 (m, 4H). MS (ES+) m/e 363.2 (M+H).

Example 276

N-(4-(1H-pyrazol-4-yl)phenyl)-2-(3,8-diazabicyclo[3.2.1]octan-8-yl)-6,7-dihydro-5H-pyrrolo[3,4-d]pyrimidin-4-amine

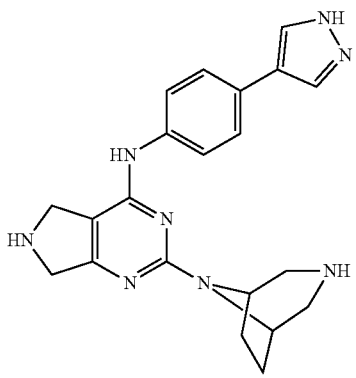 [SMILES: c1cc(-c2cn[nH]c2)ccc1Nc1nc(N2C3CCC2CNC3)nc2c1CNC2]

The reaction was conducted following general protocol A. The final residue was purified by reverse phase preparative HPLC to afford N-(4-(1H-pyrazol-4-yl)phenyl)-2-(3,8-diazabicyclo[3.2.1]octan-8-yl)-6,7-dihydro-5H-pyrrolo[3,4-d]pyrimidin-4-amine as a white solid (28%). $^1$H NMR (400 MHz, DMSO-d$_6$) δ 9.55 (s, 2H), 9.23-9.12 (m, 2H), 8.91 (s, 1H), 8.01 (s, 2H), 7.66-7.52 (m, 4H), 4.69 (s, 2H), 4.41 (s, 2H), 4.29 (s, 2H), 3.23-3013 (m, 4H), 2.07-2.02 (m, 4H). MS (ES+) m/e 389.3 (M+H).

Example 277

N-(2-(2,5-diazabicyclo[2.2.1]heptan-2-yl)-5-fluoro-6-methylpyrimidin-4-yl)-1H-indazol-5-amine

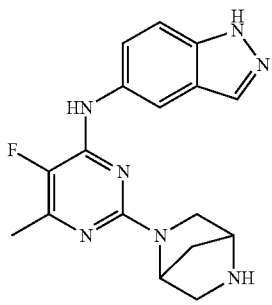 [SMILES: Cc1nc(N2CC3CC2CN3)nc(Nc2ccc3[nH]ncc3c2)c1F]

The reaction was conducted following general protocol A. The final residue was purified by reverse phase preparative HPLC to afford N-(2-(2,5-diazabicyclo[2.2.1]heptan-2-yl)-5-fluoro-6-methylpyrimidin-4-yl)-1H-indazol-5-amine as a white solid (59%). $^1$H NMR (400 MHz, DMSO-$d_6$) δ 13.04 (brs, 1H), 9.41 (brs, 1H), 9.04 (brs, 1H), 8.59 (brs, 1H), 8.15 (s, 1H), 8.03 (s, 1H), 8.63 (dd, J=9.2, 2.0 Hz, 1H), 7.49 (d, J=9.2 Hz, 1H), 4.78 (m, 1H), 4.44 (m, 1H), 3.66-3.63 (m, 1H), 3.56-3.53 (m, 1H), 3.29-3.24 (m, 2H), 2.26-2.25 (m, 3H), 2.13-2.10 (m, 1H), 1.89-1.86 (m, 1H). MS (ES+) m/e 340.1 (M+H).

Example 278

2-(3,8-diazabicyclo[3.2.1]octan-8-yl)-N-(1H-indazol-5-yl)-5,7-dihydrofuro[3,4-d]pyrimidin-4-amine

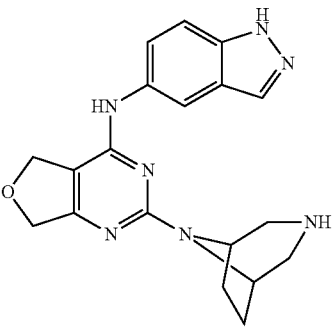 [SMILES: c1cc2[nH]ncc2cc1Nc1nc(N2C3CCC2CNC3)nc2c1COC2]

The reaction was conducted following general protocol A. The final residue was purified by reverse phase preparative HPLC to afford 2-(3,8-diazabicyclo[3.2.1]octan-8-yl)-N-(1H-indazol-5-yl)-5,7-dihydrofuro[3,4-d]pyrimidin-4-amine as a red solid (17%). $^1$H NMR (400 MHz, DMSO-$d_6$) δ 13.00 (brs, 1H), 9.14 (s, 1H), 9.05-9.02 (m, 1H), 8.85 (s, 1H), 8.06 (s, 1H), 7.99 (s, 1H), 7.51 (s, 2H), 4.89 (s, 2H), 4.76 (s, 2H), 4.65 (m, 2H), 3.18 (m, 4H), 2.10-2.00 (m, 4H). MS (ES+) m/e 364.1 (M+H).

Example 279

N-(4-(1H-pyrazol-4-yl)phenyl)-2-(3,8-diazabicyclo[3.2.1]octan-8-yl)-5,7-dihydrofuro[3,4-d]pyrimidin-4-amine

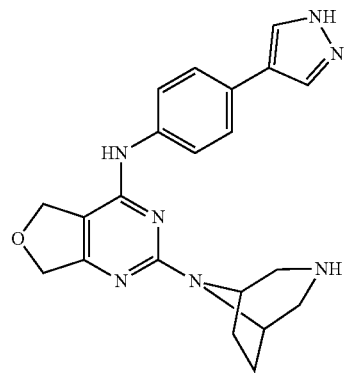 [SMILES: c1cc(-c2cn[nH]c2)ccc1Nc1nc(N2C3CCC2CNC3)nc2c1COC2]

The reaction was conducted following general protocol A. The final residue was purified by reverse phase preparative HPLC to afford N-(4-(1H-pyrazol-4-yl)phenyl)-2-(3,8-diazabicyclo[3.2.1]octan-8-yl)-5,7-dihydrofuro[3,4-d]pyrimidin-4-amine as a white solid (86%). $^1$H NMR (400 MHz, DMSO-$d_6$) δ 9.06-8.99 (m, 2H), 8.81 (brs, 1H), 8.00 (s, 2H), 7.65 (d, J=8.4 Hz, 2H), 7.57 (d, J=8.4 Hz, 2H), 4.95 (s, 2H), 4.76 (s, 2H), 4.68 (m, 2H), 3.19-3.18 (m, 4H), 2.14-2.01 (m, 4H). MS (ES+) m/e 390.1 (M+H).

Example 280

N-(2-(3,6-diazabicyclo[3.1.1]heptan-3-yl)-5-chloropyrimidin-4-yl)-1H-indazol-5-amine

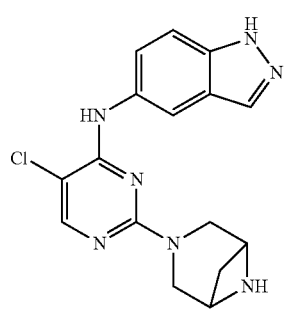 [SMILES: Clc1cnc(N2CC3CC(C2)N3)nc1Nc1ccc2[nH]ncc2c1]

The reaction was conducted following general protocol A. The final residue was purified by reverse phase preparative HPLC to afford N-(2-(3,6-diazabicyclo[3.1.1]heptan-3-yl)-5-chloropyrimidin-4-yl)-1H-indazol-5-amine as a white solid (77%). $^1$H NMR (400 MHz, DMSO-$d_6$) δ 13.06 (s, 1H), 8.77 (s, 1H), 8.29 (s, 1H), 8.10 (s, 2H), 8.04 (s, 1H), 7.65 (dd, J=8.8 Hz, 1.6 Hz, 1H), 7.48 (d, J=8.8 Hz, 1H), 3.97 (s, 2H), 3.81-3.75 (m, 4H), 2.68-2.63 (m, 1H), 1.56 (d, J=8.0 Hz, 1H). MS (ES+) m/e 342.0 (M+H).

Example 281

2-(3,8-diazabicyclo[3.2.1]octan-8-yl)-N-(4-(pyridin-4-yl)phenyl)-5,7-dihydrofuro[3,4-d]pyrimidin-4-amine

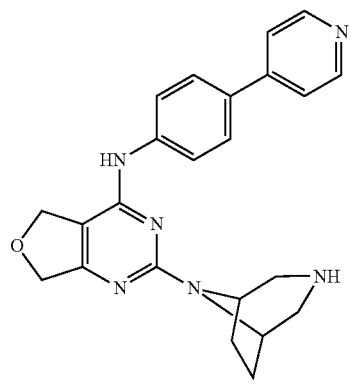 [SMILES: c1cc(-c2ccc(Nc3nc(N4C5CCC4CNC5)nc4c3COC4)cc2)ccn1]

The reaction was conducted following general protocol G. The final residue was purified by reverse phase preparative HPLC to afford 2-(3,8-diazabicyclo[3.2.1]octan-8-yl)-N-(4-(pyridin-4-yl)phenyl)-5,7-dihydrofuro[3,4-d]pyrimidin-4-amine as a white solid (27%). $^1$H NMR (400 MHz, DMSO-$d_6$) δ 9.36 (s, 1H), 9.09 (m, 1H), 8.87 (m, 1H), 8.82 (d, J=6.4 Hz, 2H), 8.16 (d, J=6.4 Hz, 2H), 8.03 (d, J=8.8 Hz, 2H), 7.93 (d, J=8.8 Hz, 2H), 5.01 (s, 2H), 4.78 (s, 2H), 4.72 (m, 2H), 3.19 (m, 4H), 2.13-2.03 (m, 4H). MS (ES+) m/e 401.1 (M+H).

Example 282

2-(3,8-diazabicyclo[3.2.1]octan-8-yl)-N-(1H-indazol-5-yl)thieno[3,2-d]pyrimidin-4-amine

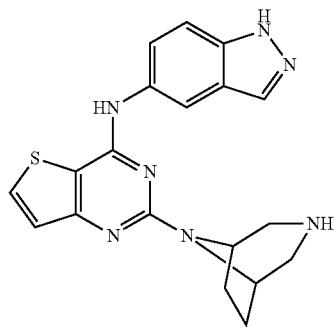 [SMILES: c1cc2nc(N3C4CCC3CNC4)nc(Nc3ccc4[nH]ncc4c3)c2s1]

The reaction was conducted following general protocol A. The final residue was purified by reverse phase preparative HPLC to afford 2-(3,8-diazabicyclo[3.2.1]octan-8-yl)-N-(1H-indazol-5-yl)thieno[3,2-d]pyrimidin-4-amine as a white solid (18%). $^1$H NMR (400 MHz, DMSO-$d_6$) δ 13.15 (s, 1H), 10.15 (s, 1H), 9.14 (s, 1H), 8.93 (s, 1H), 8.15-8.09 (m, 2H), 7.99 (s, 1H), 7.58 (s, 2H), 7.25 (d, J=5.2 Hz, 1H), 4.72 (s, 2H), 3.29-3.21 (m, 4H), 2.14-2.04 (m, 4H). MS (ES+) m/e 378.1 (M+H).

Example 283

2-(3,6-diazabicyclo[3.1.1]heptan-6-yl)-N-(1H-indazol-5-yl)-5,7-dihydrofuro[3,4-d]pyrimidin-4-amine

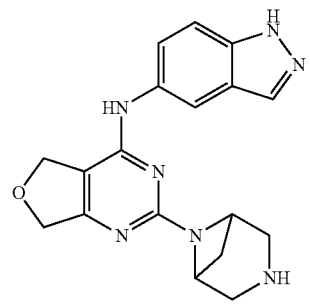 [SMILES: c1cc2[nH]ncc2cc1Nc1nc(N2C3CNCC2C3)nc2c1COC2]

The reaction was conducted following general protocol A. The final residue was purified by reverse phase preparative HPLC to afford 2-(3,6-diazabicyclo[3.1.1]heptan-6-yl)-N-(1H-indazol-5-yl)-5,7-dihydrofuro[3,4-d]pyrimidin-4-amine as a white solid (18%). $^1$H NMR (400 MHz, DMSO-$d_6$) δ 13.07 (s, 1H), 9.30-9.23 (m, 2H), 8.53 (s, 1H), 8.10 (s, 1H), 8.06 (s, 1H), 7.50 (s, 2H), 4.90 (m, 2H), 4.77 (m, 2H), 4.37 (d, J=6.0 Hz, 2H), 3.72-3.69 (m, 2H), 3.34-3.33 (m, 2H), 2.80-2.75 (m, 1H), 1.89 (d, J=9.6 Hz, 1H). MS (ES+) m/e 350.1 (M+H).

Example 284

2-(2,5-diazabicyclo[2.2.1]heptan-2-yl)-N-(1H-indazol-5-yl)-5,7-dihydrofuro[3,4-d]pyrimidin-4-amine

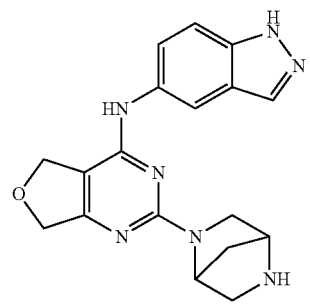 [SMILES: c1cc2[nH]ncc2cc1Nc1nc(N2CC3CC2CN3)nc2c1COC2]

The reaction was conducted following general protocol A. The final residue was purified by reverse phase preparative HPLC to afford 2-(2,5-diazabicyclo[2.2.1]heptan-2-yl)-N-(1H-indazol-5-yl)-5,7-dihydrofuro[3,4-d]pyrimidin-4-amine as a white solid (30%). $^1$H NMR (400 MHz, DMSO-$d_6$) δ 13.01 (s, 1H), 9.12 (s, 2H), 8.65 (s, 1H), 8.13-8.04 (m, 2H), 7.56-7.49 (m, 2H), 4.89-4.85 (m, 3H), 4.78-4.75 (m, 2H), 4.47 (s, 1H), 3.71-3.59 (m, 2H), 3.31-3.24 (m, 2H), 2.13 (d, J=9.6 Hz, 1H), 1.90 (d, J=10.8 Hz, 1H). MS (ES+) m/e 350.1 (M+H).

Example 292

2-(3,6-diazabicyclo[3.1.1]heptan-6-yl)-N-(4-(pyridin-4-yl)phenyl)-6,7-dihydro-5H-pyrrolo[3,4-d]pyrimidin-4-amine

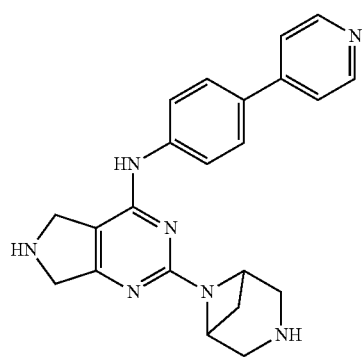 [SMILES: c1cc(-c2ccc(Nc3nc(N4C5CNCC4C5)nc4c3CNC4)cc2)ccn1]

The reaction was conducted following general protocol G. The final residue was purified by reverse phase preparative HPLC to afford 2-(3,6-diazabicyclo[3.1.1]heptan-6-yl)-N-(4-(pyridin-4-yl)phenyl)-6,7-dihydro-5H-pyrrolo[3,4-d]pyrimidin-4-amine as a yellow solid (16%). $^1$H NMR (400 MHz, DMSO-$d_6$) δ 8.76 (d, J=6.8 Hz, 2H), 8.24 (d, J=6.8 Hz, 2H), 8.01 (m, 4H), 4.68-4.57 (m, 4H), 4.45 (s, 2H), 3.94 (d, J=12.8 Hz, 2H), 3.47 (d, J=12.8 Hz, 2H), 3.05-2.99 (m, 1H), 1.97 (d, J=6.0 Hz, 1H). MS (ES+) m/e 386.0 (M+H).

Example 293

N-(2-(3,6-diazabicyclo[3.1.1]heptan-6-yl)-5-chloropyrimidin-4-yl)-4-methyl-1H-indazol-5-amine

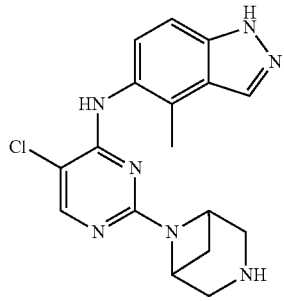 [SMILES: Cc1c(Nc2nc(N3C4CNCC3C4)ncc2Cl)ccc2[nH]ncc12]

The reaction was conducted following general protocol A. The final residue was purified by reverse phase preparative HPLC to afford N-(2-(3,6-diazabicyclo[3.1.1]heptan-6-yl)-5-chloropyrimidin-4-yl)-4-methyl-1H-indazol-5-amine as a yellow solid (16%). $^1$H NMR (400 MHz, DMSO-$d_6$) δ 8.25-8.05 (m, 2H), 7.42-7.40 (m, 1H), 7.29 (d, J=8.8 Hz, 1H), 4.29 (m, 2H), 3.70-3.68 (m, 2H), 3.31 (m, 2H), 2.86 (m, 1H), 2.49 (s, 3H), 1.80-1.78 (m, 1H). MS (ES+) m/e 356.3 (M+H).

Example 294

N-(2-(3,8-diazabicyclo[3.2.1]octan-8-yl)-5-chloropyrimidin-4-yl)-4-methyl-1H-indazol-5-amine

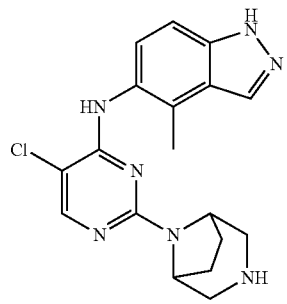 [SMILES: Cc1c(Nc2nc(N3C4CCC3CNC4)ncc2Cl)ccc2[nH]ncc12]

The reaction was conducted following general protocol A. The final residue was purified by reverse phase preparative HPLC to afford N-(2-(3,8-diazabicyclo[3.2.1]octan-8-yl)-5-chloropyrimidin-4-yl)-4-methyl-1H-indazol-5-amine as a white solid (22%). $^1$H NMR (400 MHz, DMSO-$d_6$) δ 8.19-8.10 (m, 2H), 7.47-7.39 (m, 1H), 7.35-7.26 (m, 1H), 4.51 (m, 2H), 3.26 (m, 2H), 3.18-3.15 (m, 2H), 2.50 (s, 3H), 2.16-2.15 (m, 2H), 2.00-1.98 (m, 2H). MS (ES+) m/e 370.1 (M+H).

Example 295

N-(2-(3,6-diazabicyclo[3.1.1]heptan-6-yl)-5-chloropyrimidin-4-yl)-6-fluoro-1H-indazol-5-amine

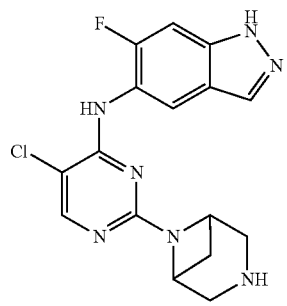 [SMILES: Fc1cc2[nH]ncc2cc1Nc1nc(N2C3CNCC2C3)ncc1Cl]

The reaction was conducted following general protocol A. The final residue was purified by reverse phase preparative HPLC to afford N-(2-(3,6-diazabicyclo[3.1.1]heptan-6-yl)-5-chloropyrimidin-4-yl)-6-fluoro-1H-indazol-5-amine as a white solid (45%). $^1$H NMR (400 MHz, DMSO-$d_6$) δ 8.15-8.11 (m, 1H), 8.08 (s, 1H), 7.90 (d, J=7.2 Hz, 1H), 7.38 (d, J=10.4 Hz, 1H), 4.32 (m, 1H), 3.77 (d, J=12.8 Hz, 2H), 3.38-3.30 (m, 2H), 2.90-2.85 (m, 1H), 1.85-1.82 (m, 1H). MS (ES+) m/e 360.1 (M+H).

Example 296

N-(2-(3,8-diazabicyclo[3.2.1]octan-8-yl)-5-chloro-pyrimidin-4-yl)-6-fluoro-1H-indazol-5-amine

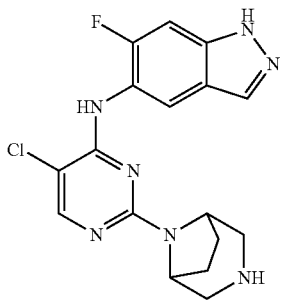 [SMILES: Fc1cc2[nH]ncc2cc1Nc1nc(N2C3CCC2CNC3)ncc1Cl]

The reaction was conducted following general protocol A. The final residue was purified by reverse phase preparative HPLC to afford N-(2-(3,8-diazabicyclo[3.2.1]octan-8-yl)-5-chloropyrimidin-4-yl)-6-fluoro-1H-indazol-5-amine as a white solid (45%). $^1$H NMR (400 MHz, DMSO-$d_6$) δ 8.12 (s, 1H), 8.09 (s, 1H), 7.90 (d, J=7.2 Hz, 1H), 7.38 (d, J=10.4 Hz, 1H), 4.56 (m, 2H), 3.32-3.26 (m, 2H), 3.19-3.12 (m, 2H), 2.25-2.10 (m, 2H), 2.00-1.92 (m, 2H). MS (ES+) m/e 374.1 (M+H).

Example 297

N-(2-(3,6-diazabicyclo[3.1.1]heptan-6-yl)-5-chloro-pyrimidin-4-yl)-6-methoxy-1H-indazol-5-amine

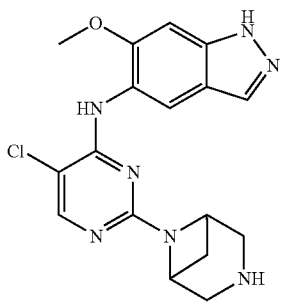 [SMILES: COc1cc2[nH]ncc2cc1Nc1nc(N2C3CNCC2C3)ncc1Cl]

The reaction was conducted following general protocol A. The final residue was purified by reverse phase preparative HPLC to afford N-(2-(3,6-diazabicyclo[3.1.1]heptan-6-yl)-5-chloropyrimidin-4-yl)-6-methoxy-1H-indazol-5-amine as a white solid (53%). $^1$H NMR (400 MHz, DMSO-$d_6$) δ 8.42-8.27 (m, 1H), 8.15-8.11 (m, 1H), 7.98 (s, 1H), 7.11 (s, 1H), 4.52 (m, 2H), 4.04-3.96 (m, 3H), 3.83 (d, J=12.8 Hz, 2H), 3.46 (d, J=12.8 Hz, 2H), 3.03-2.88 (m, 1H), 1.97-1.87 (m, 1H). MS (ES+) m/e 372.0 (M+H).

Example 298

N-(2-(3,8-diazabicyclo[3.2.1]octan-8-yl)-5-(trifluoromethyl)pyrimidin-4-yl)-1H-indazol-5-amine

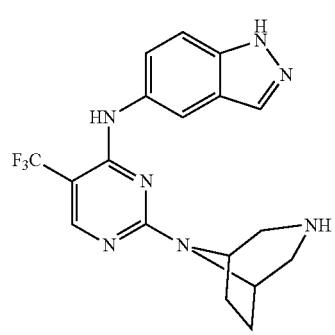 [SMILES: FC(F)(F)c1cnc(N2C3CCC2CNC3)nc1Nc1ccc2[nH]ncc2c1]

The reaction was conducted following general protocol A. The final residue was purified by reverse phase preparative HPLC to afford N-(2-(3,8-diazabicyclo[3.2.1]octan-8-yl)-5-(trifluoromethyl)pyrimidin-4-yl)-1H-indazol-5-amine as a colorless gum (53%). $^1$H NMR (400 MHz, DMSO-$d_6$) δ 13.10 (s, 1H), 9.00 (s, 1H), 8.83 (m, 2H), 8.33 (s, 1H), 8.05 (s, 1H), 7.75 (s, 1H), 7.50-7.43 (m, 2H), 4.79-4.74 (m, 1H), 4.28 (m, 1H), 3.12 (m, 4H), 2.00-1.95 (m, 4H). MS (ES+) m/e 390.1 (M+H).

Example 299

2-(3,8-diazabicyclo[3.2.1]octan-8-yl)-N-(1H-indazol-5-yl)-6-methyl-5,6,7,8-tetrahydropyrido[4,3-d]pyrimidin-4-amine

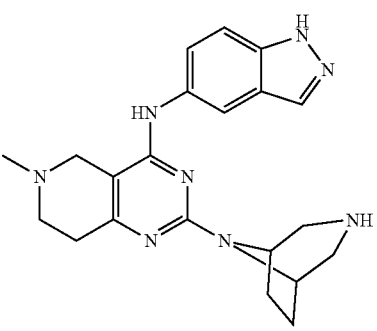 [SMILES: CN1CCc2nc(N3C4CCC3CNC4)nc(Nc3ccc4[nH]ncc4c3)c2C1]

The reaction was conducted following general protocol A. The final residue was purified by reverse phase preparative HPLC to afford 2-(3,8-diazabicyclo[3.2.1]octan-8-yl)-N-(1H-indazol-5-yl)-6-methyl-5,6,7,8-tetrahydropyrido[4,3-d]pyrimidin-4-amine as a white solid (3%). $^1$H NMR (400 MHz, DMSO-$d_6$) δ 10.69 (brs, 1H), 9.45 (s, 1H), 9.06-8.99 (m, 2H), 8.06 (s, 1H), 7.88 (s, 1H), 7.54-7.49 (m, 2H), 4.60 (s, 2H), 3.61 (m, 4H), 3.19-3.12 (m, 4H), 3.01-2.83 (m, 5H), 2.07-1.98 (m, 4H). MS (ES+) m/e 391.4 (M+H).

Example 300

N-(4-(1H-pyrazol-4-yl)phenyl)-2-(3,6-diazabicyclo[3.1.1]heptan-6-yl)-6,7-dihydro-5H-pyrrolo[3,4-d]pyrimidin-4-amine

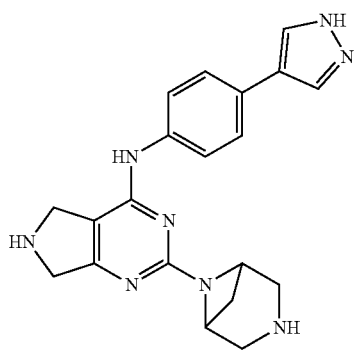 [SMILES: c1cc(-c2cn[nH]c2)ccc1Nc1nc(N2C3CNCC2C3)nc2c1CNC2]

The reaction was conducted following general protocol A. The final residue was purified by reverse phase preparative HPLC to afford N-(4-(1H-pyrazol-4-yl)phenyl)-2-(3,6-diazabicyclo[3.1.1]heptan-6-yl)-6,7-dihydro-5H-pyrrolo[3,4-d]pyrimidin-4-amine as a grey solid (4%). $^1$H NMR (400 MHz, CD$_3$OD) δ 7.97 (s, 2H), 7.66 (d, J=8.8 Hz, 2H), 7.59 (d, J=8.8 Hz, 2H), 4.53-4.51 (m, 4H), 4.41 (s, 2H), 3.90 (d, J=12.8 Hz, 2H), 3.42 (d, J=12.4 Hz, 2H), 3.01-2.96 (m, 1H), 1.92 (d, J=10.0 Hz, 1H). MS (ES+) m/e 371.4 (M+H).

Example 301

N-(2-(3,6-diazabicyclo[3.1.1]heptan-6-yl)-5-fluoro-6-methylpyrimidin-4-yl)-1H-indazol-5-amine

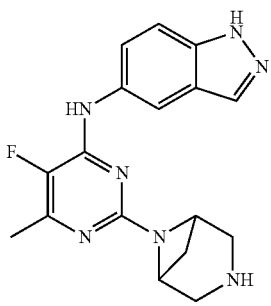 [SMILES: Cc1nc(N2C3CNCC2C3)nc(Nc2ccc3[nH]ncc3c2)c1F]

The reaction was conducted following general protocol A. The final residue was purified by reverse phase preparative HPLC to afford N-(2-(3,6-diazabicyclo[3.1.1]heptan-6-yl)-5-fluoro-6-methylpyrimidin-4-yl)-1H-indazol-5-amine as an orange solid (23%). $^1$H NMR (400 MHz, CD$_3$OD) δ 8.07 (s, 1H), 8.04 (s, 1H), 7.60-7.55 (m, 2H), 4.56 (m, 2H), 3.87 (d, J=13.2 Hz, 2H), 3.46 (d, J=12.8 Hz, 2H), 3.04-2.98 (m, 1H), 2.41 (d, J=2.8 Hz, 3H), 1.91 (m, 1H). MS (ES+) m/e 340.0 (M+H).

Example 302

N-(2-(3,8-diazabicyclo[3.2.1]octan-8-yl)-5-fluoro-6-methylpyrimidin-4-yl)-1H-indazol-5-amine

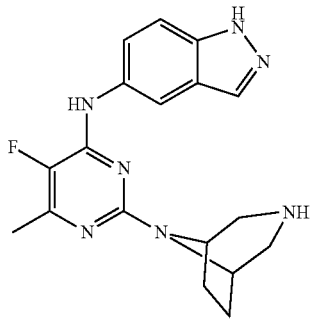 [SMILES: Cc1nc(N2C3CCC2CNC3)nc(Nc2ccc3[nH]ncc3c2)c1F]

The reaction was conducted following general protocol A. The final residue was purified by reverse phase preparative HPLC to afford N-(2-(3,8-diazabicyclo[3.2.1]octan-8-yl)-5-fluoro-6-methylpyrimidin-4-yl)-1H-indazol-5-amine as an pink solid (5%). $^1$H NMR (400 MHz, DMSO-d$_6$) δ 13.0 (s, 1H), 9.44 (s, 1H), 9.07-9.04 (m, 1H), 8.85-8.84 (m, 1H), 8.05 (s, 1H), 8.03 (s, 1H), 7.60 (dd, J=9.2, 2.0 Hz, 1H), 7.50 (d, J=8.8 Hz, 1H), 4.58 (s, 2H), 3.17-3.16 (m, 4H), 2.26 (s, 3H), 2.09-1.98 (m, 4H). MS (ES+) m/e 354.3 (M+H).

Example 303

N-(4-(1H-pyrazol-4-yl)phenyl)-2-(3,8-diazabicyclo[3.2.1]octan-8-yl)-6-methyl-5,6,7,8-tetrahydropyrido[4,3-d]pyrimidin-4-amine

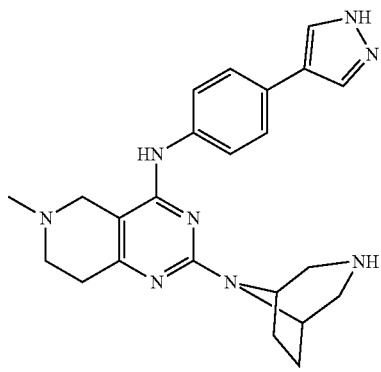 [SMILES: CN1CCc2nc(N3C4CCC3CNC4)nc(Nc3ccc(-c4cn[nH]c4)cc3)c2C1]

The reaction was conducted following general protocol A. The final residue was purified by reverse phase preparative HPLC to afford N-(4-(1H-pyrazol-4-yl)phenyl)-2-(3,8-diazabicyclo[3.2.1]octan-8-yl)-6-methyl-5,6,7,8-tetrahydropyrido[4,3-d]pyrimidin-4-amine as an pink solid (23%). $^1$H NMR (400 MHz, DMSO-d$_6$) δ 7.93 (s, 2H), 7.59 (d, J=8.8 Hz, 2H), 7.53 (d, J=8.8 Hz, 2H), 4.63 (m, 2H), 3.48 (s, 2H), 3.15-2.88 (m, 2H), 2.85-2.78 (m, 6H), 2.59 (s, 3H), 2.10-1.97 (m, 4H). MS (ES+) m/e 417.3 (M+H).

Example 304

N-(2-(3,6-diazabicyclo[3.1.1]heptan-6-yl)-5-(trifluoromethyl)pyrimidin-4-yl)-1H-indazol-5-amine

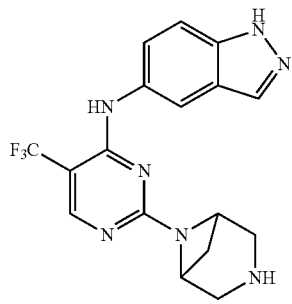 [SMILES: FC(F)(F)c1cnc(N2C3CNCC2C3)nc1Nc1ccc2[nH]ncc2c1]

The reaction was conducted following general protocol A. The final residue was purified by reverse phase preparative HPLC to afford N-(2-(3,6-diazabicyclo[3.1.1]heptan-6-yl)-5-(trifluoromethyl)pyrimidin-4-yl)-1H-indazol-5-amine as a white solid (52%). $^1$H NMR (400 MHz, DMSO-$d_6$) δ 13.07 (s, 1H), 9.22 (s, 1H), 8.87 (s, 1H), 8.45 (s, 1H), 8.35 (s, 1H), 8.05 (s, 1H), 7.76 (s, 1H), 7.50-7.48 (m, 1H), 7.41-7.39 (m, 1H), 4.38 (s, 1H), 4.05 (s, 1H), 3.56 (m, 2H), 3.29 (m, 2H) 2.72-2.67 (m, 1H), 1.78 (d, J=9.6 Hz, 1H). MS (ES+) m/e 376.1 (M+H).

Example 305

N-(2-(3,8-diazabicyclo[3.2.1]octan-8-yl)-5-chloropyrimidin-4-yl)-6-methoxy-1H-indazol-5-amine

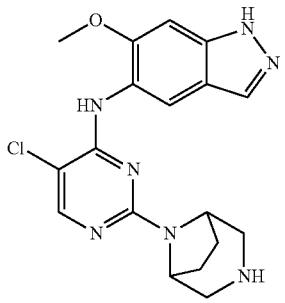 [SMILES: COc1cc2[nH]ncc2cc1Nc1nc(N2C3CCC2CNC3)ncc1Cl]

The reaction was conducted following general protocol A. The final residue was purified by reverse phase preparative HPLC to afford N-(2-(3,8-diazabicyclo[3.2.1]octan-8-yl)-5-chloropyrimidin-4-yl)-6-methoxy-1H-indazol-5-amine as a pink solid (40%). $^1$H NMR (400 MHz, CD$_3$OD) δ 8.28 (s, 1H), 8.12 (s, 1H), 8.01 (s, 1H), 7.12 (s, 1H), 4.43 (m, 2H), 3.99 (s, 3H), 3.39-3.32 (m, 2H), 3.29-3.21 (m, 2H), 2.35-2.22 (m, 2H), 2.15-2.01 (m, 2H MS (ES+) m/e 386.0 (M+H).

Example 306

2-(3,8-diazabicyclo[3.2.1]octan-8-yl)-N-(4-(pyridin-4-yl)phenyl)-6,7-dihydro-5H-pyrrolo[3,4-d]pyrimidin-4-amine

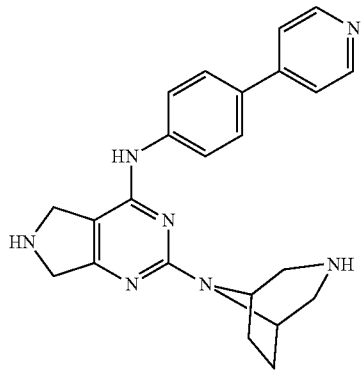 [SMILES: c1cc(-c2ccc(Nc3nc(N4C5CCC4CNC5)nc4c3CNC4)cc2)ccn1]

The reaction was conducted following general protocol G. The final residue was purified by reverse phase preparative HPLC to afford 2-(3,8-diazabicyclo[3.2.1]octan-8-yl)-N-(4-(pyridin-4-yl)phenyl)-6,7-dihydro-5H-pyrrolo[3,4-d]pyrimidin-4-amine as a yellow solid (10%). $^1$H NMR (400 MHz, DMSO-$d_6$) δ 9.76 (s, 2H), 9.57 (s, 1H), 9.43 (s, 1H), 9.09 (s, 1H), 8.85 (d, J=6.4 Hz, 2H), 8.22 (d, J=6.8 Hz, 2H), 8.06 (d, J=8.8 Hz, 2H), 7.94 (d, J=8.8 Hz, 2H), 4.73 (s, 2H), 4.49 (s, 2H), 4.34 (s, 2H), 3.25-3.16 (m, 4H), 2.09-2.06 (m, 4H). MS (ES+) m/e 400.3 (M+H).

Example 307

2-(3,6-diazabicyclo[3.1.1]heptan-6-yl)-N-(1H-indazol-5-yl)-7,8-dihydro-5H-pyrano[4,3-d]pyrimidin-4-amine

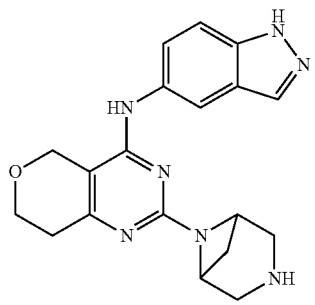 [SMILES: c1cc2[nH]ncc2cc1Nc1nc(N2C3CNCC2C3)nc2c1COCC2]

The reaction was conducted following general protocol A. The final residue was purified by reverse phase preparative HPLC to afford 2-(3,6-diazabicyclo[3.1.1]heptan-6-yl)-N-(1H-indazol-5-yl)-7,8-dihydro-5H-pyrano[4,3-d]pyrimidin-4-amine as a white solid (30%). $^1$H NMR (400 MHz, DMSO-$d_6$) δ 13.12 (s, 1H), 9.44 (s, 1H), 8.78 (s, 1H), 8.09 (s, 1H), 7.90 (s, 1H), 7.55-7.53 (m, 1H), 7.548-7.46 (m, 1H), 4.61 (s, 2H), 4.43 (s, 2H), 3.94 (t, J=5.6 Hz, 2H), 3.68 (d, J=12.4 Hz, 2H), 3.39 (d, J=9.6 Hz, 2H), 2.81-2.73 (m, 3H), 1.87 (d, J=9.6 Hz, 1H). MS (ES+) m/e 364.1 (M+H).

Example 308

N-(2-(3,6-diazabicyclo[3.1.1]heptan-6-yl)-5-cyclopropylpyrimidin-4-yl)-1H-indazol-5-amine

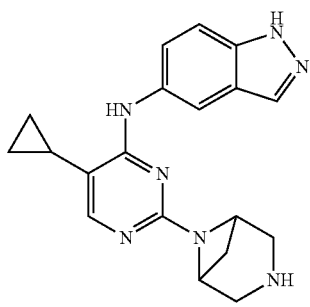 [SMILES: c1cc2[nH]ncc2cc1Nc1nc(N2C3CNCC2C3)ncc1C1CC1]

The reaction was conducted following general protocol A. The final residue was purified by reverse phase preparative HPLC to afford N-(2-(3,6-diazabicyclo[3.1.1]heptan-6-yl)-5-cyclopropylpyrimidin-4-yl)-1H-indazol-5-amine as a white solid (9%). $^1$H NMR (400 MHz, DMSO-$d_6$) δ 13.19 (s, 1H), 9.87 (s, 1H), 9.52 (s, 1H), 9.02 (s, 1H), 8.12 (d, J=0.8 Hz, 1H), 7.96 (s, 1H), 7.78 (d, J=0.8 Hz, 1H), 7.59-7.51 (m, 2H), 4.46 (m, 2H), 3.65 (m, 2H), 3.42 (d, J=10.4 Hz, 2H), 2.85-2.81 (m, 1H), 1.87 (d, J=10.4 Hz, 1H), 1.83-1.76 (m, 1H), 1.04-0.99 (m, 2H), 0.73-0.69 (m, 2H). MS (ES+) m/e 348.0 (M+H).

Example 309

N-(2-(3,8-diazabicyclo[3.2.1]octan-8-yl)-5-cyclopropylpyrimidin-4-yl)-1H-indazol-5-amine

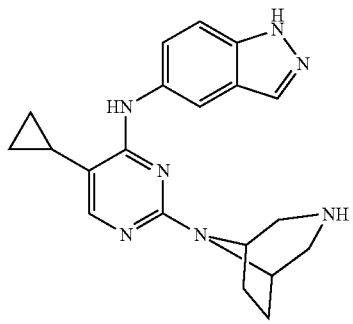 [SMILES: c1cc2[nH]ncc2cc1Nc1nc(N2C3CCC2CNC3)ncc1C1CC1]

The reaction was conducted following general protocol A. The final residue was purified by reverse phase preparative HPLC to afford N-(2-(3,8-diazabicyclo[3.2.1]octan-8-yl)-5-cyclopropylpyrimidin-4-yl)-1H-indazol-5-amine as a white solid (8%). $^1$H NMR (400 MHz, DMSO-$d_6$) δ 13.18 (s, 1H), 9.78 (s, 1H), 9.38 (s, 1H), 8.99 (s, 1H), 8.12 (s, 1H), 7.93 (s, 1H), 7.73 (s, 1H), 7.60-7.54 (m, 2H), 4.60 (s, 2H), 3.22-3.20 (m, 4H), 2.01-2.00 (m, 4H), 1.83-1.76 (m, 1H), 1.03-0.99 (m, 2H), 0.71-0.67 (m, 2H). MS (ES+) m/e 362.1 (M+H).

Example 310

2-(3,6-diazabicyclo[3.1.1]heptan-6-yl)-N-(1H-indazol-5-yl)-6,7-dihydro-5H-pyrrolo[3,4-d]pyrimidin-4-amine

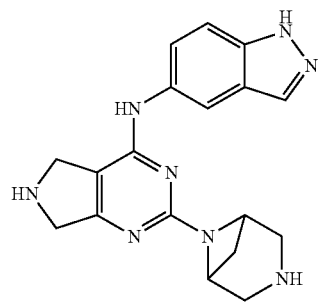 [SMILES: c1cc2[nH]ncc2cc1Nc1nc(N2C3CNCC2C3)nc2c1CNC2]

The reaction was conducted following general protocol A. The final residue was purified by reverse phase preparative HPLC to afford 2-(3,6-diazabicyclo[3.1.1]heptan-6-yl)-N-(1H-indazol-5-yl)-6,7-dihydro-5H-pyrrolo[3,4-d]pyrimidin-4-amine as a brown solid (17%). $^1$H NMR (400 MHz, DMSO-$d_6$) δ 13.07 (s, 1H), 9.59-9.40 (m, 3H), 9.24 (1, 1H), 8.70 (s, 1H), 8.09-8.06 (m, 2H), 7.53-7.48 (m, 2H), 4.36-4.29 (m, 6H), 3.35 (m, 2H), 2.78-2.75 (m, 1H) 1.89 (d, J=9.2 Hz, 1H). MS (ES+) m/e 349.1 (M+H).

Example 311

2-(3,6-diazabicyclo[3.1.1]heptan-6-yl)-N-(4-(pyridin-4-yl)phenyl)-7,8-dihydro-5H-pyrano[4,3-d]pyrimidin-4-amine

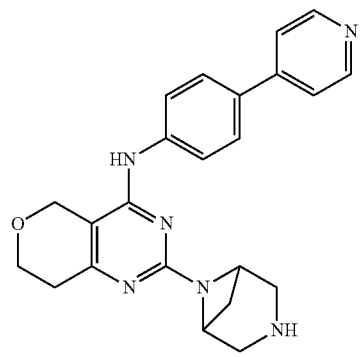 [SMILES: c1cc(-c2ccc(Nc3nc(N4C5CNCC4C5)nc4c3COCC4)cc2)ccn1]

The reaction was conducted following general protocol G. The final residue was purified by reverse phase preparative HPLC to afford 2-(3,6-diazabicyclo[3.1.1]heptan-6-yl)-N-(4-(pyridin-4-yl)phenyl)-7,8-dihydro-5H-pyrano[4,3-d]pyrimidin-4-amine as a yellow solid (30%). $^1$H NMR (400 MHz, CD$_3$OD) δ 8.56-8.54 (m, 2H), 8.38 (s, 1H), 7.83-7.77 (m, 2H), 7.75-7.71 (m, 4H), 4.66 (s, 2H), 4.48-4.46 (m, 2H), 4.02-3.99 (m, 2H), 3.87 (d, J=12.8 Hz, 2H), 3.37-3.33 (m, 2H), 2.96-2.90 (m, 1H), 2.75-2.73 (m, 2H), 1.88 (d, J=9.6 Hz, 1H). MS (ES+) m/e 401.1 (M+H).

Example 312

2-(3,6-diazabicyclo[3.1.1]heptan-6-yl)-N-(4-(pyridin-4-yl)phenyl)-5,7-dihydrofuro[3,4-d]pyrimidin-4-amine

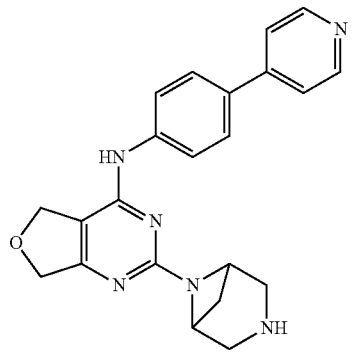 [SMILES: c1cc(-c2ccc(Nc3nc(N4C5CNCC4C5)nc4c3COC4)cc2)ccn1]

The reaction was conducted following general protocol G. The final residue was purified by reverse phase preparative HPLC to afford 2-(3,6-diazabicyclo[3.1.1]heptan-6-yl)-N-(4-(pyridin-4-yl)phenyl)-5,7-dihydrofuro[3,4-d]pyrimidin-4-amine as an off-white solid (28%). $^1$H NMR (400 MHz, CD$_3$OD) δ 8.53 (d, J=4.4 Hz, 2H), 7.93-7.90 (m, 2H), 7.75-7.71 (m, 4H), 5.02 (s, 2H), 4.81 (s, 2H), 4.38 (d, J=4 Hz, 2H), 3.57 (d, J=11.6 Hz, 2H), 2.89 (d, J=12.8 Hz, 2H), 2.78-2.2.73 (m, 1H), 1.85 (d, J=8.4 Hz, 1H). MS (ES+) m/e 387.0 (M+H).

Example 313

2-(3,6-diazabicyclo[3.1.1]heptan-6-yl)-N-(1H-indazol-5-yl)-7-methyl-5,6,7,8-tetrahydropyrido[3,4-d]pyrimidin-4-amine

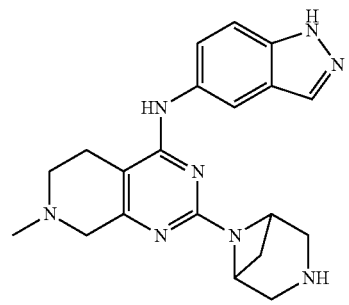 [SMILES: CN1CCc2c(nc(N3C4CNCC3C4)nc2Nc2ccc3[nH]ncc3c2)C1]

The reaction was conducted following general protocol A. The final residue was purified by reverse phase preparative HPLC to afford 2-(3,6-diazabicyclo[3.1.1]heptan-6-yl)-N-(1H-indazol-5-yl)-7-methyl-5,6,7,8-tetrahydropyrido[3,4-d]pyrimidin-4-amine as an off-white solid (18%). $^1$H NMR (400 MHz, DMSO-d$_6$) δ 13.01 (s, 1H), 10.64-10.26 (m, 1H), 9.29 (s, 1H), 8.72-8.66 (m, 2H), 8.05-8.01 (m, 2H), 7.55-7.48 (m, 2H), 4.27-4.13 (m, 4H), 3.85-3.75 (m, 2H), 3.69-3.66 (m, 2H), 3.32 (s, 2H), 2.97 (s, 3H), 2.85 (m, 2H), 2.74-2.71 (m, 1H), 1.85 (d, J=9.6 Hz, 1H). MS (ES+) m/e 377.1 (M+H).

Example 314

1-(4-((1H-indazol-5-yl)amino)-2-(3,8-diazabicyclo[3.2.1]octan-8-yl)-5,7-dihydro-6H-pyrrolo[3,4-d]pyrimidin-6-yl)ethan-1-one

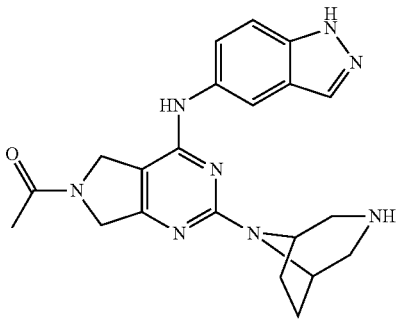 [SMILES: CC(=O)N1Cc2nc(N3C4CCC3CNC4)nc(Nc3ccc4[nH]ncc4c3)c2C1]

The reaction was conducted following general protocol A. The final residue was purified by reverse phase preparative HPLC to afford 1-(4-((1H-indazol-5-yl)amino)-2-(3,8-diazabicyclo[3.2.1]octan-8-yl)-5,7-dihydro-6H-pyrrolo[3,4-d]pyrimidin-6-yl)ethan-1-one as a pink solid (33%). $^1$H NMR (400 MHz, DMSO-d$_6$) δ 13.00 (brs, 1H), 9.15-9.09 (m, 1H), 9.00 (s, 1H), 8.83 (s, 1H), 8.06-8.03 (m, 2H), 7.59-7.55 (m, 1H), 7.54-7.48 (m, 1H), 4.66-4.62 (m, 4H), 4.47 (s, 1H), 4.37 (s, 1H), 3.18 (m, 4H), 2.08-1.99 (m, 7H). MS (ES+) m/e 405.2 (M+H).

Example 315

N-(2-(3,8-diazabicyclo[3.2.1]octan-8-yl)-6-chloro-5-methylpyrimidin-4-yl)-1H-indazol-5-amine

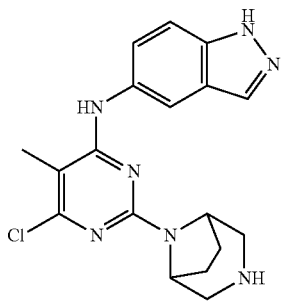 [SMILES: Cc1c(Cl)nc(N2C3CCC2CNC3)nc1Nc1ccc2[nH]ncc2c1]

The reaction was conducted following general protocol A. The final residue was purified by reverse phase preparative HPLC to afford N-(2-(3,8-diazabicyclo[3.2.1]octan-8-yl)-6-chloro-5-methylpyrimidin-4-yl)-1H-indazol-5-amine as a white solid (42%). $^1$H NMR (400 MHz, DMSO-d$_6$) δ 13.00 (s, 1H), 8.58 (s, 1H), 8.21 (s, 1H), 8.02 (s, 1H), 7.89 (s, 1H), 7.54-7.46 (m, 2H), 4.35 (s, 2H), 2.94 (d, J=11.6 Hz, 2H), 2.75 (d, J=11.2 Hz, 2H), 2.19 (s, 3H), 1.91-1.81 (m, 4H). MS (ES+) m/e 370.2 (M+H).

Example 316

N-(4-(1H-pyrazol-4-yl)phenyl)-2-(3,6-diazabicyclo[3.1.1]heptan-6-yl)-5,7-dihydrofuro[3,4-d]pyrimidin-4-amine

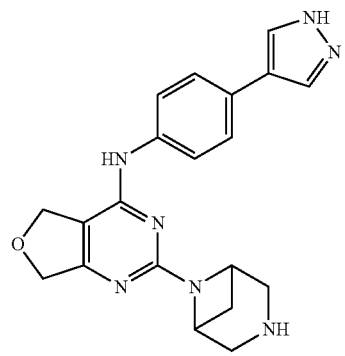 [SMILES: c1cc(-c2cn[nH]c2)ccc1Nc1nc(N2C3CNCC2C3)nc2c1COC2]

The reaction was conducted following general protocol A. The final residue was purified by reverse phase preparative HPLC to afford N-(4-(1H-pyrazol-4-yl)phenyl)-2-(3,6-diazabicyclo[3.1.1]heptan-6-yl)-5,7-dihydrofuro[3,4-d]pyrimidin-4-amine as an off-white solid (55%). $^1$H NMR (400 MHz, DMSO-$d_6$) δ 9.26 (s, 1H), 9.09 (s, 1H), 8.51 (s, 1H), 8.00 (s, 2H), 7.67 (d, J=8.8 Hz, 2H), 7.55 (d, J=8.4 Hz, 2H), 4.96 (s, 2H), 4.77 (s, 2H), 4.38-4.36 (m, 2H), 3.72-3.69 (m, 2H), 3.34 (m, 2H), 2.80-2.76 (m, 1H) 1.90-1.88 (m, 1H). MS (ES+) m/e 376.1 (M+H).

Example 317

N-(4-(1H-pyrazol-4-yl)phenyl)-2-(3,6-diazabicyclo[3.1.1]heptan-6-yl)-7,8-dihydro-5H-pyrano[4,3-d]pyrimidin-4-amine

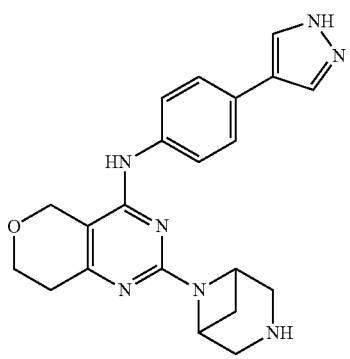 [SMILES: c1cc(-c2cn[nH]c2)ccc1Nc1nc(N2C3CNCC2C3)nc2c1COCC2]

The reaction was conducted following general protocol A. The final residue was purified by reverse phase preparative HPLC to afford N-(4-(1H-pyrazol-4-yl)phenyl)-2-(3,6-diazabicyclo[3.1.1]heptan-6-yl)-7,8-dihydro-5H-pyrano[4,3-d]pyrimidin-4-amine as an off-white solid (48%). $^1$H NMR (400 MHz, DMSO-$d_6$) δ 9.55 (s, 1H), 9.28 (s, 1H), 8.90 (s, 1H), 8.04 (s, 2H), 7.63-7.54 (m, 4H), 4.60-4.51 (m, 4H), 3.94 (t, J=5.6 Hz, 2H), 3.72-3.69 (m, 2H), 3.45-3.42 (m, 2H), 2.87-2.81 (m, 1H), 2.73 (m, 2H), 1.92-1.90 (m, 1H). MS (ES+) m/e 390.1 (M+H).

Example 318

N-(2-(3,8-diazabicyclo[3.2.1]octan-8-yl)-5-chloropyrimidin-4-yl)-6-methyl-1H-indazol-5-amine

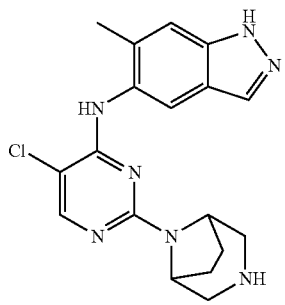 [SMILES: Cc1cc2[nH]ncc2cc1Nc1nc(N2C3CCC2CNC3)ncc1Cl]

The reaction was conducted following general protocol A. The final residue was purified by reverse phase preparative HPLC to afford N-(2-(3,8-diazabicyclo[3.2.1]octan-8-yl)-5-chloropyrimidin-4-yl)-6-methyl-1H-indazol-5-amine as a white solid (27%). $^1$H NMR (400 MHz, CD$_3$OD) δ 8.10 (s, 1H), 8.02 (s, 1H), 7.72 (s, 1H), 7.49 (s, 1H), 4.51 (s, 2H), 3.24-3.21 (m, 2H), 3.14-3.11 (m, 2H), 2.39 (s, 3H), 2.18-2.15 (m, 2H), 1.98-1.92 (m, 2H). MS (ES+) m/e 370.1 (M+H).

Example 319

N-(2-(3,8-diazabicyclo[3.2.1]octan-8-yl)-5-fluoro-6-methoxypyrimidin-4-yl)-1H-indazol-5-amine

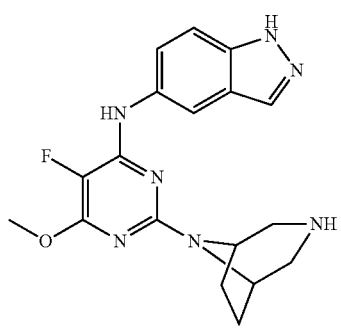 [SMILES: COc1nc(N2C3CCC2CNC3)nc(Nc2ccc3[nH]ncc3c2)c1F]

The reaction was conducted following general protocol A. The final residue was purified by reverse phase preparative HPLC to afford N-(2-(3,8-diazabicyclo[3.2.1]octan-8-yl)-5-fluoro-6-methoxypyrimidin-4-yl)-1H-indazol-5-amine as an off-white solid (18%). $^1$H NMR (400 MHz, DMSO-$d_6$) δ 12.97 (brs, 1H), 9.15 (s, 1H), 9.01 (s, 1H), 8.80 (s, 1H), 8.03 (s, 1H), 7.97 (s, 1H), 7.57 (d, J=8.8 Hz, 1H), 7.47 (d, J=8.8 Hz, 1H), 4.57 (m, 2H), 3.91 (s, 3H), 3.18 (m, 4H), 2.07-1.99 (m, 4H). MS (ES+) m/e 370.1 (M+H).

Example 320

6-((1H-indazol-5-yl)amino)-2-(3,8-diazabicyclo[3.2.1]octan-8-yl)-5-fluoropyrimidin-4-ol

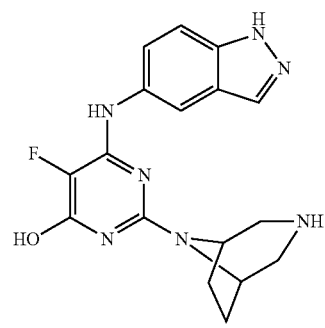 [SMILES: Oc1nc(N2C3CCC2CNC3)nc(Nc2ccc3[nH]ncc3c2)c1F]

The reaction was conducted following general protocol A. The final residue was purified by reverse phase preparative HPLC to afford 6-((1H-indazol-5-yl)amino)-2-(3,8-diazabicyclo[3.2.1]octan-8-yl)-5-fluoropyrimidin-4-ol as an off-white solid (32%). $^1$H NMR (400 MHz, DMSO-$d_6$) δ 13.01 (s, 1H), 11.28 (s, 1H), 9.12 (s, 1H), 8.90 (s, 2H), 8.01 (d, J=0.8 Hz, 1H), 7.81 (s, 1H), 7.50-7.43 (m, 2H), 4.55 (m, 2H), 3.27-3.13 (m, 4H), 2.09-1.96 (m, 4H). MS (ES+) m/e 356.2 (M+H).

Example 321

N-(2-(3,8-diazabicyclo[3.2.1]octan-8-yl)-5-chloro-6-methoxypyrimidin-4-yl)-1H-indazol-5-amine

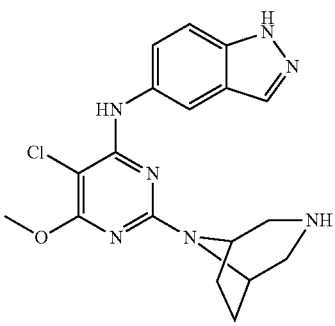 [SMILES: COc1nc(N2C3CCC2CNC3)nc(Nc2ccc3[nH]ncc3c2)c1Cl]

The reaction was conducted following general protocol A. The final residue was purified by reverse phase preparative HPLC to afford N-(2-(3,8-diazabicyclo[3.2.1]octan-8-yl)-5-chloro-6-methoxypyrimidin-4-yl)-1H-indazol-5-amine as a brown solid (41%). $^1$H NMR (400 MHz, DMSO-$d_6$) δ 13.02 (brs, 1H), 9.02 (d, J=11.2 Hz, 1H), 8.80 (s, 1H), 8.70 (s, 1H), 8.05 (s, 1H), 7.85 (d, J=1.2 Hz, 1H), 7.53-7.46 (m, 2H), 4.52 (m, 2H), 3.90 (s, 3H), 3.21-3.13 (m, 4H), 2.06-1.96 (m, 4H). MS (ES+) m/e 386.3 (M+H).

Example 322

Ethyl (3αR,8αR)-2-(4-((1H-indazol-5-yl)amino)-5-fluoropyrimidin-2-yl)octahydropyrrolo[3,4-d]azepine-3α(1H)-carboxylate

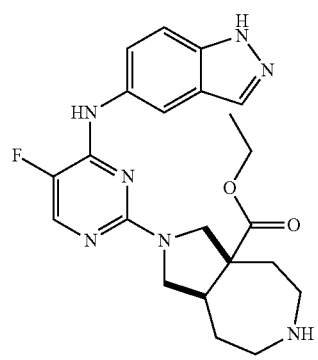

The reaction was conducted following general protocol A. The final residue was purified by reverse phase preparative HPLC to afford ethyl (3aR,8aR)-2-(4-((1H-indazol-5-yl)amino)-5-fluoropyrimidin-2-yl)octahydropyrrolo[3,4-d]azepine-3a(1H)-carboxylate as a yellow solid (10%). $^1$H NMR (400 MHz, CD$_3$OD) δ 8.10-8.09 (m, 1H), 8.08 (s, 1H), 8.00 (d, J=5.2 Hz, 1H), 7.65-7.57 (m, 2H), 4.25-4.18 (m, 3H), 3.93-3.87 (m, 1H), 3.51-3.45 (m, 4H), 3.25-3.11 (m, 3H), 2.51-2.45 (m, 1H), 2.14-1.99 (m, 3H), 1.25 (t, J=6.8 Hz, 3H). MS (ES+) m/e 440.2 (M+H).

Example 323

Ethyl (3αR,8αR)-2-(4-((1H-indazol-5-yl)amino)-5-chloropyrimidin-2-yl)octahydropyrrolo[3,4-d]azepine-3α(1H)-carboxylate

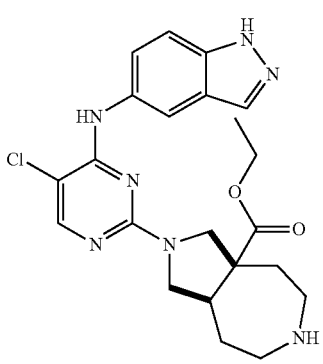

The reaction was conducted following general protocol A. The final residue was purified by reverse phase preparative HPLC to afford ethyl (3aR,8aR)-2-(4-((1H-indazol-5-yl)amino)-5-chloropyrimidin-2-yl)octahydropyrrolo[3,4-d]azepine-3a(1H)-carboxylate as a yellow solid (25%). $^1$H NMR (400 MHz, CD$_3$OD) δ 8.07 (s, 1H), 8.03 (s, 1H), 8.00 (s, 1H), 7.60-7.54 (m, 2H), 4.26-4.11 (m, 3H), 3.87 (dd, J=11.2, 8.0 Hz, 1H), 3.49-3.41 (m, 3H), 3.22-3.09 (m, 4H), 2.45 (dd, J=16.0, 6.8 Hz, 1H), 2.14-1.97 (m, 3H), 1.23 (t, J=6.8 Hz, 3H). MS (ES+) m/e 456.2 (M+H).

Example 324

N-(2-((1,5)-9-oxa-3,7-diazabicyclo[3.3.1]nonan-3-yl)-5-fluoropyrimidin-4-yl)-1H-indazol-5-amine

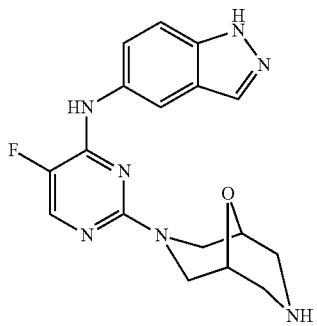 [SMILES: Fc1cnc(N2CC3CNCC(C2)O3)nc1Nc1ccc2[nH]ncc2c1]

The reaction was conducted following general protocol A. The final residue was purified by reverse phase preparative HPLC to afford N-(2-((1,5)-9-oxa-3,7-diazabicyclo[3.3.1]nonan-3-yl)-5-fluoropyrimidin-4-yl)-1H-indazol-5-amine as a yellow solid (28%). $^1$H NMR (400 MHz, CD$_3$OD) δ 8.06-8.05 (m, 2H), 8.02 (d, J=4.0 Hz, 1H), 7.64-7.55 (m, 2H), 4.33 (d, J=13.6 Hz, 2H), 4.27 (s, 2H), 3.53-3.43 (m, 3H), 3.41-3.30 (m, 2H). MS (ES+) m/e 356.3 (M+H).

Example 325

N-(2-((1,5)-9-oxa-3,7-diazabicyclo[3.3.1]nonan-3-yl)-5-chloropyrimidin-4-yl)-1H-indazol-5-amine

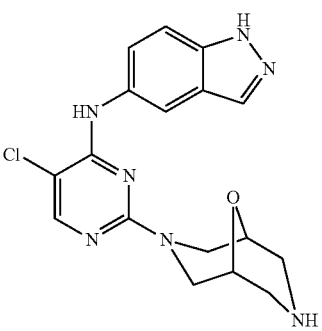 [SMILES: Clc1cnc(N2CC3CNCC(C2)O3)nc1Nc1ccc2[nH]ncc2c1]

The reaction was conducted following general protocol A. The final residue was purified by reverse phase preparative HPLC to afford N-(2-((1,5)-9-oxa-3,7-diazabicyclo[3.3.1]nonan-3-yl)-5-chloropyrimidin-4-yl)-1H-indazol-5-amine as a white solid (18%). $^1$H NMR (400 MHz, DMSO-d$_6$) δ 13.02 (s, 1H), 9.05 (d, J=12.0 Hz, 1H), 8.95 (s, 1H), 8.16 (s, 1H), 8.05-7.99 (m, 3H), 7.64 (dd, J=9.2, 2.0 Hz, 1H), 7.50 (d, J=8.8 Hz, 1H), 4.26 (d, J=13.3 Hz, 2H), 4.20 (brs, 2H), 3.34-3.28 (m, 4H), 3.21-3.18 (m, 2H). MS (ES+) m/e 372.1 (M+H).

Example 326

Ethyl 3-(4-((1H-indazol-5-yl)amino)-5-chloropyrimidin-2-yl)-3,6-diazabicyclo[3.2.1]octane-7-carboxylate

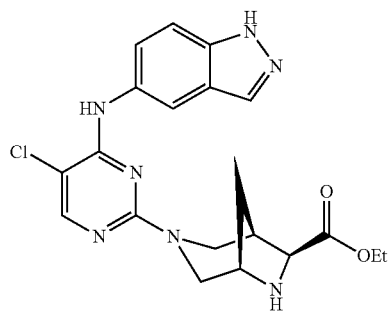 [SMILES: CCOC(=O)[C@H]1N[C@@H]2C[C@@H]1CN(c1ncc(Cl)c(Nc3ccc4[nH]ncc4c3)n1)C2]

The reaction was conducted following general protocol A. The final residue was purified by reverse phase preparative HPLC to afford ethyl 3-(4-((1H-indazol-5-yl)amino)-5-chloropyrimidin-2-yl)-3,6-diazabicyclo[3.2.1]octane-7-carboxylate as a yellow solid (23%). $^1$H NMR (400 MHz, DMSO-d$_6$) δ 8.06 (s, 1H), 8.02 (s, 1H), 7.95-7.94 (m, 1H), 7.56 (m, 2H), 4.60 (dd, J=14.0, 3.2 Hz, 1H), 4.50-4.45 (m, 2H), 4.19 (s, 1H), 4.09-3.95 (m, 1H), 3.69 (m, 1H), 3.19-3.04 (m, 2H), 2.23 (s, 2H), 0.86 (m, 3H). MS (ES+) m/e 428.2 (M+H).

Example 328

N-(2-(3a-((ethylperoxy)methyl)-6a-(trifluoromethyl)hexahydropyrrolo[3,4-c]pyrrol-2(1H)-yl)-5-fluoropyrimidin-4-yl)-1H-indazol-5-amine

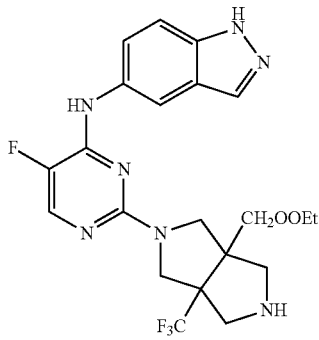

The reaction was conducted following general protocol A. The final residue was purified by reverse phase preparative HPLC to afford ethyl N-(2-(3a-((ethylperoxy)methyl)-6a-(trifluoromethyl)hexahydropyrrolo[3,4-c]pyrrol-2(1H)-yl)-5-fluoropyrimidin-4-yl)-1H-indazol-5-amine as a yellow solid (8%). $^1$H NMR (400 MHz, CD$_3$OD) δ 8.09 (d, J=1.2 Hz, 1H), 8.05 (s, 1H), 8.02 (d, J=4.8 Hz, 1H), 7.62 (dd, J=9.2, 2.0 Hz, 1H), 7.57 (d, J=8.8 Hz, 1H), 4.33-4.27 (m, 3H), 4.15 (d, J=12.8 Hz, 2H), 3.99 (d, J=12.8 Hz, 1H), 3.94 (d, J=4.0 Hz, 1H), 3.92-3.89 (m, 1H), 3.89-3.82 (m, 1H), 3.66 (d, J=12.8 Hz, 1H), 1.30 (t, J=7.2 Hz, 3H). MS (ES+) m/e 480.2 (M+H).

Example 329

2-(3,8-diazabicyclo[3.2.1]octan-8-yl)-N4-(1H-indazol-5-yl)-N6-methylpyrimidine-4,6-diamine

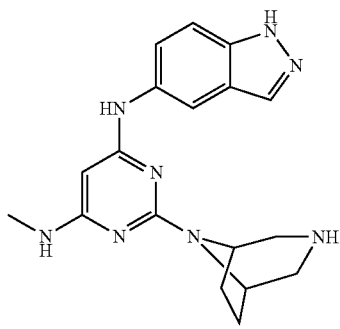 [SMILES: CNc1cc(Nc2ccc3[nH]ncc3c2)nc(N2C3CCC2CNC3)n1]

The reaction was conducted following general protocol A. The final residue was purified by reverse phase preparative HPLC to afford 2-(3,8-diazabicyclo[3.2.1]octan-8-yl)-N4-(1H-indazol-5-yl)-N6-methylpyrimidine-4,6-diamine as a yellow solid (2%). $^1$H NMR (400 MHz, DMSO-d$_6$) δ 13.00 (s, 1H), 9.06 (s, 1H), 8.83 (s, 1H), 8.02 (s, 1H), 7.82 (s, 1H), 7.50 (d, J=8.8 Hz, 1H), 7.34 (d, J=8.8 Hz, 1H), 5.22 (s, 1H), 4.69 (s, 2H), 3.21 (m, 4H), 2.74 (s, 3H), 2.11-2.00 (m, 4H). MS (ES+) m/e 351.2 (M+H).

Example 330

2-(3,8-diazabicyclo[3.2.1]octan-8-yl)-N-(1H-indazol-5-yl)quinazolin-4-amine

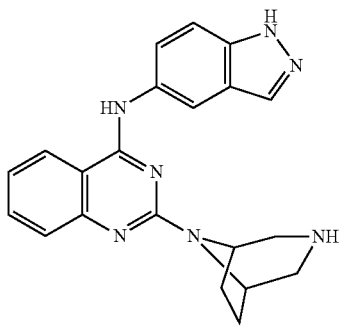 [SMILES: c1ccc2c(Nc3ccc4[nH]ncc4c3)nc(N3C4CCC3CNC4)nc2c1]

The reaction was conducted following general protocol A. The final residue was purified by reverse phase preparative HPLC to afford 2-(3,8-diazabicyclo[3.2.1]octan-8-yl)-N-(1H-indazol-5-yl)quinazolin-4-amine as a yellow solid (42%). $^1$H NMR (400 MHz, DMSO-d$_6$) δ 13.05 (brs, 1H), 9.74 (s, 1H), 8.37 (d, J=8.0 Hz, 1H), 8.23 (s, 2H), 8.09-8.08 (m, 2H), 7.70 (d, J=9.2, 2.0 Hz, 1H), 7.69-7.62 (m, 1H), 7.55 (d, J=9.2 Hz, 1H), 7.46 (d, J=8.0 Hz, 1H), 7.26 (t, J=8.4 Hz, 1H), 4.65 (s, 2H), 3.12-3.00 (m, 4H), 2.07 (m, 4H). MS (ES+) m/e 372.4 (M+H).

Example 331

2-(3,8-diazabicyclo[3.2.1]octan-8-yl)-N4-(6-fluoro-1H-indazol-5-yl)-N6,N6-dimethylpyrimidine-4,6-diamine

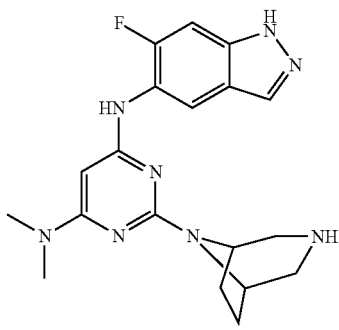 [SMILES: CN(C)c1cc(Nc2cc3cn[nH]c3cc2F)nc(N2C3CCC2CNC3)n1]

The reaction was conducted following general protocol A. The final residue was purified by reverse phase preparative HPLC to afford 2-(3,8-diazabicyclo[3.2.1]octan-8-yl)-N4-(6-fluoro-1H-indazol-5-yl)-N6,N6-dimethylpyrimidine-4,6-diamine as a white solid (29%). $^1$H NMR (400 MHz, DMSO-d$_6$) δ 13.11 (s, 1H), 9.00 (s, 1H), 8.79 (s, 1H), 8.59 (s, 1H), 8.06 (s, 1H), 7.99 (d, J=7.6 Hz, 1H), 7.41 (d, J=10.8 Hz, 1H), 5.29 (s, 1H), 4.62 (s, 2H), 3.15 (m, 4H), 2.95 (s, 6H), 2.10-1.90 (m, 4H). MS (ES+) m/e 383.3 (M+H).

Example 332

2-(3,8-diazabicyclo[3.2.1]octan-8-yl)-N4-ethyl-N6-(1H-indazol-5-yl)-N4-methylpyrimidine-4,6-diamine

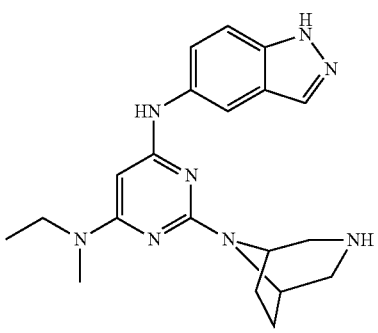 [SMILES: CCN(C)c1cc(Nc2ccc3[nH]ncc3c2)nc(N2C3CCC2CNC3)n1]

The reaction was conducted following general protocol A. The final residue was purified by reverse phase preparative HPLC to afford 2-(3,8-diazabicyclo[3.2.1]octan-8-yl)-N4-ethyl-N6-(1H-indazol-5-yl)-N4-methylpyrimidine-4,6-diamine as a yellow solid (10%). $^1$H NMR (400 MHz, DMSO-d$_6$) δ 12.92 (brs, 1H), 8.87 (s, 2H), 8.72 (s, 1H), 7.99 (s, 1H), 7.89 (s, 1H), 7.46 (d, J=8.8 Hz, 1H), 7.36 (d, J=8.8 Hz, 1H), 5.28 (m, 1H), 4.67 (m, 2H), 3.47 (m, 2H), 3.18 (m, 4H), 2.91 (s, 3H), 2.09-1.98 (m, 4H), 1.05 (t, J=6.8 Hz, 3H). MS (ES+) m/e 379.3 (M+H).

Example 333

6-((1H-indazol-5-yl)amino)-2-(3,8-diazabicyclo[3.2.1]octan-8-yl)-5-methylpyrimidine-4-carbonitrile

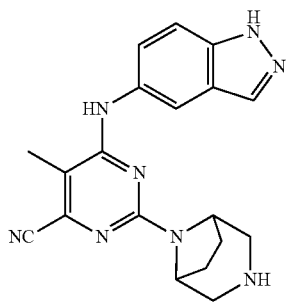 [SMILES: Cc1c(C#N)nc(N2C3CCC2CNC3)nc1Nc1ccc2[nH]ncc2c1]

The reaction was conducted following general protocol A. The final residue was purified by reverse phase preparative HPLC to afford 6-((1H-indazol-5-yl)amino)-2-(3,8-diazabicyclo[3.2.1]octan-8-yl)-5-methylpyrimidine-4-carbonitrile as a yellow solid (4%). $^1$H NMR (400 MHz, DMSO-d$_6$) δ 13.08 (s, 1H), 9.02 (s, 2H), 8.79 (s, 1H), 8.08 (s, 1H), 7.92 (s, 1H), 7.56-7.51 (m, 2H), 4.51 (m, 2H), 3.14 (m, 4H), 2.32 (s, 3H), 2.08-1.95 (m, 4H). MS (ES+) m/e 361.3 (M+H).

Example 334

N-(5-fluoro-2-(5-(methylamino)-2-azabicyclo[2.2.1]heptan-2-yl)pyrimidin-4-yl)-1H-indazol-5-amine

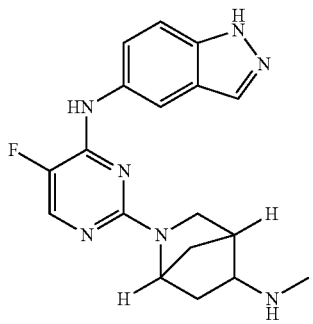 [SMILES: CNC1CC2CC1CN2c1ncc(F)c(Nc2ccc3[nH]ncc3c2)n1]

Step 1: A solution of N-(2-chloro-5-fluoropyrimidin-4-yl)-1H-indazol-5-amine (1 equiv), tert-butyl (2-azabicyclo[2.2.1]heptan-5-yl)carbamateamine (1 equiv) and DIPEA (2 equiv) in DMSO was stirred at 110° C. for 16 hours. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl (2-(4-((1H-indazol-5-yl)amino)-5-fluoropyrimidin-2-yl)-2-azabicyclo[2.2.1]heptan-5-yl)carbamate as a yellow oil (98% yield).

Step 2: To a solution of tert-butyl (2-(4-((1H-indazol-5-yl)amino)-5-fluoropyrimidin-2-yl)-2-azabicyclo[2.2.1]heptan-5-yl)carbamate (1 equiv) in THF was added LAH (2 equiv). The mixture was stirred at 70° C. for 19 hours. The reaction mixture was cooled down to room temperature and diluted with H$_2$O (1 mL), 15% aqueous NaOH (1 mL) and H$_2$O (3 mL). The resulting mixture was extracted with EtOAc. The combined organic layers were washed with brine, dried over Na$_2$SO$_4$, filtered and concentrated under reduced pressure. The final residue was purified by reverse phase preparative HPLC to afford N-(5-fluoro-2-(5-(methylamino)-2-azabicyclo[2.2.1]heptan-2-yl)pyrimidin-4-yl)-1H-indazol-5-amine as a yellow solid (12%). $^1$H NMR (400 MHz, CD$_3$OD) δ 8.11 (s, 1H), 8.08 (s, 1H), 7.97 (d, J=5.2 Hz, 1H), 7.65-7.56 (m, 2H), 4.60 (s, 1H), 3.77-3.69 (m, 1H), 3.67-3.61 (m, 1H), 3.60-3.54 (m, 1H), 3.11 (m, 1H), 2.73 (s, 3H), 2.34-2.28 (m, 1H), 2.04-2.01 (m, 1H), 1.90-1.87 (m, 1H), 1.74-1.68 (m, 1H). MS (ES+) m/e 354.4 (M+H).

Example 335

N-(2-(5-(dimethylamino)-2-azabicyclo[2.2.1]heptan-2-yl)-5-fluoropyrimidin-4-yl)-1H-indazol-5-amine

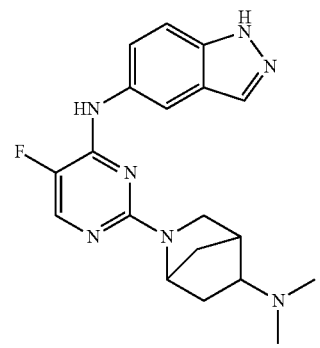 [SMILES: CN(C)C1CC2CC1CN2c1ncc(F)c(Nc2ccc3[nH]ncc3c2)n1]

The reaction was conducted following general protocol F. The final residue was purified by reverse phase preparative HPLC to afford N-(2-(5-(dimethylamino)-2-azabicyclo[2.2.1]heptan-2-yl)-5-fluoropyrimidin-4-yl)-1H-indazol-5-amine as a white solid (8%). $^1$H NMR (400 MHz, CD$_3$OD) δ 8.24 (s, 1H), 7.98 (s, 1H), 7.76 (d, J=4.0 Hz, 1H), 7.68 (d, J=8.8 Hz, 1H), 7.49 (d, J=9.2 Hz, 1H), 4.47 (s, 1H), 3.62 (d, J=10.0 Hz, 1H), 3.37 (d, J=10.9 Hz, 1H), 2.74 (s, 1H), 2.51-2.43 (m, 1H), 2.19 (s, 6H), 2.01-1.95 (m, 1H), 1.81 (d, J=10.0 Hz, 1H), 1.70 (d, J=9.6 Hz, 1H), 1.44-1.40 (m, 1H). MS (ES+) m/e 368.3 (M+H).

Example 336

2-(3,8-diazabicyclo[3.2.1]octan-8-yl)-N$^4$-(1H-indazol-5-yl)-N$^6$,N$^6$-dimethylpyrimidine-4,6-diamine

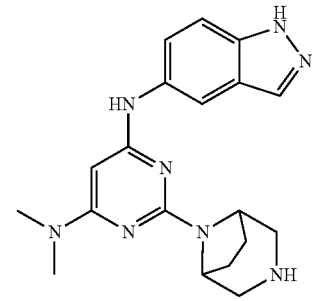 [SMILES: CN(C)c1cc(Nc2ccc3[nH]ncc3c2)nc(N2C3CCC2CNC3)n1]

The reaction was conducted following general protocol A. The final residue was purified by reverse phase preparative HPLC to afford 2-(3,8-diazabicyclo[3.2.1]octan-8-yl)-N⁴-(1H-indazol-5-yl)-N⁶,N⁶-dimethylpyrimidine-4,6-diamine as a yellow solid (33%). ¹H NMR (400 MHz, DMSO-d₆) δ 12.99 (brs, 1H), 9.13 (s, 2H), 8.88 (s, 1H), 8.01 (s, 1H), 7.87 (s, 1H), 7.49-7.36 (m, 2H), 5.30 (s, 1H), 4.71 (s, 2H), 3.20 (m, 4H), 2.97 (s, 6H), 2.16-1.94 (m, 4H). MS (ES+) m/e 365.3 (M+H).

Example 337

N-(2-(3-(dimethylamino)-8-azabicyclo[3.2.1]octan-8-yl)pyrimidin-4-yl)-1H-indazol-5-amine

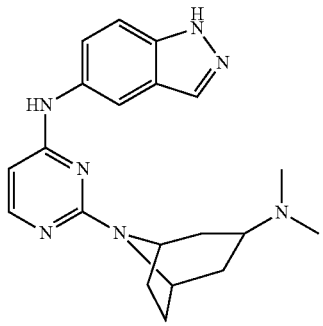 [SMILES: CN(C)C1CC2CCC(C1)N2c1nccc(Nc2ccc3[nH]ncc3c2)n1]

The reaction was conducted following general protocol F. The final residue was purified by reverse phase preparative HPLC to afford N-(2-(3-(dimethylamino)-8-azabicyclo[3.2.1]octan-8-yl)pyrimidin-4-yl)-1H-indazol-5-amine as a white solid (10%). ¹H NMR (400 MHz, CD3OD) δ 8.09 (s, 1H), 7.98 (s, 1H), 7.83 (d, J=6.0 Hz, 1H), 7.53-7.47 (m, 2H), 6.03 (d, J=6.0 Hz, 1H), 4.70 (s, 2H), 2.84-2.76 (m, 1H), 2.23 (s, 6H), 2.12-2.01 (m, 2H), 1.91-1.81 (m, 4H), 1.79-1.70 (m, 2H). MS (ES+) m/e 364.3 (M+H).

Example 338

Ethyl 2-(4-((1H-indazol-5-yl)amino)-5-chloropyrimidin-2-yl)-6a-(trifluoromethyl)hexahydropyrrolo[3,4-c]pyrrole-3a(1H)-carboxylate

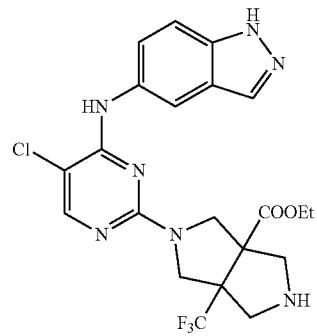 [SMILES: CCOC(=O)C12CNCC1(C(F)(F)F)CN(c1ncc(Cl)c(Nc3ccc4[nH]ncc4c3)n1)C2]

The reaction was conducted following general protocol A. The final residue was purified by reverse phase preparative HPLC to afford ethyl 2-(4-((1H-indazol-5-yl)amino)-5-chloropyrimidin-2-yl)-6a-(trifluoromethyl)hexahydropyrrolo[3,4-c]pyrrole-3a(1H)-carboxylate as a yellow solid (38%). ¹H NMR (400 MHz, CD₃OD) δ 8.06 (s, 1H), 8.04 (s, 1H), 7.99 (s, 1H), 7.59-7.54 (m, 2H), 4.30-4.25 (m, 3H), 4.12-4.09 (m, 2H), 3.93-3.79 (m, 4H), 3.62-3.60 (m, 1H), 1.28 (t, J=7.2 Hz, 3H). MS (ES+) m/e 496.2 (M+H).

Example 339

Ethyl 3-(4-((1H-indazol-5-yl)amino)-5-fluoropyrimidin-2-yl)-3,6-diazabicyclo[3.2.1]octane-7-carboxylate

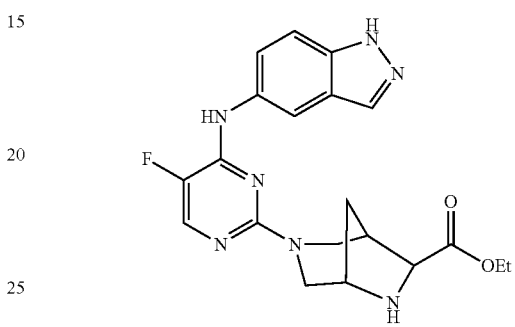

The reaction was conducted following general protocol A. The final residue was purified by reverse phase preparative HPLC to afford ethyl 3-(4-((1H-indazol-5-yl)amino)-5-fluoropyrimidin-2-yl)-3,6-diazabicyclo[3.2.1]octane-7-carboxylate as a yellow solid (30%). ¹H NMR (400 MHz, CD₃OD) δ 8.07 (s, 1H), 8.05-8.02 (m, 1H), 7.97 (d, J=4.4 Hz, 1H), 7.62-7.56 (m, 2H), 4.56-4.43 (m, 3H), 4.24 (s, 1H), 4.08-3.98 (m, 1H), 3.71 (s, 1H), 3.26 (m, 1H), 3.19 (m, 1H), 3.08 (m, 1H), 2.25 (s, 2H), 0.85 (t, J=5.6 Hz, 3H). MS (ES+) m/e 412.2 (M+H).

Example 340

N-(2-(3,8-diazabicyclo[3.2.1]octan-8-yl)-5-chloro-6-(trifluoromethyl)pyrimidin-4-yl)-1H-indazol-5-amine

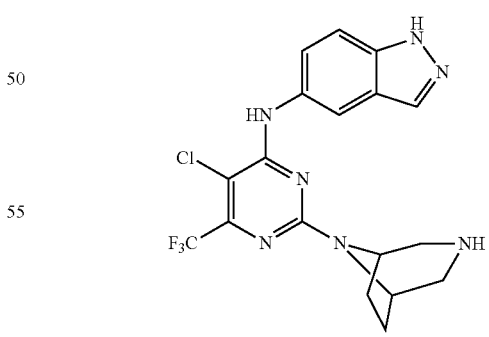

The reaction was conducted following general protocol A. The final residue was purified by reverse phase preparative HPLC to afford N-(2-(3,8-diazabicyclo[3.2.1]octan-8-yl)-5-chloro-6-(trifluoromethyl)pyrimidin-4-yl)-1H-indazol-5-amine as a white solid (41%). ¹H NMR (400 MHz, DMSO-d₆) δ 13.11 (s, 1H), 9.49 (s, 1H), 8.91 (s, 2H), 8.08 (s, 1H), 7.87 (s, 1H), 7.53 (s, 2H), 4.49 (m, 2H), 3.22-3.13 (m, 4H), 2.09-1.95 (m, 4H). MS (ES+) m/e 424.1 (M+H).

Example 341

N-(2-(3,8-diazabicyclo[3.2.1]octan-8-yl)-6-(trifluoromethyl)pyrimidin-4-yl)-1H-indazol-5-amine

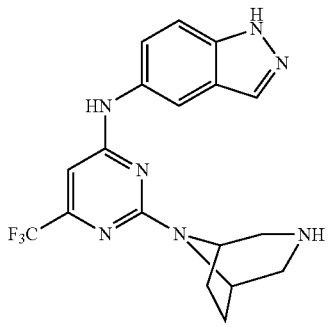 [SMILES: FC(F)(F)c1cc(Nc2ccc3[nH]ncc3c2)nc(N2C3CCC2CNC3)n1]

A solution of N-(2-(3,8-diazabicyclo[3.2.1]octan-8-yl)-5-chloro-6-(trifluoromethyl)pyrimidin-4-yl)-1H-indazol-5-amine (1 equiv) and 10% Pd on carbon in MeOH were stirred at 50 C for 39 h under $H_2$ (50 psi). The reaction mixture was filtered through celite pad and filtrate was concentrated under reduced. The residue was dissolved in MeOH and 10% Pd on carbon followed by HCl (36% purity) were added. The reaction mixture was filtered through celite pad and filtrate was concentrated under reduced. The final residue was purified by reverse phase preparative HPLC to afford N-(2-(3,8-diazabicyclo[3.2.1]octan-8-yl)-6-(trifluoromethyl)pyrimidin-4-yl)-1H-indazol-5-amine as a white solid (41%). $^1$H NMR (400 MHz, DMSO-$d_6$) δ 13.03 (s, 1H), 9.73 (s, 1H), 8.27 (s, 2H), 8.09 (s, 1H), 8.04 (s, 1H), 7.54-7.46 (m, 2H), 6.34 (s, 1H), 4.51 (m, 2H), 2.89-2.67 (m, 4H), 2.00-1.92 (m, 4H). MS (ES+) m/e 390.3 (M+H).

Example 342

Ethyl 2-(3,8-diazabicyclo[3.2.1]octan-8-yl)-5-fluoro-$N^4$-(1H-indazol-5-yl)-$N^6$,$N^6$-dimethylpyrimidine-4,6-diamine

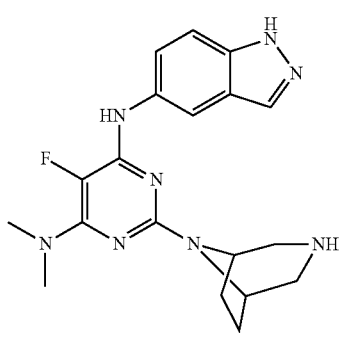 [SMILES: CN(C)c1nc(N2C3CCC2CNC3)nc(Nc2ccc3[nH]ncc3c2)c1F]

The reaction was conducted following general protocol A. The final residue was purified by reverse phase preparative HPLC to afford ethyl 2-(3,8-diazabicyclo[3.2.1]octan-8-yl)-5-fluoro-$N^4$-(1H-indazol-5-yl)-$N^6$,$N^6$-dimethylpyrimidine-4,6-diamine as a white solid (30%). $^1$H NMR (400 MHz, CD$_3$OD) δ 7.98 (d, J=1.6 Hz, 1H), 7.94 (s, 1H), 7.56 (dd, J=8.8, 1.6 Hz, 1H), 7.44 (d, J=8.8 Hz, 1H), 4.50 (s, 2H), 3.15-3.12 (m, 8H), 2.74 (d, J=6.4 Hz, 2H), 2.09-1.90 (m, 4H). MS (ES+) m/e 383.4 (M+H).

Example 343

4-((1H-indazol-5-yl)amino)-2-(3,8-diazabicyclo[3.2.1]octan-8-yl)-6-methylpyrimidine-5-carbonitrile

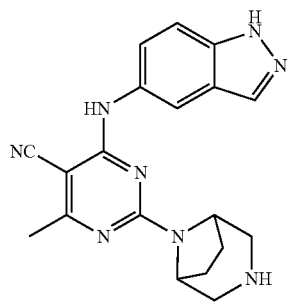 [SMILES: Cc1nc(N2C3CCC2CNC3)nc(Nc2ccc3[nH]ncc3c2)c1C#N]

The reaction was conducted following general protocol A. The final residue was purified by reverse phase preparative HPLC to afford 4-((1H-indazol-5-yl)amino)-2-(3,8-diazabicyclo[3.2.1]octan-8-yl)-6-methylpyrimidine-5-carbonitrile as a white solid (30%). $^1$H NMR (400 MHz, DMSO-$d_6$) δ 13.01 (s, 1H), 9.40 (s, 1H), 9.08 (s, 1H), 8.84 (s, 1H), 8.05 (s, 1H), 7.84 (s, 1H), 7.51-7.47 (m, 2H), 4.80 (m, 1H), 4.45 (m, 1H), 3.17 (m, 4H), 2.41 (s, 3H), 2.03-1.96 (m, 4H). MS (ES+) m/e 361.3 (M+H).

Example 344

2-(3,8-diazabicyclo[3.2.1]octan-8-yl)-5-chloro-$N^4$-(1H-indazol-5-yl)-$N^6$,$N^6$-dimethylpyrimidine-4,6-diamine

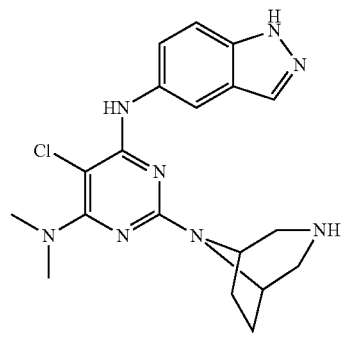 [SMILES: CN(C)c1nc(N2C3CCC2CNC3)nc(Nc2ccc3[nH]ncc3c2)c1Cl]

The reaction was conducted following general protocol A. The final residue was purified by reverse phase preparative HPLC to afford 2-(3,8-diazabicyclo[3.2.1]octan-8-yl)-5-chloro-$N^4$-(1H-indazol-5-yl)-$N^6$,$N^6$-dimethylpyrimidine-4,6-diamine as a brown solid (9%). $^1$H NMR (400 MHz, DMSO-$d_6$) δ 12.94 (brs, 1H), 8.34 (s, 1H), 8.26 (s, 1H), 7.97 (s, 1H), 7.87 (s, 1H), 7.54-7.40 (m, 2H), 4.34 (s, 2H), 2.99 (s, 6H), 2.94-2.87 (m, 2H), 2.66-2.64 (m, 2H), 1.92-1.78 (m, 4H). MS (ES+) m/e 399.1 (M+H).

Example 345

2-(piperazin-1-yl)-N-(3-(pyridin-4-yl)phenyl)pyrimidin-4-amine

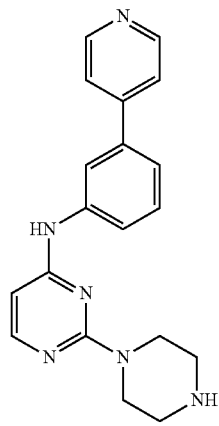 [SMILES: c1cc(Nc2ccnc(N3CCNCC3)n2)cc(-c2ccncc2)c1]

The reaction was conducted following general protocol G. The final residue was purified by reverse phase preparative HPLC to afford 2-(piperazin-1-yl)-N-(3-(pyridin-4-yl)phenyl)pyrimidin-4-amine as a white solid (33%). $^1$H NMR (400 MHz, DMSO-$d_6$) δ 11.17 (s, 1H), 9.49 (s, 2H), 8.94 (d, J=6.0 Hz, 2H), 8.29 (s, 1H), 8.20 (d, J=5.6 Hz, 2H), 8.01 (d, J=6.8 Hz, 1H), 7.86 (d, J=7.2 Hz, 1H), 7.77 (d, J=7.6 Hz, 1H), 7.69-7.62 (m, 1H), 6.55 (d, J=6.4 Hz, 1H), 4.02 (s, 4H), 3.25 (s, 4H). MS (ES+) m/e 333.0 (M+H).

Example 346

2-(piperazin-1-yl)-N-(3-(pyridin-3-yl)phenyl)pyrimidin-4-amine

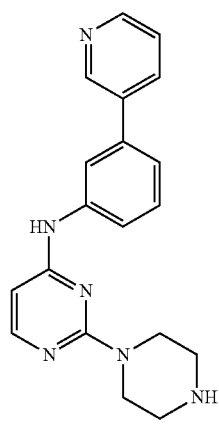 [SMILES: c1cncc(-c2cccc(Nc3ccnc(N4CCNCC4)n3)c2)c1]

The reaction was conducted following general protocol G. The final residue was purified by reverse phase preparative HPLC to afford 2-(piperazin-1-yl)-N-(3-(pyridin-3-yl)phenyl)pyrimidin-4-amine as a white solid (35%). $^1$H NMR (400 MHz, DMSO-$d_6$) δ 11.42 (s, 1H), 9.64 (s, 2H), 9.11 (s, 1H), 8.85 (s, 1H), 8.59 (d, J=8.2 Hz, 1H), 8.15 (s, 1H), 7.98 (d, J=7.2 Hz, 2H), 7.79 (s, 1H), 7.69-7.58 (m, 2H), 6.63 (d, J=6.0 Hz, 1H), 4.06 (s, 4H), 3.26 (s, 4H). MS (ES+) m/e 333.2 (M+H).

Example 347

N-(3-(1H-pyrazol-4-yl)phenyl)-2-(piperazin-1-yl)pyrimidin-4-amine

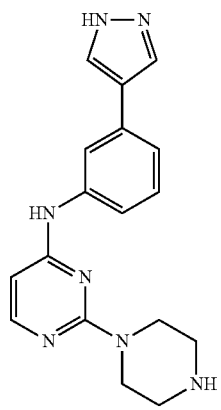 [SMILES: c1cc(Nc2ccnc(N3CCNCC3)n2)cc(-c2cn[nH]c2)c1]

The reaction was conducted following general protocol G. The final residue was purified by reverse phase preparative HPLC to afford N-(3-(1H-pyrazol-4-yl)phenyl)-2-(piperazin-1-yl)pyrimidin-4-amine as a white solid (18%). $^1$H NMR (400 MHz, DMSO-$d_6$) δ 9.26 (s, 1H), 8.04 (s, 1H), 7.98-7.88 (m, 3H), 7.37-7.18 (m, 3H), 6.04 (d, J=5.6 Hz, 1H), 3.66 (s, 4H), 2.73 (s, 4H). MS (ES+) m/e 322.2 (M+H).

Example 349

5-(4-((2-(piperazin-1-yl)pyrimidin-4-yl)amino)phenyl)pyridin-2(1H)-one

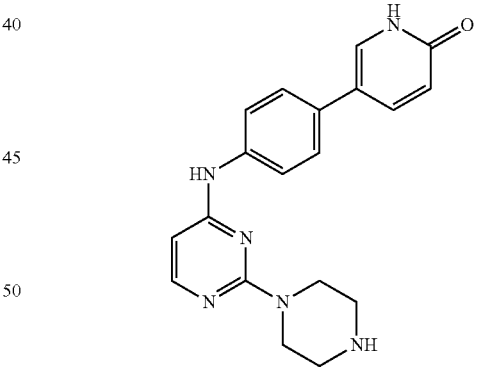

Step 1: To a solution of tert-butyl 4-(4-((4-bromophenyl)amino)pyrimidin-2-yl)piperazine-1-carboxylate (1 equiv) and compound (6-methoxypyridin-3-yl)boronic acid (1 equiv) in dioxane and H$_2$O was added Pd(dppf)Cl$_2$ (84.15 mg) and K$_3$PO$_4$ (732.33 mg) under N$_2$ at 23° C. The reaction mixture was heated to 100° C. and stirred for 16 hours. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl 4-(4-((4-(6-methoxypyridin-3-yl)phenyl)amino)pyrimidin-2-yl)piperazine-1-carboxylate.

Step 2: 4: A mixture of compound tert-butyl 4-(4-((4-(6-methoxypyridin-3-yl)phenyl)amino)pyrimidin-2-yl)piperazine-1-carboxylate (1 equiv) in HBr was stirred at 100° C. for 16 hours. The final residue was purified by reverse phase preparative HPLC to afford 5-(4-((2-(piperazin-1-yl)pyrimidin-4-yl)amino)phenyl)pyridin-2(1H)-one as a white solid (53%). $^1$H NMR (400 MHz, DMSO-d$_6$) δ 9.29 (s, 1H), 7.92 (d, J=5.6 Hz, 1H), 7.82 (dd, J=9.6, 2.4 Hz, 1H), 7.68 (s, 1H), 7.66 (s, 2H), 7.50 (d, J=8.4 Hz, 2H), 6.41 (d, J=9.2 Hz, 1H), 6.02 (d, J=5.6 Hz, 1H), 3.62 (brs, 4H), 2.72 (brs, 4H). MS (ES+) m/e 349.2 (M+H).

Example 350

N-(4-(6-aminopyridin-3-yl)phenyl)-2-(piperazin-1-yl)pyrimidin-4-amine

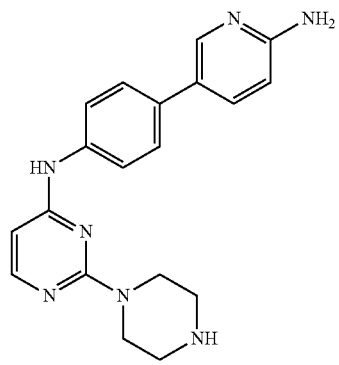 [SMILES: Nc1ccc(-c2ccc(Nc3ccnc(N4CCNCC4)n3)cc2)cn1]

Step 1: A mixture of compound tert-butyl 4-(4-((4-bromophenyl)amino)pyrimidin-2-yl)piperazine-1-carboxylate (1 equiv), KOAc (3 equiv), B(Pin)$_2$ (1.5 equiv) and Pd(dppf)Cl$_2$ (0.1 equiv) in dioxane was stirred at 100° C. under N$_2$ for 16 hrs. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl 4-(4-((4-(4,4,5,5-tetramethyl-1,3,2-dioxaborolan-2-yl)phenyl)amino)pyrimidin-2-yl)piperazine-1-carboxylate.

Step 2: To mixture of compound tert-butyl 4-(4-((4-(4,4,5,5-tetramethyl-1,3,2-dioxaborolan-2-yl)phenyl)amino)pyrimidin-2-yl)piperazine-1-carboxylate (1 equiv), 5-bromopyridin-2-amine (0.1 equiv), Pd(PPh$_3$)$_4$ (0.1 equiv), K$_3$PO$_4$ (3 equiv) in DCE and H$_2$O was stirred at 140° C. under microwave irradiation for 20 min. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl 4-(4-((4-(6-aminopyridin-3-yl)phenyl)amino)pyrimidin-2-yl)piperazine-1-carboxylate.

Step 3: A mixture of compound tert-butyl 4-(4-((4-(6-aminopyridin-3-yl)phenyl)amino)pyrimidin-2-yl)piperazine-1-carboxylate (1 equiv) in HCl methanol mixture was stirred at 20° C. for 2 hours. The final residue was purified by reverse phase preparative HPLC to afford N-(4-(6-aminopyridin-3-yl)phenyl)-2-(piperazin-1-yl)pyrimidin-4-amine as a white solid. $^1$H NMR (400 MHz, DMSO-d$_6$) δ 9.26 (s, 1H), 8.22 (s, 1H), 7.92 (d, J=5.6 Hz, 1H), 7.69 (d, J=6.0 Hz, 1H), 7.67 (d, J=8.8 Hz, 2H), 7.51 (d, J=8.8 Hz, 2H), 6.51 (d, J=5.6 Hz, 1H), 6.03 (d, J=6.0 Hz, 1H), 3.63 (t, J=4.4 Hz, 4H), 2.73 (t, J=4.4 Hz, 4H). MS (ES+) m/e 348.0 (M+H).

Example 351

N-(4-(1H-imidazol-5-yl)phenyl)-2-(piperazin-1-yl)pyrimidin-4-amine

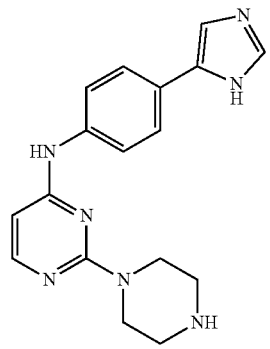 [SMILES: c1cc(Nc2ccc(-c3cnc[nH]3)cc2)nc(N2CCNCC2)n1]

Step 1: A mixture of compound tert-butyl 4-(4-((4-(4,4,5,5-tetramethyl-1,3,2-dioxaborolan-2-yl)phenyl)amino)pyrimidin-2-yl)piperazine-1-carboxylate (1 equiv), K$_3$PO$_4$ (2 equiv), 4-bromo-1-((2-(trimethylsilyl)ethoxy)methyl)-1H-imidazole (1 equiv) and Pd(dppf)Cl$_2$ (0.1 equiv) in dioxane was stirred at 100° C. under N$_2$ for 16 hrs. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl 4-(4-((4-(1-((2-(trimethylsilyl)ethoxy)methyl)-1H-imidazol-4-yl)phenyl)amino)pyrimidin-2-yl)piperazine-1-carboxylate.

Step 2: A mixture of compound tert-butyl 4-(4-((4-(1-((2-(trimethylsilyl)ethoxy)methyl)-1H-imidazol-4-yl)phenyl)amino)pyrimidin-2-yl)piperazine-1-carboxylate (1 equiv) in 6M HCl was stirred at 100° C. for 16 hours. The final residue was purified by reverse phase preparative HPLC to afford N-(4-(1H-imidazol-5-yl)phenyl)-2-(piperazin-1-yl)pyrimidin-4-amine as a white solid (57%). $^1$H NMR (400 MHz, DMSO-d$_6$) δ 12.07 (s, 1H), 9.22 (s, 1H), 7.92 (d, J=5.6 Hz, 1H), 7.67-7.61 (m, 5H), 7.51 (s, 1H), 6.03 (d, J=5.6 Hz, 1H), 3.64 (t, J=4.8 Hz, 4H), 2.75 (t, J=4.8 Hz, 4H). MS (ES+) m/e 322.2 (M+H).

Example 353

2-(piperazin-1-yl)-N-(4-(thiazol-5-yl)phenyl)pyrimidin-4-amine

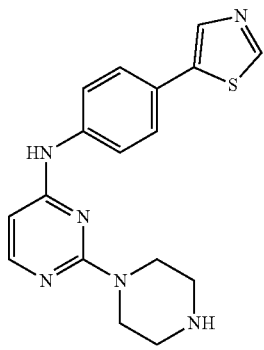 [SMILES: c1cc(Nc2ccc(-c3cncs3)cc2)nc(N2CCNCC2)n1]

Step 1: A mixture of compound tert-butyl 4-(4-((4-(4,4,5,5-tetramethyl-1,3,2-dioxaborolan-2-yl)phenyl)amino)pyrimidin-2-yl)piperazine-1-carboxylate (1 equiv), K₃PO₄ (2 equiv), 5-bromothiazole (1 equiv) and Pd(dppf)Cl₂ (0.1 equiv) in dioxane water was stirred at 100° C. under N₂ for 16 hrs. The reaction mixture was cooled down to room temperature and quenched by the addition of water, extracted with EtOAc. The combined organics were dried with Na₂SO₄, filtered and solvent removed under reduced pressure. The residue was purified by silica gel chromatography to afford tert-butyl 4-(4-((4-(thiazol-5-yl)phenyl)amino)pyrimidin-2-yl)piperazine-1-carboxylate.

Step 2: A mixture of compound tert-butyl 4-(4-((4-(thiazol-5-yl)phenyl)amino)pyrimidin-2-yl)piperazine-1-carboxylate (1 equiv) in TFA/DCM mixture was stirred at 20° C. for 2 hours. The final residue was purified by reverse phase preparative HPLC to afford 2-(piperazin-1-yl)-N-(4-(thiazol-5-yl)phenyl)pyrimidin-4-amine as a white solid (53%). ¹H NMR (400 MHz, DMSO-d₆) δ 9.42 (s, 1H), 9.02 (s, 1H), 8.23 (s, 1H), 7.96 (d, J=5.6 Hz, 1H), 7.74 (d, J=8.8 Hz, 2H), 7.64 (d, J=8.8 Hz, 2H), 6.05 (d, J=5.6 Hz, 1H), 3.64 (t, J=4.8 Hz, 4H), 2.74 (t, J=4.8 Hz, 4H). MS (ES+) m/e 339.0 (M+H).

Example 354

N-(4-(4H-1,2,4-triazol-3-yl)phenyl)-2-(piperazin-1-yl)pyrimidin-4-amine

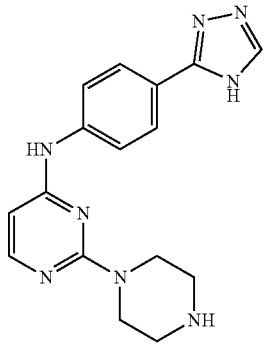 [SMILES: c1cc(Nc2ccc(-c3nnc[nH]3)cc2)nc(N2CCNCC2)n1]

The reaction was conducted following general protocol A. The final residue was purified by reverse phase preparative HPLC to afford N-(4-(4H-1,2,4-triazol-3-yl)phenyl)-2-(piperazin-1-yl)pyrimidin-4-amine as an white solid (50%). ¹H NMR (400 MHz, DMSO-d₆) δ 9.44 (s, 1H), 8.31 (s, 1H), 7.97-7.93 (m, 3H), 7.76 (d, J=8.8 Hz, 2H), 6.07 (d, J=5.6 Hz, 1H), 3.64 (brs, 4H), 2.74 (brs, 4H). MS (ES+) m/e 323.1 (M+H).

Example 355

4-(4-((2-(piperazin-1-yl)pyrimidin-4-yl)amino)phenyl)thiazol-2-amine

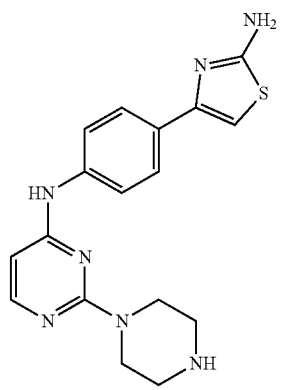 [SMILES: Nc1nc(-c2ccc(Nc3ccnc(N4CCNCC4)n3)cc2)cs1]

The reaction was conducted following general protocol A. The final residue was purified by reverse phase preparative HPLC to afford 4-(4-((2-(piperazin-1-yl)pyrimidin-4-yl)amino)phenyl)thiazol-2-amine as an white solid (51%). ¹H NMR (400 MHz, DMSO-d₆) δ 9.27 (s, 1H), 7.92 (d, J=5.6 Hz, 1H), 7.73 (d, J=8.8 Hz, 2H), 7.62 (d, J=8.8 Hz, 2H), 6.98 (s, 2H), 6.87 (s, 1H), 6.03 (d, J=5.6 Hz, 1H), 3.63 (t, J=4.8 Hz, 4H), 2.74 (t, J=4.8 Hz, 4H). MS (ES+) m/e 354.1 (M+H).

Example 356

5-(4-((2-(piperazin-1-yl)pyrimidin-4-yl)amino)phenyl)-1,3,4-thiadiazol-2-amine

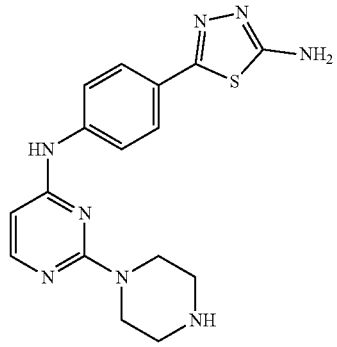 [SMILES: Nc1nnc(-c2ccc(Nc3ccnc(N4CCNCC4)n3)cc2)s1]

The reaction was conducted following general protocol A. The final residue was purified by reverse phase preparative HPLC to afford 5-(4-((2-(piperazin-1-yl)pyrimidin-4-yl)amino)phenyl)-1,3,4-thiadiazol-2-amine as an white solid (23%). $^1$H NMR (400 MHz, DMSO-d$_6$) δ 9.59 (s, 1H), 8.25 (s, 2H), 8.00 (d, J=5.6 Hz, 1H), 7.74 (d, J=8.8 Hz, 2H), 7.70 (d, J=8.8 Hz, 2H), 7.31 (s, 2H), 6.13 (d, J=5.6 Hz, 1H), 3.81 (t, J=4.8 Hz, 4H), 3.00 (t, J=4.8 Hz, 4H). MS (ES+) m/e 355.1 (M+H).

Example 357

6-(4-((2-(piperazin-1-yl)pyrimidin-4-yl)amino)phenyl)pyridazin-3 (2H)-one

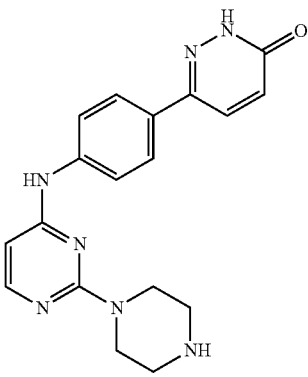 [SMILES: O=c1ccc(-c2ccc(Nc3ccnc(N4CCNCC4)n3)cc2)n[nH]1]

Step 1: To a solution of tert-butyl 4-(4-((4-(4,4,5,5-tetramethyl-1,3,2-dioxaborolan-2-yl)phenyl)amino)pyrimidin-2-yl)piperazine-1-carboxylate (1 equiv) and compound 3-chloro-6-methoxypyridazine (1 equiv) in DMF and H$_2$O was added Pd(dppf)Cl$_2$ (0.1 equiv) and K$_2$CO$_3$ (2 equiv) under N$_2$ at 23° C. The reaction mixture was heated to 100° C. and stirred for 16 hours. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl 4-(4-((4-(6-methoxypyridazin-3-yl)phenyl)amino)pyrimidin-2-yl)piperazine-1-carboxylate.

Step 2: 4: A mixture of compound tert-butyl 4-(4-((4-(6-methoxypyridazin-3-yl)phenyl)amino)pyrimidin-2-yl)piperazine-1-carboxylate (1 equiv) in hydrochloric acid was stirred at 100° C. for 16 hours. The final residue was purified by reverse phase preparative HPLC to afford 6-(4-((2-(piperazin-1-yl)pyrimidin-4-yl)amino)phenyl)pyridazin-3 (2H)-one as a yellow solid (8%). $^1$H NMR (400 MHz, DMSO-d$_6$) δ 9.44 (s, 1H), 8.02 (d, J=10.0 Hz, 1H), 7.96 (d, J=5.6 Hz, 1H), 7.82 (d, J=8.8 Hz 2H), 7.75 (d, J=8.8 Hz, 2H), 6.95 (d, J=10.0 Hz, 1H), 6.06 (d, J=5.6 Hz, 1H), 3.63 (brs, 4H), 2.74 (brs, 4H). MS (ES+) m/e 350.1 (M+H).

Example 358

N-(4-(oxazol-5-yl)phenyl)-2-(piperazin-1-yl)pyrimidin-4-amine

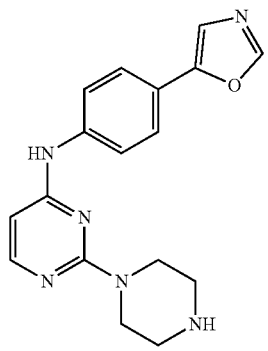 [SMILES: c1cc(Nc2ccc(-c3cnco3)cc2)nc(N2CCNCC2)n1]

The reaction was conducted following general protocol A. The final residue was purified by reverse phase preparative HPLC to afford N-(4-(oxazol-5-yl)phenyl)-2-(piperazin-1-yl)pyrimidin-4-amine as a yellow solid (18%). $^1$H NMR (400 MHz, DMSO-d$_6$) δ 9.45 (s, 1H), 8.36 (s, 1H), 7.94 (d, J=5.6 Hz, 1H), 7.78-7.72 (m, 2H), 7.69-7.63 (m, 2H), 7.55 (s, 1H), 6.05 (d, J=5.6 Hz, 1H), 3.62 (brs, 4H), 2.73 (brs, 4H). MS (ES+) m/e 323.1 (M+H).

Example 359

N-(4-(2-aminopyridin-4-yl)phenyl)-2-(piperazin-1-yl)pyrimidin-4-amine

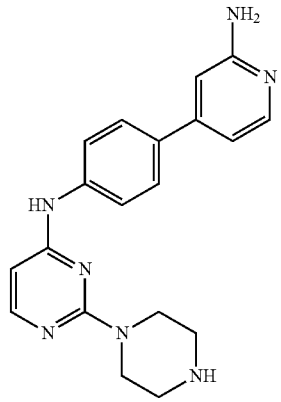 [SMILES: Nc1cc(-c2ccc(Nc3ccnc(N4CCNCC4)n3)cc2)ccn1]

Step 1: To a solution of tert-butyl 4-(4-((4-(4,4,5,5-tetramethyl-1,3,2-dioxaborolan-2-yl)phenyl)amino)pyrimidin-2-yl)piperazine-1-carboxylate (1 equiv) and 4-bromopyridin-2-amine (1 equiv) in dioxane and H$_2$O was added Pd(dppf)Cl$_2$ (0.1 equiv) and K$_2$CO$_3$ (2 equiv) under N$_2$ at 23° C. The reaction mixture was heated to 100° C. and stirred for 16 hours. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl 4-(4-((4-(2-aminopyridin-4-yl)phenyl)amino)pyrimidin-2-yl)piperazine-1-carboxylate.

259

Step 2: A mixture of compound tert-butyl 4-(4-((4-(2-aminopyridin-4-yl)phenyl)amino)pyrimidin-2-yl)piperazine-1-carboxylate (1 equiv) in hydrochloric acid and ethyl acetate was stirred at 25° C. for 2 hours. The final residue was purified by reverse phase preparative HPLC to afford N-(4-(2-aminopyridin-4-yl)phenyl)-2-(piperazin-1-yl)pyrimidin-4-amine a yellow solid (37%). $^1$H NMR (400 MHz, CD$_3$OD) 6.91 (t, J=5.6 Hz, 2H), 7.72 (d, J=8.8, 2H), 7.636 (d, J=8.8, 2H), 6.89 (dd, J=6.6, 1.6 Hz, 1H), 6.83 (s, 1H), 6.11 (d, J=5.6 Hz, 1H), 3.76-3.86 (m, 4H), 2.90-3.02 (m, 4H). MS (ES+) m/e 348.1 (M+H).

Example 360

4-(4-((2-(piperazin-1-yl)pyrimidin-4-yl)amino)phenyl)pyridin-2(1H)-one

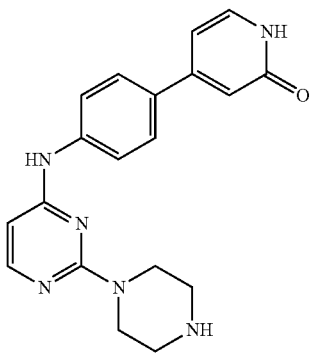 [SMILES: O=c1cc(-c2ccc(Nc3ccnc(N4CCNCC4)n3)cc2)cc[nH]1]

Step 1: To a solution of tert-butyl 4-(4-((4-bromophenyl)amino)pyrimidin-2-yl)piperazine-1-carboxylate (1 equiv) and (2-methoxypyridin-4-yl)boronic acid (1 equiv) in dioxane and H$_2$O was added Pd(dppf)Cl$_2$ (0.1 equiv) and K$_3$PO$_4$ (2 equiv) under N$_2$ at 23° C. The reaction mixture was heated to 90° C. and stirred for 16 hours. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl 4-(4-((4-(2-methoxypyridin-4-yl)phenyl)amino)pyrimidin-2-yl)piperazine-1-carboxylate.

Step 2: A mixture of compound tert-butyl 4-(4-((4-(2-methoxypyridin-4-yl)phenyl)amino)pyrimidin-2-yl)piperazine-1-carboxylate (1 equiv) in hydrochloric acid was stirred at 100° C. for 16 hours. The final residue was purified by reverse phase preparative HPLC to afford 4-(4-((2-(piperazin-1-yl)pyrimidin-4-yl)amino)phenyl)pyridin-2(1H)-one as a white solid (9%). $^1$H NMR (400 MHz, DMSO-d$_6$) δ 9.51 (brs, 1H), 7.96 (d, J=5.6 Hz, 1H), 7.76 (d, J=8.4 Hz, 2H), 7.67 (d, J=8.0 Hz, 2H), 7.41 (d, J=6.8 Hz, 1H), 6.57 (s, 1H), 6.54 (d, J=6.8 Hz, 1H), 6.08 (d, J=5.6 Hz, 1H), 3.64 (brs, 4H), 2.74 (brs, 4H). MS (ES+) m/e 349.1 (M+H).

260

Example 361

5-(4-((2-(piperazin-1-yl)pyrimidin-4-yl)amino)phenyl)thiazol-2-amine

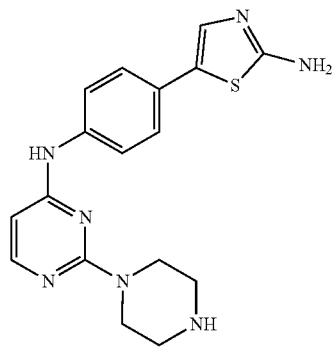 [SMILES: Nc1ncc(-c2ccc(Nc3ccnc(N4CCNCC4)n3)cc2)s1]

The reaction was conducted following general protocol A. The final residue was purified by reverse phase preparative HPLC to afford 5-(4-((2-(piperazin-1-yl)pyrimidin-4-yl)amino)phenyl)thiazol-2-amine as a yellow solid (18%). $^1$H NMR (400 MHz, DMSO-d$_6$) δ 9.41 (s, 1H), 8.27 (s, 2H), 7.97 (d, J=5.6 Hz, 1H), 7.96 (d, J=8.4 Hz, 2H), 7.38 (d, J=8.4 Hz, 2H), 7.29 (s, 1H), 7.05 (s, 2H), 6.09 (d, J=5.6 Hz, 1H), 3.83 (br.s, 4H), 3.04 (br.s, 4H). MS (ES+) m/e 354.1 (M+H).

Example 362

5-(4-((2-(piperazin-1-yl)pyrimidin-4-yl)amino)phenyl)-1,3,4-oxadiazol-2-amine

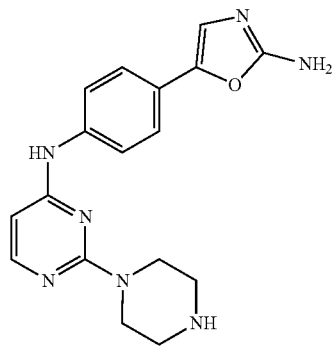 [SMILES: Nc1ncc(-c2ccc(Nc3ccnc(N4CCNCC4)n3)cc2)o1]

The reaction was conducted following general protocol A. The final residue was purified by reverse phase preparative HPLC to afford 5-(4-((2-(piperazin-1-yl)pyrimidin-4-yl)amino)phenyl)-1,3,4-oxadiazol-2-amine as a yellow solid (6%). $^1$H NMR (400 MHz, DMSO-d$_6$) δ 9.54 (s, 1H), 7.98 (d, J=5.6 Hz, 1H), 7.79 (d, J=8.8 Hz, 2H), 7.727 (d, J=8.8, 2H), 7.13 (s, 2H), 6.08 (d, J=5.6 Hz, 1H), 3.68-3.60 (m, 4H), 2.79-2.70 (m, 4H). MS (ES+) m/e 339.2 (M+H).

Example 363

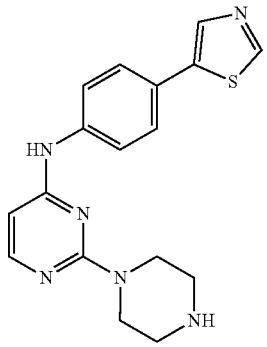

The reaction was conducted following general protocol A. The final residue was purified by reverse phase preparative HPLC to afford 5-(4-((2-(piperazin-1-yl)pyrimidin-4-yl)amino)phenyl)-1,3,4-oxadiazol-2-amine as a yellow solid (6%). $^1$H NMR (400 MHz, DMSO-$d_6$) δ 9.54 (s, 1H), 7.98 (d, J=5.6 Hz, 1H), 7.79 (d, J=8.8 Hz, 2H), 7.727 (d, J=8.8, 2H), 7.13 (s, 2H), 6.08 (d, J=5.6 Hz, 1H), 3.68-3.60 (m, 4H), 2.79-2.70 (m, 4H). MS (ES+) m/e 339.2 (M+H).

Example 364

5-((2-(piperazin-1-yl)pyrimidin-4-yl)amino)-1,3-dihydro-2H-benzo[d]imidazol-2-one

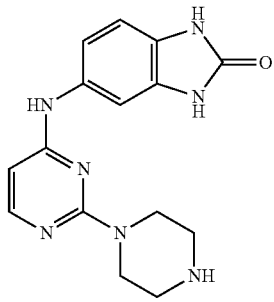 [SMILES: O=c1[nH]c2ccc(Nc3ccnc(N4CCNCC4)n3)cc2[nH]1]

The reaction was conducted following general protocol A. The final residue was purified by reverse phase preparative HPLC to afford 5-((2-(piperazin-1-yl)pyrimidin-4-yl)amino)-1,3-dihydro-2H-benzo[d]imidazol-2-one as a yellow solid (11%). $^1$H NMR (400 MHz, DMSO-$d_6$) δ 10.64 (s, 1H), 10.45 (s, 1H), 9.03 (s, 1H), 7.86 (d, J=5.2 Hz, 1H), 7.50 (s, 1H), 6.97 (d, J=8.0 Hz, 1H), 6.84 (d, J=8.4 Hz, 1H), 5.95 (d, J=5.6 Hz, 1H), 3.60 (t, J=4.4 Hz, 4H), 2.68 (t, J=4.4 Hz, 4H). MS (ES+) m/e 312.1 (M+H).

Example 365

5-((2-(piperazin-1-yl)pyrimidin-4-yl)amino)indolin-2-one

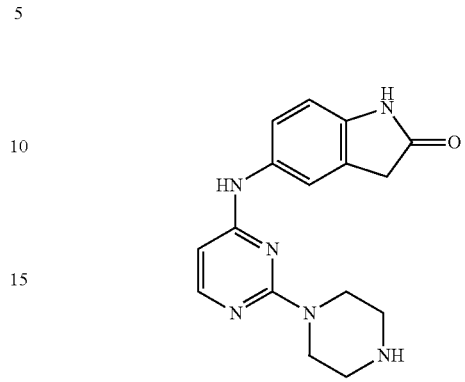

The reaction was conducted following general protocol A. The final residue was purified by reverse phase preparative HPLC to afford 5-((2-(piperazin-1-yl)pyrimidin-4-yl)amino)indolin-2-one as a white solid (24%). $^1$H NMR (400 MHz, DMSO-$d_6$) δ 10.28 (s, 1H), 9.00 (s, 1H), 7.86 (d, J=5.6 Hz, 1H), 7.43 (s, 1H), 7.35 (d, J=8.0 Hz, 1H), 6.75 (d, J=8.4 Hz, 1H), 5.93 (d, J=6.0 Hz, 1H), 3.59 (t, J=4.4 Hz, 4H), 3.47 (s, 1H), 2.71 (t, J=4.4 Hz, 4H). MS (ES+) m/e 311.1 (M+H).

Example 366

N-(4-(3H-imidazo[4,5-b]pyridin-7-yl)phenyl)-2-(piperazin-1-yl)pyrimidin-4-amine

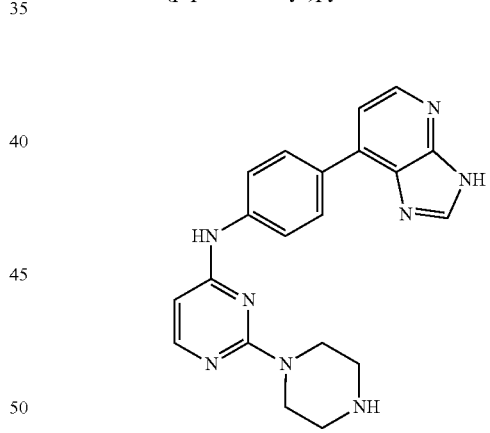

Step 1: To a solution of tert-butyl 4-(4-((4-(4,4,5,5-tetramethyl-1,3,2-dioxaborolan-2-yl)phenyl)amino)pyrimidin-2-yl)piperazine-1-carboxylate (1 equiv) and 7-chloro-3-(4-methoxybenzyl)-3H-imidazo[4,5-b]pyridine (1 equiv) in dioxane and H$_2$O was added Pd(dppf)Cl$_2$ (0.1 equiv) and K$_2$CO$_3$ (2 equiv) under N$_2$ at 23° C. The reaction mixture was heated to 100° C. and stirred for 16 hours. The reaction mixture was cooled down to room temperature and quenched by the addition of water, extracted with EtOAc. The combined organics were dried with Na$_2$SO$_4$, filtered and solvent removed under reduced pressure. The residue was purified by silica gel chromatography to afford tert-butyl 4-(4-((4-(3-(4-methoxybenzyl)-3H-imidazo[4,5-b]pyridin-7-yl)phenyl)amino)pyrimidin-2-yl)piperazine-1-carboxylate.

Step 2: A mixture of compound tert-butyl 4-(4-((4-(3-(4-methoxybenzyl)-3H-imidazo[4,5-b]pyridin-7-yl)phenyl)amino)pyrimidin-2-yl)piperazine-1-carboxylate (1 equiv) in trifluoroacetic acid and DCM was stirred at 25° C. for 2 hours. The final residue was purified by reverse phase preparative HPLC to afford N-(4-(3H-imidazo[4,5-b]pyridin-7-yl)phenyl)-2-(piperazin-1-yl)pyrimidin-4-amine a white solid (20%). $^1$H NMR (400 MHz, DMSO-d$_6$) δ 9.48 (s, 1H), 8.45 (s, 1H), 8.34 (d, J=5.2 Hz, 2H), 7.97 (d, J=5.6 Hz, 1H), 7.83 (d, J=8.4 Hz, 2H), 7.52 (brs, 1H), 6.09 (d, J=5.6 Hz, 1H), 3.66 (brs, 4H), 2.75 (brs, 4H) MS (ES+) m/e 373.1 (M+H).

Example 367

N-(4-(1,3,4-oxadiazol-2-yl)phenyl)-2-(piperazin-1-yl)pyrimidin-4-amine

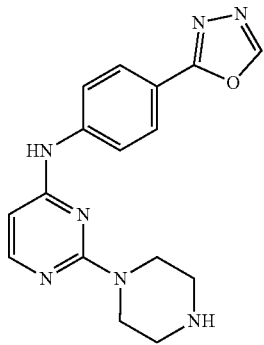

The reaction was conducted following general protocol A. The final residue was purified by reverse phase preparative HPLC to afford N-(4-(1,3,4-oxadiazol-2-yl)phenyl)-2-(piperazin-1-yl)pyrimidin-4-amine as a white solid (21%). $^1$H NMR (400 MHz, DMSO-d$_6$) δ 9.72 (s, 1H), 9.27 (s, 1H), 8.27 (brs, 1H), 8.02 (d, J=5.6 Hz, 1H), 7.97 (d, J=8.4 Hz, 2H), 7.87 (d, J=8.4 Hz, 2H), 6.14 (d, J=5.6 Hz, 1H), 3.73 (brs, 4H), 2.88 (brs, 4H). MS (ES+) m/z 324.1 (M+H).

Example 368

N-(4-(1H-pyrrolo[2,3-b]pyridin-4-yl)phenyl)-2-(piperazin-1-yl)pyrimidin-4-amine

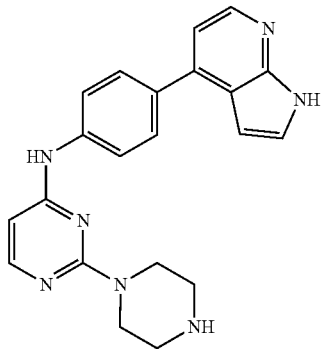 [SMILES: c1cc(Nc2ccc(-c3ccnc4[nH]ccc34)cc2)nc(N2CCNCC2)n1]

Step 1: Compound 4-(4-nitrophenyl)-1H-pyrrolo[2,3-b]pyridine (1 equiv), Fe powder (5 equiv) and NH$_4$Cl (1.2 equiv) in ethanol:water (5/1) was stirred at 90° C. for 2 hrs. The mixture was diluted with MeOH, filtered, and solids were washed with MeOH. The filtrate was concentrated. The residue was dissolved in EtOAc and washed with water. The aqueous layer was extracted with EtOAc. The combined organic layer was dried over Na$_2$SO$_4$ and concentrated to afford 4-(1H-pyrrolo[2,3-b]pyridin-4-yl)aniline Step 2: A mixture of compound 4-(1H-pyrrolo[2,3-b]pyridin-4-yl)aniline (1 equiv), compound 2,4-dichloropyrimidine (1.3 equiv) and DIPEA (2 equiv) in n-BuOH was stirred at 100° C. for 16 hrs. The mixture was concentrated to give compound N-(4-(1H-pyrrolo[2,3-b]pyridin-4-yl)phenyl)-2-chloropyrimidin-4-amine which was used in the next step directly.

Step 3: The mixture of compound N-(4-(1H-pyrrolo[2,3-b]pyridin-4-yl)phenyl)-2-chloropyrimidin-4-amine (1 equiv), tert-butyl piperazine-1-carboxylate (1.2 equiv) and DIPEA (2 equiv) in DMF (10.00 mL) was stirred at 110° C. for 16 hrs. The mixture was purified via pre-HPLC to give compound tert-butyl 4-(4-((4-(1H-pyrrolo[2,3-b]pyridin-4-yl)phenyl)amino)pyrimidin-2-yl)piperazine-1-carboxylate as a yellow solid Step 4: A mixture of compound tert-butyl 4-(4-((4-(1H-pyrrolo[2,3-b]pyridin-4-yl)phenyl)amino)pyrimidin-2-yl)piperazine-1-carboxylate (1 equiv) in trifluoroacetic acid and DCM was stirred at 25° C. for 2 hours. The final residue was purified by reverse phase preparative HPLC to afford N-(4-(1H-pyrrolo[2,3-b]pyridin-4-yl)phenyl)-2-(piperazin-1-yl)pyrimidin-4-amine a white solid (14%). $^1$H NMR (400 MHz, CD$_3$OD) δ 8.23 (d, J=4.8 Hz, 1H), 7.93 (d, J=6.0 Hz, 1H), 7.81-7.76 (m, 4H), 7.45 (d, J=3.6 Hz, 1H), 7.22 (d, J=5.2 Hz, 1H), 6.73 (d, J=3.6 Hz, 1H), 6.13 (d, J=5.6 Hz, 1H), 3.80 (t, J=5.2 Hz, 4H), 2.92 (t, J=5.2 Hz, 4H). MS (ES+) m/e 372.1 (M+H).

Example 369

N-(2-(piperazin-1-yl)pyrimidin-4-yl)-1H-pyrrolo[2,3-b]pyridin-5-amine

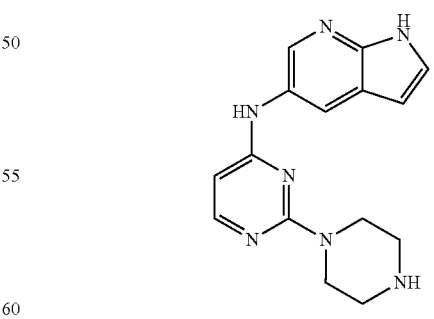

The reaction was conducted following general protocol C. The final residue was purified by reverse phase preparative HPLC to afford N-(2-(piperazin-1-yl)pyrimidin-4-yl)-1H-pyrrolo[2,3-b]pyridin-5-amine as a white solid (7%). MS (ES+) m/z 296.1 (M+H).

Example 370

N-(2-(1,4-diazepan-1-yl)pyrimidin-4-yl)-1H-pyrrolo[2,3-b]pyridin-5-amine

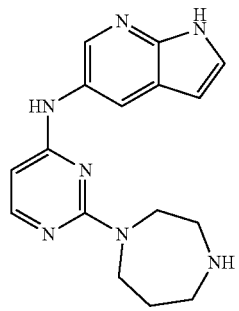 [SMILES: c1cc(Nc2cnc3[nH]ccc3c2)nc(N2CCCNCC2)n1]

The reaction was conducted following general protocol C. The final residue was purified by reverse phase preparative HPLC to afford N-(2-(1,4-diazepan-1-yl)pyrimidin-4-yl)-1H-pyrrolo[2,3-b]pyridin-5-amine as a white solid (9%). MS (ES+) m/z 310.1 (M+H).

Example 371

Methods
Determination of Compound's ROCK Inhibitory Activity In Vitro (Z'Lyte Assay).

Recombinant ROCK1 (amino acids 1-535) and ROCK2 (amino acids 1-552) proteins were purchased from ThermoFisher Scientific. Compound's activities were measured by Z'-lyte kinase kit (ThermoFisher Scientific) and $IC_{50}$ was calculated Determination of Compounds ROCK Inhibitory Activity in A7R5Cells.

Rat aortic smooth muscle cell line, A7R5, cells were seeded with density of 5,000 cells/well in a 96-well plates for 24 hours and subsequently treated for 90 min with testing compounds. Cells were then fixed and processed according to the In-Cell ELISA Colorimetric Detection Kit manual (Thermo Scientific).

NIH3T3 Cells Acta2-Promoter Driven-Luciferase Assay.
A NIH3T3 cell line stably expressing a luciferase reporter driven by the human ACTA2 gene promoter (−1000-1 bp) was established (NIH3T3-Acta2-luciferase). The cells were plated to confluence and treated with the test compounds plus TGFβ1 for 24 hr. Cells were then lysed and luciferase activity was measured using the LightSwitch luciferase kit from Active Motif.

Results
ROCK Inhibitors of the Invention Potently Inhibited ROCK Kinase Activity In Vitro and in Cells.

As shown in FIG. 1a, Kadmon ROCKi at lower than 10 nanomolar concentrations potently inhibited the activity of both isoforms of ROCK in vitro as measured by the Z'-Lyte kit.

An A7R5 in-cell Elisa assay was performed. A7R5 cells were treated with 9 points 2 fold serial dilution of compounds and ppMlc (T18/S19) levels were determined to calculate cellular IC50 values of the compounds. Compounds of the invention gave in cell IC50s under 100 nM. See FIG. 1b.

A7R5 cells were treated with the compound of Example 192 for 90 min and ppMlc (T18/S19) levels were visualized by western blotting. Example 192 at 110 nM efficiently blocked phosphorylation of ROCK targets MLC and MYPT1.

In vitro activities for the compounds were measured with Z'-lyte kinase kit (ThermoFisher Scientific). The percent inhibition rate was calculated by normalizing the kinase activity value obtained with 1 μM compound treatment against DMSO control value and then applied to the formula, [1-(compound/DMSO)]×100%. IC50s were calculated using the nonlinear regression curve fit function of the GraphPad Prism software with kinase activities data measured with 9 points 2-fold serial dilution of compounds treatment. In cell pMLC IC50s were calculated with data obtained from A7R5 cell experiments. A7R5 cells were treated with 9 points 2-fold serial dilution of compounds and ppMlc (T18/S19) levels were determined to calculate cellular IC50 values of the compounds using the nonlinear regression curve fit function of the GraphPad Prism software. NIH3T3 cells stably expressing ACTA2-promoter-driven-luciferase were applied to measure ROCK compounds functional IC50s in cells. Cells were plated in 96 well plates to confluence and treated with 9 points serial dilution of compounds in combination with TGFβ1 for 24 hr. Luciferase activities were measured and compound's IC50s were calculated using the nonlinear regression curve fit function of the GraphPad Prism software.

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 210 | 0 [3 μM] | | 41.9 [3 μM] | | 73.4 [10 μM] | 589.0 | |
| 202 | 88.3 [3 μM] | | 88.4 [3 μM] | | 13.8 [10 μM] | | |
| 40 | | | | | 13.4 [10 μM] | | |
| 41 | | >10000 | | | 9.96 [10 μM] | | |
| 42 | | | | | 9.1 [10 μM] | | |
| 225 | 98.3 [3 μM] | 98 | 80.9 [3 μM] | | 78.0 [10 μM] | 532.0 | |
| 226 | | | | | 67.7 [10 μM] | | |
| 227 | | | | | 83.4 [10 μM] | | |

-continued

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 228 | 100.7 [3 μM] | 3 | 98.5 [3 μM] | 4 | 83.0 [10 μM] | 69.0 | 151 |
| 229 | | 77 | | | 81.0 [10 μM] | | |
| 230 | | | | | 16.1 [10 μM] | | |
| 232 | 103.7 [3 μM] | 22 | 100.1 [3 μM] | 75 | 93.0 [10 μM] | 129.0 | |
| 252 | | | | | 65.0 [10 μM] | 1173.0 | |
| 253 | | | | | 41.5 [10 μM] | | |
| 255 | | | | | 72.0 [10 μM] | 1355.0 | |
| 256 | | | | | 84.5 [10 μM] | 1557.0 | |
| 257 | | | | | 85.6 [10 μM] | 2072.0 | |
| 258 | | | | | 26.0 [10 μM] | | |
| 224 | | | | | 48.0 [10 μM] | 3348.0 | |
| 3 | | | | | 54.4 [10 μM] | | |
| 4 | | 139 | | | 95.3 [10 μM] | 312.0 | |
| 5 | 102.3 [3 μM] | 54 | 98.3 [3 μM] | | 86.0 [10 μM] | 63.0 | |
| 6 | 85.7 [1 μM] | | | | 94.6 [10 μM] | 1800.0 | |
| 7 | 96 [1 μM] | 107 | | 65 | 98.3 [10 μM] | 460.0 | |
| 8 | 83.3 [1 μM] | | | | 89.0 [10 μM] | 1596.0 | |
| 9 | 98.7 [1 μM] | | | | 93.5 [10 μM] | 1200.0 | |
| 10 | 98 [0.5 μM] | 20 | 94 [0.5 μM] | | 90.0 [10 μM] | 565.0 | |
| 11 | 93 [0.5 μM] | 31 | 76 [0.5 μM] | | 89.0 [10 μM] | 1123.0 | |
| 12 | 97.3 [1 μM] | | | | 95.0 [10 μM] | 839.0 | |
| 260 | | | | | 18.0 [10 μM] | | |
| 261 | 74 [1 μM] | | | | 86.0 [10 μM] | 1878.0 | |
| 262 | | | | | 87.0 [10 μM] | 3650.0 | |
| 263 | 101 [1 μM] | | | | 82.0 [10 μM] | 1392.0 | |
| 264 | 92.8 [1 μM] | 30 | | | 60.2 [10 μM] | 514.0 | |
| 265 | 71.2 [1 μM] | | | | 80.0 [10 μM] | 1367.0 | |
| 266 | | | | | 74.0 [10 μM] | 3147.0 | |
| 267 | 52.3 [1 μM] | | | | 70.0 [10 μM] | | |
| 268 | | | | | 63.7 [10 μM] | 3721.0 | |
| 2 | | | | | 72.4 [10 μM] | 2501.0 | |
| 235 | 94.4 [1 μM] | 54 | | | | 510.0 | |
| 236 | | | | | 80.8 [10 μM] | 4688.0 | |
| 237 | | 104 | | 63 | 68.2 [10 μM] | 423.0 | 2348 |
| 238 | | 17 | | 55 | 70.0 [10 μM] | 215.0 | |
| 240 | 84.5 [1 μM] | | | | 78.1 [10 μM] | 1108.0 | |
| 241 | 85.2 [1 μM] | | | | 81.0 [10 μM] | 954.0 | |

-continued

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 203 | 98 [3 μM] | 57 | 89.1 [3 μM] | 46 | 63.5 [10 μM] | 561 | |
| 57 | 93.4 [3 μM] | | 17.4 [3 μM] | | 60.6 [10 μM] | 1218 | |
| 45 | 98.8 [3 μM] | 649 | 99 [3 μM] | 307 | | 2121 | |
| 43 | 98.8 [3 μM] | 120 | 99 [3 μM] | 135 | | 730 | |
| 58 | 98.8 [3 μM] | 144 | 99 [3 μM] | 192 | | 1079 | |
| 239 | 100 [3 μM] | >1000 | 100 [3 μM] | >1000 | | 6351 | |
| 245 | 100 [3 μM] | >1000 | 100 [3 μM] | >1000 | | 8222 | |
| 247 | 100 [3 μM] | 407 | 100 [3 μM] | 132 | | 1960 | |
| 59 | 100 [3 μM] | 902 | 100 [3 μM] | 671 | | 4778 | |
| 60 | 100 [3 μM] | 450 | 100 [3 μM] | 660 | | 3439 | |
| 61 | 100 [3 μM] | >1000 | 100 [3 μM] | >1000 | | 8166 | |
| 62 | 100 [3 μM] | 177.2 | 100 [3 μM] | 179.3 | | 1299 | |
| 248 | 100 [3 μM] | 43.92 | 100 [3 μM] | 36.02 | | 968 | |
| 63 | 100 [3 μM] | >1000 | 100 [3 μM] | >1000 | | 25130 | |
| 249 | | >1000 | | >1000 | 33.6 [10 μM] | | |
| 250 | | >1000 | | >1000 | 50.4 [10 μM] | 5438 | |
| 251 | | 160 | | 57 | 66.9 [10 μM] | 614 | |
| 271 | | >1000 | | >1000 | 28.3 [10 μM] | | |
| 214 | | 26 | | 38 | 63 [10 μM] | 323 | 1253 |
| 215 | | 37 | | 40 | 68.5 [10 μM] | 201 | 1221; 1780 |
| 64 | | 240 | | 325 | 63.9 [10 μM] | 1037 | |
| 65 | | 353 | | 98 | 47.8 [10 μM] | 1985 | |
| 178 | | 159 | | 388 | 47.5 [10 μM] | 706 | |
| 18 | | 206 | | 332 | 11 [10 μM] | | |
| 179 | 77.6 [1 μM] | | | | 67.4 [10 μM] | 1543 | |
| 140 | 88 [1 μM] | | | | 63.5 [10 μM] | 734 | |
| 180 | 73.8 [1 μM] | | | | 62.6 [10 μM] | 1455 | |
| 204 | | 85 | | 20 | 70 [10 μM] | 231 | 1780 |
| 205 | | 61 | | | 55.05 [10 μM] | 415 | 1275 |
| 91 | 47.9 [1 μM] | | | | 46.72 [10 μM] | | |
| 141 | | | | | 54.87 [10 μM] | 2892 | |
| 142 | | | | | 37.45 [10 μM] | | |
| 30 | 90.6 [1 μM] | | | | 56.41 [10 μM] | 1122 | |
| 31 | 78.1 [1 μM] | | | | 57.97 [10 μM] | 1854 | |
| 181 | | | | | 36.50 [10 μM] | | |
| 182 | | | | | 30.22 [10 μM] | | |
| 183 | | | | | 43.09 [10 μM] | | |

-continued

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 184 | | | | | 34.13 [10 µM] | | |
| 185 | 19.7 [1 µM] | | | | 41.60 [10 µM] | | |
| 186 | 47.8 [1 µM] | | | | 47.72 [10 µM] | | |
| 187 | | 111 | | 58 | 59.83 [10 µM] | 665 | |
| 108 | | | | | 47.29 [10 µM] | | |
| 32 | 44.6 [1 µM] | | | | 53.71 [10 µM] | 3949 | |
| 47 | 33.1 [1 µM] | | | | 45.56 [10 µM] | | |
| 48 | | | | | 51.08 [10 µM] | 2579 | |
| 49 | 50.6 [1 µM] | | | | 46.34 [10 µM] | | |
| 92 | | | | | 19.64 [10 µM] | | |
| 93 | | | | | 21.06 [10 µM] | | |
| 94 | | | | | 19.25 [10 µM] | | |
| 95 | 61 [1 µM] | | | | 46.73 [10 µM] | | |
| 143 | 59.3 [1 µM] | | | | 49.78 [10 µM] | 2151 | |
| 144 | | | | | 45.57 [10 µM] | | |
| 145 | | | | | 42.36 [10 µM] | | |
| 146 | 71.8 [1 µM] | | | | 50.24 [10 µM] | 2063 | |
| 188 | 44.9 [1 µM] | | | | 47.92 [10 µM] | | |
| 96 | 27.2 [1 µM] | | | | 14.35 [10 µM] | | |
| 109 | 68.4 [1 µM] | | | | 52.27 [10 µM] | 1883 | |
| 110 | 67.5 [1 µM] | | | | 50.86 [10 µM] | 1392 | |
| 111 | 31.8 [1 µM] | | | | 43.98 [10 µM] | | |
| 112 | | | | | 56.91 [10 µM] | 1288 | |
| 147 | 37.6 [1 µM] | | | | 47.8 [10 µM] | | |
| 148 | 55.1 [1 µM] | | | | 46 [10 µM] | | |
| 149 | 71.4 [1 µM] | | | | 49.4 [10 µM] | | |
| 197 | | 437 | | | 53.8 [10 µM] | 581 | |
| 13 | 58.1 [1 µM] | | | | 51.1 [10 µM] | 1488 | |
| 14 | 33.3 [1 µM] | | | | 48.9 [10 µM] | | |
| 97 | 54 [1 µM] | | | | 52.5 [10 µM] | 2337 | |
| 15 | 8 [1 µM] | | | | 26.4 [10 µM] | | |
| 206 | | 198 | | | 52.9 [10 µM] | 519 | |
| 16 | | | | | 32.1 [10 µM] | | |
| 50 | | | | | 35.5 [10 µM] | | |
| 51 | 29.3 [1 µM] | | | | 39.4 [10 µM] | | |
| 98 | 0 [1 µM] | | | | 17.4 [10 µM] | | |
| 19 | 4.6 [1 µM] | | | | 31.8 [10 µM] | | |

-continued

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 20 | | | | | 37.6 [10 μM] | | |
| 189 | 14 [0.5 μM] | | 18 [0.5 μM] | | 33.4 [10 μM] | 637 | |
| 52 | | | | | 29.5 [10 μM] | | |
| 99 | | | | | 29.6 [10 μM] | | |
| 113 | 58.1 [1 μM] | | | | 47.5 [10 μM] | 2880 | |
| 150 | 43.2 [1 μM] | | | | 44.4 [10 μM] | 4971 | |
| 207 | 91 [1 μM] | 104 | | 41 | 52.3 [10 μM] | 351 | 1262 |
| 21 | | | | | 21.1 [10 μM] | | |
| 151 | 87.4 [1 μM] | 80 | | | 55.1 [10 μM] | | |
| 22 | 76.5 [1 μM] | | | | 54.2 [10 μM] | 1390 | |
| 190 | 41 [1 μM] | | | | 45.9 [10 μM] | | |
| 114 | 82 [1 μM] | | | | 48.7 [10 μM] | | |
| 115 | 64.2 [1 μM] | | | | 48.2 [10 μM] | | |
| 152 | 77 [1 μM] | | | | 50.7 [10 μM] | 1033 | |
| 191 | 67 [1 μM] | | | | 50.6 [10 μM] | 1852 | |
| 100 | 47.5 [1 μM] | | | | 46.4 [10 μM] | | |
| 116 | 81.9 [1 μM] | | | | 51.6 [10 μM] | 1018 | |
| 53 | 74.5 [1 μM] | | | | 51.3 [10 μM] | 1718 | |
| 23 | 29.5 [1 μM] | | | | 46.4 [10 μM] | | |
| 208 | | 135 | | 49 | 58.3 [10 μM] | 313 | 1512 |
| 90 | 73.8 [1 μM] | | | | 54.2 [10 μM] | 2203 | |
| 24 | | | | | 22.6 [10 μM] | | |
| 25 | 52.9 [1 μM] | | | | 48.3 [10 μM] | | |
| 101 | | | | | 19.2 [10 μM] | | 7527 |
| 102 | 48.5 [1 μM] | 1095 | | | 43.5 [10 μM] | | |
| 54 | 58.5 [1 μM] | | | | 50.1 [10 μM] | 1701 | |
| 103 | | | | | 38.3 [10 μM] | | |
| 55 | 83.3 [1 μM] | | | | 52.2 [10 μM] | 998 | |
| 199 | | 151 | | | 49.6 [10 μM] | 525 | |
| 200 | | 1.6 | | 28 | 49.8 [10 μM] | 275 | 1601 |
| 26 | 33.5 [1 μM] | | | | 39.9 [10 μM] | | |
| 216 | | 70 | | | 42.6 [1 μM] | 517 | 1380 |
| 66 | 86.3 [1 μM] | 380 | | | 17.5 [1 μM] | | |
| 201 | | 27 | | 37 | 50.1 [1 μM] | 168 | 1635 |
| 67 | 99.2 [1 μM] | 45 | | | 31.4 [1 μM] | 1363 | |
| 27 | 71.3 [1 μM] | | | | 16.8 [1 μM] | | |
| 117 | | 45 | | 15 | 50.6 [1 μM] | 168 | 1274 |

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 68 | | 294 | | 35.4 | 1009 [1 μM] | | |
| 69 | 52 [0.5 μM] | | 67 [0.5 μM] | | 19.3 [1 μM] | | |
| 209 | | 34 | | 5 | 53.2 [1 μM] | 47 | 332 |
| 192 | | 12 | | 5 | 53.5 [1 μM] | 98 | 189 |
| 104 | 82.9 [1 μM] | | | | 31.6 [1 μM] | 997 | |
| 105 | 53.9 [1 μM] | | | | 15.1 [1 μM] | | |
| 217 | | 28 | | 6 | 51.2 [1 μM] | 127 | 963 |
| 218 | 99.5 [1 μM] | | | 65 | 53 [1 μM] | 430 | 6113 |
| 193 | 84.4 [1 μM] | 282 | | | 32.5 [1 μM] | 788 | |
| 106 | 34.1 [1 μM] | | | | 12.8 [1 μM] | | |
| 153 | | 556 | | | 23.8 [1 μM] | | |
| 219 | | 41 | | 18 | 46.6 [1 μM] | 77 | 613 |
| 154 | 98.5 [1 μM] | 245 | | | 36.2 [1 μM] | 433 | 2912 |
| 196 | 39 [0.5 μM] | | 37 [0.5 μM] | | 17.6 [1 μM] | | |
| 56 | 87.1 [1 μM] | | | | 29 [1 μM] | | |
| 155 | 82.1 [1 μM] | | | | 25 [1 μM] | | |
| 220 | | 5.9 | | 3.1 | 45.1 [1 μM] | 74 | 167 |
| 28 | 45 [1 μM] | | | | 11.8 [1 μM] | | |
| 156 | | | | | 7.1 [1 μM] | | |
| 157 | | 89 | | | 27.2 [1 μM] | | |
| 221 | | 3.7 | | | 39.6 [1 μM] | 50 | 243 |
| 118 | 95.6 [1 μM] | 90 | | | 32.9 [1 μM] | 382 | 3727 |
| 211 | 103.8 [1 μM] | 0.9 | | 2.9 | 35.8 [1 μM] | 66 | 437 |
| 119 | 90.1 [1 μM] | | | | 17.7 [1 μM] | | |
| 212 | 91.9 [1 μM] | | | | 16.1 [1 μM] | | |
| 120 | 93.1 [1 μM] | | | | 23.4 [1 μM] | | |
| 158 | | | | | −1.1 [1 μM] | | |
| 121 | | | | | −7.3 [1 μM] | | |
| 70 | | | | | −9.7 [1 μM] | | |
| 159 | | | | | −12.2 [1 μM] | | |
| 71 | | | | | −12.8 [1 μM] | | |
| 107 | 98.3 [1 μM] | | | | 26 [1 μM] | | |
| 194 | 98.3 [1 μM] | 23 | | 41 | 31.6 [1 μM] | 176 | 1536 |
| 195 | 66 [1 μM] | 405 | | | −3.1 [1 μM] | | |
| 213 | 101.2 [1 μM] | 1.6 | | 0.2 | 34 [1 μM] | 60 | 230 |
| 122 | | | | | −6.8 [1 μM] | | |
| 160 | | | | | 5.9 [1 μM] | | |

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 161 | | | | | 2.6 [1 µM] | | |
| 162 | | | | | 16.7 [1 µM] | | |
| 163 | | | | | −7.8 [1 µM] | | |
| 164 | | | | | −8.3 [1 µM] | | |
| 165 | | | | | −10.2 [1 µM] | | |
| 72 | | | | | −6.7 [1 µM] | | |
| 73 | | | | | −4.8 [1 µM] | | |
| 74 | | | | | 2.7 [1 µM] | | |
| 75 | | | | | −8.7 [1 µM] | | |
| 76 | | | | | 0 [1 µM] | | |
| 77 | | | | | −2.9 [1 µM] | | |
| 123 | | | | | −0.8 [1 µM] | | |
| 124 | | | | | −7.6 [1 µM] | | |
| 125 | | | | | 0.7 [1 µM] | | |
| 126 | | | | | −12.3 [1 µM] | | |
| 127 | | | | | −7.2 [1 µM] | | |
| 128 | | | | | −8.3 [1 µM] | | |
| 29 | 102.4 [1 µM] | | | 42 | 39.1 [1 µM] | 147 | 1087 |
| 198 | 104.5 [1 µM] | 5 | | 4.1 | 38 [1 µM] | 57 | 413 |
| 166 | 100.2 [1 µM] | | | | 34.3 [1 µM] | 259 | 2043 |
| 167 | 88.2 [1 µM] | | | | 22.5 [1 µM] | | |
| 168 | | | | | 12.2 [1 µM] | | |
| 169 | 99.5 [1 µM] | | | | 30.9 [1 µM] | 395 | 1832 |
| 170 | 99.1 [1 µM] | 27 | | | 31.5 [1 µM] | 274 | 572 |
| 78 | 99.1 [1 µM] | | | | 20.3 [1 µM] | | |
| 79 | | | | | 9.8 [1 µM] | | |
| 80 | | | | | 11.9 [1 µM] | | |
| 81 | | | | | 13.2 [1 µM] | | |
| 82 | | 12 | | | 42.5 [1 µM] | 572 | 3420 |
| 173 | 17.6 [1 µM] | | | | 1.3 [1 µM] | | |
| 84 | 22.2 [1 µM] | | | | 0.7 [1 µM] | | |
| 174 | | 35 | | | 26.3 [1 µM] | | |
| 85 | 98 [1 µM] | | | | 17.3 [1 µM] | | |
| 129 | 101.2 [1 µM] | 18 | | | 50.6 [1 µM] | 377 | 2918 |
| 130 | 93.4 [1 µM] | | | | 27.7 [1 µM] | | |
| 131 | 74.1 [1 µM] | | | | 12.7 [1 µM] | | |
| 132 | 81.8 [1 µM] | 245 | | | 19.6 [1 µM] | | |

-continued

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 133 | 15.2 [1 μM] | | | | 3.1 [1 μM] | | |
| 134 | | 11 | | | 29.9 [1 μM] | | |
| 135 | | 9.7 | | | 48.4 [1 μM] | 400 | 2072 |
| 222 | 102.4 [1 μM] | 4.9 | | | 58.2 [1 μM] | 122 | 520 |
| 87 | 7.6 [1 μM] | | | | 5.8 [1 μM] | | |
| 176 | 0 [1 μM] | | | | 14.5 [1 μM] | | |
| 138 | 9.1 [1 μM] | | | | 15.2 [1 μM] | | |
| 280 | | 263 | | | 26.6 [1 μM] | | |
| 284 | 30 [0.5 μM] | NA | 25 [0.5 μM] | | 24.1 [1 μM] | | |
| 283 | 101 [0.5 μM] | <0.1 | 101 [0.5 μM] | | 25.8 [1 μM] | | |
| 39 | 64 [0.5 μM] | | 67 [0.5 μM] | | 6.6 [1 μM] | | |
| 277 | | 3.7 | | | 63.4 [1 μM] | 45 | 245 |
| 278 | | 6.6 | | | 59.9 [1 μM] | 199 | 1438 |
| 281 | 10 [0.5 μM] | 2570 | 14 [0.5 μM] | | 10.4 [1 μM] | | |
| 279 | 85 [0.5 μM] | 40 | 76 [0.5 μM] | | | | |
| 282 | 99 [0.5 μM] | <0.1 | 101 [0.5 μM] | | | | |
| 274 | 99 [0.5 μM] | 0.4 | 101 [0.5 μM] | | | | |
| 46 | 98 [0.5 μM] | 1 | 98 [0.5 μM] | | | | |
| 275 | 90 [0.5 μM] | 1.2 | 95 [0.5 μM] | | | | |
| 243 | 80 [0.5 μM] | 56 | 67 [0.5 μM] | | | | |
| 276 | 91 [0.5 μM] | 2.3 | 88 [0.5 μM] | | | | |
| 37 | | 2873 | | | | 7057 | >10,000 |
| 34 | 101.3 [3 μM] | 29 | 101.7 [3 μM] | 31 | 62.4 [10 μM] | 393.0 | |
| 35 | 98.9 [3 μM] | 15 | 100 [3 μM] | 16 | 68.1 [10 μM] | 416.0 | |
| 273 | 85.6 [3 μM] | | 89.1 [3 μM] | | 44.1 [10 μM] | | |
| 272 | 85.8 [3 μM] | | 88.5 [3 μM] | | 53.3 [10 μM] | | |
| 17 | | | | | 11.2 [1 μM] | | |
| 38 | 63.1 [1 μM] | 451 | | | 9.2 [1 μM] | | |
| 44 | 72.7 [1 μM] | 220 | | | 13.2 [1 μM] | | |
| 83 | | | | | 2.1 [1 μM] | | |
| 86 | | | | | 377.49 [1 μM] | | |
| 88 | 13.8 [1 μM] | | | | 5.6 [1 μM] | | |
| 89 | 12.7 [1 μM] | | | | 20.1 [1 μM] | | |
| 136 | | | | | 1.1 [1 μM] | | |
| 137 | 21.6 [1 μM] | | | | 24.4 [1 μM] | | |
| 254 | | 1230 | | | 16.24 [10 μM] | | |
| 259 | | >10000 | | | 6.48 [10 μM] | | |

-continued

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 269 | | 1653 | | | −5.7, −7.2 [10 µM] | | |
| 270 | | 1426 | | | −6.9, −8.9 [10 µM] | | |
| 139 | | 9.3 | | | 2.2 [1 µM] | | |
| 171 | | | | | −9.6 [1 µM] | | |
| 172 | | | | | −9.9 [1 µM] | | |
| 175 | 10.5 [1 µM] | | | | | | |
| 177 | 9.5 [1 µM] | | | | 10.2 [1 µM] | | |
| 223 | | 15.76 | | | >10000 [10 µM] | | |
| 231 | | 276 | | >10000 | 94.24, 63.4 [10 µM] | 335 | |
| 233 | | 217 | | >10000 | 95.1 [10 µM] | 712 | |
| 234 | | 1800 | | | 55.6 [10 µM] | | |
| 242 | | 747 | | | 41.2 [10 µM] | | |
| 244 | | >10000 | | | 0.8 [10 µM] | | |
| 246 | 0 | | | | 1.8 [10 µM] | | |
| 33 | | >10,000 | | | | | |
| 292 | 10 [0.5 µM] | | | | | | |
| 293 | 1 [0.5 µM] | | | | | | |
| 294 | 0 [0.5 µM] | | | | | | |
| 295 | 98 [0.5 µM] | 45 | | | | 646 | 2206 |
| 296 | 90 [0.5 µM] | 110 | | | | 860 | 3123 |
| 297 | 87 [0.5 µM] | 84 | | | | 1429 | 3791 |
| 298 | | 75 | | | | 1516 | >5,000 |
| 299 | 70 [0.5 µM] | 34 | | | | 1196 | >10,000 |
| 300 | 68 [0.5 µM] | 54 | | | | >10000 | >10,000 |
| 301 | 100 [0.5 µM] | 0.4 | | | | 16 | 178 |
| 302 | 98 [0.5 µM] | 2.2 | 99 [0.5 µM] | | | 35 | 229 |
| 303 | | 257 | | | | >10000 | NA |
| 304 | | 17 | | | | 413 | 980 |
| 305 | 83 [0.5 µM] | 160 | | | | 1411 | 3811 |
| 306 | | >1000 | | | | >10000 | NA |
| 307 | | 2.6 | | | | 977 | 2048 |
| 308 | | 15 | | | | 377 | 1241 |
| 309 | | 117 | | | | 917 | 3333 |
| 310 | | 3.8 | | | | >5,000 | >5,000 |
| 311 | | >1000 | | | | N/A | N/A |
| 312 | | >1000 | | | | N/A | N/A |
| 313 | 99 [0.5 µM] | 14 | 94 [0.5 µM] | | | 3033 | |
| 314 | 94 [0.5 µM] | 80 | 81 [0.5 µM] | | | >5000 | >5000 |
| 315 | | 26 | | | | 168 | 1949 |
| 316 | 85 [0.5 µM] | 27 | 90 [0.5 µM] | | | 2421 | >10000 |
| 317 | 75 [0.5 µM] | 38 | 70 [0.5 µM] | | | >10,000 | >10,000 |
| 318 | 50 [0.5 µM] | | | | | | |

-continued

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 319 | 100 [0.5 μM] | 1.1 | 98 [0.5 μM] | | | 18; 49 | 59 |
| 321 | 100 [0.5 μM] | 8 | 98 [0.5 μM] | | | 74 | 114 |
| 322 | 29 [0.5 μM] | | 17 [0.5 μM] | | | | |
| 320 | 97 [0.5 μM] | 18 | 95 [0.5 μM] | 8.7 | | >5,000 | >5,000 |
| 323 | 29 [0.5 μM] | | 17 [0.5 μM] | | | | |
| 324 | 71 | 268 | | | | 2079 | 1373 |
| 325 | 25 [0.5 μM] | | | | | | |
| 326 | 64 [0.5 μM] | 305 | | | | 6288 | >10,000 |
| 328 | 7 [0.5 μM] | | 8 [0.5 μM] | | | | |
| 329 | | 1.8 | | | | | 90 |
| 330 | | 11 | | | | | |
| 331 | | 5.9 | | | | | 318 |
| 332 | | 1.2 | | | | 18 | 80 |
| 333 | | 44 | | | | 577 | 1597 |
| 334 | | 121 | | | | 889 | 1650 |
| 335 | | >1000 | | | | | |
| 336 | 103 [0.5 μM] | 3.6 | 99 [0.5 μM] | | | 25 | 116 |
| 337 | | >1000 | | | | | |
| 338 | 13 [0.5 μM] | | 3 [0.5 μM] | | | | |
| 339 | 75 [0.5 μM] | 211 | 56 [0.5 μM] | | | | |
| 340 | | 20 | | | | 362 | 894 |
| 341 | | 5.8 | | | | 27 | 58 |
| 342 | | 0.1 | | | | 26 | 1950 |
| 343 | | 5.6 | | | | 127 | 223 |
| 344 | | 1.7 | | | | 82 | 192 |
| 345 | | | | | 23.7 [10 μM] | | |
| 346 | | >10000 | | >10000 | 12.3 [10 μM] | | |
| 349 | | | | | 4.21 [10 μM] | | |
| 350 | | 3700 | | | 14.81 [10 μM] | | |
| 347 | | >10000 | | | 16.96 [10 μM] | | |
| 351 | | >10000 | | | 7.8 [10 μM] | | |
| 353 | | >10000 | | | 25.55 [10 μM] | | |
| 354 | | >10000 | | | 6.4 [10 μM] | | |
| 355 | | >10000 | | | 21.93 [10 μM] | | |
| 356 | | >10000 | | | 6.59 [10 μM] | | |
| 357 | | 1900 | | | 6.35 [10 μM] | | |
| 358 | | >10000 | | | 24.32 [10 μM] | | |
| 359 | | >10000 | | | 21.75 [10 μM] | | |
| 360 | | 5200 | | | 1.69 [10 μM] | | |
| 361 | | >10000 | | | 2.02 [10 μM] | | |
| 362 | | | | | 5.14 [10 μM] | | |
| 363 | | | | | 10.22 [10 μM] | | |
| 364 | | | | | 6.18 [10 μM] | | |

-continued

| Ex. # | ROCK2 % inh. @ [conc] | ROCK2 IC50 (nM) | ROCK1 % inh. @ [conc] | ROCK1 IC50 (nM) | pMLC % inh A7R5 @ [conc] | pMLC IC50 (nM) A7R5 | NIH3T3 Acta2-luc, IC50 (nM) |
|---|---|---|---|---|---|---|---|
| 365 | >10000 | | | | 5.72 [10 µM] | | |
| 366 | | | | | 4.95 [10 µM] | | |
| 367 | | | | | 7.2 [10 µM] | | |
| 368 | | 1050 | | | 91.26 [10 µM] | | 1627 |
| 369 | | | | | 0.9 [10 µM] | | |
| 370 | | 6268 | | | 5.8 [10 µM] | | |

Example 372

ROCK Inhibitors of the Invention Inhibited ROCK Kinase Driven F-Actin Polymerization in Cells.

Dynamic transition between monomeric globular (G-actin) and polymerized filamentous actin (F-actin) states in cells are governed primarily by Rho/ROCK pathway. Inhibition of RhoGTPase or its effector kinase ROCKs can lead to disruption of filamentous actin structure stress fibers in cells. FIG. 2a showed that silencing of ROCKs expression in cultured fibroblasts by transfection of targeting siRNAs significantly reduced F-actin contents. Pharmacological inhibition of ROCK activity in CCD18lu human lung fibroblasts using a ROCK inhibitor of the invention (Example 228) phenotypically copied gene silencing, as shown in FIG. 2b. This result underscores the importance of ROCK activity in controlling cellular actin dynamics and corresponding nuclear signaling events.

Example 373

ROCK Inhibitors of the Invention Prevent Nuclear Translocation of Fibrogenic Transcription Coactivator MKL1.

Monomeric G-actin binds to the transcriptional coactivator megakaryoblastic leukemia 1 (MKL1 or MRTF) and prevents it from translocating to the nucleus and activating transcription. Activation of the Rho/ROCK pathway depletes cellular G-actin by polymerizing into filamentous form, leading to nuclear translocation of MKL1, and activating MKL1-dependent serum response factor (SRF) driven gene expression.

The Example 228 compound abolished nuclear accumulation of MKL1 in cultured human lung fibroblasts. CCD18Lu human lung fibroblasts were treated with the ROCK inhibitor (3 µM) for 3 hours and fixed and stained for MKL1, F-actin and DAPI. The ROCK inhibitor efficiently cleared stress fiber formation while blocked nuclear accumulation of MKL1. See FIG. 3.

Example 374

ROCK Inhibitors of the Invention Dampened Pro-Fibrotic Gene Expressions

Expression of α-smooth-muscle-actin (αSMA, or Acta2) by fibroblasts is a key marker indicating the transdifferentiation of fibroblasts to more pro-fibrotic myofibroblasts exemplified by increased expression of fibrogenic factors, such as connective tissue growth factor (CTGF) and collagens. Mechanotransduction along with fibrogenic cytokines, including TGFβ signaling all lead to expression of αSMA and contribute to myofibroblast differentiation, proliferation and sustained survival.

As shown in FIG. 4a, ROCK inhibitor strongly inhibited αSMA expression induced by rigid matrix. HFF cells were cultured on Prime Coat dishes coated with silicone gel with increasing rigidities (2 KPa or 30 KPa). Cells were treated for 24 hours with compounds and mRNA expressions were quantified by Taqman qPCR.

TGFβ1 induced αSMA expression was decreased by ROCK inhibitor. LL24 cells were treated for 24 hours and mRNA expressions were quantified by Taqman qPCR. ROCK inhibitor decreased basal, as well as TGFβ1 induced, expression of αSMA in human lung fibroblasts. See FIG. 4b. And correspondingly, αSMA protein levels were reduced by longer incubations of ROCKi in a dose dependent manner as seen in FIG. 4c. CCD18Lu human lung fibroblasts were cultured on plastic substrate for 5 days with or without inhibitors. αSMA and control proteins were visualized by western blots.

ROCK inhibitors can be effectively rank ordered by ACTA2-promoter-driven-luciferase reporter cell assay. NIH3T3 cells stably expressing ACTA2-promoter-driven-luciferase were plated in 96 well plates to confluence and treated with 9 points serial dilution of compounds in combination with TGFβ1 for 24 hr. Luciferase activities were measured and compound's IC50s were calculated. By this assay multiple compounds of the invention gave IC50s under 200 nM. See FIG. 4d.

Example 375

ROCK Inhibitors Inhibited Integrin Dependent Latent TGFβ Activation

Figure 5:
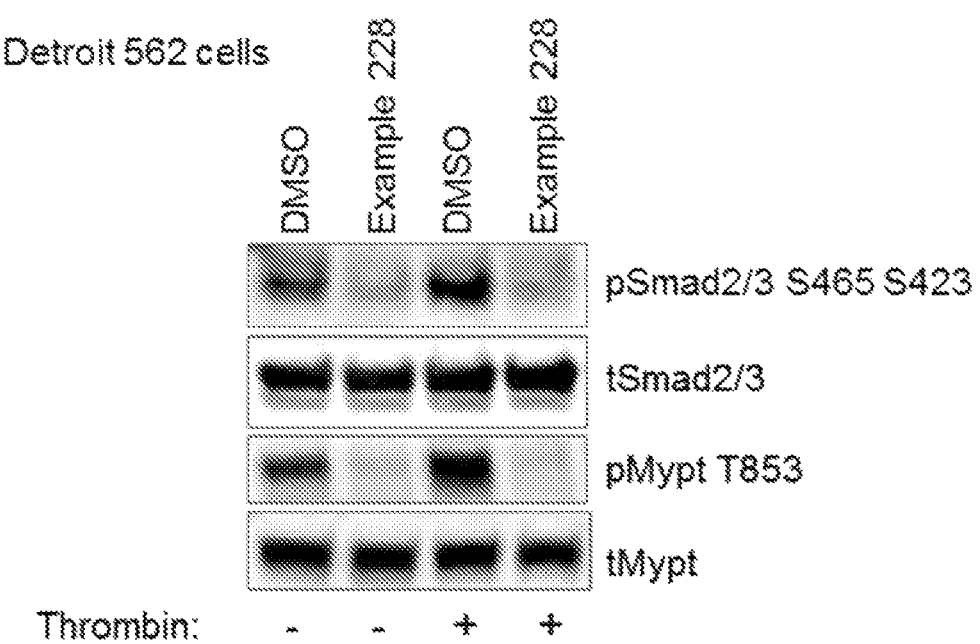
FIG. 5. ROCK inhibitor (Example 228) blocked integrin αvβ6 mediated latent TGFβ activation. Integrin αvβ6 positive cell line Detroit 562 cells were plated and treated with compounds in combination with par1 ligand thrombin for 2 hours, lysed and activation of TGFβ signaling was detected by phosphorylation of transcription factors Smad2/3.

Integrin αvβ6 mediated latent TGFβ activation requires ROCK activity (Jenkins et al., 2006). Activation of the latent TGF3 complex is a key step in regulating the biological availability of this molecule and its subsequent activities. Under tissue injury, extracellular protease cleavage of cell membrane receptor protease-activated receptor 1 (par1) leads to activation of Rho/ROCK, which in turn activates latent ECM associated TGFβ through cell membrane integrin αvβ6. Hence, ROCK inhibition decreased par1 ligand thrombin induced TGFβ signaling in Detroit 562 integrin αvβ6 positive cell line, which was evident by the reduced level of phosphorylated smad2/3 as shown in FIG. 5. Integrin αvβ6 positive cell line Detroit 562 cells were plated and treated with compounds in combination with par1 ligand thrombin for 2 hours, lysed and activation of TGFβ signaling was detected by phosphorylation of transcription factors Smad2/3.

Example 376

ROCK Inhibitors Inhibited Pro-Senescence Extracellular Matrix Protein CCN1 Expression Myofibroblasts isolated from IPF patients' lung show senescence characteristics. While they were resistant to apoptosis signals, they were highly active in metabolism and persistently produced large amounts of ECM proteins (Kurundkar et al., 2016). Under fibrotic condition, fed by mechanotransduction and TGFβ stimulation, the aberrant myofibroblasts release yet under studied pro-senescence ECM-associated proteins. One such protein appears to be CCN1 (or CYR61).

Figure 6:
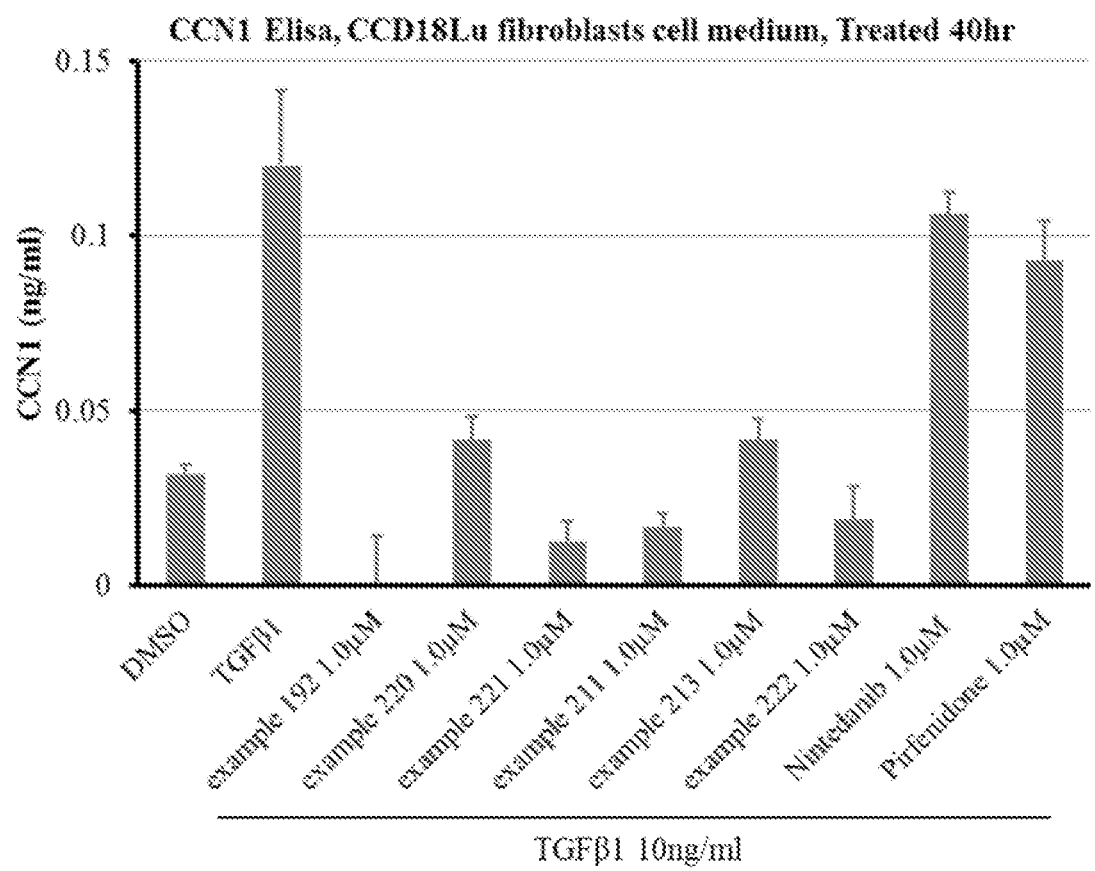
FIG. 6. CCN1 ELISA in CCD18Lu fibroblasts cell culture medium. Cells were treated with ROCK inhibitor in combination with TGF3 for 40 hr. CCN1 contents were measured using human CCN1 ELISA kit from R&D Systems.

Treatment of human lung fibroblast with ROCK inhibitor under TGFβ induction, strongly inhibited secreted CCN1 proteins, demonstrated by cell culture medium ELISA assay as shown in FIG. 6. CCD18Lu fibroblasts cells were treated with ROCK inhibitor in combination with TGF3 for 40 hr. CCN1 contents were measured using human CCN1 ELISA kit from R&D Systems. These results suggest that ROCK inhibitors could dampen pro-survival, pro-senescent signals of myofibroblasts under fibrotic conditions.

Example 377

ROCK Inhibitors Preserved Epithelial and Endothelial Structural Integrities.

In fibrotic disease progression, the initial damage occurs to organ epithelial layers. The injured epithelial cells go through apoptosis, stimulate innate immune reactions and disrupt underlying vascular endothelial barrier function. Extravascular coagulation driven by activated thrombin pathway is a hallmark of tissue injury. Thus, protection of epithelial integrity, blockade of thrombin induced extravascular coagulation and corresponding downstream signaling have important functions in prevention of fibrosis initiation and spreading.

Under calcium chelation shock, ROCK inhibitors of the invention efficiently protected the polarized MDCK cells layer integrity. See FIG. 7a. MDCK cells were cultured in confluence for 3 days and extracellular calcium was chelated by adding 5 mM of EGTA under with or without ROCK inhibitor conditions. Cellular junctional integrity was visualized by immunofluorescent staining of adhesion molecule p120. F-actin and nucleus were counterstained. The ROCK inhibitors protected epithelial junctional integrity. See FIG. 7a.

With thrombin stimulation, the ROCK inhibitor (Example 228) potently inhibited thrombin induced phosphorylation of the contractile protein MLC in endothelial cell line SVEC4-10. See FIG. 7b. Mouse endothelial cell line SVEC4-10 was cultured and treated with increasing doses of thrombin in combination with ROCK inhibitor for 10 min. ppMLC signal was detected by western blot. The ROCK inhibitor blocked thrombin induced MLC phosphorylation. See FIG. 7b. Collectively, the above data strongly supports the ROCK inhibitors of the invention as an effective intervention in fibrotic diseases.

Example 378

Therapeutic Efficacy of Compounds in Bleomycin Induced Lung Fibrosis in Mice

Male C57B/L6 mice were housed for acclimation for no less than 7 days. After acclimation period, animals were randomly assigned to treatment groups. On day 0, mice were anesthetized with 5% isoflurane by inhalation for 10-15 mins and then suspended by their front teeth on a wire attached to a fixed animal operating plate. 50 µL of saline or bleomycin solution was administered via intratracheal instillation. Mice in treatment groups were intratracheally instilled with bleomycin hydrochloride (BLM) 2.0 U/kg (mg/kg) in sterile saline. On day 7 following bleomycin administration, half of the animals in vehicle group were sacrificed to establish a baseline for the level of fibrosis at the treatment initiation. Mice in normal control group received saline by p.o. once daily from Day 7 to Day 20. Treatment group mice received the compound dosed orally once daily from Day 7 to Day 20.

On Day 20, 2-3 hours posted the last dose, all mice were sacrificed. Lungs were gently lavaged via the tracheal cannula with 0.8 mL of PBS containing 1% BSA and 0.6 mM EDTA. After the lavage, lung tissues were collected from each animal. The lung tissues were divided into 3 parts: the large lobe of right part was fixed with 10% neutral formalin for paraffin embedding and histopathology. The remained lobes of right parts were snap-frozen and protein lysates were prepared for target engagement analysis.

Example 379

Prophylactic Efficacy of Compounds in Bleomycin Induced Lung Fibrosis in Mice

Male C57B/L6 mice were ear tagged and weighed prior to the start of the study. Treatment group animals were treated with the compound on day −1 pre-bleomycin and all subsequent days post-bleomycin administration. On day 0, animals in disease groups received 1.5 U/kg dose of bleomycin via oropharyngeal route. The non-bleomycin control group received sterile saline. Animals were closely monitored daily till the end of the study. On day 21 following bleomycin administration, all animals were euthanized and blood, lung, and bronchoalveolar lavage (BAL) fluid were collected. Blood samples were used for plasma preparation; total leukocytes were counted in BAL fluid; and lungs were fixed in 10% neutral buffered formalin for histopathological analysis.

Example 380

Unilateral Ureteral Obstruction (UUO)-Induced Renal Fibrosis Model in Mice

Male C57B/L6 mice were anesthetized with Isoflurane and placed in dorsal recumbency and the abdominal region was shaved and prepared for surgery with alternating scrub wipes of iodine or chlorhexidine scrub and 70% isopropyl alcohol. A small midline incision was made in the abdomen and the left ureter identified and dissected free of surrounding tissue. A double ligature (5 mm apart) was placed and secured just below the left kidney, thus ligating the ureter. For sham animals, the ureter were identified and dissected free of surround tissue, but not ligated. All animals were monitored closely for 3 days.

Starting on Day 0 and continuing through Day 10, mice were dosed via oral gavage (PO) with test article or vehicle. The control drug group animals were dosed on Days 0, 2, 4, 6, and 8. All animals were euthanized via $CO_2$ asphyxiation on Day 10. Upon sacrifice, blood was collected for the preparation of whole blood and plasma, and both kidneys were removed, photographed, and weighed. Both kidneys were dissected and fixed in 10% formalin for histological analysis, and a portion was snap frozen in liquid nitrogen and stored at −80° C. The formalin-fixed kidney sections were processed for routine histological evaluation. Longitudinal (coronal) sections were obtained from the samples and slides were stained with hematoxylin and eosin, Masson's Trichrome for histological examination of fibrosis.

Example 381

Histamine-Induced Vascular Permeability Model in Mice 7-8 weeks old Balb/c female mice were acclimated at least 3 days, and randomly assigned to groups. Animals were injected i.v. with 1% Evans Blue at a dose 100 μl/mouse. 10 minutes later animals in disease groups were given 1 μg of histamine in 20 μl PBS intradermally on the back and sacrificed 20 minutes after administration. 20 μl PBS were injected intradermal into the animal back in sham control. Vehicle and test articles were dosed via oral gavage accordingly. Positive control salbutamol was administered 15 minutes before Evans blue.

20 minutes post challenge with histamine, animals were euthanized. The skin was then inverted, the lesion diameters were measured. The area of the lesion was calculated and expressed in square millimeters. Following diameter measurements, Evan's Blue dye was extracted from the skin tissue and the optical density was measured. Data are calculated against a spiked in Evan's Blue standard curve.

Example 382

Figure 8:
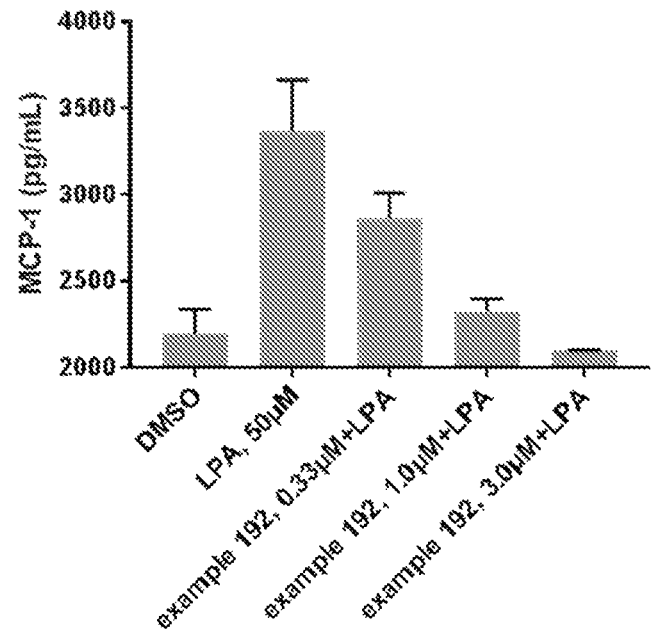
FIG. 8. ROCK inhibitor is active in blockade of fibrotic agent LPA or thrombin induced monocyte chemoattractant protein-1 (MCP-1 or chemokine C—C motif ligand 2, CCL2) secretion from endothelial cells. Mouse endothelial SVEC-10 cells were treated with 50 µM LPA or 5 U/ml thrombin in combination with or without ROCK inhibition for 24 hr and secreted MCP-1 level was measured with ELISA.
Figure 8:
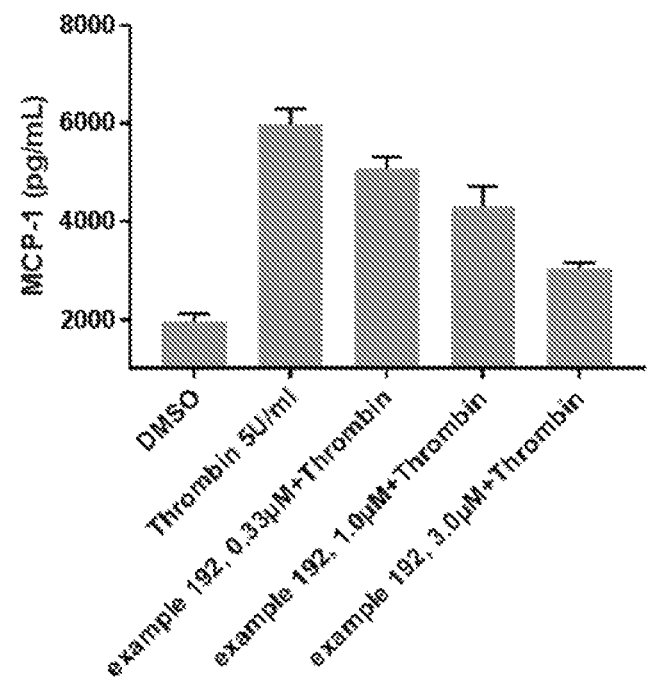

ROCK Inhibitor Blocks the Inflammatory Chemokine MCP-1 Secretion from Endothelial Cells Tissue damage induced inflammation and wound healing response exacerbate fibrotic disease progression. Multiple fibrotic agents, including LPA and thrombin not only activate ROCK pathway in fibroblasts, also could stimulate endothelial cells to release cytokines and chemokines to orchestrate the wound healing, or in diseased condition fibrosis development. Thus, inhibiting abnormal chemokine secretion is beneficial to fibrotic (and inflammatory) disease control. ROCK inhibitors could effectively block enhanced secretion of MCP-1 in endothelial cells induced by exogenous factors. As demonstrated in FIG. 8, increased doses of ROCK inhibitor lowered MCP-1 detected in the cell medium when mouse SVEC4-10 endothelial cells were stimulated with LPA or thrombin in the presence of ROCK inhibitor for 24 hour, quantified by ELISA. It highlights the potential application of ROCK inhibitors in fibrotic and inflammatory disease areas.

Example 383

Figures 9, 9A:
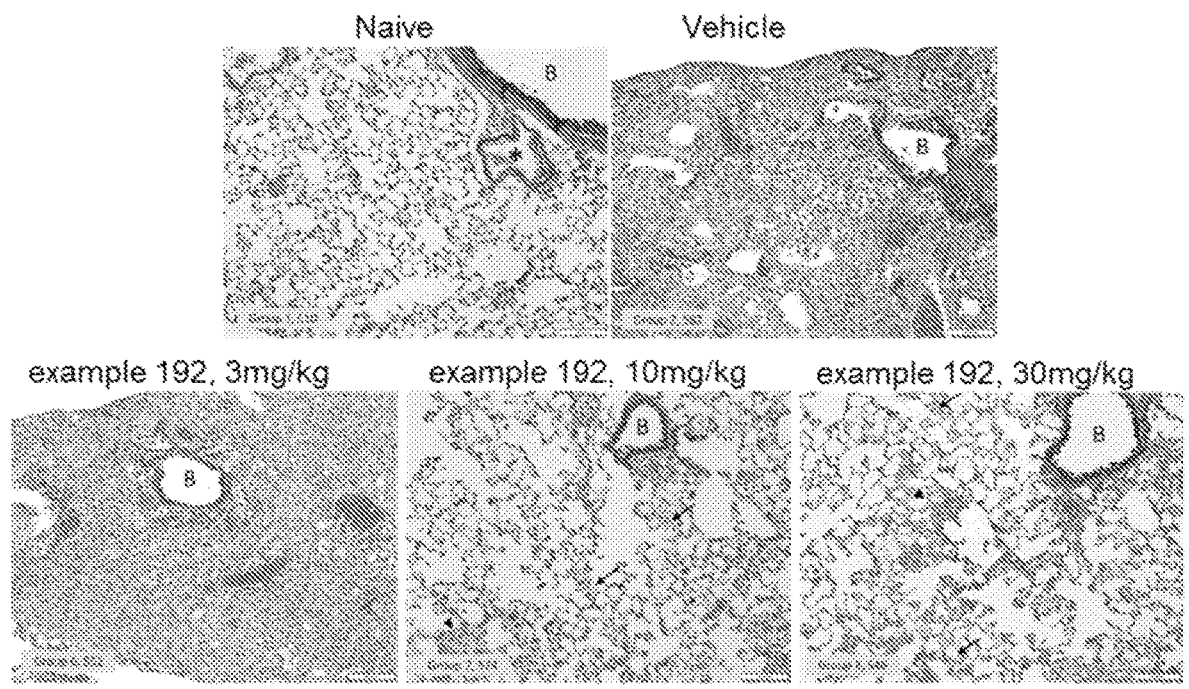
FIG. 9a. ROCK inhibitor is active in a mouse model of pulmonary fibrosis. Representative images of lung sections stained with Masson's trichrome to visualized fibrosis in the lungs of mice following 21-day treatment with ROCK inhibitor in the bleomycin-induced lung injury model.

ROCK Inhibitor is Effective in Lowering Multiple Fibrotic Indices in the Bleomycin Induced Pulmonary Fibrosis Model in Mice Based on the strong anti-fibrotic cellular activity of ROCK inhibitors of this invention, the ability of such inhibitors to attenuate fibrosis in the in vivo setting was assessed in several mouse models of disease. Including the bleomycin induced model of pulmonary fibrosis. Following the intratracheal instillation of bleomycin mice were orally administered ROCK inhibitor at dose of either 3 mg/kg, 10 mg/kg or 30 mg/kg. control animal received vehicle only in the same once daily administration schedule. Following 20 days of treatment the animals were sacrificed and lungs were removed, weighted and fixed for histopathological evaluation. FIG. 9a shows representative images of Masson's Trichrome stained lung sections at 10× objective from each treatment group. While in the treatment groups fibrotic mass formation (arrowhead), thickened alveolar septae and knot-like formation (arrow) was still present all were less severe compared to bleomycin induced controls. (B=bronchiole). Overall ROCK inhibitor improved lung architecture and collagen deposition in a dose dependent manner in this model. With mice receiving doses ≥10 mg/kg showing clear and statistically significant improvements.

Figures 9, 9B:
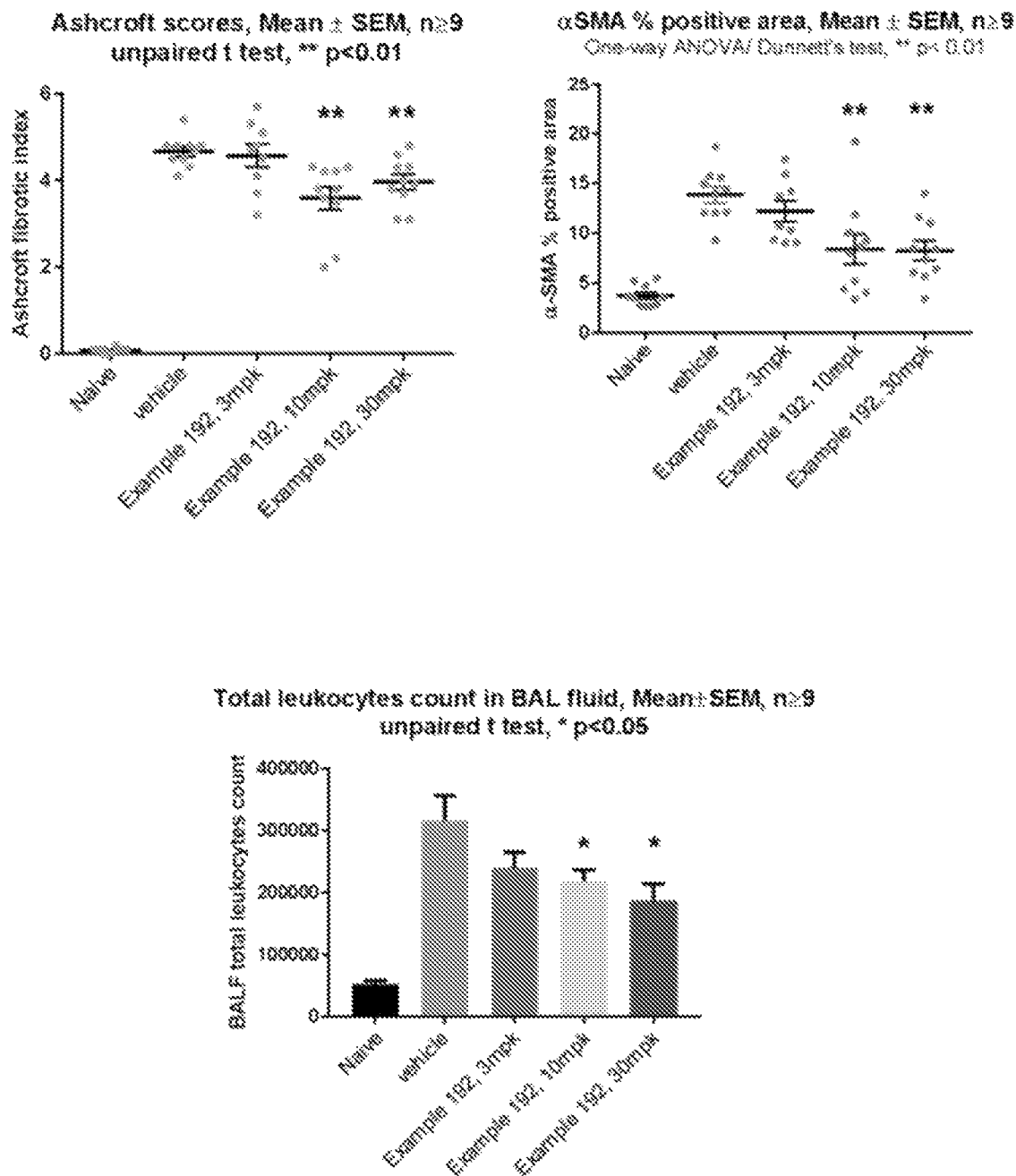
FIG. 9b. Quantitation of the positive activity of ROCK inhibitor in an in vivo model of pulmonary fibrosis. Ashcroft fibrotic indices, α-smooth muscle actin (αSMA) percentage positive area and total leukocytes count in bronchoalveolar lavage fluid obtained from lungs of mice in the bleomycin lung fibrosis model treated with compound of Example 192.

The improvement in the overall lung fibrosis, α-smooth muscle actin (αSMA) percentage positive area and total leukocytes count in bronchoalveolar lavage fluid was quantitated by applying the Ashcoft score criteria to the histopathology images, IHC quantitation and flowcytometry respectively. Administration of ≥10 mg/kg ROCK inhibitor resulted in substantially less fibrosis and lower inflammatory leukocytes infiltration compared to vehicle treated controls, as indicated by lower group mean fibrotic indices, αSMA positive area and total leukocytes count in bronchoalveolar lavage fluid. See FIG. 9b.

Example 384

Figures 10, 10A:
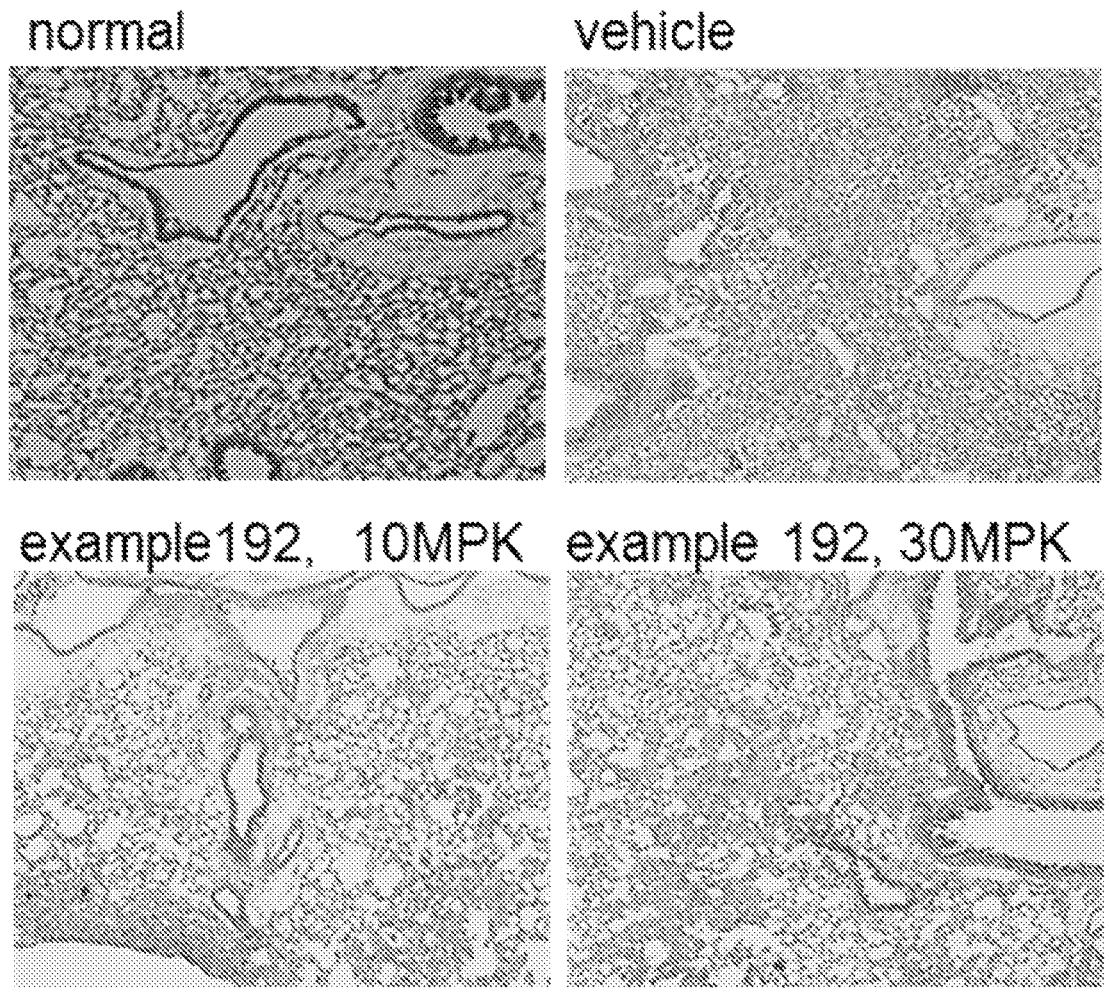
FIG. 10a. ROCK inhibitor is therapeutically active in a mouse model of pulmonary fibrosis. Representative images of lung sections stained with Masson's trichrome to visualized fibrosis in the lungs of mice following therapeutic treatment with ROCK inhibitor in the bleomycin-induced lung injury model.

ROCK Inhibition is Effective at Lowering Fibrosis Scores when Administered Therapeutically in the Bleomycin Induced Pulmonary Fibrosis Model in Mice The activity of ROCK inhibitors in attenuating pulmonary fibrosis in a therapeutic dosing setting was assessed in a bleomycin-induced model, following intratracheal bleomycin installation to induce lung tissue damage and consequent fibrosis of the lung. 7 days after bleomycin instillation, which allowed for the fibrosis to be established prior to the treatment initiation, mice were treated with the compound or vehicle control. All mice were sacrificed on day 20 and lungs were collected. The large lobe of the right lung was fixed with 10% neutral formalin, sectioned and stained with Masson's Trichrome. Clear anti-fibrotic effects were observed in 10 mg/kg and 30 mg/kg ROCK inhibitor treatment groups, as evidenced by the lower collagen contents and the decreased Masson's trichrome staining scores. See FIG. 10a.

Figures 10, 10B:
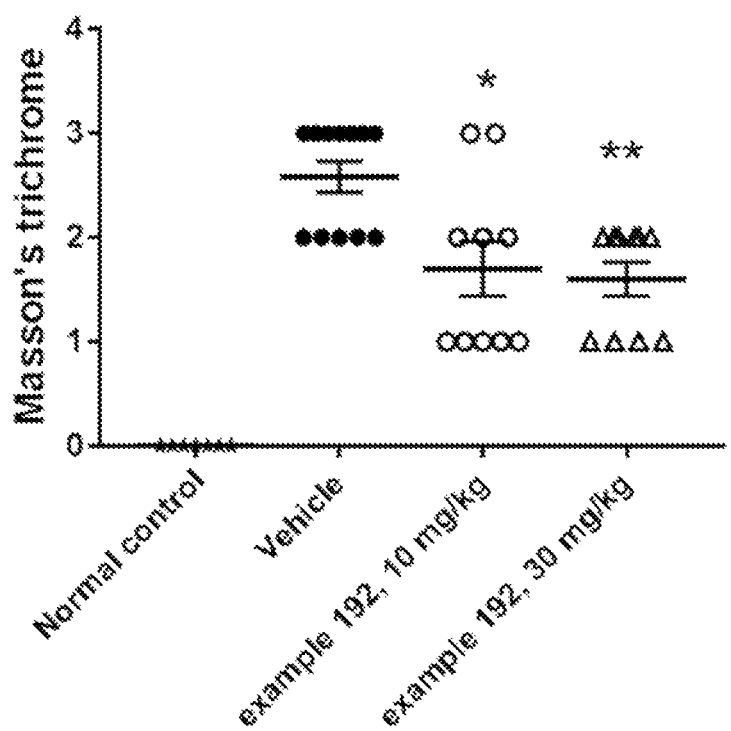
FIG. 10b. Quantitation of the decrease in the fibrosis index in the histopathological analysis of the images from ROCK inhibitor and vehicle treated mice in the bleomycin-induced lung injury model.

The improvement in the overall lung fibrosis was quantitated for each animal in the control and treatment groups. See FIG. 10b. Masson's trichrome-stained sections of the lungs from individual mice with group means, and standard errors of the means (SEM) are shown. The scores of normal control mice were 0. The collagen amounts in the lungs from compound example 192 treated mice were significantly lower.

In addition to the determination of the therapeutic activity of ROCK inhibition in the pulmonary fibrosis model, target engagement and the extent of ROCK inhibition in the lung of drug treated animals were also determined. Protein extracts were prepared from the snap frozen lung samples and separated on SDS-PAGE and analyzed by Western blotting. ROCK kinase direct target, phosphorylated myosin-binding subunit of myosin phosphatase (MYPT, pT853) and a ROCK pathway regulated protein CCN1 expression levels were detected. Administration of ROCK inhibitor of Example 192 blocked ROCK kinase activity in bleomycin treated mouse lungs, as shown by the reduction of phosphorylated MYPT levels and CCN1 total protein levels.

Figures 10, 10C:
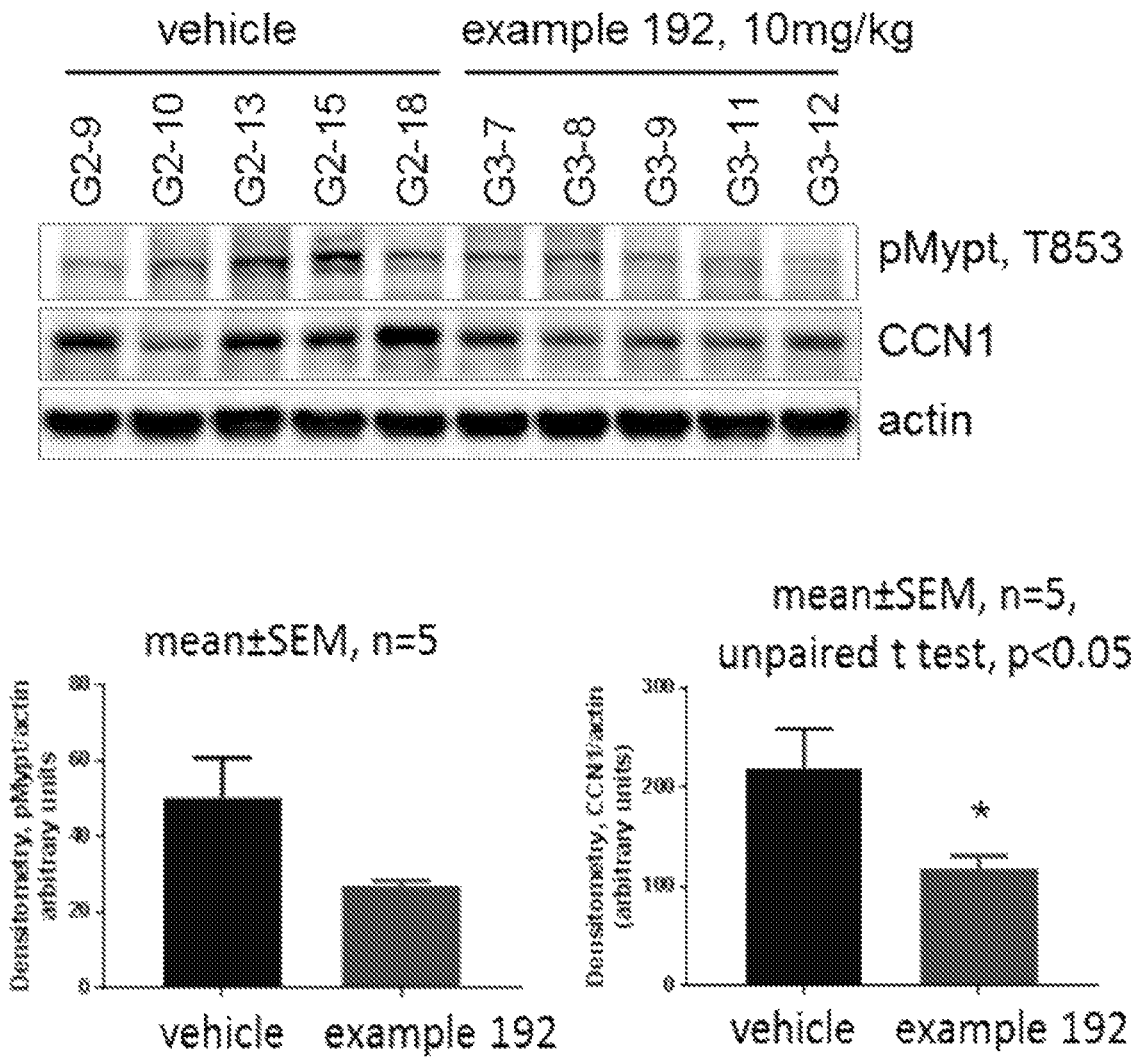
FIG. 10c. ROCK target engagement analysis in the lung tissue from the bleomycin-induced pulmonary fibrosis model. Western blotting and quantitation of the image shows a reduction in the ROCK target phosphorylation and the reduction of the CCN1 protein levels (a direct result of ROCK inhibition) in the mice treated with ROCK inhibitor of Example 192.

Western blot results were quantitated by the Image J densitometry program. See. FIG. 10c.

Example 385

Administration of ROCK Inhibitor Attenuated Fibrosis in a Unilateral Ureteral Obstruction (UUO) Induced Renal Fibrosis Model in Mice.

To assess the activity of ROCK inhibitors in modulation of additional organ fibrosis in an in vivo setting, ROCK inhibitor was tested in a UUO model of renal fibrosis. Following surgical ureteral obstruction, the kidney underdoes massive necrotic changes along with the induction of fibrosis. Drug was administered via oral gavage at doses of 3 mg/kg BID, 6 mg/kg BID and 10 mg/kg QD starting 2 hr. prior to ligation surgery. The animals were sacrificed on Day 10 following surgery and the extent of fibrosis was determined by histopathological analysis of fixed kidney sections stained with Masson's trichrome. The middle third of each kidney from groups treated with ROCK inhibitor or control treatment was collected, fixed in NBF, and processed for histopathology. See FIG. 11a. The urinary space of the renal pelvis (U), medulla (M), and cortex (C) are labeled. Increased staining for collagen (arrows) is present between tubules (interstitium) of the peripapillary area near the urinary space and extends into the medulla.

The improvement in the kidney fibrosis following UUO was quantitated based on the individual image scores by a pathologist blinded to the group assignments. Scores assigned to each parameter in Masson's trichrome-stained sections of the obstructed kidney from individual mouse with group means, and standard errors of the means (SEM) are shown in FIG. 11b. Scores for each parameter in kidneys from mice in the sham-operated control group were 0. The amount of interstitial collagen (increased staining, interstitial) in the obstructed kidney was significantly lower ($*p<0.05$ and $**p<0.01$) in all groups treated with ROCK inhibitor of Example 192. The improvement in the renal fibrosis following ROCK inhibitor treatment suggests that additional fibrotic indications could benefit from pharmacological intervention in the ROCK signaling pathways.

Example 386

ROCK Inhibition Stabilizes the Endothelial Barrier Function in a Histamine-Induced Vascular Permeability Model in Mice In addition to the damage sustained by the organ epithelium, in fibrotic disease, damage also occurs to the endothelial cells, causing destabilization of the endothelial barrier and capillary leakage, both hallmarks of fibrotic tissues. ROCK signaling pathway is upregulated in the injured endothelial cells and lead to further barrier destabilization and vascular leakage. The involvement of ROCK in the induction of vascular leakage allowed us to hypothesize that the administration of ROCK inhibitor could stabilize such vascular barrier function in vivo. We tested the efficacy of blocking ROCK inhibitor activity following single dose administration in a model of histamine-induced dermal vascular leakage in mice. In this model intradermal injection of histamine rapidly induced extravasation of Evan's Blue dye at the site of histamine administration. Administration of ROCK inhibitor of Example 192 1 hr. prior to histamine injection blocked the vascular permeability induced by histamine in a dose dependent manner, suggesting that in addition to the anti-fibrotic activity, ROCK inhibitions of this invention could also be utilized in disease associated with induced vascular permeability. FIG. 12a shows representative images of Evan's Blue dye extravasation induced by histamine.

The extent of compound efficacy was quantitated by calculating both the overall skin spot area and the amount of Evans Blue dye permeating the skin. 20 Minutes post challenge with histamine, animals were euthanized, the lesion diameters were measured. The area of the lesion was calculated and expressed in square millimeters. Following diameter measurements, Evan's Blue dye was extracted from the skin tissue and the optical density was measured. Data are calculated against a spiked in Evan's Blue standard curve. $**$ $p<0.01$ vs Vehicle group using one-way ANOVA followed by Dunnette post-test. See FIG. 12b.

BIBLIOGRAPHY

Jenkins, R. G., Su, X., Su, G., Scotton, C. J., Camerer, E., Laurent, G. J., Davis, G. E., Chambers, R. C., Matthay, M. A., and Sheppard, D. (2006). Ligation of protease-activated receptor 1 enhances alpha(v)beta6 integrin-dependent TGF-beta activation and promotes acute lung injury. J Clin Invest 116, 1606-1614.

Julian, L., and Olson, M. F. (2014). Rho-associated coiled-coil containing kinases (ROCK): structure, regulation, and functions. Small GTPases 5, e29846.

Kurundkar, A. R., Kurundkar, D., Rangarajan, S., Locy, M. L., Zhou, Y., Liu, R. M., Zmijewski, J., and Thannickal, V. J. (2016). The matricellular protein CCN1 enhances TGF-beta1/SMAD3-dependent profibrotic signaling in fibroblasts and contributes to fibrogenic responses to lung injury. FASEB J 30, 2135-2150.

Moraes, C. (2015). Between a rock and a soft place: recent progress in understanding matrix mechanics. Integr Biol (Camb) 7, 736-739.

The invention claimed is:
1. A compound having the formula IIj:

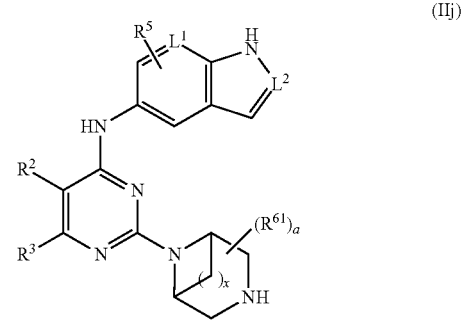

(IIj)

wherein:
each of $L^1$ and $L^2$ are independently selected from N and CH;
$R^2$ is selected from the group consisting of H, halo, hydroxy, —NRR', —(CH$_2$)$_g$NRR',
—O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;
$R^3$ is selected from the group consisting of H, halo, hydroxy, —NRR', —(CH$_2$)$_g$NRR',
—O—(CH$_2$)$_g$NRR', —C(═O)—NRR', cyano, lower alkyl, $C_3$-$C_6$ cyclic alkyl, lower alkoxy, $C_1$-$C_3$ perfluoro alkyl, $C_1$-$C_3$ perfluoro alkoxy and carboxyl;

alternatively R² and R³ are taken together to form a 4- to 7-membered fused ring having from 0 to 3 ring heteroatoms, and is unsubstituted or is substituted with halo, hydroxyl, amino, —C(=O)-lower alkyl, lower alkyl, and lower alkoxy;

R⁵ is selected from H, halo, hydroxy, —NRR', —(CH₂)_gNRR', —O—(CH₂), NRR', —C(=O)—NRR', cyano, lower alkyl, C₃-C₆ cyclic alkyl, lower alkoxy, C₁-C₃ perfluoro alkyl, C₁-C₃ perfluoro alkoxy and carboxyl;

each R⁶¹ is independently selected from the group consisting of H, halo, hydroxy, lower alkyl, substituted lower alkyl, lower alkoxy, aryl, aralkyl, heterocycle, —NRR',
—(CH₂)_fNRR', —O—(CH₂)_gNRR', —C(=O)—NRR', —C(=O)—OR, cyano, lower alkyl, C₃-C₆ cyclic alkyl, C₁-C₃ perfluoro alkyl, C₁-C₃ perfluoro alkoxy and carboxyl;

each R is independently selected from H and lower alkyl,
each R' is independently selected from H, lower alkyl, aryl, substituted aryl, aralkyl, and
substituted aralkyl;
a is selected from 0 to 3;
each f is independently 1 to 3;
each g is independently 2 or 3; and
x is selected from 1 to 3; or a pharmaceutically-acceptable salt thereof.

2. The compound according to claim 1, having the formula IIk:

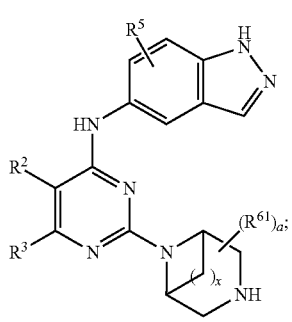

(IIk)

or a pharmaceutically-acceptable salt thereof.
3. A compound having the formula:

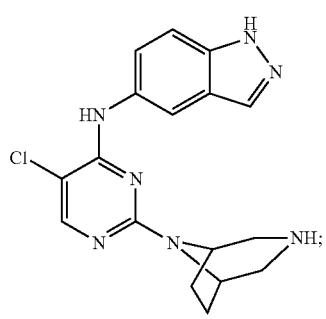 [SMILES: Clc1cnc(N2C3CCC2CNC3)nc1Nc1ccc2[nH]ncc2c1]

or a pharmaceutically-acceptable salt thereof.
4. A method of treating a fibrotic disorder in a subject comprising administering to the subject a therapeutically effective amount of a compound according to claim 1; or a pharmaceutically-acceptable salt thereof, wherein the fibrotic disorder is selected from pulmonary fibrosis, renal fibrosis, and lung fibrosis.

5. The method of claim 4, wherein the pulmonary fibrosis is idiopathic pulmonary fibrosis.

6. A method of treating a disorder related to the inhibition of Rho Associated Coiled-Coil Containing Protein Kinases in a subject comprising administering to the subject a therapeutically effective amount of a compound according claim 1; or a pharmaceutically-acceptable salt thereof.

7. A method of treating glaucoma in a subject comprising administering to the subject a therapeutically effective amount of a compound according claim 1; or a pharmaceutically-acceptable salt thereof.

8. A method of treating a disorder related to the inhibition of Rho Associated Coiled-Coil Containing Protein Kinases in a subject comprising administering to the subject a therapeutically effective amount of a compound according to claim 3; or a pharmaceutically-acceptable salt thereof.

9. A method of treating a fibrotic disorder in a subject comprising administering to the subject a therapeutically effective amount of a compound according to claim 3; or a pharmaceutically-acceptable salt thereof, wherein the fibrotic disorder is selected from pulmonary fibrosis, renal fibrosis, and lung fibrosis.

10. A compound according to claim 3, which is:

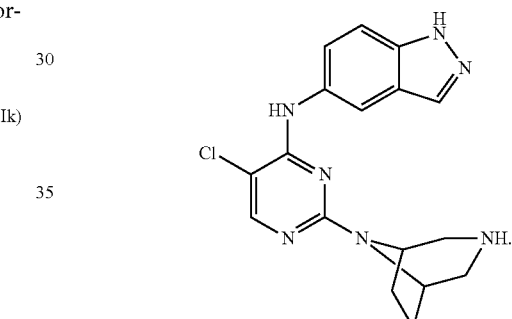

11. The compound according to claim 3, or a pharmaceutically-acceptable salt thereof, wherein the pharmaceutically-acceptable salt is a hydrochloride salt.

12. A pharmaceutical composition comprising a therapeutically effective amount of the compound of claim 3, or a pharmaceutically acceptable salt thereof, formulated with one or more pharmaceutically acceptable excipients.

13. A pharmaceutical composition comprising a therapeutically effective amount of the hydrochloride salt of the compound of claim 3, formulated with one or more pharmaceutically acceptable excipients.

14. A pharmaceutical composition comprising a therapeutically effective amount of the compound of claim 3, or a pharmaceutically acceptable salt thereof, formulated with one or more pharmaceutically acceptable carriers.

15. The pharmaceutical composition according to claim 14 formulated as a solid dosage form for oral administration.

16. A method of treating pulmonary fibrosis in a subject comprising administering to the subject a therapeutically effective amount of a compound according to claim 3, or a pharmaceutically-acceptable salt thereof.

17. The method of claim 16, wherein the pulmonary fibrosis is idiopathic pulmonary fibrosis.

* * * * *

UNITED STATES PATENT AND TRADEMARK OFFICE
CERTIFICATE OF CORRECTION

PATENT NO.        : 11,613,531 B2
APPLICATION NO.   : 16/641465
DATED             : March 28, 2023
INVENTOR(S)       : Eduardas Skucas et al.

It is certified that error appears in the above-identified patent and that said Letters Patent is hereby corrected as shown below:

In the Claims

Claim 1, Column 293, Line 7, "-$(CH_2)_g$NRR', -O-$(CH_2)$, NRR', -C(=O)-" should read -- -$(CH_2)_j$NRR', -O-$(CH_2)_g$NRR', -C(=O)- --

Signed and Sealed this
Twenty-seventh Day of June, 2023

Katherine Kelly Vidal
*Director of the United States Patent and Trademark Office*